(12) United States Patent
Conklin et al.

(10) Patent No.: US 12,345,709 B2
(45) Date of Patent: *Jul. 1, 2025

(54) CLAUDIN18 ANTIBODIES AND METHODS OF TREATING CANCER

(71) Applicant: The Regents of the University of California, Oakland, CA (US)

(72) Inventors: Dylan Conklin, Los Angeles, CA (US); Martina S. McDermott, Los Angeles, CA (US); Neil A. O'Brien, Los Angeles, CA (US); Michael J. Palazzolo, Los Angeles, CA (US); Dennis Slamon, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 374 days.

This patent is subject to a terminal disclaimer.

(21) Appl. No.: 17/627,540

(22) PCT Filed: Jul. 17, 2020

(86) PCT No.: PCT/US2020/042573
§ 371 (c)(1),
(2) Date: Jan. 14, 2022

(87) PCT Pub. No.: WO2021/011885
PCT Pub. Date: Jan. 21, 2021

(65) Prior Publication Data
US 2022/0372133 A1    Nov. 24, 2022

Related U.S. Application Data

(60) Provisional application No. 62/875,416, filed on Jul. 17, 2019.

(51) Int. Cl.
| | | |
|---|---|---|
| *G01N 33/574* | (2006.01) | |
| *A61K 47/68* | (2017.01) | |
| *A61P 1/18* | (2006.01) | |
| *A61P 35/00* | (2006.01) | |
| *C07K 16/28* | (2006.01) | |
| *G01N 33/68* | (2006.01) | |
| *A61K 39/00* | (2006.01) | |

(52) U.S. Cl.
CPC .... *G01N 33/57407* (2013.01); *A61K 47/68031* (2023.08); *A61K 47/6849* (2017.08); *A61P 1/18* (2018.01); *A61P 35/00* (2018.01); *C07K 16/28* (2013.01); *C07K 16/2809* (2013.01); *G01N 33/57438* (2013.01); *G01N 33/57492* (2013.01); *G01N 33/68* (2013.01); *A61K 2039/505* (2013.01); *C07K 2317/24* (2013.01); *C07K 2317/31* (2013.01); *C07K 2317/56* (2013.01); *C07K 2317/77* (2013.01); *C07K 2317/92* (2013.01)

(58) Field of Classification Search
CPC .. C07K 16/28; C07K 16/2809; C07K 2317/24; C07K 2317/31; C07K 2317/56; C07K 2317/77; C07K 2317/92; A61K 47/6803; A61K 47/6849; A61K 2039/505; A61P 1/18; A61P 35/00; G01N 33/57438; G01N 33/57492; G01N 33/68

See application file for complete search history.

(56) References Cited

U.S. PATENT DOCUMENTS

| | | |
|---|---|---|
| 11,834,499 B1 | 12/2023 | Conklin et al. |
| 2016/0008465 A1 | 1/2016 | Sahin et al. |

FOREIGN PATENT DOCUMENTS

| | | | | |
|---|---|---|---|---|
| CN | 109762067 A | 5/2019 | | |
| WO | WO-2008/145338 A2 | 12/2008 | | |
| WO | WO-2014/146778 A1 | 9/2014 | | |
| WO | WO-2016/165762 A1 | 10/2016 | | |
| WO | WO-2018/054484 A1 | 3/2018 | | |
| WO | WO-2018/054973 A1 | 3/2018 | | |
| WO | WO 2019/173420 | * | 3/2019 | ........... A61K 39/395 |
| WO | WO-2020/025792 A1 | 2/2020 | | |
| WO | WO-2021/011885 A1 | 1/2021 | | |

OTHER PUBLICATIONS

Mariuzza (Annu. Rev. Biophys. Biophys. Chem., 16: 139-159, 1987, IDS).*
McCarthy et al. (J. Immunol. Methods, 251(1-2): 137-149, 2001, IDS).*
Lin et al. (African Journal of Biotechnology, 10(79):18294-18302, 2011, IDS).*
International Search Report and Written Opinion for International Application No. PCT/US2020/042573 dated Oct. 20, 2020.
Lin et al., "Improved affinity of a chicken single-chain antibody to avian infectious bronchitis virus by site-directed mutagenesis of complementarity-determining region H3." *African journal of biotechnology* 10.79: 18294-18302 (2011).
Mariuzza et al., "The structural basis of antigen-antibody recognition." *Annual review of biophysics and biophysical chemistry* 16.1: 139-159 (1987).
McCarthy et al., "Altering the fine specificity of an anti-Legionella single chain antibody by a single amino acid insertion", Journal of immunological methods 251(1-2): 137-149 (2001).

(Continued)

*Primary Examiner* — Nelson B Moseley, II
(74) *Attorney, Agent, or Firm* — Foley Hoag LLP; Janine S. Ladislaw; Thi K. Dio

(57) ABSTRACT

The present disclosure provides antigen-binding proteins which bind to Claudin-18.2 (CLDN18.2); bispecific antigen-binding proteins which bind to CLDN18.2 and a second antigen; and conjugates thereof. In various aspects, the antigen-binding proteins bind to Extracellular Loop 1 (EL1) of the extracellular domain of CLDN18.2. Related polypeptides, nucleic acids, vectors, host cells, and conjugates are further provided herein. Kits and pharmaceutical compositions comprising such entities are moreover provided. Also provided are methods of making an antigen-binding protein and methods of treating a subject having cancer.

15 Claims, 44 Drawing Sheets

Specification includes a Sequence Listing.

(56) References Cited

OTHER PUBLICATIONS

Extended European Search Report for EP Application No. 20839947.7 dated Jul. 17, 2023.
Kyuno et al., "Claudin-18.2 as a therapeutic target in cancers: cumulative findings from basic research and clinical trials" Tissue Barriers, 10(1): 16 pages (2022).
Singh et al., "Anti-claudin 18.2 antibody as new targeted therapy for advanced gastric cancer" Journal of Hematology and Oncology, 10:105 (2017).
Robin et al., "Restricted diversity of antigen binding residues of antibodies revealed by computational alanine scanning of 227 antibody-antigen complexes," Journal of Molecular Biology 426 (2014): 3729-3743.
Rudikoff et al., "K chain joining segments and structural diversity of antibody combining sites," PNAS 77.7 (1980): 4270-4274.

* cited by examiner

| CELL LINE ID | CELL LINE NAME | CONTEXT | GENE 1 | GENE 2 |
|---|---|---|---|---|
| PN022 | HUPT4 | Pancreas | 285.62 | 2.14 |
| UG002 | KATO III | Upper GI | 246.53 | 0 |
| UG023 | SNU601 | Upper GI | 245.64 | 3.12 |
| UG009 | NUGC 4 | Upper GI | 144.16 | 0 |
| UG026 | SNU620 | Upper GI | 27.06 | 0 |
| PN024 | PATU 8988S | Pancreas | 24.32 | 0 |
| CL015 | SKCO1 | Colon | 14.48 | 0 |
| UG027 | SNU520 | Upper GI | 13.16 | 1.21 |
| OV020 | OV-90 | Ovarian | 6.93 | 99.53 |
| UG003 | OE19 | Upper GI | 6.02 | 0 |
| OV032 | PEO14 | Ovarian | 3.18 | 0 |
| PN023 | DAN G | Pancreas | 1.82 | 0 |
| CL002 | LOVO | Colon | 1.8 | 0 |
| CL029 | SW1116 | Colon | 1.73 | 0 |
| HN015 | UMSCC 19 | Head and Neck | 1.68 | 0 |
| LG013 | H810 | Lung | 1.67 | 0 |
| UG006 | IM95 | Upper GI | 1.54 | 0 |
| MM019 | MOLP-2 | Myeloma | 1.48 | 0 |
| UG008 | OE33 | Upper GI | 1.36 | 0 |
| CL016 | LS513 | Colon | 1.09 | 0 |

Fig. 3

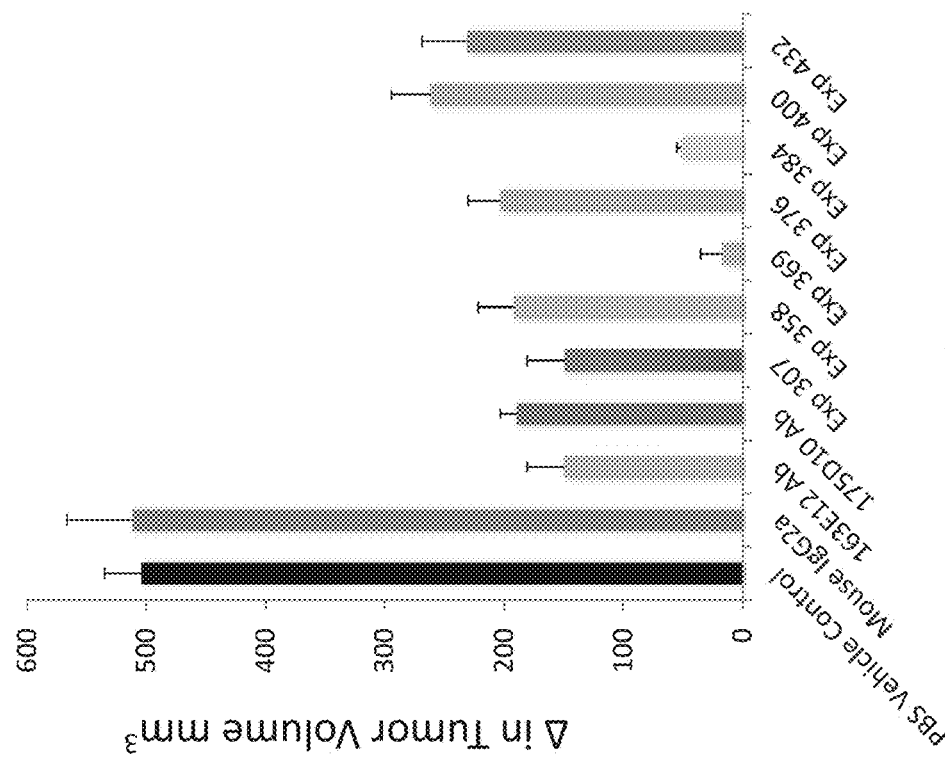
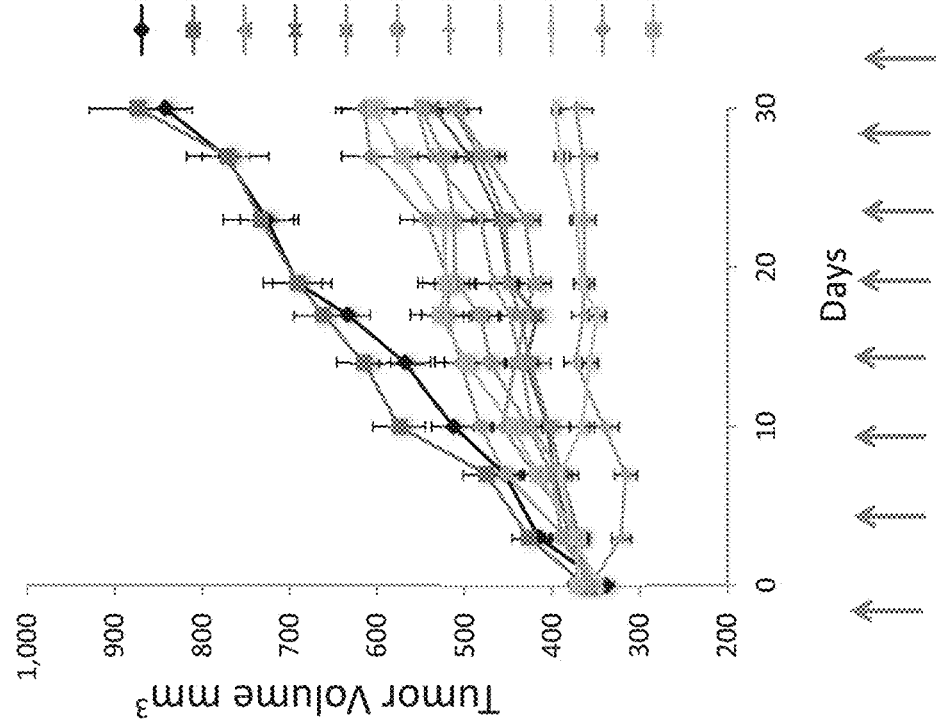
Fig. 5A
Fig. 5B

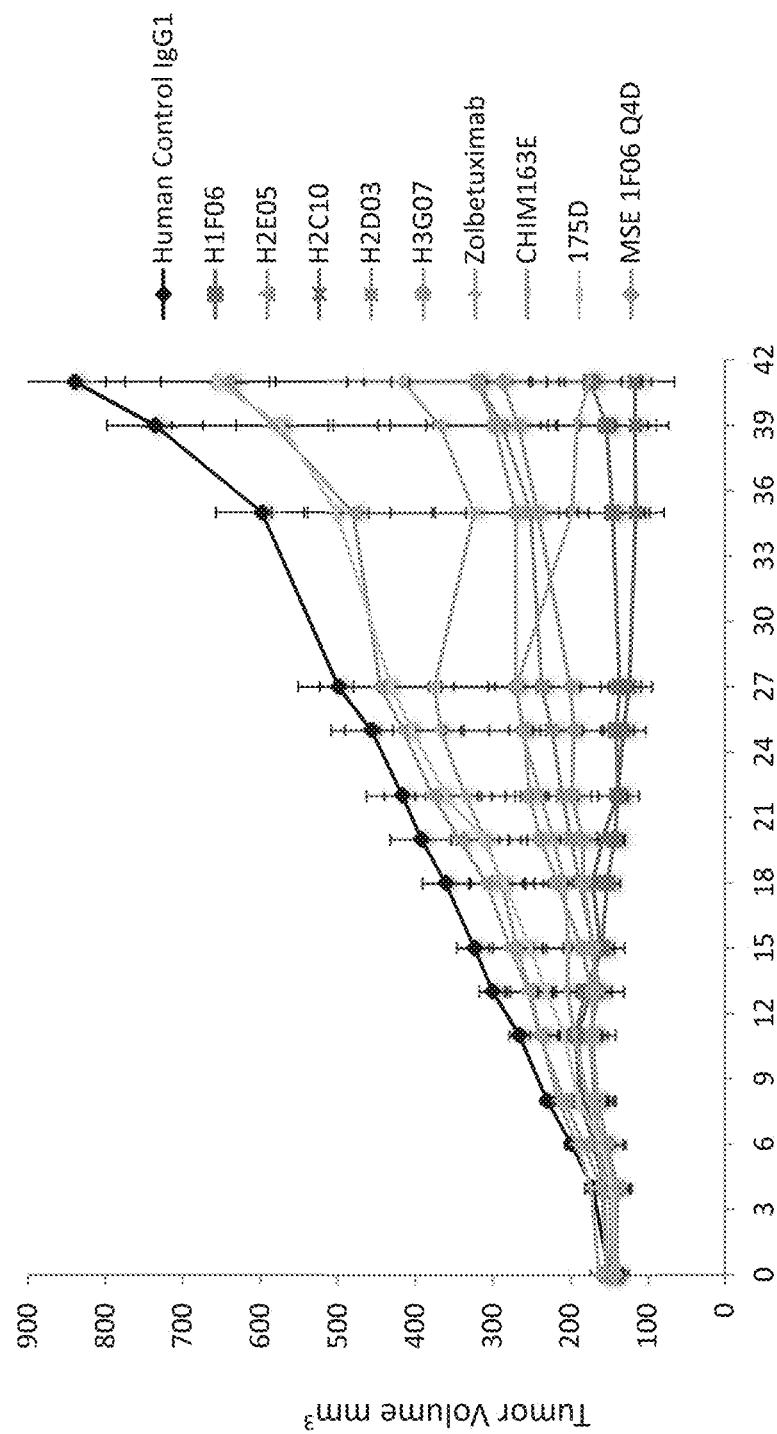
Fig. 7A  *In vivo humanized antibody screen; HUPT4 Day 42*

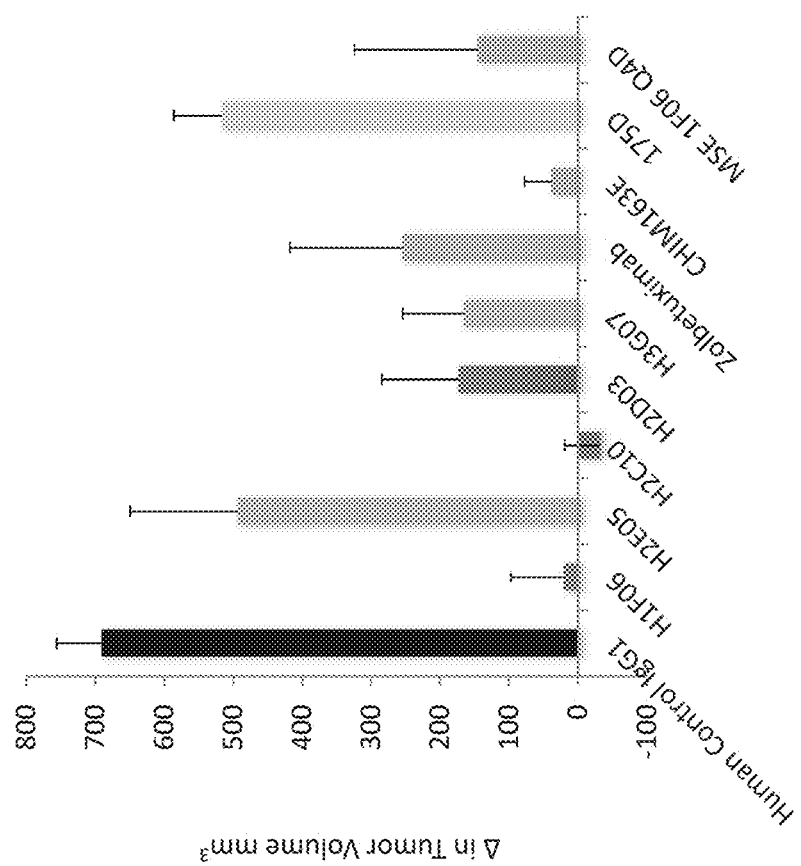
Fig. 7B  In vivo humanized antibody screen; HUPT4 Day 42

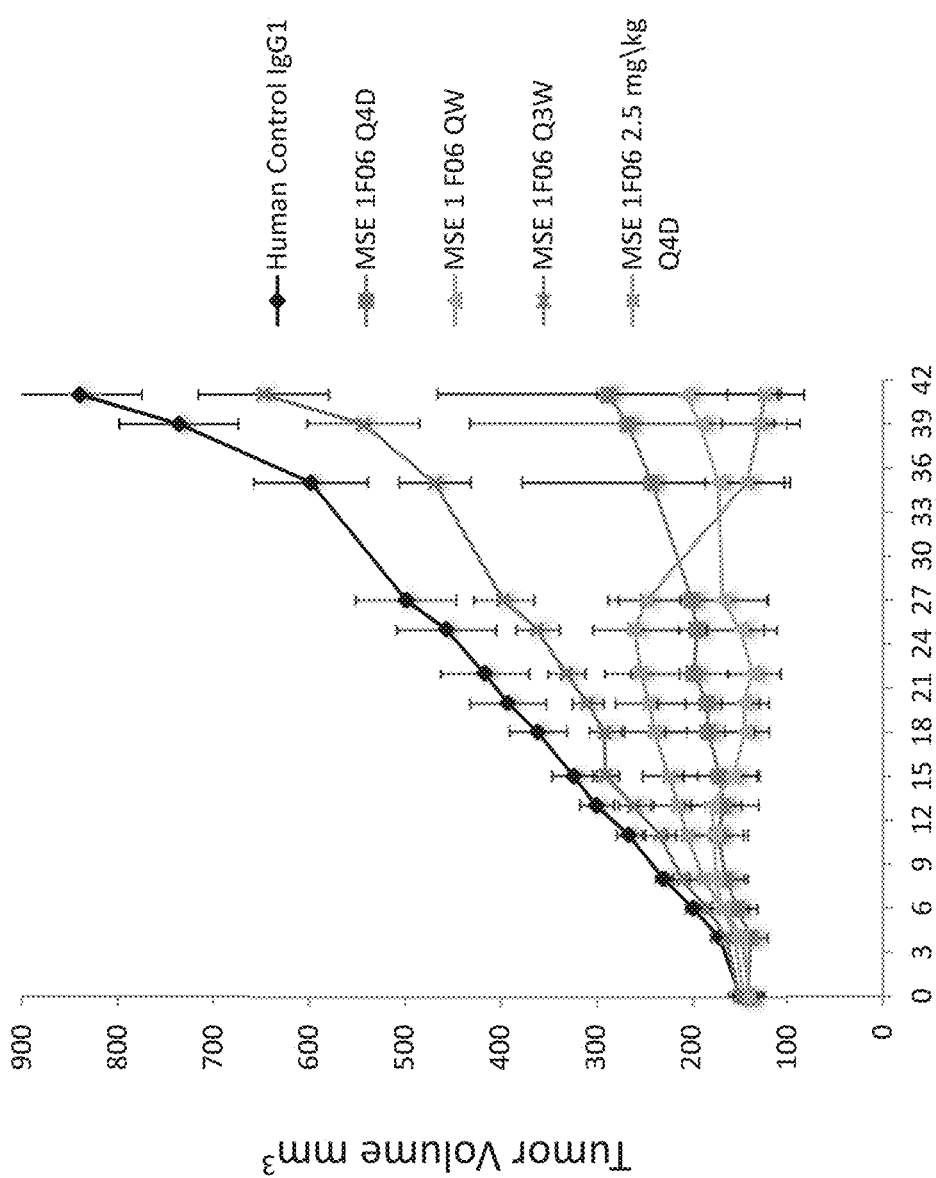
Fig. 8A Dose Scheduling; HUPT4 Day 42

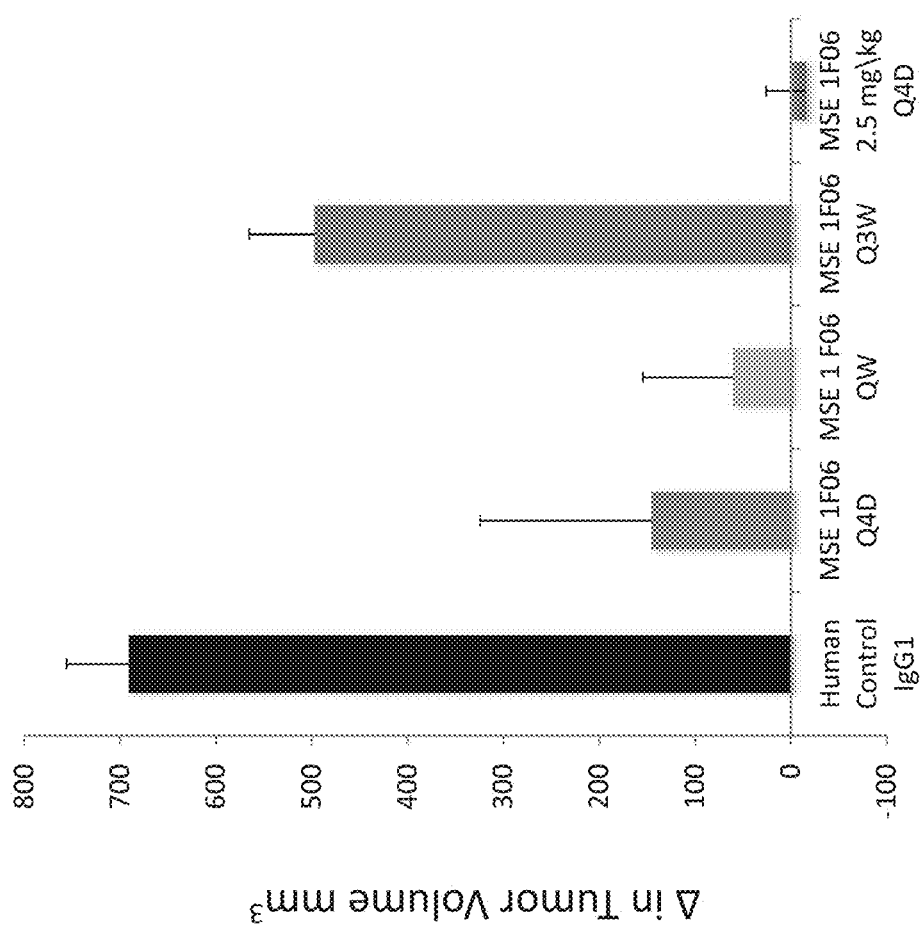
Fig. 8B Dose Scheduling; HUPT4 Day 42

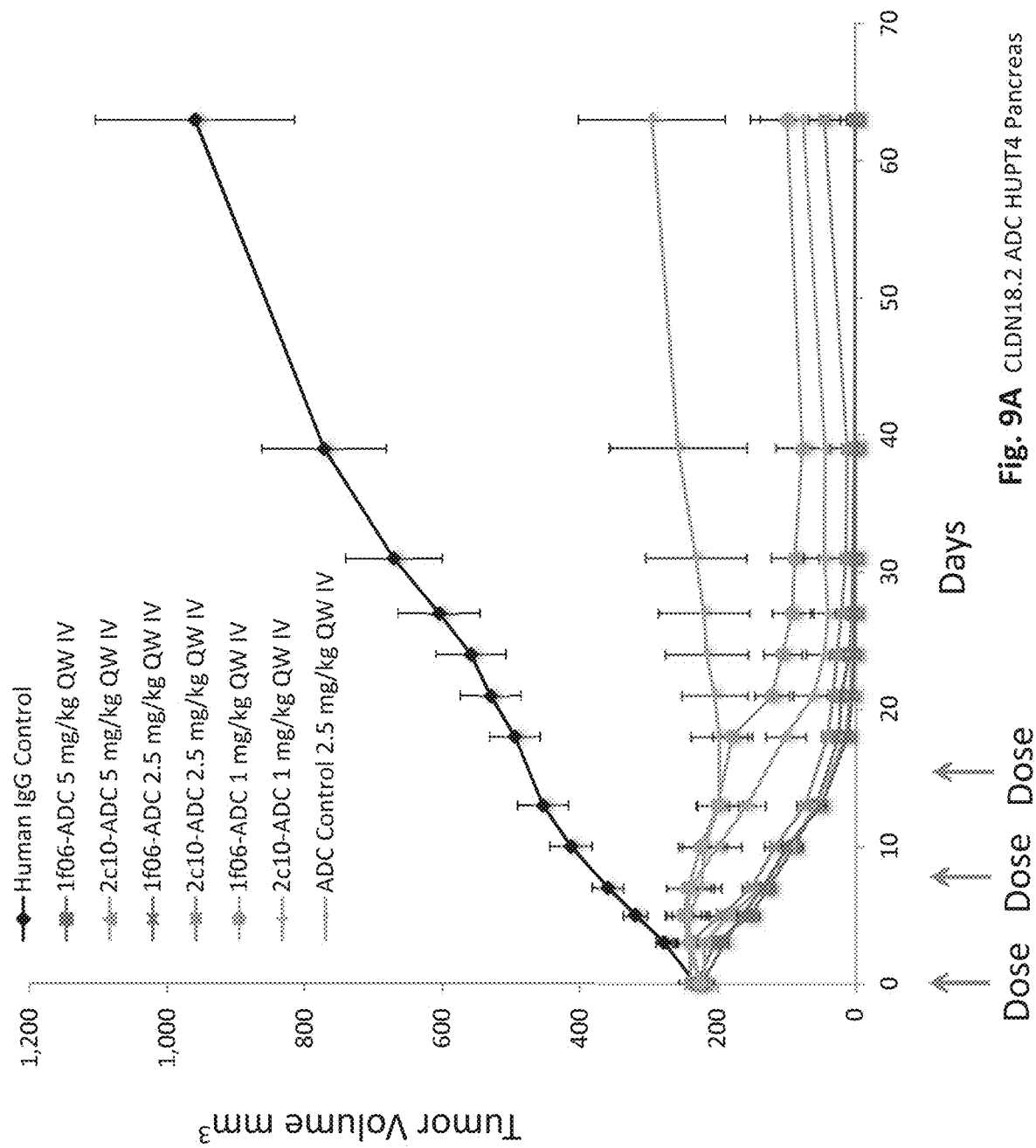
Fig. 9A CLDN18.2 ADC HUPT4 Pancreas

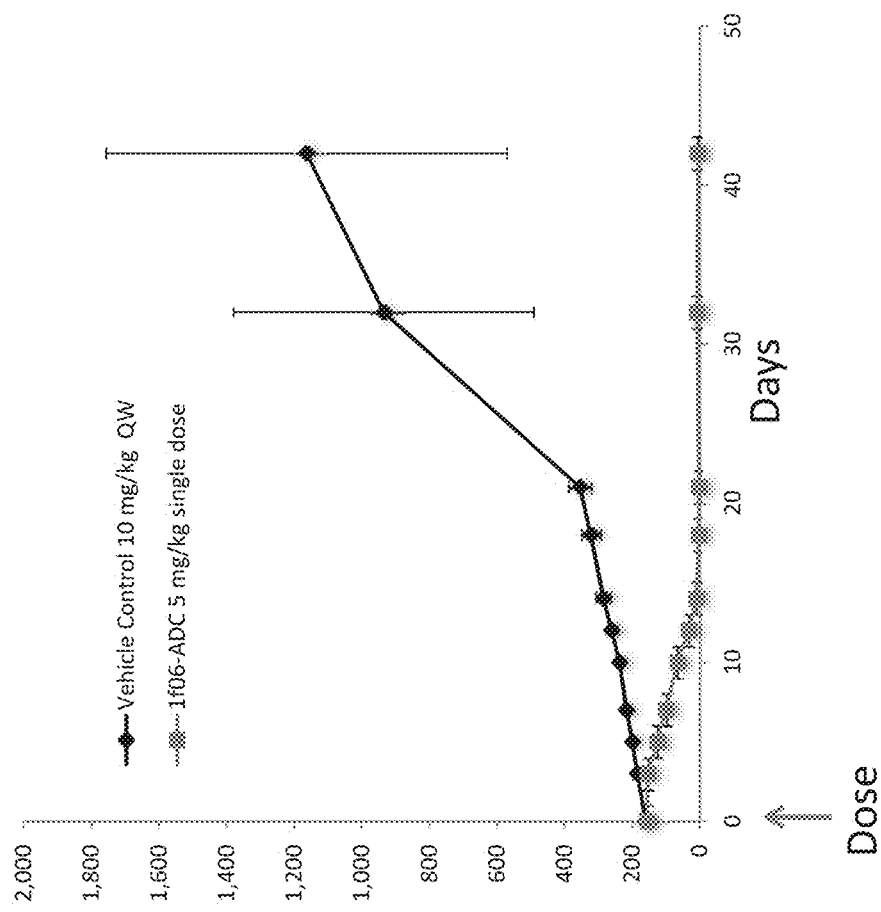
Fig. 9B CLDN18.2 ADC HUPT4 Pancreas

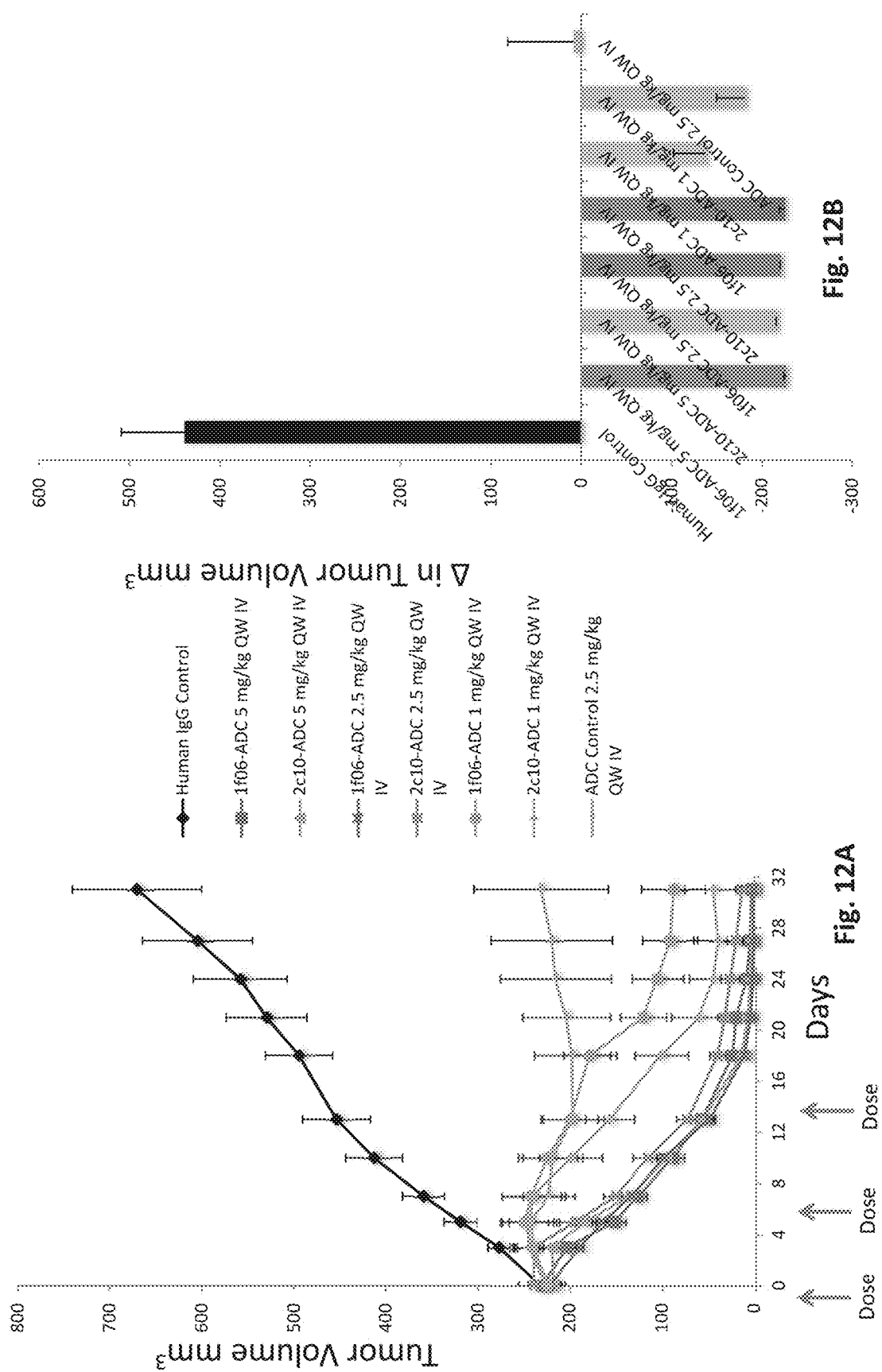

Fig. 13

| SEQ ID NO: | Ab Clone | Amino Acid Sequence |
|---|---|---|
| | | Light Chain Variable Region |
| 11 | 307 | DIVMTQSPSSLTVTTGEKVTMSCKSSQSLLNSGNQKNYLSWYQQIPGQPPKLLIFYWASTRESGVPDRFTGSGS GTDFTLTISNVQAEDLAVYYCQNDYSYPFTFGAGTKLELR |
| 13 | 369 | DILMTQSPSSLFVTAGEKVTMTCKSSQSLLNSGNQKNYLTWYQQKPGQPPKLLIYWASSRESGVPDRFTGSGS GTDFTLTISSVQAEDLAVYYCQNDYSYPFTFGAGTKLELK |
| 15 | 376 | DIVMTQSPSSLTVTAGEKVTMSCKSSQSLLNSGNQKNYLTWYQQKPGQPPKLLIYWASTRESGVPDRFTGSGS GTGFTLTISSVQAEDLAVYYCQNDYSFPFTFGAGTKLELK |
| 17 | 358 | DIVMTQSPSSLTVTAGEKVTMSCKSSQSLFNSGNQRNYLTWYQQKPGQPPKLLIYWASTRESGVPDRFTGSGS GTGFTLTISSVQAEDLAFYYCQNVIYPLTFGLGTKLELR |
| 19 | 384 | DIVMTQSPSSLTVTAGEKVTMSCKSSQSLLNSGNQKNYLTWYQQRPGQPPKLLIYWASTRESGVPDRFTGSGS GTDFTLTISSVQAEDLAVYCCQNNYYPFTFGGGTKLGIK |
| 21 | 360 | DIVMTQSPSSLAVTAGEQVTMSCKSSQSLLNSGNQKNYLTWYQQKPGQPPKLLIYWASIRQSGVPDRFTGSGS GTDFTLTISSVQAEDLAVYYCQLNDYGFPLTFGAGTKLELK |
| 23 | 432 | DIVMTQSPSSLTVTAREKVTMTCKSSQSLLNSGNQKNYLTWYQQKPGQPPKLLIYWASTRESGVPDRFTGSGS GTDFTLTISSVQAEDLAVYYCQNAYYPFTFGGGTKLEIK |
| 25 | 400 | DVVMTQSPSSLTVTAGEKVTMSCKSSQSLLNSGNQRSYLTWYQQKPGQPPKLLIYWASTRESGAPDRFTGSGS GADFTLTISSVQAEDLAIYYCQNNYNYPFTFGSGTKLEIK |
| 27 | 331 | DIVMTQSPSSLTVTAGEKVTMSCKSSQSLLNSGNQKNYLTWYQQKPGQPPKLLFYWASTKKSGVPDRFTGSGS RTDFTLTISSVQAEDLAVYYCLNDYSFPLTFGAGTKLELK |
| 29 | 347 | DIVMTQSPSSLTVTGEQVTMSCKSSQSLLNSGNQKNYLTWYQQKPGQPPKLLIYWASTRQSGVPDRFTGSGS GTDFTLTISSVQAEDLTVYYCLNDYSFPLTFGAGTKLELK |
| 31 | 339 | DIVMTQSPSSLTVTISSAQAADLAVYYCLNDYSFPLFFGGGTKLEIK DIVMTQSPSSLTVTAGEKVTMTCKSSQSLLNSGNQKNYLTWYQQKPGQPPKLLIYWASTGASGVPDRFTGSGS |
| 33 | 301 | DIVMTQSPSSLTVTAGEKVTMDCKSSQSLLNSGNQKNYLTWYQQKSGQPPKLLIYWASIRKSGVPDRFTGSGS GTDFTLTISSVQAEDLAVYYCLNDYSFPLTFGAGTKLELK |
| 35 | 392 | QIVLTQSPAIMSASPGQKVTITCSASSTINYMHWYQQKLGSSPKLMIYDTSKLAPGVPARFSGSGSGTSYSLT ISSMEAEDAASYFCHQWSSYPPTFGSGTKLEIK |
| 37 | 416 | DIQMTQTTSSLSASLGDRVTISCRASQDISNYLNWYQQKPDGTVKLLIYYTSRLHSGVPSRFSGSGSGTDYSL TISNLEPEDIATYYCQHYSKLPPTFGSGTKLEIK |
| 39 | 409 | DIVITQDELSNPVTSGESVSLSCRSSKSLLYKDGKTYLNWFLQRPGQSPQLLVYWMSTRASGVSDRFSGSGSG TDFTLEISRVKAEDVGVYYCQQVVYPYTFGSGTKLEIK |
| 41 | 424 | DIVMTQSPSSLTVTAGEKVTMSCKSSQSLLNSGNQKNYLTWYQQKPGQPPKLLIYWASTRESGVPDRFTGSGS GTDFTLTISSVQAEDLAVYYCQNDYSYPFTFGSGTKLEIK |
| 58 | Benchmark 1-175D10 | |

Fig. 13, cont.

| SEQ ID NO: | Ab Clone | Amino Acid Sequence |
|---|---|---|
| 60 | Benchmark 2-163E12 | DIVMTQSPSSLTVTAGEKVTMSCKSSQSLLNSGNQKNYLTWYQQKPGQPPKLLIYWASTRESGVPDRFTGSGS GTDFTLTISSVQAEDLAVYYCQNDYSYPLTFGAGTKLELK |
| 62 | Benchmark 3-zoletuximab | DIVMTQSPSSLTVTAGEKVTMSCKSSQSLLNSGNQKNYLTWYQQKPGQPPKLLIYWASTRESGVPDRFTGSGS GTDFTLTISSVQAEDLAVYYCQNDYSYPFTFGSGTKLEIK |
| | Heavy Chain Variable Region | |
| 10 | 307 | DVKLVESGGGLVKPGGSLKLSCAASGFTFSSYTMSWVRQTPEKRLEWVATIIGGSYTYYPDSVKGRFTISRD NAKNTLYLQMSSLKSEDTAMYYCTRLVKGNAMDYWGQGTSVAVSS |
| 12 | 369 | DVKLVESGGGLVKPGGSLKLSCAASGFTFTSYTMSWVRQTPEKRLEWVATIIGGSYTYYPDSVKGRFTISRD NAKNTLYLQMSSLKSEDTAMYYCTRLVKGNAMDYWGQGTSVTVSS |
| 14 | 376 | DVKLVESGGGLVKPGGSLKLSCAASGFTFSSYTMSWVRQTPEKRLYWVATISSGVSYTYYPDSVKGRFTISRD NAKNTLYLQMSSLKSEDTAMYYCTRLITKGNAMDYWGQGTSVTVSS |
| 16 | 358 | VVQLVESGGDFVQPGGSRKLSCAVSGFTFSSFGMHWVRQAPEKGLEWVAYISSGTTNIYYADTVKGRFFVSRD NFKNSLFLHMTSLRSEDTAMYYCVRSGYYGNSLDYWGQGTPLLVSS |
| 18 | 384 | QVQLQQSGAELARPGASVKLSCKASDYTFTSYISWVKQRTGQLEWIGEIYPRNGNTYYNEKFKGKATLTAD KSSSTAYMELRSLTSEDSAVYFCARSYYGNSFAYWGQGTLVTVSA |
| 20 | 360 | VVQLQQSGPELVKPGASVKMSCKASGYTFTSYLMHWVRQKPGLGLDWIGYINPYNDGTNYNAKFIDKATLTSD KTSSTAYMELSSLTSEDSAIYYCTRGDYWGQGTSVTVSS |
| 22 | 432 | QIQLQQSGAELARPRASVKLSCKASGYTFTSDVISWVKQRPGQGLEWIGESYLRNGNTYYNENFKGKATLTAD KSSSTAYMELRSLITSEDSAVYFCARSYGNSFAYWGQGTLVTVSA |
| 24 | 400 | QVQLKESGPGLIVAPSQSLSITCTVSGFSLNSYGVSWVRQPPGKGLEWLGVIWGDGSTNYHSALKSRLNINKDK SKSQVFLKLNSLQTDDTATYYCARPTRGNAMDYWGQGTSVTVSS |
| 26 | 331 | EVQLQQSGPELVKPGASVRMSCKASGYTFTSYIMHWVKQKPGQGPEWMGYINPYNDGTNYNEKFKDKATLTSD KSSSTAYMDLSSLTSEDSAVYYCTRGDYWGQGTSVTVSS |
| 28 | 347 | EVQLQQSGPELVKPGASVKMSCKASGYTFTSYLIHWVKQKPGQGLEWIGYINPYNDATYYNEKFKAKATLTSD KSSSTAYMELSSLTSEDTAIYYCTRGDYWSQGTSVTVSS |
| 30 | 339 | EVQLQQSGPELVKPGASVKMSCKASGYTFTSYVMHWVKQKPGQGLEWIGYFNPYNDDTKYNEKFKGKATLTSD KSSSTAYMDLSSLITSEDSAVYYCTRGDYWGQGTSVTVSS |
| 32 | 301 | VVQLQQSGPELVKPGASVKMSCKASGYTFTSFLIHWVRQKPGLGLEWIGYINPYDYGINYNVKFMDKVTLTSD KTSSTAYMELSSLTSADSAIYYCTRGDYWGQGTSVTVSS |
| 34 | 392 | EVQLQQSGPELVKPGASVKMSCKASGFTFTSYVMHWVKQKSGQGLEWIGYINPYNDDIKYNAKFEDKATLTSD RSSSTAYMELSSLTSDDSAVYFCTRGDYWGQGTLTVSS |
| 36 | 416 | EFQLQQSGPELVKPGASVKISCKASVYSFTGYNMNWVKQSNGKSLEWIGVINPYNGNTYYNEKFKGKATLTVD QSSSTAYMQLNSLITSEDSAVYYCARSEDYYNIRGASWGQGTLVTVSA |
| 38 | 409 | QVQLQQSGAELARPGASVKLISEDSAVYFCATGVITTVIPTDWYFDVWGTGTTVSS KSSSTAYMELRSLTSEDSAVYFCATGVITTVIPTDWYFDVWGTGTTVSS |

Fig. 13, cont.

| SEQ ID NO: | Ab Clone | Amino Acid Sequence |
|---|---|---|
| 40 | 424 | EVQLQQSGPELVKPGASVKISCKASGYSFTVYYMNWVKQSPEKSLEWIGEINPSTGGTTYNPKFKAKATLTVD KSSSTAYMQLKSLTSEDSALYFCVRWADYWGQGTTLTVSS |
| 59 | Benchmark 1 | QVQLQQPGAELVRPGASVKLSCKASGYTFTSYWINWVKQRPGQGLEWIGNIYPSDSYTNYNQKFKDKATLTVD KSSSTAYMQLSSPTSEDSAVYYCTRSWRGNSFDYWGQGTTLTVSS |
| 61 | Benchmark 2 | QVQLQQSGAELARPGASVKLSCKASGYTFTDYYINWVKQRTGQGLEWIGEIYPGSGNTYYNEKFKGKATLTAD KSSSTAYMQLSSLTSEDSAVYFCARSYGAFDYWGQGTTLTVSS |
| 148 | Benchmark 2-1 | QIQLVQSGPELKKPGETVKISCKASGYTFTNYGMNWVKQAPGKGLKWMGWINTNTGEPTYAEEFKGRFAFSLE TSASTAYLQINNLKNEDTATYFCARLGFGNAMDYWGQGTSVTVSS |
| 63 | Benchmark 3-zoletuximab | QVQLQQPGAELVRPGASVKLSCKASGYTFTSYWINWVKQRPGQGLEWIGNIYPSDSYTNYNQKFKDKATLTVD KSSSTAYMQLSSPTSEDSAVYYCTRSWRGNSFDYWGQGTTLTVSS |
| | | Humanized Light Chain Variable Region |
| 43 | HuAb307-1 (L1) | DIVMTQSPDSLAVSLGERATINCKSSQSLLNSGNQKNYLSWYQQKPGQPPKLLIYWASTRESGVPDRFSGSGS GTDFTLTISSLQAEDVAVYYCQNDYSYPFTFGQGTKLEIK |
| 44 | HuAb307-2 (L2) | DIVMTQSPDSLAVSLGERATINCKSSQSLLNSGNQKNYLSWYQQKPGQPPKLLFYWASTRESGVPDRFSGSGS GTDFTLTISSLQAEDVAVYYCQNDYSYPFTFGQGTKLEIK |
| 45 | HuAb307-3 (L3) | QVQLQQSGAELARPGASVKLSCKASGYTFTDYYINWVKQRTGQGLEWIGEIYPGSGNTYYNEKFKGKATLTAD KSSSTAYMQLSSLTSEDSAVYFCARSYGAFDYWGQGTTLTVSS |
| 47 | HuAb376-1 (L1) | DIVMTQSPDSLAVSLGERVTMNCKSSQSLLNSGNQKNYLTWYQQKPGQPPKLLIYWASTRESGVPDRFSGSGS GTDFTLTISSLQAEDVAVYYCQNDYSYPFTFGQGTKLEIK |
| 48 | HuAb376-2 (L2) | DIVMTQSPDSLAVSLGERVTMNCKSSQSLFNSGNQRNYLTWYQQKPGQPPKLLIYWASTRESGVPDRFSGSGS GTDFTLTISSVQAEDVAVYYCQNVIYPLTFGQGTKLEIK |
| 149 | HuAb358-1 (L1) | DIVMTQSPDSLAVSLGERVTMNCKSSQSLFNSGNQRNYLTWYQQKPGQPPKLLIYWASTRESGVPDRFSGSGS GTDFTLTISSLQAEDVAVYYCQNVIYPLTFGQGTKLEIK |
| 150 | HuAb358-2 (L2) | DIVMTQSPDSLAVSLGERVTMNCKSSQSLFNSGNQRNYLTWYQQKPGQPPKLLIYWASIRQSGVPDRFSGSGS GTDFTLTISSVQAEDVAVYYCQNVIYPLTFGQGTKLEIK |
| 53 | HuAb360-1 (L1) | DIVMTQSPDSLAVSLGERVTMNCKSSQSLLNSGNQKNYLTWYQQKPGQPPKLLIYWASIRQSGVPDRFSGSGS GTDFTLTISSLQAEDVAVYYCLNDYGFPLTFGQGTKLEIK |
| 54 | HuAb360-2 (L2) | DIVMTQSPDSLAVSLGERVTMNCKSSQSLLNSGNQKNYLTWYQQKPGQPPKLLIYWASIRQSGVPDRFSGSGS GTDFTLTISSVQAEDVAVYYCLNDYGFPLTFGQGTKLEIK |
| 53 | HuAb360-3 (L1) | DIVMTQSPDSLAVSLGERVTMNCKSSQSLLNSGNQKNYLTWYQQKPGQPPKLLIYWASIRQSGVPDRFSGSGS GTDFTLTISSLQAEDVAVYYCLNDYGFPLTFGQGTKLEIK |
| 54 | HuAb360-4 (L2) | DIVMTQSPDSLAVSLGERVTMNCKSSQSLLNSGNQKNYLTWYQQKPGQPPKLLIYWASIRQSGVPDRFSGSGS GTDFTLTISSVQAEDVAVYYCLNDYGFPLTFGQGTKLEIK |
| 53 | HuAb360-5 (L1) | DIVMTQSPDSLAVSLGERVTMNCKSSQSLLNSGNQKNYLTWYQQKPGQPPKLLIYWASIRQSGVPDRFSGSGS GTDFTLTISSLQAEDVAVYYCLNDYGFPLTFGQGTKLEIK |

Fig. 13, cont.

| SEQ ID NO: | Ab Clone | Amino Acid Sequence |
|---|---|---|
| 54 | HuAb360-6 (L2) | DIVMTQSPDSLAVSLGERVTMNCKSSQSLLNSGNQKNYLTWYQQKPGQPPKLLIYWASIRQSGVPDRFSGSGS GTDFTLTISSVQAEDVAVYYCLNDYGFPLTFGQGTKLEIK |
| 50 | HuAb432-1 (L1) | DIVMTQSPDSLAVSLGERATINCKSTQSLLNSGNQKNYLTWYQQKPGQPPKLLIYWASTRESGVPDRFSGSGS GTDFTIHISSLQAEDVAVYYCQNAYYYPFTFGQGTKLEIK |
| 51 | HuAb432-2 (L2) | DIVMTQSPDSLAVSLGERVTMNCKSTQSLLNSGNQKNYLTWYQQKPGQPPKLLIYWASTRESGVPDRFSGSGS GTDFTLTISSVQAEDVAVYYCQNAYYYPFTFGQGTKLEIK |
| 50 | HuAb432-3 (L1) | DIVMTQSPDSLAVSLGERATINCKSTQSLLNSGNQKNYLTWYQQKPGQPPKLLIYWASTRESGVPDRFSGSGS GTDFTLTISSLQAEDVAVYYCQNAYYYPFTFGQGTKLEIK |
| 51 | HuAb432-4 (L2) | DIVMTQSPDSLAVSLGERVTMNCKSTQSLLNSGNQKNYLTWYQQKPGQPPKLLIYWASTRESGVPDRFSGSGS GTDFTLTISSVQAEDVAVYYCQNAYYYPFTFGQGTKLEIK |
| | | Humanized Heavy Chain Variable Region |
| 42 | HuAb307-1 (H2) | EVQLLESGGGLVQPGGSLRLSCAASGFTFSSYTMSWVRQAPGKGLEWVATIIGGSYTYYADSVKGRFTISRD NSKNTLYLQMNSLRAEDTAVYYCTRLIVKGNAMDYWGQGTLVTVSS |
| 42 | HuAb307-2 (H2) | EVQLLESGGGLVQPGGSLRLSCAASGFTFSSYTMSWVRQAPGKGLEWVATIIGGSYTYYADSVKGRFTISRD NSKNTLYLQMNSLRAEDTAVYYCTRLIVKGNAMDYWGQGTLVTVSS |
| 42 | HuAb307-3 (H2) | EVQLLESGGGLVQPGGSLRLSCAASGFTFSSYTMSWVRQAPGKGLEWVATIIGGSYTYYADSVKGRFTISRD NSKNTLYLQMNSLRAEDTAVYYCTRLIVKGNAMDYWGQGTLVTVSS |
| 46 | HuAb376-1 (H2) | EVQLLESGGGLVQPGGSLRLSCAASGFTFSSYTMSWVRQAPGKGLEWVATISSGVSYTYYADSVKGRFTISRD NSKNTLYLQMNSLRAEDTAVYYCTRLTKGNAMDYWGQGTLVTVSS |
| 46 | HuAb376-2 (H2) | EVQLLESGGGLVQPGGSLRLSCAVSGFTFSSFGM4HWVRQAPGKGLEWVAYISSGTTNIYYADSVKGRFTVSRD NAKNSLYLQMNSLRAEDTAVYYCVRSGYYGNSLDYWGQGTLVTVSS |
| 131 | HuAb358-1 (H2) | EVQLLESGGGLVQPGGSLRLSCAVSGFTFSSFGMHWVRQAPGKGLEWVAYISSGTTNIYYADSVKGRFTISRD NAKNSLYLQMNSLRAEDTAVYYCVRSGYYGNSLDYWGQGTLVTVSS |
| 131 | HuAb358-2 (H2) | EVQLLESGGGLVQPGGSLRLSCAVSGFTFSSFGMHWVRQAPGKGLEWVAYISSGTTNIYYADSVKGRFTISRD NAKNSLYLQMNSLRAEDTAVYYCVRSGYYGNSLDYWGQGTLVTVSS |
| 52 | HuAb360-1 (H2) | QVQLVQSGAEVKKPGASVKVSCKASGYTFTSYLMHWVRQAPGQGLEWIGYINPYNDGTNYAQKFQGRVTMTSD TSTSTVYMELSSLRSEDTAVYYCTRGDYWGQGTLVTVSS |
| 52 | HuAb360-2 (H2) | QVQLVQSGAEVKKPGASVKVSCKASGYTFTSYLMHWVRQAPGQGLEWIGYINPYNDGTNYAQKFQGRVTMTSD TSTSTVYMELSSLRSEDTAVYYCTRGDYWGQGTLVTVSS |
| 55 | HuAb360-3 (H3) | QVQLVQSGAEVKKPGASVKMSCKASGYTFTSYLMHWVRQAPGQGLEWIGYINPYNDGTNYAQKFQGRATLTSD TSTSTAYMELSSLRSEDTAVYYCTRGDYWGQGTLVTVSS |
| 55 | HuAb360-4 (H3) | QVQLVQSGAEVKKPGASVKMSCKASGYTFTSYLMHWVRQAPGQGLEWIGYINPYNDGTNYAQKFQGRATLTSD TSTSTAYMELSSLRSEDTAVYYCTRGDYWGQGTLVTVSS |
| 56 | HuAb360-5 (H4) | QVQLVQSGAEVKKPGASVKMSCKASGYTFTSYLMHWVRQAPGQGLEWIGYINPYNDGTNYAQKFQGRATLTSD KSTSTAYMELSSLRSEDTAVYYCTRGDYWGQGTLVTVSS |

Fig. 13, cont.

| SEQ ID NO: | Ab Clone | Amino Acid Sequence |
|---|---|---|
| 56 | HuAb360-6 (H4) | QVQLVQSGAEVKKPGASVKMSCKASGYTFTSYLMHWVRQAPGQGLEWIGYINPYNDGTNYAQKFQGRATLTSD KSTSTAYMELSSLRSEDTAVYYCTRGDYWGQGTLVTVSS |
| 57 | HuAb432-1 (H1) | QVQLVQSGAEVKKPGSSVKVSCKASGYTFTSDVISWVRQAPGQGLEWMGESYLRNGNTYYAQKFQGRVTITAD KSTSTAYMELSSLRSEDTAVYYCARSYYGNSFAYWGQGTLVTVSS |
| 57 | HuAb432-2 (H1) | QVQLVQSGAEVKKPGSSVKVSCKASGYTFTSDVISWVRQAPGQGLEWMGESYLRNGNTYYAQKFQGRVTITAD KSTSTAYMELSSLRSEDTAVYYCARSYYGNSFAYWGQGTLVTVSS |
| 49 | HuAb432-3 (H2) | QVQLVQSGAEVKKPGSSVKLSCKASGYTFTSDVISWVRQAPGQGLEWIGESYLRNGNTYYAQKFQGRATLTAD KSTSTAYMELSSLRSEDTAVYYCARSYYGNSFAYWGQGTLVTVSS |
| 49 | HuAb432-4 (H2) | QVQLVQSGAEVKKPGSSVKLSCKASGYTFTSDVISWVRQAPGQGLEWIGESYLRNGNTYYAQKFQGRATLTAD KSTSTAYMELSSLRSEDTAVYYCARSYYGNSFAYWGQGTLVTVSS |

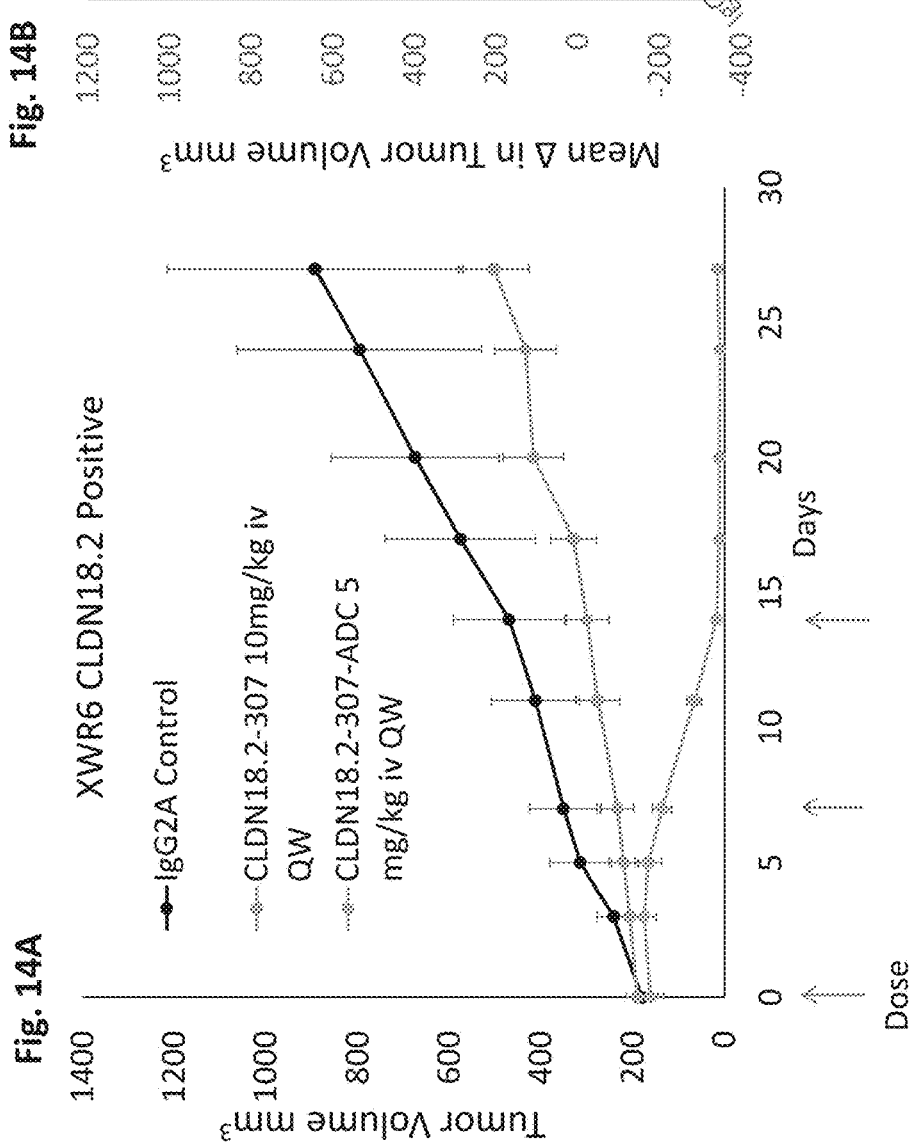
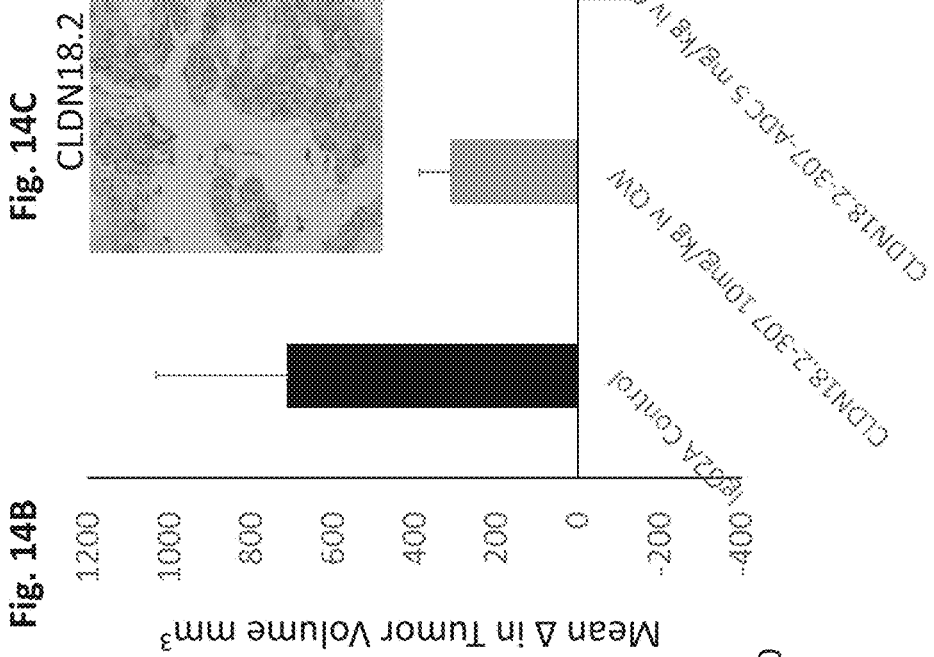
Fig. 14A
Fig. 14B
Fig. 14C CLDN18.2

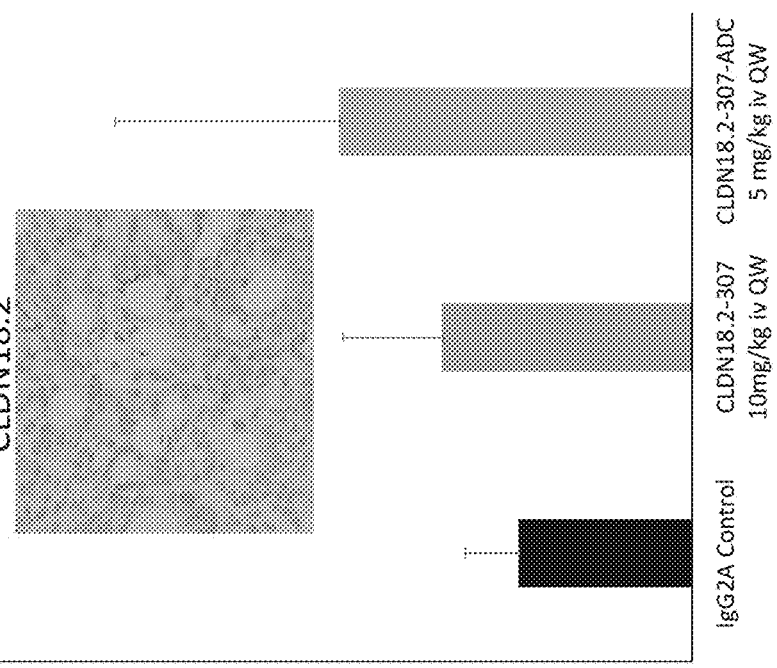
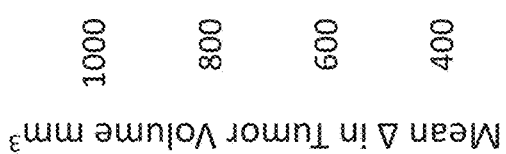
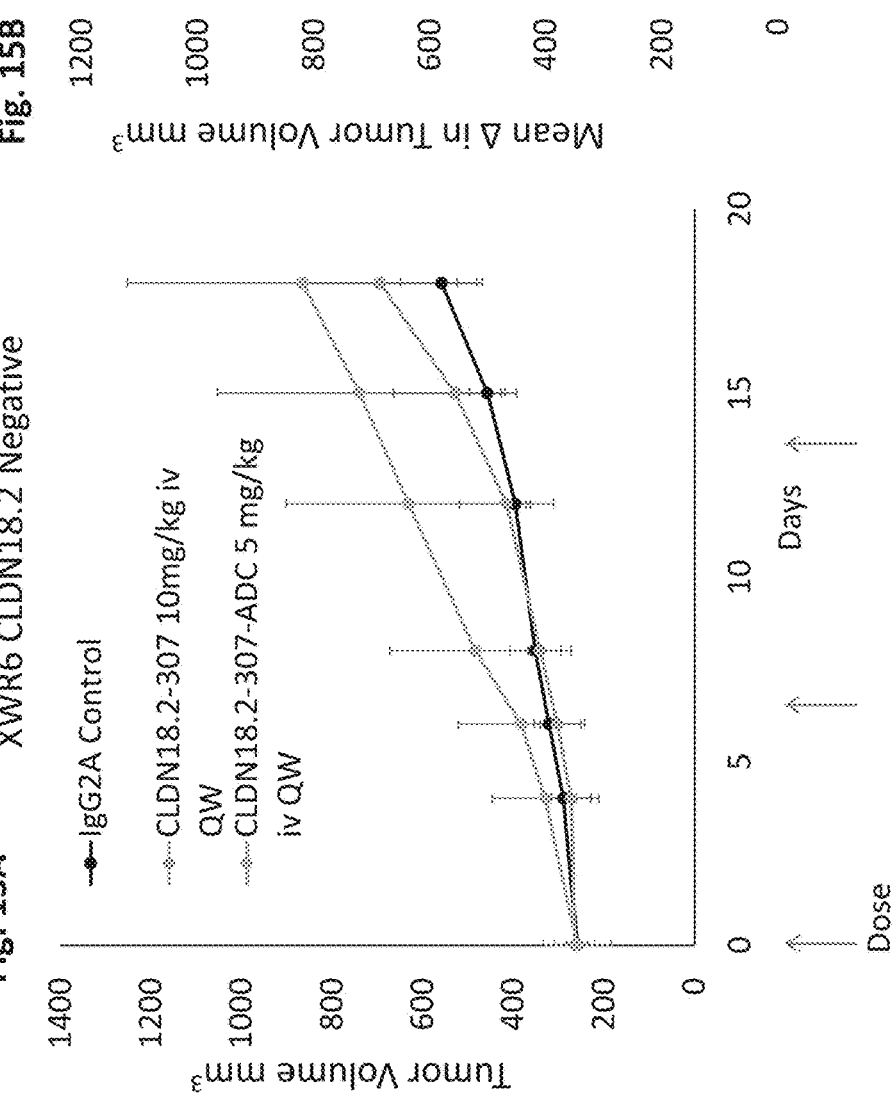

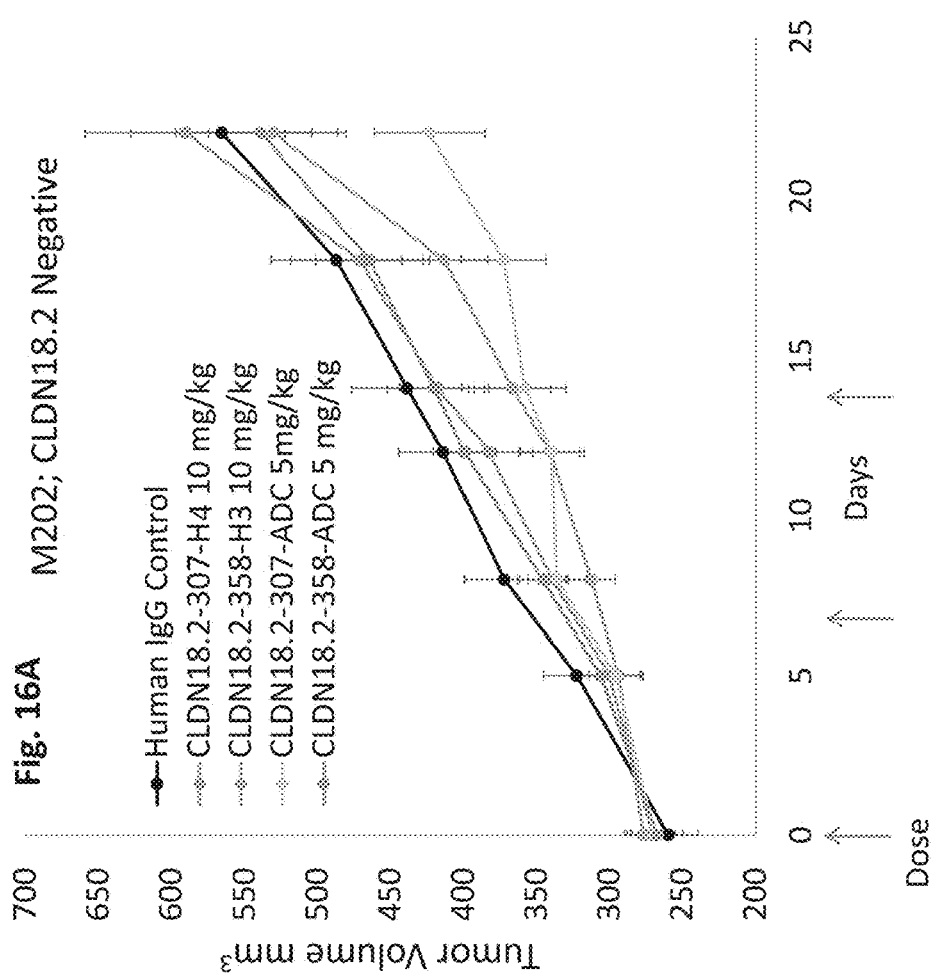
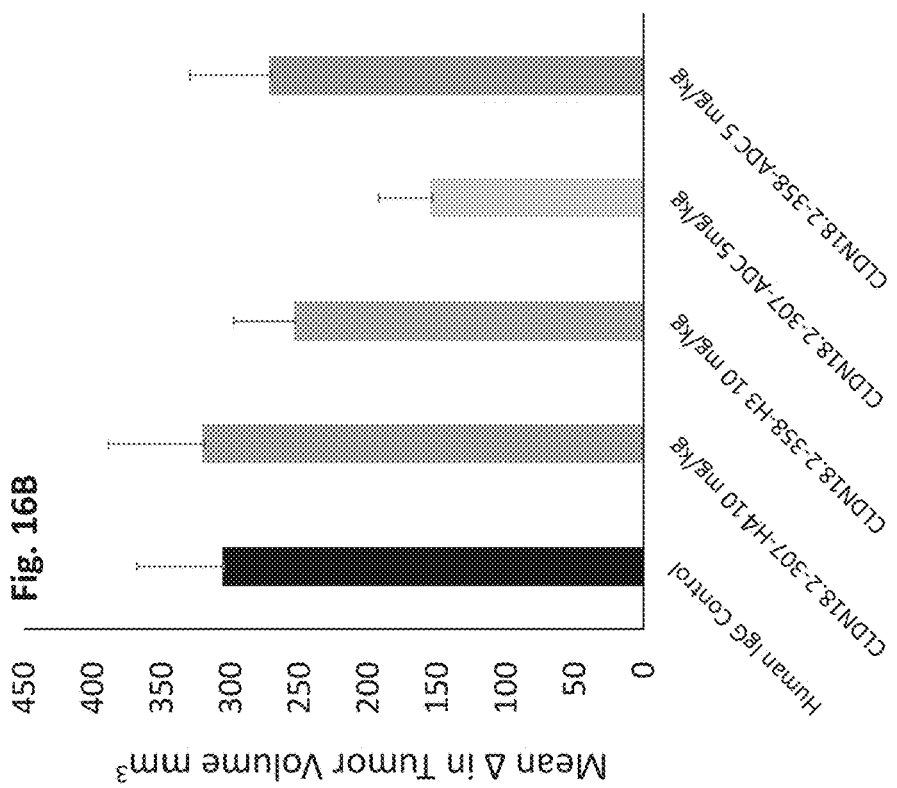

Fig. 17

| SEQ ID NO | Name | Description | Sequence |
|---|---|---|---|
| 131 | 02-0358-4h_VH | 02-0358-4h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGNSLDYYWGQGTLVTVSS |
| 135 | 02-0358-4h_VL | 02-0358-4h antibody | DIVMTQSPDSLAVSLGERVTMNCKSSQSLFQSSGNQRNYLTWYQQKPGQPPKLLIYWASTRESGVPDRFSGSGSGTDFTLTISSVQAEDVAVYYCQNVYIYPLTFGQGTKLEIK |
| 131 | 02-0358-5h_VH | 02-0358-5h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGNSLDYYWGQGTLVTVSS |
| 136 | 02-0358-5h_VL | 02-0358-5h antibody | DIVMTQSPDSLAVSLGERVTMNCKSSQSLFSSGNQRNYLTWYQQKPGQPPKLLIYWASSTRESGVPDRFSGSGSGTDFTLTISSVQAEDVAVYYCQNVYIYPLTFGQGTKLEIK |
| 133 | 02-0358-6h_VH | 02-0358-6h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGSLDYWGQGTLVTVSS |
| 137 | 02-0358-6h_VL | 02-0358-6h antibody | DIVMTQSPDSLAVSLGERVTMNCKSSQSLFNSSGNQRNYLTWYQQKPGQPPKLLIYWASSTRESGVPDRFSGSGSGTDFTLTISSVQAEDVAVYYCQNVYIYPLTFGQGTKLEIK |
| 134 | 02-0358-7h_VH | 02-0358-7h antibody | EVQLVESGGGLVQPGGSLRLSCAVSGFTFSSFGMHWVRQAPGKGLEWVAYISSGTTNIYYADSVKGRFTVSRDNAKNSLYIQMNSLRAEDTAVYYCVRSGYYGSLDYWGQGTLVTVSS |
| 137 | 02-0358-7h_VL | 02-0358-7h antibody | DIVMTQSPDSLAVSLGERVTMNCKSSQSLFNSSGNQRNYLTWYQQKPGQPPKLLIYWASSTRESGVPDRFSGSGSGTDFTLTISSVQAEDVAVYYCQNVYIYPLTFGQGTKLEIK |
| 133 | 02-0358-8h_VH | 02-0358-8h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGQSLDYWGQGTLVTVSS |
| 135 | 02-0358-8h_VL | 02-0358-8h antibody | DIVMTQSPDSLAVSLGERVTMNCKSSQSLFQSSGNQRNYLTWYQQKPGQPPKLLIYWASSTRESGVPDRFSGSGSGTDFTLTISSVQAEDVAVYYCQNVYIYPLTFGQGTKLEIK |
| 132 | 02-0358-9h_VH | 02-0358-9h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGSLDYWGQGTLVTVSS |
| 136 | 02-0358-9h_VL | 02-0358-9h antibody | DIVMTQSPDSLAVSLGERVTMNCKSSQSLFSSGNQRNYLTWYQQKPGQPPKLLIYWASSTRESGVPDRFSGSGSGTDFTLTISSVQAEDVAVYYCQNVYIYPLTFGQGTKLEIK |
| 134 | 02-0358-10h_VH | 02-0358-10h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGSLDYWGQGTLVTVSS |
| 136 | 02-0358-10h_VL | 02-0358-10h antibody | DIVMTQSPDSLAVSLGERVTMNCKSSQSLFSSGNQRNYLTWYQQKPGQPPKLLIYWASSTRESGVPDRFSGSGSGTDFTLTISSVQAEDVAVYYCQNVYIYPLTFGQGTKLEIK |
| 134 | 02-0358-11h_VH | 02-0358-11h antibody | EVQLVESGGGLVQPGGSLRLSCAVSGFTFSSFGMHWVRQAPGKGLEWVAYISSGTTNIYYADSVKGRFTISRDNSKNTLYLQMNSLRAEDTAVYYCVRSGYYGSLDYWGQGTLVTVSS |
| 136 | 02-0358-11h_VL | 02-0358-11h antibody | DIVMTQSPDSLAVSLGERVTMNCKSSQSLFSSGNQRNYLTWYQQKPGQPPKLLIYWASSTRESGVPDRFSGSGSGTDFTLTISSVQAEDVAVYYCQNVYIYPLTFGQGTKLEIK |
| 42 | 02-h1F06-5h_VH | 02-h1F06-5h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGNAMDYWGQGTLVTVSS |
| 140 | 02-h1F06-5h_VL | 02-h1F06-5h antibody | DIVMTQSPDSLAVSLGERVTMNCKSSQSLLSSGNQKNYLSWYQQKPGQPPKLIFYWASTRESGVPDRFSGSGSGTDFTLTISSVQAEDVAVYYCQQNDYSYPFTFGQGTKLEIK |
| 42 | 02-h1F06-6h_VH | 02-h1F06-6h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGNAMDYWGQGTLVTVSS |
| 141 | 02-h1F06-6h_VL | 02-h1F06-6h antibody | DIVMTQSPDSLAVSLGERVTMNCKSSQSLLSSGNKNYLSWYQQKPGQPPKLIFYWASTRESGVPDRFSGSGSGTDFTLTISSVQAEDVAVYYCQQNDYSYPFTFGQGTKLEIK |
| 138 | 02-h1F06-7h_VH | 02-h1F06-7h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGQAMDYWGQGTLVTVSS |
| 142 | 02-h1F06-7h_VL | 02-h1F06-7h antibody | DIVMTQSPDSLAVSLGERVTMNCKSSQSLLNSGNKNYLSWYQQKPGKGLEWVATIWGGSYTYYADSVKGRFTISRDNSKNTLYLQMNSLRAEDTAVYYCQQNDYSYPFTFGQGTKLEIK |
| 138 | 02-h1F06-8h_VH | 02-h1F06-8h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGQAMDYWGQGTLVTVSS |
| 140 | 02-h1F06-8h_VL | 02-h1F06-8h antibody | DIVMTQSPDSLAVSLGERVTMNCKSSQSLLQSSGNKNYLSWYQQKPGQPPKLIFYWASTRESGVPDRFSGSGSGTDFTLTISSVQAEDVAVYYCQQNDYSYPFTFGQGTKLEIK |
| 138 | 02-h1F06-9h_VH | 02-h1F06-9h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGQAMDYWGQGTLVTVSS |
| 141 | 02-h1F06-9h_VL | 02-h1F06-9h antibody | DIVMTQSPDSLAVSLGERVTMNCKSSQSLLSSGNKNYLSWYQQKPGQPPKLIFYWASTRESGVPDRFSGSGSGTDFTLTISSVQAEDVAVYYCQQNDYSYPFTFGQGTKLEIK |
| 139 | 02-h1F06-10h_VH | 02-h1F06-10h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGSAMDYWGQGTLVTVSS |
| 142 | 02-h1F06-10h_VL | 02-h1F06-10h antibody | DIVMTQSPDSLAVSLGERVTMNCKSSQSLLNSGNKNYLSWYQQKPGQPPKLIFYWASTRESGVPDRFSGSGSGTDFTLTISSVQAEDVAVYYCQQNDYSYPFTFGQGTKLEIK |
| 139 | 02-h1F06-11h_VH | 02-h1F06-11h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGSAMDYWGQGTLVTVSS |
| 140 | 02-h1F06-11h_VL | 02-h1F06-11h antibody | DIVMTQSPDSLAVSLGERVTMNCKSSQSLLSSGNKNYLSWYQQKPGQPPKLIFYWASTRESGVPDRFSGSGSGTDFTLTISSVQAEDVAVYYCQQNDYSYPFTFGQGTKLEIK |
| 139 | 02-h1F06-12h_VH | 02-h1F06-12h antibody | EVQLLESGGGLVQPGGSLRLSCAASGFTFSSYTMSWVRQAPGKGLEWVATIWGSGNKNYLSWYQQKPGQPPKLIFYWASTIWGGSYTYYADSVKGRFTISRDNSKNTLYLQMNSLRAEDTAVYYCTRLVKGSAMDYWGQGTLVTVSS |
| 141 | 02-h1F06-12h_VL | 02-h1F06-12h antibody | DIVMTQSPDSLAVSLGERVTMNCKSSQSLLSSGNKNYLSWYQQKPGQPPKLIFYWASTRESGVPDRFSGSGSGTDFTLTISSVQAEDVAVYYCQQNDYSYPFTFGQGTKLEIK |

Fig. 18

| Group ID | Name | | | | | | | | | | | | | |
|---|---|---|---|---|---|---|---|---|---|---|---|---|---|---|
| | 358 Jun 10162018 | 8,323.00 | 8,164.00 | 9,679.00 | | | 3,663,369.0 | 8,851.0 | 9,954.5 | 8,714.0 | 1,538,407.0 | 1,483,036.0 | 655,824.5 | 700.00 | 133.62 |
| U2761EH060-1 | 02-0358-4h | 9,743.00 | 9,875.00 | 9,163.00 | | | 2,280,899.0 | 15,099.5 | 10,721.5 | 11,716.0 | 1,634,110.0 | 1,459,323.0 | 433,762.0 | 574.82 | 93.97 |
| U2761EH060-2 | 02-0358-5h | 9,627.00 | 8,763.00 | 9,020.00 | | | 2,198,515.5 | 12,521.0 | 10,424.0 | 10,362.5 | 1,643,079.0 | 1,607,770.0 | 512,497.0 | 573.89 | 110.99 |
| U2761EH060-3 | 02-0358-6h | 9,256.00 | 9,969.00 | 8,441.00 | | | 691,375.0 | 12,774.0 | 10,568.0 | 10,456.0 | 1,437,921.0 | 1,041,623.0 | 222,124.0 | 434.71 | 79.94 |
| U2761EH060-4 | 02-0358-7h | 13,061.00 | 10,058.00 | 8,687.00 | | | 1,207,647.0 | 13,544.5 | 9,470.0 | 9,566.0 | 1,486,990.0 | 1,324,881.0 | 252,917.5 | 448.98 | 94.07 |
| U2761EH060-5 | 02-0358-8h | 11,052.00 | 11,712.50 | 8,051.50 | | | 463,876.0 | 12,614.0 | 8,445.0 | 8,869.0 | 888,216.0 | 649,161.0 | 193,841.0 | 228.71 | 57.95 |
| U2761EH060-6 | 02-0358-9h | 8,931.00 | 8,258.00 | 8,188.00 | | | 755,247.5 | 9,069.0 | 7,454.5 | 9,414.5 | 1,464,129.0 | 924,009.5 | 33,989.0 | 452.61 | 99.38 |
| U340LEH060-1 | 02-0358-10h | 9,988.50 | 9,849.50 | 7,017.00 | | | 447,864.0 | 8,366.0 | 8,391.0 | 8,197.5 | 782,883.0 | 539,386.0 | 27,118.0 | 274.37 | 54.07 |
| U340LEH060-2 | 02-0358-11h | 9,060.50 | 9,481.50 | 8,169.00 | | | 448,173.0 | 10,883.5 | 8,545.0 | 8,995.0 | 1,355,931.5 | 1,077,192.5 | 90,925.0 | 456.24 | 88.80 |
| | 307 Jun 07022018 | 10,207.00 | 7,785.00 | 10,070.00 | | | 882,289.0 | 10,194.5 | 10,266.0 | 9,137.0 | 1,668,181.0 | 1,518,551.0 | 357,802.0 | 480.23 | 119.76 |
| U505BEH130-2 | 02-h1F06-5h | 7,865.00 | 10,928.00 | 9,805.00 | | | 469,344.0 | 10,221.5 | 8,942.5 | 11,408.0 | 1,665,867.0 | 1,606,587.0 | 437,194.5 | 408.12 | 121.34 |
| U505BEH130-3 | 02-h1F06-6h | 8,109.00 | 10,555.00 | 8,628.00 | | | 1,101,019.5 | 8,874.0 | 8,055.0 | 10,555.0 | 1,845,893.5 | 1,693,376.5 | 412,621.0 | 443.94 | 136.51 |
| U505BEH130-4 | 02-h1F06-7h | 8,392.00 | 11,628.00 | 7,914.00 | | | 1,106,724.0 | 8,991.0 | 8,895.0 | 10,695.0 | 373,477.5 | 213,932.0 | 55,716.0 | 335.64 | 22.50 |
| U505BEH130-5 | 02-h1F06-8h | 11,460.50 | 10,362.00 | 8,408.00 | | | 574,195.5 | 10,637.5 | 7,571.0 | 9,893.0 | 217,507.0 | 91,583.0 | 33,043.0 | 165.62 | 12.17 |
| U519NEH130-1 | 02-h1F06-9h | 8,538.50 | 10,288.00 | 8,196.50 | | | 1,088,188.0 | 7,685.0 | 7,225.5 | 10,005.0 | 576,193.0 | 359,285.0 | 188,556.5 | 273.10 | 45.11 |
| U519NEH130-2 | 02-h1F06-10h | 13,151.50 | 9,047.50 | 7,776.50 | | | 565,415.0 | 10,404.5 | 7,012.0 | 8,390.0 | 101,787.0 | 42,834.5 | 20,990.0 | 201.79 | 6.42 |
| U519NEH130-3 | 02-h1F06-11h | 8,251.00 | 9,627.00 | 7,177.00 | | | 48,044.0 | 7,569.5 | 7,203.5 | 8,228.0 | 16,637.0 | 11,092.0 | 7,142.5 | 39.99 | 1.52 |
| U519NEH130-4 | 02-h1F06-12h | 8,384.00 | 9,948.50 | 8,416.00 | | | 437,912.0 | 7,197.0 | 7,266.0 | 9,325.0 | 154,905.0 | 63,210.5 | 17,154.5 | 183.38 | 9.99 |

Fig. 19

| Cell Line | 02-0307-h4- AF647 10ug | 02-0307-h4- AF647 1ug | 02-0307-h4- AF647 0.1ug | 02-0358-h3- AF647 10ug | 02-0358-h3- AF647 1ug | 02-0358-h3- AF647 0.1ug | 02-0307-h6- AF647 10ug | 02-0307-h6- AF647 1ug | 02-0307-h6- AF647 0.1ug | 02-0358-h5- AF647 10ug | 02-0358-h5- AF647 1ug | 02-0358-h5- AF647 0.1ug |
|---|---|---|---|---|---|---|---|---|---|---|---|---|
| HEK293T parental | 12,759.00 | 5,328.00 | 3,276.00 | 16,812.50 | 4,198.00 | 3,268.00 | 22,390.50 | 9,051.00 | 2,726.00 | 29,683.50 | 8,287.00 | 3,589.50 |
| HEK293T human CLDN18.2 mGFP clone C12 | 3,670,336.00 | 4,311,651.00 | 578,978.00 | 3,920,868.00 | 2,704,978.00 | 542,378.00 | 7,956,859.50 | 7,335,815.00 | 4,029,889.00 | 7,049,930.50 | 6,956,234.00 | 3,801,790.00 |
| HEK293T human CLDN18.1 mGFP 2B14 | 76,882.00 | 54,053.50 | 52,064.00 | 99,053.00 | 55,250.00 | 50,394.00 | 155,836.00 | 68,751.00 | 53,053.50 | 140,467.00 | 64,830.00 | 52,692.00 |
| HEK293T mouse CLDN18.2 mGFP mass pop | 6,934,857.00 | 4,027,796.50 | 472,034.50 | 5,928,398.00 | 2,287,345.50 | 285,031.00 | 9,668,803.00 | 9,439,164.00 | 2,345,982.00 | 9,496,393.00 | 8,763,806.00 | 2,517,805.00 |
| HEK293T dogCLDN18 moxGFP mass pop | 10,150.00 | 6,025.50 | 3,862.00 | 11,728.50 | 4,232.00 | 3,705.00 | 21,807.00 | 9,480.00 | 3,691.00 | 20,562.00 | 8,759.00 | 4,696.00 |
| HEK293T rat CLDN18 moxGFP Clone 5 | 13,790.00 | 7,323.00 | 3,807.50 | 16,723.50 | 5,067.00 | 3,715.50 | 30,657.50 | 10,860.00 | 3,601.00 | 31,180.00 | 12,384.00 | 4,580.00 |

Fig. 21A

| CLDN18.2 hAb | KD | | | Expression Level | | | Equilibrium Curves | Cell Model | Detached by |
|---|---|---|---|---|---|---|---|---|---|
| | KD | Error% | 95% Confidence Interval (CI) | Expression Level | 95% Confidence Interval (CI) | | | | |
| pNK-307-h1F06-4 | 3.65nM | 2.35 | 2.12nM - 6.47nM | 2.085E+06 | 1.498E+06 - 3.195E+06 | | 500pM, 2nM, 10nM | HEK293T-CLDN18.2-mGFP C12 | Versene |
| pNK-358-h2C10-3 | 3.00nM | 1.84 | 2.03nM - 4.44nM | 4.963E+06 | 3.869E+06 - 6.623E+06 | | 500pM, 2nM, 10nM | HEK293T-CLDN18.2-mGFP C12 | Versene |
| #307-6h | 1.42nM | 7.72 | 0.18nM - 11.91nM | 3.024E+06 | 1.642E+06 - 1.474E+07 | | 500pM and 10nM | HEK293T-CLDN18.2-mGFP C12 | Versene |
| #358-5h | 1.81nM | 7.19 | 0.43nM - 6.90nM | 2.922E+06 | 1.561E+06 - 7.021E+06 | | 500pM and 10nM | HEK293T-CLDN18.2-mGFP C12 | Versene |
| pNK-307-h1F06-4 | 0.69nM | 3.57 | 0.31nM - 1.34nM | 3.313E+05 | 2.558E+05 - 4.458E+05 | | 1nM, 20nM | HUPT4 | Versene |
| pNK-358-h2C10-3 | 1.70nM | 3.73 | 0.87nM - 3.23nM | 4.085E+05 | 2.934E+05 - 6.197E+05 | | 1nM, 20nM | HUPT4 | Versene |
| #307-6h | 0.93nM | 2.72 | 0.58nM - 1.43nM | 3.454E+05 | 2.760E+05 - 4.410E+05 | | 1nM, 20nM | HUPT4 | Versene |
| #358-5h | 0.67nM | 3.90 | 0.28nM - 1.32nM | 3.059E+05 | 2.212E+05 - 4.487E+05 | | 1nM, 20nM | HUPT4 | Versene |

Fig. 21B

| | Cell Line Name | KinExA 4000 | | | Quantum Flow |
|---|---|---|---|---|---|
| | | Histology | Average Expression Level (EL) | 95% Confidence Interval (CI) | Average ABC (Bivalent Binding) (ABC Monovalent x2) |
| | | | | EL Low / EL High | |
| Artificial Overexpressing Line | 293T-CLDN18.2-mGFP C12 | Artificial | 3,534,000 | 2,683,500 / 4,909,000 | 1,664,395 |
| CLDN18.2 Positive Native Cell Lines | HUPT4 | Pancreas | 460,700 | 361,850 / 599,200 | 188,201 |
| | NUGC4 | Upper GI | 452,950 | 288,550 / 823,350 | 212,069 |
| | KATOIII | Upper GI | 514,350 | 293,450 / 845,400 | 161,738 |
| | PATU89885 | Pancreas | 394,800 | 216,650 / 606,250 | 102,503 |

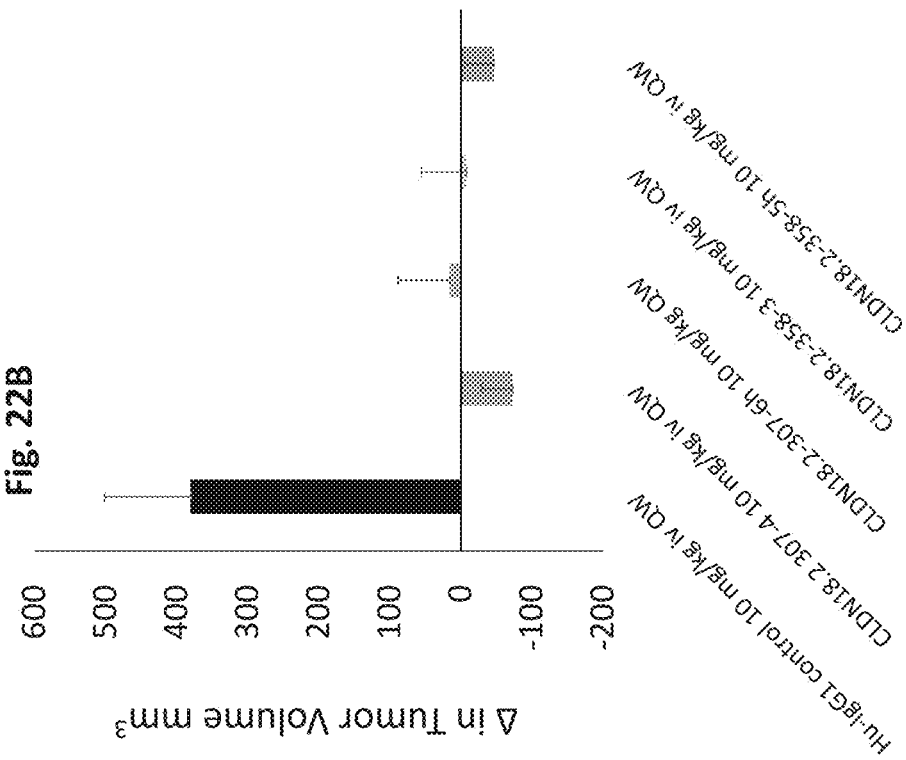
Fig. 22B
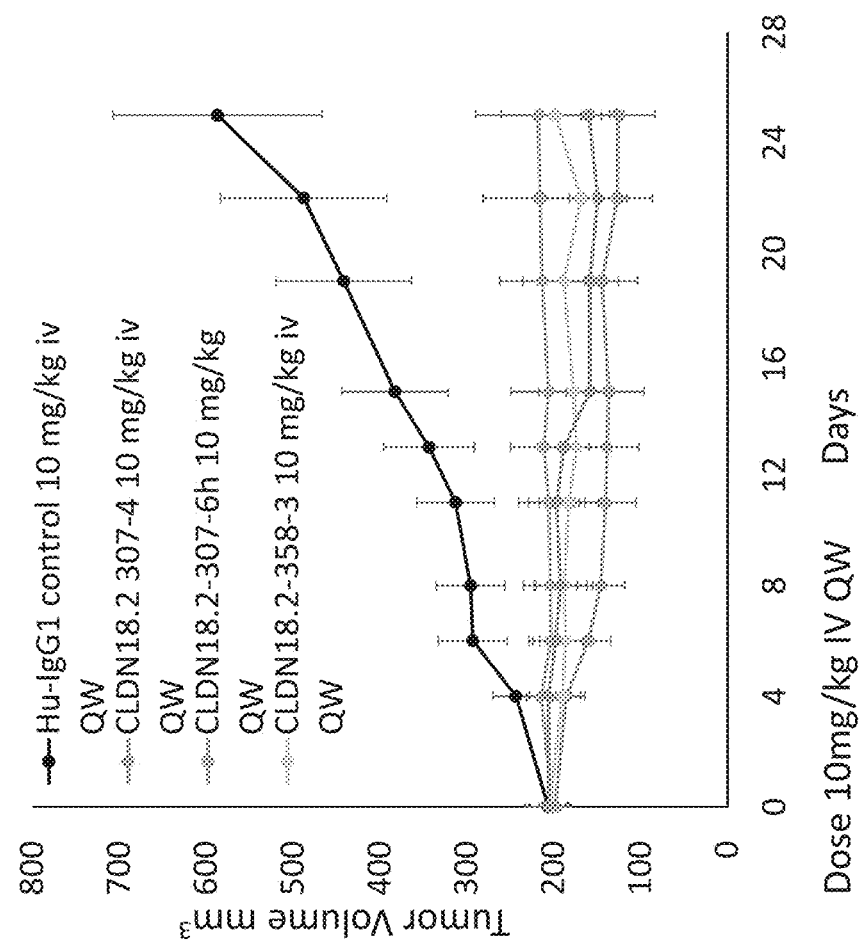
Fig. 22A HUPT4 Pancreas Cell Line Xenograft

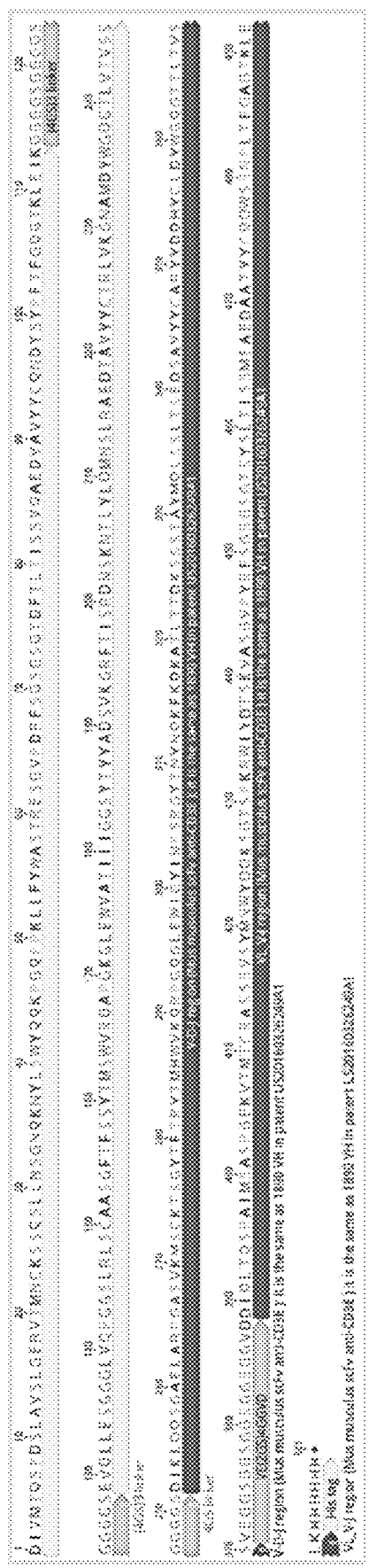
Fig. 23A  02-0307-h4-Bs (SEQ ID NO: 143)
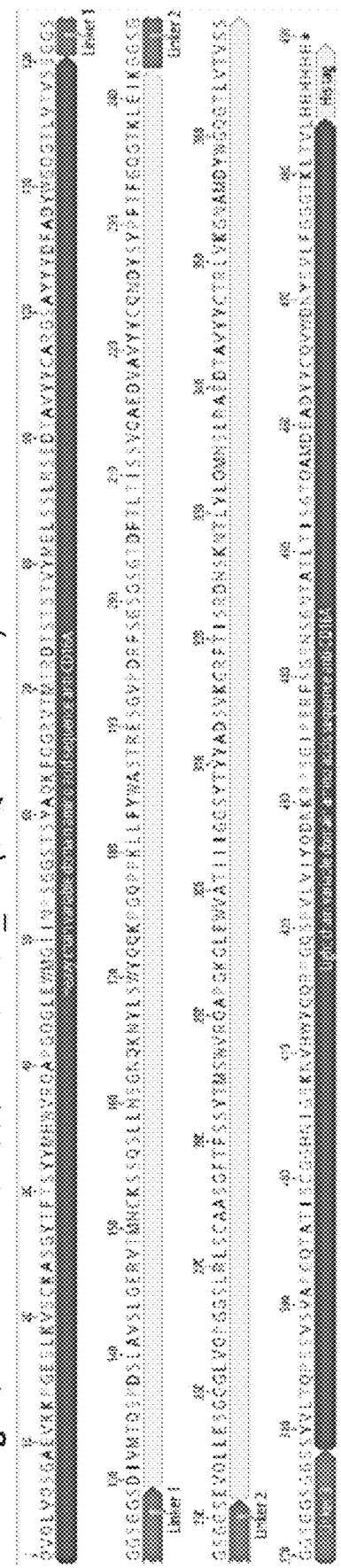
Fig. 23B  02-0307-h4-CD16A_His (SEQ ID NO: 144)

Fig. 23C

| Name | Description | Sequence |
|---|---|---|
| 02-0307-h4-Bs SEQ ID NO: 143 | CLDN18.2 - CD3E BiTE (Bispecific T cell engager) | DIVMTQSPDSLAVSLGERVTMNCKSSQSLLNSGNQKNYLSWYQQKPGQPPKLLFYWASTRESGVPDRFSGSGSGTDFTLTISSVQAEDVAVYYCQNDYSYPFTFGQGTKLEIKGGGGSGGGGSGGGGSEVQLLESGGGLVQPGGSLRLSCAASGFTFSSYTMSWVRQAPGKGLEWVATIHGGSYTYYADSVKGRFTISRDNSKNTLYLQMNSLRAEDTAVYYCTRLVKGNAMDYWGQGTLVTVSSGGGGSDIKLQQSGAELARPGASVKMSCKTSGYTFTRYTMHWVKQRPGQGLEWIGYINPSRGYTNYNQKFKDKATLTTDKSSSTAYMQLSSLTSEDSAVYCARYYDDHYCLDYWGQGTTLTVSSVEGGSGGSGGSGGSGGVDDIQLTQSPAIMSASPGEKVTMTCRASSSVSYMNWYQQKSGTSPKRWIYDTSKVASGVPYRFSGSGSGTSYSLTISSMEAEDAATYYCQQWSSNPLTFGAGTKLELKHHHHHH* |
| 02-0307-h4-CD16A_His SEQ ID NO: 144 | CLDN18.2 - CD16A TandAb | QVQLVQSGAEVKKPGESLKVSCKASGYTFTSYYMHWVRQAPGQGLEWMGIINPSGGSTSYAQKFQGRVTMTRDTSTSTVYMELSSLRSEDTAVYYCARGSAYYYDFADYWGQGTLVTVSSGGGGSGGGGSDIVMTQSPDSLAVSLGERVTMNCKSSQSLLNSGNQKNYLSWYQQKPGQPPKLLFYWASTRESGVPDRFSGSGSGTDFTLTISSVQAEDVAVYYCQNDYSYPFTFGQGTKLEIKGGGSGGGSGGGSEVQLLESGGGLVQPGGSLRLSCAASGFTFSSYTMSWVRQAPGKGLEWVATIHGGSYTYYADSVKGRFTISRDNSKNTLYLQMNSLRAEDTAVYYCTRLVKGNAMDYWGQGTLVTVSSGGGSGGGSSVVLTQPSSVSVAPGQTATISCGGHNIGSKNVHWYQQRPGQSPVLVIYQDNKRPSGIPERFSGSNSGNTATLTISGTQAMDEADYYCQVWDNYSVLFGGGTKLTVLHHHHHH* |
| 02-0358-h3-Bs SEQ ID NO: 145 | CLDN18.2 - CD3E BiTE | DIVMTQSPDSLAVSLGERVTMNCKSSQSLLNSGNQRNYLTWYQQKPGQPPKLLIYWASTRESGVPDRFSGSGSGTDFTLTISSVQAEDVAVYYCQNVYIYPLTFGQGTKLEIKGGGGSGGGGSGGGGSEVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRRSGYYGNSLDYWGQGTLVTVSSGGGGSDIKLQQSGAELARPGASVKMSCKTSGYTFTRYTMHWVKQRPGQGLEWIGYINPSRGYTNYNQKFKDKATLTTDKSSSTAYMQLSSLTSEDSAVYYCARYYDDHYCLDYWGQGTTLTVSSVEGGSGGSGGSGGSGGVDDIQLTQSPAIMSASPGEKVTMTCRASSSVSYMNWYQQKSGTSPKRWIYDTSKVASGVPYRFSGSGSGTSYSLTISSMEAEDAATYYCQQWSSNPLTFGAGTKLELKHHHHHH* |
| 02-0358-h3-CD16A-His SEQ ID NO: 146 | CLDN18.2 - CD16A TandAb | QVQLVQSGAEVKKPGESLKVSCKASGYTFTSYYMHWVRQAPGQGLEWMGIINPSGGSTSYAQKFQGRVTMTRDTSTSTVYMELSSLRSEDTAVYYCARGSAYYYDFADYWGQGTLVTVSSGGGGSGGGGSDIVMTQSPDSLAVSLGERVTMNCKSSQSLFNSGNQRNYLTWYQQKPGQPPKLLIYWASTRESGVPDRFSGSGSGTDFTLTISSVQAEDVAVYYCQNVYIYPLTFGQGTKLEIKGGGSGGGSGGGSEVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRRSGYYGNSLDYWGQGTLVTVSSGGGSGGGSSVVLTQPSSVSVAPGQTATISCGGHNIGSKNVHWYQQRPGQSPVLVIYQDNKRPSGIPERFSGSNSGNTATLTISGTQAMDEADYYCQVWDNYSVLFGGGTKLTVLHHHHHH* |

Fig. 25A  Flow Assay of Purifed BiTE diabody (2ug/reaction) flow assay, trypsin to detach cells

|  | anti-his 2o only | 307-CD16A-BiTE his tagged | 358-CD16A-BiTE his tagged | AFM13 (CD16A-CD30 BiTE) his tagged |
|---|---|---|---|---|
| ARK2 cells | 35,124.48 | 37,108.71 | 17,564.03 | 37,777.38 |
| HUPT4 cells | 12,730.43 | 72,589.71 | 41,612.48 | 15,728.04 |
| Jurkat-Lucia-NFAT-CD16 cells | 18,863.83 | 85,725.83 | 111,262.28 | 76,513.58 |

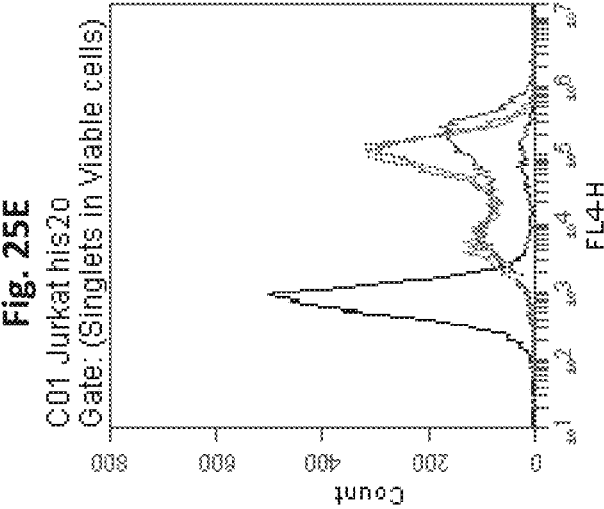
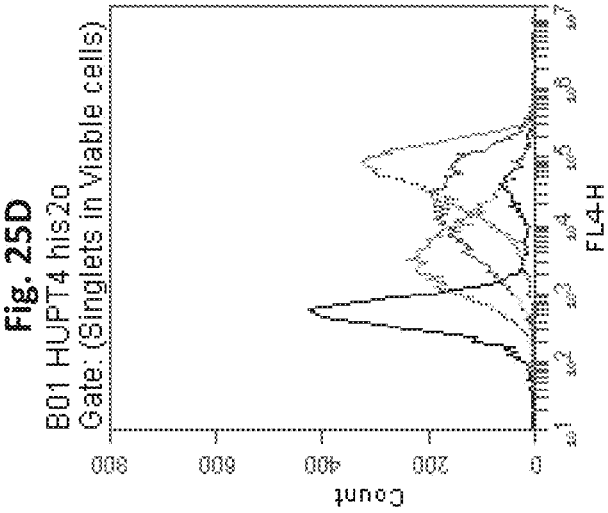
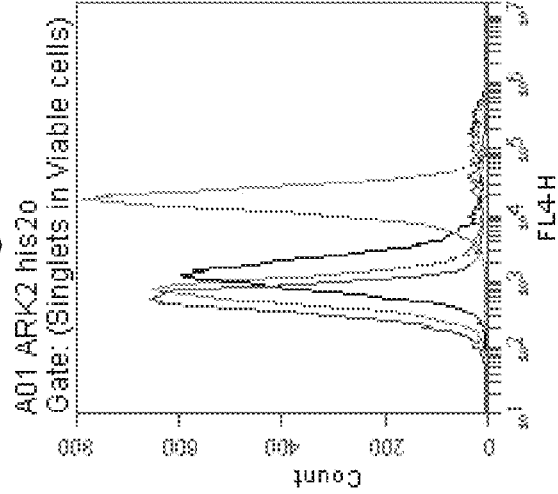

Fig. 26A Flow assay for Tandab 307-CD16A and Tandab 358-CD16A 09/18/2019

| | only anti-his 2o AF647 652513 | Tandab 307-CD16A-his 090519 | Tandab 307-CD16A-his 090519 | Tandab 358-CD16A-his 090519 | Tandab AFM13-his 090519 |
|---|---|---|---|---|---|
| ARK2 (CLDN18.2-) | 36,416.11 | 28,480.06 | | 25,080.61 | 39,787.16 |
| HUPT4 (CLDN18.2+) | 12,046.33 | 152,355.14 | | 27,623.41 | 8,939.97 |
| Jurkat Lucia CD16A | 7,290.88 | 21,167.48 | | 8,175.19 | 23,503.69 |

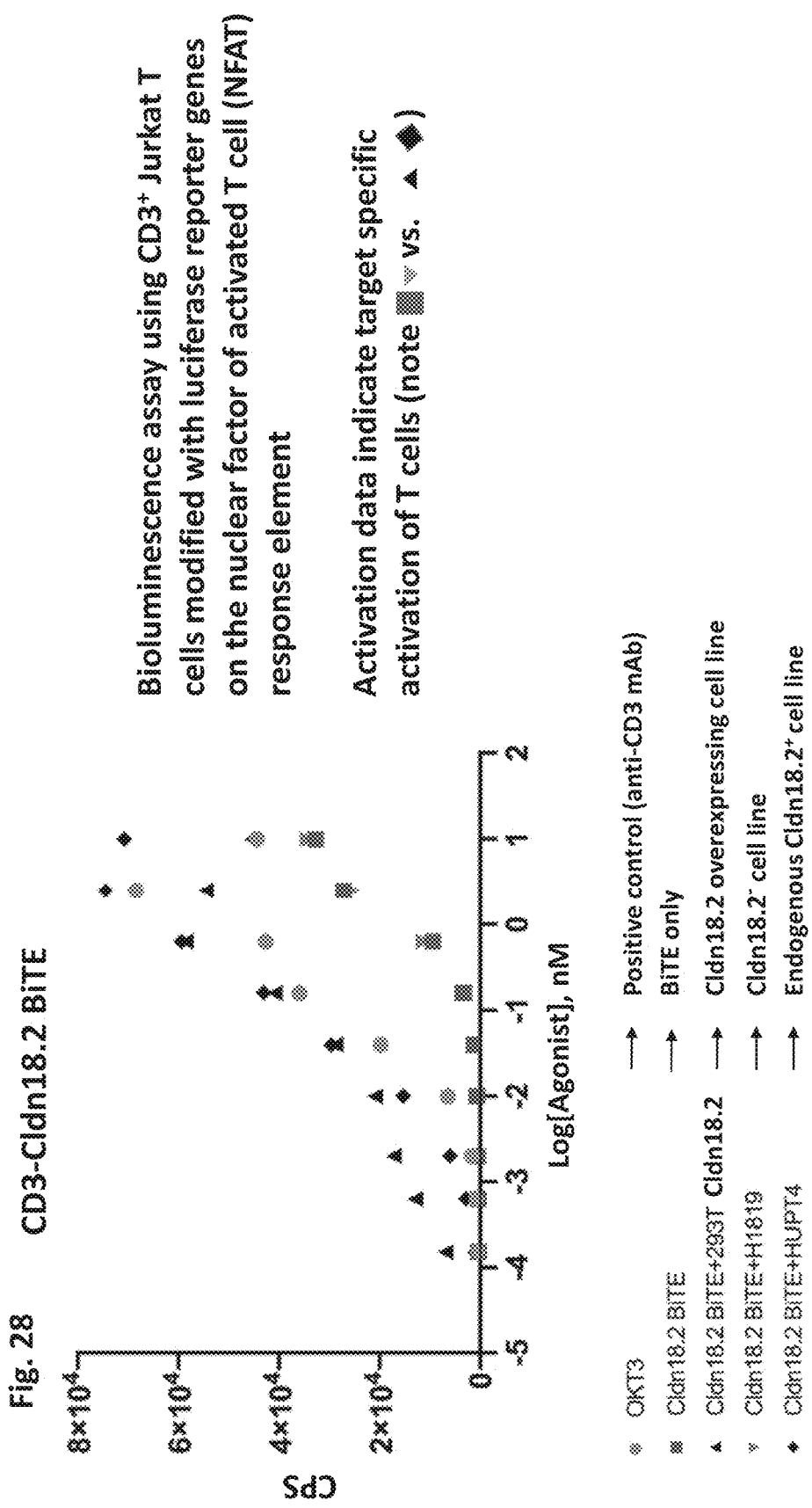

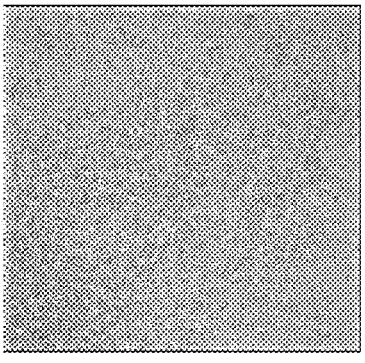
Fig. 30A 125 ng/mL Blincyto
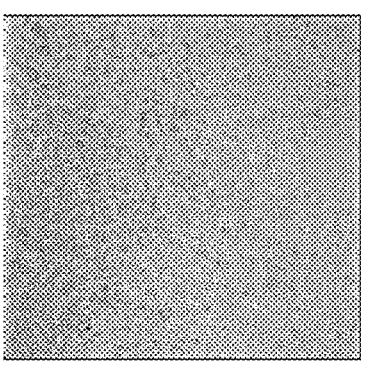
Fig. 30B 12.5 ng/mL Blincyto
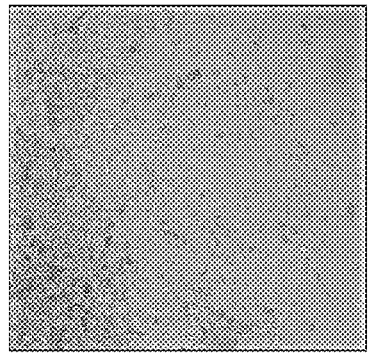
Fig. 30C 1.25 ng/mL Blincyto
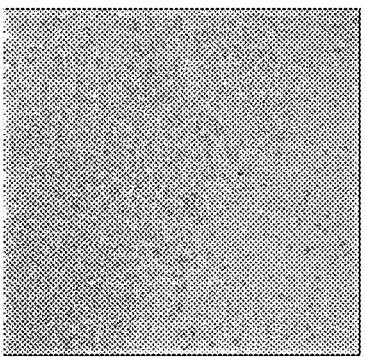
Fig. 30D 125 ng/mL p307 BiTE
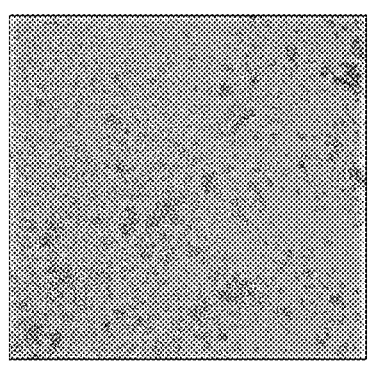
Fig. 30E 12.5 ng/mL p307 BiTE
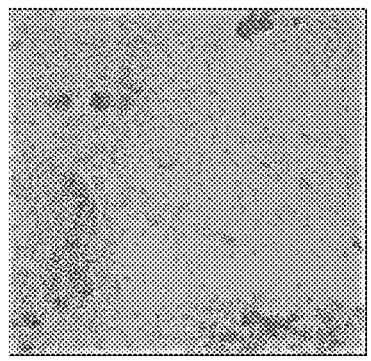
Fig. 30F 1.25 ng/mL p307 BiTE

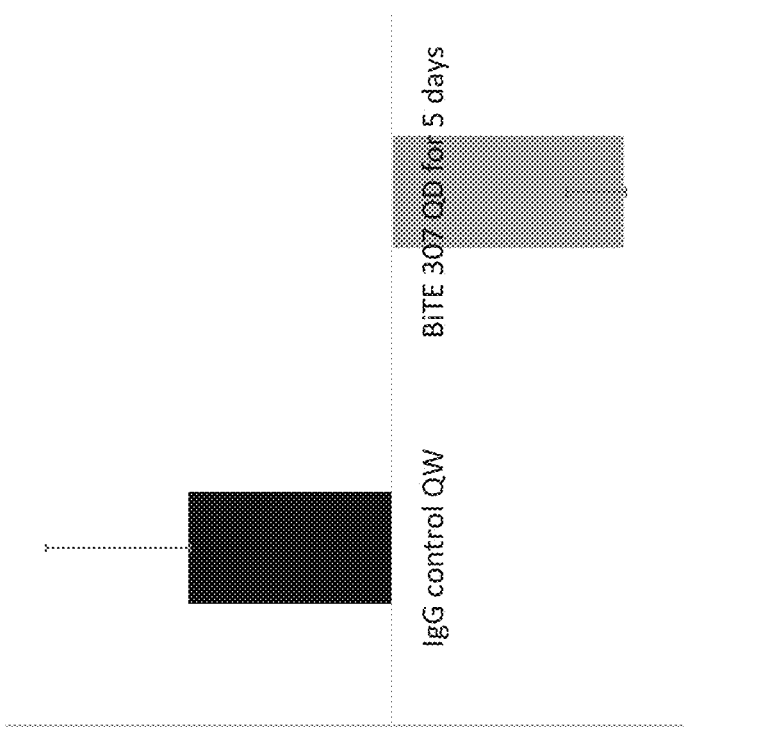
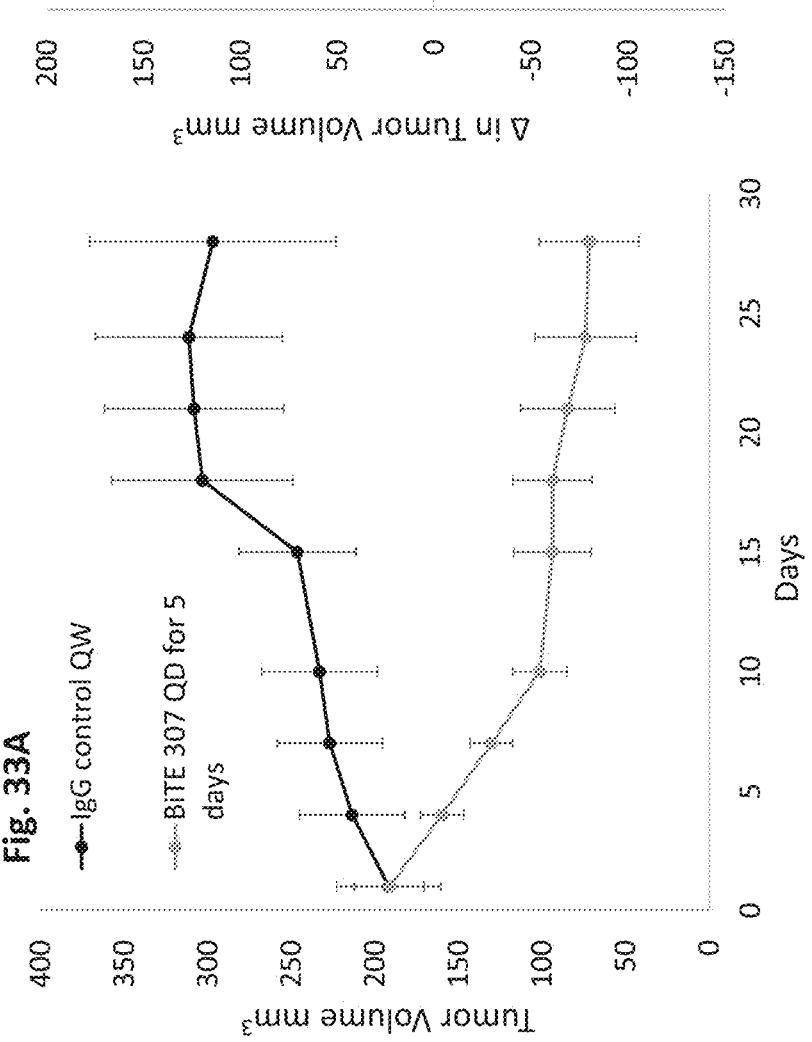

SEQUENCE LISTING

<160> NUMBER OF SEQ ID NOS: 159

<210> SEQ ID NO 1
<211> LENGTH: 261
<212> TYPE: PRT
<213> ORGANISM: Homo sapiens

<400> SEQUENCE: 1

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
```

```
                    180                 185                 190
Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 2
<211> LENGTH: 261
<212> TYPE: PRT
<213> ORGANISM: Homo sapiens

<400> SEQUENCE: 2

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 3
<211> LENGTH: 264
```

```
<212> TYPE: PRT
<213> ORGANISM: Mus musculus

<400> SEQUENCE: 3

Met Ser Val Thr Ala Cys Gln Gly Leu Gly Phe Val Ser Leu Ile
1               5                   10                  15

Gly Phe Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Val Ile Gly Ile Leu Val
                85                  90                  95

Ser Ile Phe Ala Leu Lys Cys Ile Arg Ile Gly Ser Met Asp Asp Ser
            100                 105                 110

Ala Lys Ala Lys Met Thr Leu Thr Ser Gly Ile Leu Phe Ile Ile Ser
            115                 120                 125

Gly Ile Cys Ala Ile Ile Gly Val Ser Val Phe Ala Asn Met Leu Val
            130                 135                 140

Thr Asn Phe Trp Met Ser Thr Ala Asn Met Tyr Ser Gly Met Gly Gly
145                 150                 155                 160

Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
            180                 185                 190

Val Met Met Cys Ile Ala Cys Arg Gly Leu Thr Pro Asp Asp Ser Asn
            195                 200                 205

Phe Lys Ala Val Ser Tyr His Ala Ser Gly Gln Asn Val Ala Tyr Arg
            210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Glu Gln Ser
                245                 250                 255

His Pro Thr Lys Tyr Asp Tyr Val
            260

<210> SEQ ID NO 4
<211> LENGTH: 22
<212> TYPE: PRT
<213> ORGANISM: Homo sapiens

<400> SEQUENCE: 4

Gly Leu Trp Arg Ser Cys Val Arg Glu Ser Ser Gly Phe Thr Glu Cys
1               5                   10                  15

Arg Phe Tyr Phe Thr Leu
            20

<210> SEQ ID NO 5
<211> LENGTH: 24
<212> TYPE: PRT
<213> ORGANISM: Homo sapiens

<400> SEQUENCE: 5

Gln Gly Leu Trp Arg Ser Cys Val Arg Glu Ser Ser Gly Phe Thr Glu
```

```
                 1               5                  10                  15
Cys Arg Gly Tyr Phe Thr Leu Lys
                20

<210> SEQ ID NO 6
<211> LENGTH: 26
<212> TYPE: PRT
<213> ORGANISM: Homo sapiens

<400> SEQUENCE: 6

Asp Gln Trp Ser Thr Gln Asp Leu Tyr Asn Asn Pro Val Thr Ala Val
1               5                  10                  15

Phe Asn Tyr Gln Gly Leu Trp Arg Ser Cys
                20                  25

<210> SEQ ID NO 7
<211> LENGTH: 18
<212> TYPE: PRT
<213> ORGANISM: Homo sapiens

<400> SEQUENCE: 7

Cys Arg Gly Tyr Phe Thr Leu Leu Phe Leu Pro Ala Met Leu Gln Ala
1               5                  10                  15

Val Arg

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Cys Val Thr Asn Phe Trp Met Ser Thr Ala Asn Met Tyr Thr Gly Met
1               5                  10                  15

Gly Gly Met Val Gln Thr Val Gln Thr Arg Tyr Thr Phe Gly Ala
                20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Thr Asn Phe Trp Met Ser Thr Ala Asn Met Tyr Thr Gly Met Gly
1               5                  10                  15

Gly Met Val Gln Thr Val Gln Thr Arg Tyr Thr Phe Gly Ala Cys
                20                  25                  30

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Val Lys Leu Val Glu Ser Gly Gly Gly Leu Val Lys Pro Gly Gly
1               5                  10                  15
```

```
Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
            35                  40                  45

Ala Thr Ile Ile Ile Gly Gly Ser Tyr Thr Tyr Tyr Pro Asp Ser Val
 50                      55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Leu Val Lys Gly Asn Ala Met Asp Tyr Trp Gly Gln Gly Thr
            100                 105                 110

Ser Val Ala Val Ser Ser
        115

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Met Thr Gln Ser Pro Ser Ser Leu Thr Val Thr Thr Gly
 1               5                  10                  15

Glu Lys Val Thr Met Ser Cys Lys Ser Ser Gln Ser Leu Leu Asn Ser
            20                  25                  30

Gly Asn Gln Lys Asn Tyr Leu Ser Trp Tyr Gln Gln Ile Pro Gly Gln
            35                  40                  45

Pro Pro Lys Leu Leu Phe Tyr Trp Ala Ser Thr Arg Glu Ser Gly Val
 50                      55                  60

Pro Asp Arg Phe Thr Gly Ser Gly Ser Gly Thr Asp Phe Thr Leu Thr
 65                  70                  75                  80

Ile Ser Asn Val Gln Ala Glu Asp Leu Ala Val Tyr Tyr Cys Gln Asn
                 85                  90                  95

Asp Tyr Ser Tyr Pro Phe Thr Phe Gly Ala Gly Thr Lys Leu Glu Leu
            100                 105                 110

Arg

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Thr Ser Tyr
            20                  25                  30

Thr Met Ser Trp Val Arg Gln Thr Pro Glu Lys Arg Leu Glu Trp Val
            35                  40                  45

Ala Thr Ile Ile Ile Gly Gly Ser Tyr Thr Tyr Tyr Pro Asp Ser Val
 50                      55                  60
```

-continued

```
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Leu Val Lys Gly Asn Ala Met Asp Tyr Trp Gly Gln Gly Thr
            100                 105                 110

Ser Val Thr Val Ser Ser
            115
```

<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Asp Ile Leu Met Thr Gln Ser Pro Ser Ser Leu Thr Val Thr Ala Gly
 1               5                  10                  15

Glu Lys Val Thr Met Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ser Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Phe Thr Phe Gly Ala Gly Thr Lys Leu Glu Leu
            100                 105                 110

Lys
```

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Tyr Trp Val
        35                  40                  45

Ala Thr Ile Ser Ser Gly Val Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Leu Thr Lys Gly Asn Ala Met Asp Tyr Trp Gly Gln Gly Thr
            100                 105                 110

Ser Val Thr Val Ser Ser
```

-continued

115

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Gly Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ala Gly Thr Lys Leu Glu Leu
            100                 105                 110

Lys

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Val Val Gln Leu Val Glu Ser Gly Gly Asp Phe Val Gln Pro Gly Gly
1               5                   10                  15

Ser Arg Lys Leu Ser Cys Ala Val Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Thr Thr Asn Ile Tyr Tyr Ala Asp Thr Val
    50                  55                  60

Lys Gly Arg Phe Thr Val Ser Arg Asp Asn Pro Lys Asn Ser Leu Phe
65                  70                  75                  80

Leu His Met Thr Ser Leu Arg Ser Glu Asp Thr Ala Met Tyr Tyr Cys
                85                  90                  95

Val Arg Ser Gly Tyr Tyr Gly Asn Ser Leu Asp Tyr Trp Gly Gln Gly
            100                 105                 110

Thr Pro Leu Thr Val Ser Ser
        115

<210> SEQ ID NO 17
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 17

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Gly Phe Thr Leu Thr
65                  70                  75                  80

Ile Ser Ser Val Gln Ala Glu Asp Leu Ala Phe Tyr Tyr Cys Gln Asn
                85                  90                  95

Val Tyr Ile Tyr Pro Leu Thr Phe Gly Leu Gly Thr Lys Leu Glu Leu
            100                 105                 110

Arg

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Ser Gly Ala Glu Leu Ala Arg Pro Gly Ala
1               5                   10                  15

Ser Val Lys Leu Ser Cys Lys Ala Ser Asp Tyr Thr Phe Thr Ser Tyr
            20                  25                  30

Val Ile Ser Trp Val Lys Gln Arg Thr Gly Gln Gly Leu Glu Trp Ile
        35                  40                  45

Gly Glu Ile Tyr Pro Arg Asn Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Ser Tyr Tyr Gly Asn Ser Phe Ala Tyr Trp Gly Gln Gly Thr
            100                 105                 110

Leu Val Thr Val Ser Ala
        115

<210> SEQ ID NO 19
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Arg Pro Gly Gln

```
                35                  40                  45
Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Cys Cys Gln Asn
                 85                  90                  95

Asn Tyr Tyr Pro Phe Thr Phe Gly Gly Gly Thr Lys Leu Gly Ile
                100                 105                 110

Lys

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                 20                  25                  30

Leu Met His Trp Val Arg Gln Lys Pro Gly Leu Gly Leu Asp Trp Ile
                 35                  40                  45

Gly Tyr Ile Asn Pro Tyr Asn Asp Gly Thr Asn Tyr Asn Ala Lys Phe
 50                  55                  60

Ile Asp Lys Ala Thr Leu Thr Ser Asp Lys Thr Ser Ser Thr Ala Tyr
 65                  70                  75                  80

Met Glu Leu Ser Ser Leu Thr Ser Glu Asp Ser Ala Ile Tyr Tyr Cys
                 85                  90                  95

Thr Arg Gly Asp Tyr Trp Gly Gln Gly Thr Ser Val Thr Val Ser Ser
                100                 105                 110

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Pro Ser Ser Leu Ala Val Thr Ala Gly
 1               5                  10                  15

Glu Gln Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
                 35                  40                  45

Pro Pro Lys Leu Leu Ile Tyr Trp Ala Ser Ile Arg Gln Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Leu Asn
                 85                  90                  95

Asp Tyr Gly Phe Pro Leu Thr Phe Gly Ala Gly Thr Lys Leu Glu Leu
                100                 105                 110
```

Lys

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ile Gln Leu Gln Gln Ser Gly Ala Glu Leu Ala Arg Pro Arg Ala
1               5                   10                  15

Ser Val Lys Leu Ser Cys Lys Ala Ser Gly Tyr Thr Phe Thr Ser Asp
                20                  25                  30

Val Ile Ser Trp Val Lys Gln Arg Pro Gly Gln Gly Leu Glu Trp Ile
            35                  40                  45

Gly Glu Ser Tyr Leu Arg Asn Gly Asn Thr Tyr Tyr Asn Glu Asn Phe
        50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Ser Tyr Tyr Gly Asn Ser Phe Ala Tyr Trp Gly Gln Gly Thr
                100                 105                 110

Leu Val Thr Val Ser Ala
            115

<210> SEQ ID NO 23
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Met Thr Gln Ser Pro Ser Ser Leu Thr Val Thr Ala Arg
1               5                   10                  15

Glu Lys Val Thr Met Asn Cys Lys Ser Thr Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Tyr Tyr Pro Phe Thr Phe Gly Gly Gly Thr Lys Leu Glu Ile
                100                 105                 110

Lys

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 24

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asn Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Asn Ile Asn Lys Asp Lys Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Arg Pro Thr Arg Gly Asn Ala Met Asp Tyr Trp Gly Gln Gly Thr Ser
            100                 105                 110

Val Thr Val Ser Ser
        115

<210> SEQ ID NO 25
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Val Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
            20                  25                  30

Gly Asn Gln Arg Ser Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Ala
    50                  55                  60

Pro Asp Arg Phe Thr Gly Ser Gly Ser Gly Ala Asp Phe Thr Leu Thr
65                  70                  75                  80

Ile Ser Ser Val Gln Ala Glu Asp Leu Ala Ile Tyr Tyr Cys Gln Asn
                85                  90                  95

Asn Tyr Asn Tyr Pro Phe Thr Phe Gly Ser Gly Thr Lys Leu Glu Ile
            100                 105                 110

Lys

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

Ile Met His Trp Val Lys Gln Lys Pro Gly Gln Gly Pro Glu Trp Met
            35                  40                  45

Gly Tyr Ile Asn Pro Tyr Asn Asp Gly Thr Asn Tyr Asn Glu Lys Phe
 50                  55                  60

Lys Asp Lys Ala Thr Leu Thr Ser Asp Lys Ser Ser Ser Thr Ala Tyr
 65                  70                  75                  80

Met Asp Leu Ser Ser Leu Thr Ser Glu Asp Ser Ala Val Tyr Tyr Cys
                 85                  90                  95

Thr Arg Gly Asp Tyr Trp Gly Gln Gly Thr Ser Val Thr Val Ser Ser
                100                 105                 110

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
                35                  40                  45

Pro Pro Lys Leu Leu Phe Tyr Trp Ala Ser Thr Lys Lys Ser Gly Val
 50                  55                  60

Pro Asp Arg Phe Thr Gly Ser Gly Ser Arg Thr Asp Phe Thr Leu Thr
 65                  70                  75                  80

Ile Ser Ser Val Gln Ala Glu Asp Leu Ala Val Tyr Tyr Cys Leu Asn
                 85                  90                  95

Asp Tyr Ser Phe Pro Leu Thr Phe Gly Ala Gly Thr Lys Leu Glu Leu
                100                 105                 110

Lys

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Leu Ile His Trp Val Lys Gln Lys Pro Gly Gln Gly Leu Glu Trp Ile
                35                  40                  45

Gly Tyr Ile Asn Pro Tyr Asn Asp Ala Thr Tyr Tyr Asn Glu Lys Phe
 50                  55                  60

Lys Ala Lys Ala Thr Leu Thr Ser Asp Lys Ser Ser Ser Thr Ala Tyr
 65                  70                  75                  80

Met Glu Leu Ser Ser Leu Thr Ser Glu Asp Thr Ala Ile Tyr Tyr Cys
                 85                  90                  95

Thr Arg Gly Asp Tyr Trp Ser Gln Gly Thr Ser Val Thr Val Ser Ser

<210> SEQ ID NO 29
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Thr Val Tyr Tyr Cys Leu Asn
                85                  90                  95

Asp Tyr Ser Phe Pro Leu Thr Phe Gly Ala Gly Thr Lys Leu Glu Leu
            100                 105                 110

Lys

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (95)..(95)
<223> OTHER INFORMATION: Any naturally occurring amino acid

<400> SEQUENCE: 30

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Phe Asn Pro Tyr Asn Asp Asp Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Asp Ser Ala Val Tyr Xaa Cys
                85                  90                  95

Thr Arg Gly Asp Tyr Trp Gly Gln Gly Thr Ser Val Thr Val Ser Ser
            100                 105                 110

<210> SEQ ID NO 31
<211> LENGTH: 113
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 31

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Gly Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Ala Gln Ala Ala Asp Leu Ala Val Tyr Tyr Cys Leu Asn
                85                  90                  95

Asp Tyr Ser Phe Pro Leu Thr Phe Gly Ala Gly Thr Lys Leu Glu Leu
            100                 105                 110

Lys

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Val Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Phe
            20                  25                  30

Leu Ile His Trp Val Arg Gln Lys Pro Gly Leu Gly Leu Glu Trp Ile
        35                  40                  45

Gly Tyr Ile Asn Pro Tyr Asp Tyr Gly Ile Asn Tyr Asn Val Lys Phe
    50                  55                  60

Met Asp Lys Val Thr Leu Thr Ser Asp Lys Thr Ser Ser Thr Ala Tyr
65                  70                  75                  80

Met Glu Leu Ser Ser Leu Thr Ser Ala Asp Ser Ala Ile Tyr Tyr Cys
                85                  90                  95

Thr Arg Gly Asp Tyr Trp Gly Gln Gly Thr Ser Val Ile Val Ser Ser
            100                 105                 110

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Val Met Thr Gln Ser Pro Ser Ser Leu Ala Val Thr Thr Gly
1               5                   10                  15

Glu Gln Val Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Thr Gly Gln
        35                  40                  45

-continued

Ser Pro Lys Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Leu Asn
                85                  90                  95

Asp Tyr Gly Phe Pro Leu Thr Phe Gly Ala Gly Thr Lys Leu Glu Leu
                100                 105                 110

Lys

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Ser Tyr
                20                  25                  30

Val Met His Trp Val Lys Gln Lys Ser Gly Gln Gly Leu Glu Trp Ile
            35                  40                  45

Gly Tyr Ile Asn Pro Tyr Asn Asp Asp Ile Lys Tyr Asn Ala Lys Phe
    50                  55                  60

Glu Asp Lys Ala Thr Leu Thr Ser Asp Arg Ser Ser Thr Ala Tyr
65                  70                  75                  80

Met Glu Leu Ser Ser Leu Thr Ser Asp Asp Ser Ala Val Tyr Phe Cys
                85                  90                  95

Thr Arg Gly Asp Tyr Trp Gly Gln Gly Thr Thr Leu Thr Val Ser Ser
                100                 105                 110

<210> SEQ ID NO 35
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Met Thr Gln Ser Pro Ser Ser Leu Thr Val Thr Thr Gly
1               5                   10                  15

Glu Lys Val Thr Met Asp Cys Lys Ser Ser Gln Ser Leu Leu Asn Ser
                20                  25                  30

Gly Asn Gln Lys Asn Tyr Leu Thr Trp Tyr Gln Gln Lys Ser Gly Gln
            35                  40                  45

Pro Pro Lys Leu Leu Ile Tyr Trp Ala Ser Ile Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Leu Asn
                85                  90                  95

Asp Tyr Ser Phe Pro Leu Thr Phe Gly Ala Gly Thr Lys Leu Glu Leu
                100                 105                 110

Lys

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Phe Gln Leu Gln Gln Ser Gly Pro Glu Leu Val Lys Pro Gly Ala
1               5                   10                  15

Ser Val Lys Ile Ser Cys Lys Ala Ser Val Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Val Ile Asn Pro Asn Tyr Gly Asn Thr Asn Tyr Asn Gln Arg Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Glu Asp Tyr Tyr Asn Ile Arg Gly Ala Ser Trp Gly Gln
            100                 105                 110

Gly Thr Leu Val Thr Val Ser Ala
        115                 120

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Thr Ile Asn Tyr Met
            20                  25                  30

His Trp Tyr Gln Gln Lys Leu Gly Ser Ser Pro Lys Leu Trp Ile Tyr
        35                  40                  45

Asp Thr Ser Lys Leu Ala Pro Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Pro Thr
                85                  90                  95

Phe Gly Ser Gly Thr Lys Leu Glu Leu Lys
            100                 105

<210> SEQ ID NO 38
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Ser Pro Arg Ser Gly Asn Thr Tyr Tyr Asn Glu Lys Phe
50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Thr Gly Val Ile Thr Thr Val Ile Pro Thr Asp Trp Tyr Phe Asp
            100                 105                 110

Val Trp Gly Thr Gly Thr Thr Val Thr Val Ser Ser
        115                 120

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln His Tyr Ser Lys Leu Pro Pro
                85                  90                  95

Thr Phe Gly Ser Gly Thr Lys Leu Glu Ile Lys
            100                 105

<210> SEQ ID NO 40
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Val Tyr
            20                  25                  30

Tyr Met Asn Trp Val Lys Gln Ser Pro Glu Lys Ser Leu Glu Trp Ile
        35                  40                  45

Gly Glu Ile Asn Pro Ser Thr Gly Gly Thr Thr Tyr Asn Pro Lys Phe
50                  55                  60
```

```
Lys Ala Lys Ala Thr Leu Thr Val Asp Lys Ser Ser Thr Ala Tyr
65                  70                  75                  80

Met Gln Leu Lys Ser Leu Thr Ser Glu Asp Ser Ala Ile Tyr Phe Cys
                85                  90                  95

Val Arg Trp Ala Asp Tyr Trp Gly Gln Gly Thr Thr Leu Thr Val Ser
            100                 105                 110

Ser
```

<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 41

```
Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
                20                  25                  30

Asp Gly Lys Thr Tyr Leu Asn Trp Phe Leu Gln Arg Pro Gly Gln Ser
            35                  40                  45

Pro Gln Leu Leu Val Tyr Trp Met Ser Thr Arg Ala Ser Gly Val Ser
50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Val
                85                  90                  95

Val Tyr Tyr Pro Tyr Thr Phe Gly Ser Gly Thr Lys Leu Glu Ile Lys
            100                 105                 110
```

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Ala Pro Gly Lys Gly Leu Glu Trp Val
            35                  40                  45

Ala Thr Ile Ile Ile Gly Gly Ser Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Leu Val Lys Gly Asn Ala Met Asp Tyr Trp Gly Gln Gly Thr
            100                 105                 110

Leu Val Thr Val Ser Ser
            115
```

```
<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ser Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Val Met Thr Gln Ser Pro Asp Ser Leu Ala Val Ser Leu Gly
```

-continued

```
              1               5                  10                 15
              Glu Arg Val Thr Met Asn Cys Lys Ser Ser Gln Ser Leu Leu Asn Ser
                       20                  25                  30
              Gly Asn Gln Lys Asn Tyr Leu Ser Trp Tyr Gln Gln Lys Pro Gly Gln
                       35                  40                  45
              Pro Pro Lys Leu Leu Phe Tyr Trp Ala Ser Thr Arg Glu Ser Gly Val
                       50                  55                  60
              Pro Asp Arg Phe Ser Gly Ser Gly Ser Gly Thr Asp Phe Thr Leu Thr
              65                  70                  75                  80
              Ile Ser Ser Val Gln Ala Glu Asp Val Ala Val Tyr Tyr Cys Gln Asn
                                85                  90                  95
              Asp Tyr Ser Tyr Pro Phe Thr Phe Gly Gln Gly Thr Lys Leu Glu Ile
                                100                 105                 110
              Lys
```

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
              Glu Val Gln Leu Leu Glu Ser Gly Gly Gly Leu Val Gln Pro Gly Gly
              1               5                  10                 15
              Ser Leu Arg Leu Ser Cys Ala Ala Ser Gly Phe Thr Phe Ser Ser Tyr
                       20                  25                  30
              Thr Met Ser Trp Val Arg Gln Ala Pro Gly Lys Gly Leu Glu Trp Val
                       35                  40                  45
              Ala Thr Ile Ser Ser Gly Val Ser Tyr Thr Tyr Tyr Ala Asp Ser Val
                       50                  55                  60
              Lys Gly Arg Phe Thr Ile Ser Arg Asp Asn Ser Lys Asn Thr Leu Tyr
              65                  70                  75                  80
              Leu Gln Met Asn Ser Leu Arg Ala Glu Asp Thr Ala Val Tyr Tyr Cys
                                85                  90                  95
              Thr Arg Leu Thr Lys Gly Asn Ala Met Asp Tyr Trp Gly Gln Gly Thr
                                100                 105                 110
              Leu Val Thr Val Ser Ser
                       115
```

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
              Asp Ile Val Met Thr Gln Ser Pro Asp Ser Leu Ala Val Ser Leu Gly
              1               5                  10                 15
              Glu Arg Ala Thr Ile Asn Cys Lys Ser Ser Gln Ser Leu Leu Asn Ser
                       20                  25                  30
              Gly Asn Gln Lys Asn Tyr Leu Thr Trp Tyr Gln Gln Lys Pro Gly Gln
                       35                  40                  45
              Pro Pro Lys Leu Leu Ile Tyr Trp Ala Ser Thr Arg Glu Ser Gly Val
                       50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Phe Thr Phe Gly Gln Gly Thr Lys Leu Glu Ile
            100                 105                 110

Lys

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Asp Ser Leu Ala Val Ser Leu Gly
  1               5                  10                  15

Glu Arg Val Thr Met Asn Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Asn
                 85                  90                  95

Asp Tyr Ser Tyr Pro Phe Thr Phe Gly Gln Gly Thr Lys Leu Glu Ile
            100                 105                 110

Lys

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ser
  1               5                  10                  15

Ser Val Lys Leu Ser Cys Lys Ala Ser Gly Tyr Thr Phe Thr Ser Asp
                 20                  25                  30

Val Ile Ser Trp Val Arg Gln Ala Pro Gly Gln Gly Leu Glu Trp Ile
             35                  40                  45

Gly Glu Ser Tyr Leu Arg Asn Gly Asn Thr Tyr Tyr Ala Gln Lys Phe
 50                  55                  60

Gln Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Tyr Tyr Gly Asn Ser Phe Ala Tyr Trp Gly Gln Gly Thr
            100                 105                 110

Leu Val Thr Val Ser Ser
```

115

<210> SEQ ID NO 50
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ser Thr Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Tyr Pro Phe Thr Phe Gly Gln Gly Thr Lys Leu Glu Ile
            100                 105                 110

Lys

<210> SEQ ID NO 51
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Asp Ser Leu Ala Val Ser Leu Gly
1               5                   10                  15

Glu Arg Val Thr Met Asn Cys Lys Ser Thr Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Ala Tyr Tyr Tyr Pro Phe Thr Phe Gly Gln Gly Thr Lys Leu Glu Ile
            100                 105                 110

Lys

<210> SEQ ID NO 52
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Leu Met His Trp Val Arg Gln Ala Pro Gly Gln Gly Leu Glu Trp Ile
        35                  40                  45

Gly Tyr Ile Asn Pro Tyr Asn Asp Gly Thr Asn Tyr Ala Gln Lys Phe
    50                  55                  60

Gln Gly Arg Val Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Asp Tyr Trp Gly Gln Gly Thr Leu Val Thr Val Ser Ser
            100                 105                 110

<210> SEQ ID NO 53
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Leu Asn
                85                  90                  95

Asp Tyr Gly Phe Pro Leu Thr Phe Gly Gln Gly Thr Lys Leu Glu Ile
            100                 105                 110

Lys

<210> SEQ ID NO 54
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Gln Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Leu Asn
                 85                  90                  95

Asp Tyr Gly Phe Pro Leu Thr Phe Gly Gln Gly Thr Lys Leu Glu Ile
            100                 105                 110

Lys

<210> SEQ ID NO 55
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
                20                  25                  30

Leu Met His Trp Val Arg Gln Ala Pro Gly Gln Gly Leu Glu Trp Ile
            35                  40                  45

Gly Tyr Ile Asn Pro Tyr Asn Asp Gly Thr Asn Tyr Ala Gln Lys Phe
50                  55                  60

Gln Gly Arg Ala Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Tyr Trp Gly Gln Gly Thr Leu Val Thr Val Ser Ser
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
                20                  25                  30

Leu Met His Trp Val Arg Gln Ala Pro Gly Gln Gly Leu Glu Trp Ile
            35                  40                  45

Gly Tyr Ile Asn Pro Tyr Asn Asp Gly Thr Asn Tyr Ala Gln Lys Phe
50                  55                  60

Gln Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Tyr Trp Gly Gln Gly Thr Leu Val Thr Val Ser Ser
            100                 105                 110

<210> SEQ ID NO 57
<211> LENGTH: 118
```

<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asp
            20                  25                  30

Val Ile Ser Trp Val Arg Gln Ala Pro Gly Gln Gly Leu Glu Trp Met
        35                  40                  45

Gly Glu Ser Tyr Leu Arg Asn Gly Asn Thr Tyr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Gly Asn Ser Phe Ala Tyr Trp Gly Gln Gly Thr
            100                 105                 110

Leu Val Thr Val Ser Ser
            115

<210> SEQ ID NO 58
<211> LENGTH: 113
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Translation of PCR product

<400> SEQUENCE: 58

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Translation of PCR product

```
<400> SEQUENCE: 59

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 60
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Translation of PCR product

<400> SEQUENCE: 60

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 61
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Translation of PCR product

<400> SEQUENCE: 61

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
```

```
                 20                  25                  30
Tyr Ile Asn Trp Val Lys Gln Arg Thr Gly Gln Gly Leu Glu Trp Ile
             35                  40                  45

Gly Glu Ile Tyr Pro Gly Ser Gly Asn Thr Tyr Tyr Asn Glu Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Ser Tyr Gly Ala Phe Asp Tyr Trp Gly Gln Gly Thr Thr Leu
            100                 105                 110

Thr Val Ser Ser
            115

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Translation of PCR product

<400> SEQUENCE: 62

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Phe Thr Phe Gly Ser Gly Thr Lys Leu Glu Ile
            100                 105                 110

Lys

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Translation of PCR product

<400> SEQUENCE: 63

Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Thr Phe Thr Ser Tyr
                 20                  25                  30

Trp Ile Asn Trp Val Lys Gln Arg Pro Gly Gln Gly Leu Glu Trp Ile
             35                  40                  45

Gly Asn Ile Tyr Pro Ser Asp Ser Tyr Thr Asn Tyr Asn Gln Lys Phe
```

```
                    50                  55                  60
Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Ser Trp Arg Gly Asn Ser Phe Asp Tyr Trp Gly Gln Gly Thr
            100                 105                 110

Thr Leu Thr Val Ser Ser
        115
```

<210> SEQ ID NO 64
<211> LENGTH: 10
<212> TYPE: PRT
<213> ORGANISM: Mus musculus

<400> SEQUENCE: 64

```
Gly Phe Thr Phe Ser Ser Tyr Thr Met Ser
 1               5                  10
```

<210> SEQ ID NO 65
<211> LENGTH: 10
<212> TYPE: PRT
<213> ORGANISM: Mus musculus

<400> SEQUENCE: 65

```
Thr Ile Ile Ile Gly Gly Ser Tyr Thr Tyr
 1               5                  10
```

<210> SEQ ID NO 66
<211> LENGTH: 9
<212> TYPE: PRT
<213> ORGANISM: Mus musculus

<400> SEQUENCE: 66

```
Leu Val Lys Gly Asn Ala Met Asp Tyr
 1               5
```

<210> SEQ ID NO 67
<211> LENGTH: 10
<212> TYPE: PRT
<213> ORGANISM: Mus musculus

<400> SEQUENCE: 67

```
Thr Ile Ser Ser Gly Val Ser Tyr Thr Tyr
 1               5                  10
```

<210> SEQ ID NO 68
<211> LENGTH: 9
<212> TYPE: PRT
<213> ORGANISM: Mus musculus

<400> SEQUENCE: 68

```
Leu Thr Lys Gly Asn Ala Met Asp Tyr
 1               5
```

<210> SEQ ID NO 69
<211> LENGTH: 10
<212> TYPE: PRT
<213> ORGANISM: Mus musculus

<400> SEQUENCE: 69

```
Gly Phe Thr Phe Ser Ser Phe Gly Met His
 1               5                  10
```

<210> SEQ ID NO 70
<211> LENGTH: 10
<212> TYPE: PRT
<213> ORGANISM: Mus musculus

<400> SEQUENCE: 70

Tyr Ile Ser Ser Gly Thr Thr Asn Ile Tyr
1               5                   10

<210> SEQ ID NO 71
<211> LENGTH: 10
<212> TYPE: PRT
<213> ORGANISM: Mus musculus

<400> SEQUENCE: 71

Ser Gly Tyr Tyr Gly Asn Ser Leu Asp Tyr
1               5                   10

<210> SEQ ID NO 72
<211> LENGTH: 10
<212> TYPE: PRT
<213> ORGANISM: Mus musculus

<400> SEQUENCE: 72

Gly Tyr Thr Phe Thr Ser Tyr Leu Met His
1               5                   10

<210> SEQ ID NO 73
<211> LENGTH: 10
<212> TYPE: PRT
<213> ORGANISM: Mus musculus

<400> SEQUENCE: 73

Tyr Ile Asn Pro Tyr Asn Asp Gly Thr Asn
1               5                   10

<210> SEQ ID NO 74
<211> LENGTH: 3
<212> TYPE: PRT
<213> ORGANISM: Mus musculus

<400> SEQUENCE: 74

Gly Asp Tyr
1

<210> SEQ ID NO 75
<211> LENGTH: 10
<212> TYPE: PRT
<213> ORGANISM: Mus musculus

<400> SEQUENCE: 75

Gly Tyr Thr Phe Thr Ser Asp Val Ile Ser
1               5                   10

<210> SEQ ID NO 76
<211> LENGTH: 10
<212> TYPE: PRT
<213> ORGANISM: Mus musculus

<400> SEQUENCE: 76

Glu Ser Tyr Leu Arg Asn Gly Asn Thr Tyr
1               5                   10

-continued

```
<210> SEQ ID NO 77
<211> LENGTH: 9
<212> TYPE: PRT
<213> ORGANISM: Mus musculus

<400> SEQUENCE: 77

Ser Tyr Tyr Gly Asn Ser Phe Ala Tyr
1               5

<210> SEQ ID NO 78
<211> LENGTH: 17
<212> TYPE: PRT
<213> ORGANISM: Mus musculus

<400> SEQUENCE: 78

Lys Ser Ser Gln Ser Leu Leu Asn Ser Gly Asn Gln Lys Asn Tyr Leu
1               5                   10                  15

Ser

<210> SEQ ID NO 79
<211> LENGTH: 7
<212> TYPE: PRT
<213> ORGANISM: Mus musculus

<400> SEQUENCE: 79

Trp Ala Ser Thr Arg Glu Ser
1               5

<210> SEQ ID NO 80
<211> LENGTH: 9
<212> TYPE: PRT
<213> ORGANISM: Mus musculus

<400> SEQUENCE: 80

Gln Asn Asp Tyr Ser Tyr Pro Phe Thr
1               5

<210> SEQ ID NO 81
<211> LENGTH: 17
<212> TYPE: PRT
<213> ORGANISM: Mus musculus

<400> SEQUENCE: 81

Lys Ser Ser Gln Ser Leu Leu Asn Ser Gly Asn Gln Lys Asn Tyr Leu
1               5                   10                  15

Thr

<210> SEQ ID NO 82
<211> LENGTH: 17
<212> TYPE: PRT
<213> ORGANISM: Mus musculus

<400> SEQUENCE: 82

Lys Ser Ser Gln Ser Leu Phe Asn Ser Gly Asn Gln Arg Asn Tyr Leu
1               5                   10                  15

Thr

<210> SEQ ID NO 83
<211> LENGTH: 9
<212> TYPE: PRT
<213> ORGANISM: Mus musculus

<400> SEQUENCE: 83
```

```
Gln Asn Val Tyr Ile Tyr Pro Leu Thr
1               5

<210> SEQ ID NO 84
<211> LENGTH: 7
<212> TYPE: PRT
<213> ORGANISM: Mus musculus

<400> SEQUENCE: 84

Trp Ala Ser Ile Arg Gln Ser
1               5

<210> SEQ ID NO 85
<211> LENGTH: 9
<212> TYPE: PRT
<213> ORGANISM: Mus musculus

<400> SEQUENCE: 85

Leu Asn Asp Tyr Gly Phe Pro Leu Thr
1               5

<210> SEQ ID NO 86
<211> LENGTH: 17
<212> TYPE: PRT
<213> ORGANISM: Mus musculus

<400> SEQUENCE: 86

Lys Ser Thr Gln Ser Leu Leu Asn Ser Gly Asn Gln Lys Asn Tyr Leu
1               5                   10                  15

Thr

<210> SEQ ID NO 87
<211> LENGTH: 9
<212> TYPE: PRT
<213> ORGANISM: Mus musculus

<400> SEQUENCE: 87

Gln Asn Ala Tyr Tyr Tyr Pro Phe Thr
1               5

<210> SEQ ID NO 88
<211> LENGTH: 10
<212> TYPE: PRT
<213> ORGANISM: Mus musculus

<400> SEQUENCE: 88

Gly Phe Thr Phe Thr Ser Tyr Thr Met Ser
1               5                   10

<210> SEQ ID NO 89
<211> LENGTH: 10
<212> TYPE: PRT
<213> ORGANISM: Mus musculus

<400> SEQUENCE: 89

Asp Tyr Thr Phe Thr Ser Tyr Val Ile Ser
1               5                   10

<210> SEQ ID NO 90
<211> LENGTH: 10
<212> TYPE: PRT
<213> ORGANISM: Mus musculus

<400> SEQUENCE: 90
```

```
Glu Ile Tyr Pro Arg Asn Gly Asn Thr Tyr
1               5                   10

<210> SEQ ID NO 91
<211> LENGTH: 10
<212> TYPE: PRT
<213> ORGANISM: Mus musculus

<400> SEQUENCE: 91

Gly Phe Ser Leu Asn Ser Tyr Gly Val Ser
1               5                   10

<210> SEQ ID NO 92
<211> LENGTH: 9
<212> TYPE: PRT
<213> ORGANISM: Mus musculus

<400> SEQUENCE: 92

Val Ile Trp Gly Asp Gly Ser Thr Asn
1               5

<210> SEQ ID NO 93
<211> LENGTH: 9
<212> TYPE: PRT
<213> ORGANISM: Mus musculus

<400> SEQUENCE: 93

Pro Thr Arg Gly Asn Ala Met Asp Tyr
1               5

<210> SEQ ID NO 94
<211> LENGTH: 10
<212> TYPE: PRT
<213> ORGANISM: Mus musculus

<400> SEQUENCE: 94

Gly Tyr Thr Phe Thr Ser Tyr Ile Met His
1               5                   10

<210> SEQ ID NO 95
<211> LENGTH: 10
<212> TYPE: PRT
<213> ORGANISM: Mus musculus

<400> SEQUENCE: 95

Gly Tyr Thr Phe Thr Ser Tyr Leu Ile His
1               5                   10

<210> SEQ ID NO 96
<211> LENGTH: 10
<212> TYPE: PRT
<213> ORGANISM: Mus musculus

<400> SEQUENCE: 96

Tyr Ile Asn Pro Tyr Asn Asp Ala Thr Tyr
1               5                   10

<210> SEQ ID NO 97
<211> LENGTH: 10
<212> TYPE: PRT
<213> ORGANISM: Mus musculus

<400> SEQUENCE: 97

Gly Tyr Thr Phe Thr Ser Tyr Val Met His
1               5                   10
```

<210> SEQ ID NO 98
<211> LENGTH: 10
<212> TYPE: PRT
<213> ORGANISM: Mus musculus

<400> SEQUENCE: 98

Tyr Phe Asn Pro Tyr Asn Asp Asp Thr Lys
1               5                   10

<210> SEQ ID NO 99
<211> LENGTH: 10
<212> TYPE: PRT
<213> ORGANISM: Mus musculus

<400> SEQUENCE: 99

Gly Tyr Thr Phe Thr Ser Phe Leu Ile His
1               5                   10

<210> SEQ ID NO 100
<211> LENGTH: 10
<212> TYPE: PRT
<213> ORGANISM: Mus musculus

<400> SEQUENCE: 100

Tyr Ile Asn Pro Tyr Asp Tyr Gly Ile Asn
1               5                   10

<210> SEQ ID NO 101
<211> LENGTH: 10
<212> TYPE: PRT
<213> ORGANISM: Mus musculus

<400> SEQUENCE: 101

Gly Phe Thr Phe Thr Ser Tyr Val Met His
1               5                   10

<210> SEQ ID NO 102
<211> LENGTH: 10
<212> TYPE: PRT
<213> ORGANISM: Mus musculus

<400> SEQUENCE: 102

Tyr Ile Asn Pro Tyr Asn Asp Asp Ile Lys
1               5                   10

<210> SEQ ID NO 103
<211> LENGTH: 10
<212> TYPE: PRT
<213> ORGANISM: Mus musculus

<400> SEQUENCE: 103

Val Tyr Ser Phe Thr Gly Tyr Asn Met Asn
1               5                   10

<210> SEQ ID NO 104
<211> LENGTH: 10
<212> TYPE: PRT
<213> ORGANISM: Mus musculus

<400> SEQUENCE: 104

Val Ile Asn Pro Asn Tyr Gly Asn Thr Asn
1               5                   10

<210> SEQ ID NO 105
<211> LENGTH: 11
<212> TYPE: PRT
<213> ORGANISM: Mus musculus

<400> SEQUENCE: 105

Ser Glu Asp Tyr Tyr Asn Ile Arg Gly Ala Ser
1               5                   10

<210> SEQ ID NO 106
<211> LENGTH: 10
<212> TYPE: PRT
<213> ORGANISM: Mus musculus

<400> SEQUENCE: 106

Gly Tyr Thr Phe Thr Ser Tyr Gly Ile Ser
1               5                   10

<210> SEQ ID NO 107
<211> LENGTH: 10
<212> TYPE: PRT
<213> ORGANISM: Mus musculus

<400> SEQUENCE: 107

Glu Ile Ser Pro Arg Ser Gly Asn Thr Tyr
1               5                   10

<210> SEQ ID NO 108
<211> LENGTH: 15
<212> TYPE: PRT
<213> ORGANISM: Mus musculus

<400> SEQUENCE: 108

Gly Val Ile Thr Thr Val Ile Pro Thr Asp Trp Tyr Phe Asp Val
1               5                   10                  15

<210> SEQ ID NO 109
<211> LENGTH: 10
<212> TYPE: PRT
<213> ORGANISM: Mus musculus

<400> SEQUENCE: 109

Gly Tyr Ser Phe Thr Val Tyr Tyr Met Asn
1               5                   10

<210> SEQ ID NO 110
<211> LENGTH: 10
<212> TYPE: PRT
<213> ORGANISM: Mus musculus

<400> SEQUENCE: 110

Glu Ile Asn Pro Ser Thr Gly Gly Thr Thr
1               5                   10

<210> SEQ ID NO 111
<211> LENGTH: 4
<212> TYPE: PRT
<213> ORGANISM: Mus musculus

<400> SEQUENCE: 111

Trp Ala Asp Tyr
1

<210> SEQ ID NO 112
<211> LENGTH: 7

```
<212> TYPE: PRT
<213> ORGANISM: Mus musculus

<400> SEQUENCE: 112

Trp Ala Ser Ser Arg Glu Ser
1               5

<210> SEQ ID NO 113
<211> LENGTH: 9
<212> TYPE: PRT
<213> ORGANISM: Mus musculus

<400> SEQUENCE: 113

Gln Asn Asn Tyr Tyr Tyr Pro Phe Thr
1               5

<210> SEQ ID NO 114
<211> LENGTH: 17
<212> TYPE: PRT
<213> ORGANISM: Mus musculus

<400> SEQUENCE: 114

Lys Ser Ser Gln Ser Leu Leu Asn Ser Gly Asn Gln Arg Ser Tyr Leu
1               5                   10                  15

Thr

<210> SEQ ID NO 115
<211> LENGTH: 9
<212> TYPE: PRT
<213> ORGANISM: Mus musculus

<400> SEQUENCE: 115

Gln Asn Asn Tyr Asn Tyr Pro Phe Thr
1               5

<210> SEQ ID NO 116
<211> LENGTH: 7
<212> TYPE: PRT
<213> ORGANISM: Mus musculus

<400> SEQUENCE: 116

Trp Ala Ser Thr Lys Lys Ser
1               5

<210> SEQ ID NO 117
<211> LENGTH: 9
<212> TYPE: PRT
<213> ORGANISM: Mus musculus

<400> SEQUENCE: 117

Leu Asn Asp Tyr Ser Phe Pro Leu Thr
1               5

<210> SEQ ID NO 118
<211> LENGTH: 7
<212> TYPE: PRT
<213> ORGANISM: Mus musculus

<400> SEQUENCE: 118

Trp Ala Ser Thr Arg Gln Ser
1               5

<210> SEQ ID NO 119
<211> LENGTH: 7
```

<212> TYPE: PRT
<213> ORGANISM: Mus musculus

<400> SEQUENCE: 119

Trp Ala Ser Thr Gly Ala Ser
1               5

<210> SEQ ID NO 120
<211> LENGTH: 10
<212> TYPE: PRT
<213> ORGANISM: Mus musculus

<400> SEQUENCE: 120

Ser Ala Ser Ser Thr Ile Asn Tyr Met His
1               5                   10

<210> SEQ ID NO 121
<211> LENGTH: 7
<212> TYPE: PRT
<213> ORGANISM: Mus musculus

<400> SEQUENCE: 121

Asp Thr Ser Lys Leu Ala Pro
1               5

<210> SEQ ID NO 122
<211> LENGTH: 9
<212> TYPE: PRT
<213> ORGANISM: Mus musculus

<400> SEQUENCE: 122

His Gln Trp Ser Ser Tyr Pro Pro Thr
1               5

<210> SEQ ID NO 123
<211> LENGTH: 11
<212> TYPE: PRT
<213> ORGANISM: Mus musculus

<400> SEQUENCE: 123

Arg Ala Ser Gln Asp Ile Ser Asn Tyr Leu Asn
1               5                   10

<210> SEQ ID NO 124
<211> LENGTH: 7
<212> TYPE: PRT
<213> ORGANISM: Mus musculus

<400> SEQUENCE: 124

Tyr Thr Ser Arg Leu His Ser
1               5

<210> SEQ ID NO 125
<211> LENGTH: 9
<212> TYPE: PRT
<213> ORGANISM: Mus musculus

<400> SEQUENCE: 125

Gln His Tyr Ser Lys Leu Pro Pro Thr
1               5

<210> SEQ ID NO 126
<211> LENGTH: 16
<212> TYPE: PRT
<213> ORGANISM: Mus musculus -continued

<400> SEQUENCE: 126

Arg Ser Ser Lys Ser Leu Leu Tyr Lys Asp Gly Lys Thr Tyr Leu Asn
1               5                   10                  15

<210> SEQ ID NO 127
<211> LENGTH: 7
<212> TYPE: PRT
<213> ORGANISM: Mus musculus

<400> SEQUENCE: 127

Trp Met Ser Thr Arg Ala Ser
1               5

<210> SEQ ID NO 128
<211> LENGTH: 9
<212> TYPE: PRT
<213> ORGANISM: Mus musculus

<400> SEQUENCE: 128

Gln Gln Val Val Tyr Tyr Pro Tyr Thr
1               5

<210> SEQ ID NO 129
<211> LENGTH: 7
<212> TYPE: PRT
<213> ORGANISM: Mus musculus

<400> SEQUENCE: 129

Trp Ala Ser Ile Arg Lys Ser
1               5

<210> SEQ ID NO 130
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Ser Ser
                20                  25                  30

Gly Asn Gln Lys Asn Tyr Leu Ser Trp Tyr Gln Gln Lys Pro Gly Gln
            35                  40                  45

Pro Pro Lys Leu Leu Phe Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 131
<211> LENGTH: 119
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Thr Thr Asn Ile Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Gly Tyr Tyr Gly Asn Ser Leu Asp Tyr Trp Gly Gln Gly
            100                 105                 110

Thr Leu Val Thr Val Ser Ser
        115

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 132

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Phe Ser Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Val Tyr Ile Tyr Pro Leu Thr Phe Gly Gln Gly Thr Lys Leu Glu Ile
            100                 105                 110

Lys

<210> SEQ ID NO 133
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Phe
            20                  25                  30

```
Gly Met His Trp Val Arg Gln Ala Pro Gly Lys Gly Leu Glu Trp Val
        35                  40                  45

Ala Tyr Ile Ser Ser Gly Thr Thr Asn Ile Tyr Tyr Ala Asp Ser Val
 50                  55                  60

Lys Gly Arg Phe Thr Val Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
            85                  90                  95

Val Arg Ser Gly Tyr Tyr Gly Gln Ser Leu Asp Tyr Trp Gly Gln Gly
                100                 105                 110

Thr Leu Val Thr Val Ser Ser
        115

<210> SEQ ID NO 134
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ser Phe
                20                  25                  30

Gly Met His Trp Val Arg Gln Ala Pro Gly Lys Gly Leu Glu Trp Val
        35                  40                  45

Ala Tyr Ile Ser Ser Gly Thr Thr Asn Ile Tyr Tyr Ala Asp Ser Val
 50                  55                  60

Lys Gly Arg Phe Thr Val Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
            85                  90                  95

Val Arg Ser Gly Tyr Tyr Gly Ser Ser Leu Asp Tyr Trp Gly Gln Gly
                100                 105                 110

Thr Leu Val Thr Val Ser Ser
        115

<210> SEQ ID NO 135
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Val Met Thr Gln Ser Pro Asp Ser Leu Ala Val Ser Leu Gly
 1               5                  10                  15

Glu Arg Val Thr Met Asn Cys Lys Ser Ser Gln Ser Leu Phe Gln Ser
                20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80
```

Ile Ser Ser Val Gln Ala Glu Asp Val Ala Val Tyr Tyr Cys Gln Asn
                85                  90                  95

Val Tyr Ile Tyr Pro Leu Thr Phe Gly Gln Gly Thr Lys Leu Glu Ile
            100                 105                 110

Lys

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Phe Ser Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Val Tyr Ile Tyr Pro Leu Thr Phe Gly Gln Gly Thr Lys Leu Glu Ile
            100                 105                 110

Lys

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Val Tyr Ile Tyr Pro Leu Thr Phe Gly Gln Gly Thr Lys Leu Glu Ile
            100                 105                 110

Lys

<210> SEQ ID NO 138

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Thr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Thr | Ile | Ile | Ile | Gly | Gly | Ser | Tyr | Thr | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Arg | Leu | Val | Lys | Gly | Gln | Ala | Met | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | | 115 | | |

```
<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Thr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Thr | Ile | Ile | Ile | Gly | Gly | Ser | Tyr | Thr | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Arg | Leu | Val | Lys | Gly | Ser | Ala | Met | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | | 115 | | |

```
<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

```
Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Gln Ser
            20                  25                  30

Gly Asn Gln Lys Asn Tyr Leu Ser Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 141
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Ser Ser
            20                  25                  30

Gly Asn Gln Lys Asn Tyr Leu Ser Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Ser Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Asn
                 85                  90                  95

Asp Tyr Ser Tyr Pro Phe Thr Phe Gly Gln Gly Thr Lys Leu Glu Ile
            100                 105                 110

Lys

<210> SEQ ID NO 143
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Val Met Thr Gln Ser Pro Asp Ser Leu Ala Val Ser Leu Gly
  1               5                  10                  15

Glu Arg Val Thr Met Asn Cys Lys Ser Ser Gln Ser Leu Leu Asn Ser
                 20                  25                  30

Gly Asn Gln Lys Asn Tyr Leu Ser Trp Tyr Gln Gln Lys Pro Gly Gln
             35                  40                  45

Pro Pro Lys Leu Leu Phe Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Asn
                 85                  90                  95

Asp Tyr Ser Tyr Pro Phe Thr Phe Gly Gln Gly Thr Lys Leu Glu Ile
            100                 105                 110

Lys Gly Gly Gly Gly Ser Gly Gly Gly Ser Gly Gly Gly Gly Ser
            115                 120                 125

Glu Val Gln Leu Leu Glu Ser Gly Gly Leu Val Gln Pro Gly Gly
            130                 135                 140

Ser Leu Arg Leu Ser Cys Ala Ala Ser Gly Phe Thr Phe Ser Ser Tyr
145                 150                 155                 160

Thr Met Ser Trp Val Arg Gln Ala Pro Gly Lys Gly Leu Glu Trp Val
                165                 170                 175

Ala Thr Ile Ile Ile Gly Gly Ser Tyr Thr Tyr Tyr Ala Asp Ser Val
            180                 185                 190

Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Val Tyr Tyr Cys
            210                 215                 220

Thr Arg Leu Val Lys Gly Asn Ala Met Asp Tyr Trp Gly Gln Gly Thr
225                 230                 235                 240

Leu Val Thr Val Ser Ser Gly Gly Gly Ser Asp Ile Lys Leu Gln
                245                 250                 255

Gln Ser Gly Ala Glu Leu Ala Arg Pro Gly Ala Ser Val Lys Met Ser
            260                 265                 270

Cys Lys Thr Ser Gly Tyr Thr Phe Thr Arg Tyr Thr Met His Trp Val
            275                 280                 285

Lys Gln Arg Pro Gly Gln Gly Leu Glu Trp Ile Gly Tyr Ile Asn Pro
290                 295                 300
```

```
Ser Arg Gly Tyr Thr Asn Tyr Asn Gln Lys Phe Lys Asp Lys Ala Thr
305                 310                 315                 320

Leu Thr Thr Asp Lys Ser Ser Ser Thr Ala Tyr Met Gln Leu Ser Ser
                325                 330                 335

Leu Thr Ser Glu Asp Ser Ala Val Tyr Tyr Cys Ala Arg Tyr Tyr Asp
            340                 345                 350

Asp His Tyr Cys Leu Asp Tyr Trp Gly Gln Gly Thr Thr Leu Thr Val
        355                 360                 365

Ser Ser Val Glu Gly Gly Ser Gly Gly Ser Gly Gly Ser Gly Gly Ser
    370                 375                 380

Gly Gly Val Asp Asp Ile Gln Leu Thr Gln Ser Pro Ala Ile Met Ser
385                 390                 395                 400

Ala Ser Pro Gly Glu Lys Val Thr Met Thr Cys Arg Ala Ser Ser Ser
                405                 410                 415

Val Ser Tyr Met Asn Trp Tyr Gln Gln Lys Ser Gly Thr Ser Pro Lys
            420                 425                 430

Arg Trp Ile Tyr Asp Thr Ser Lys Val Ala Ser Gly Val Pro Tyr Arg
        435                 440                 445

Phe Ser Gly Ser Gly Ser Gly Thr Ser Tyr Ser Leu Thr Ile Ser Ser
    450                 455                 460

Met Glu Ala Glu Asp Ala Ala Thr Tyr Tyr Cys Gln Gln Trp Ser Ser
465                 470                 475                 480

Asn Pro Leu Thr Phe Gly Ala Gly Thr Lys Leu Glu Leu Lys His His
                485                 490                 495

His His His His
            500

<210> SEQ ID NO 144
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
                100                 105                 110

Gly Thr Leu Val Thr Val Ser Ser Gly Gly Ser Gly Gly Ser Gly Gly
            115                 120                 125

Ser Asp Ile Val Met Thr Gln Ser Pro Asp Ser Leu Ala Val Ser Leu
        130                 135                 140

Gly Glu Arg Val Thr Met Asn Cys Lys Ser Ser Gln Ser Leu Leu Asn
```

```
            145                 150                 155                 160
Ser Gly Asn Gln Lys Asn Tyr Leu Ser Trp Tyr Gln Gln Lys Pro Gly
                165                 170                 175

Gln Pro Pro Lys Leu Leu Phe Tyr Trp Ala Ser Thr Arg Glu Ser Gly
                180                 185                 190

Val Pro Asp Arg Phe Ser Gly Ser Gly Ser Gly Thr Asp Phe Thr Leu
                195                 200                 205

Thr Ile Ser Ser Val Gln Ala Glu Asp Val Ala Val Tyr Tyr Cys Gln
210                 215                 220

Asn Asp Tyr Ser Tyr Pro Phe Thr Phe Gly Gln Gly Thr Lys Leu Glu
225                 230                 235                 240

Ile Lys Gly Gly Ser Gly Gly Ser Gly Gly Ser Glu Val Gln Leu Leu
                245                 250                 255

Glu Ser Gly Gly Gly Leu Val Gln Pro Gly Gly Ser Leu Arg Leu Ser
                260                 265                 270

Cys Ala Ala Ser Gly Phe Thr Phe Ser Ser Tyr Thr Met Ser Trp Val
                275                 280                 285

Arg Gln Ala Pro Gly Lys Gly Leu Glu Trp Val Ala Thr Ile Ile Ile
            290                 295                 300

Gly Gly Ser Tyr Thr Tyr Tyr Ala Asp Ser Val Lys Gly Arg Phe Thr
305                 310                 315                 320

Ile Ser Arg Asp Asn Ser Lys Asn Thr Leu Tyr Leu Gln Met Asn Ser
                325                 330                 335

Leu Arg Ala Glu Asp Thr Ala Val Tyr Tyr Cys Thr Arg Leu Val Lys
                340                 345                 350

Gly Asn Ala Met Asp Tyr Trp Gly Gln Gly Thr Leu Val Thr Val Ser
                355                 360                 365

Ser Gly Gly Ser Gly Gly Ser Gly Gly Ser Ser Tyr Val Leu Thr Gln
                370                 375                 380

Pro Ser Ser Val Ser Val Ala Pro Gly Gln Thr Ala Thr Ile Ser Cys
385                 390                 395                 400

Gly Gly His Asn Ile Gly Ser Lys Asn Val His Trp Tyr Gln Gln Arg
                405                 410                 415

Pro Gly Gln Ser Pro Val Leu Val Ile Tyr Gln Asp Asn Lys Arg Pro
                420                 425                 430

Ser Gly Ile Pro Glu Arg Phe Ser Gly Ser Asn Ser Gly Asn Thr Ala
                435                 440                 445

Thr Leu Thr Ile Ser Gly Thr Gln Ala Met Asp Glu Ala Asp Tyr Tyr
                450                 455                 460

Cys Gln Val Trp Asp Asn Tyr Ser Val Leu Phe Gly Gly Gly Thr Lys
465                 470                 475                 480

Leu Thr Val Leu His His His His His
                485                 490

<210> SEQ ID NO 145
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Val Met Thr Gln Ser Pro Asp Ser Leu Ala Val Ser Leu Gly
1               5                   10                  15
```

```
Glu Arg Val Thr Met Asn Cys Lys Ser Ser Gln Ser Leu Phe Asn Ser
                 20                  25                  30

Gly Asn Gln Arg Asn Tyr Leu Thr Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Thr Asp Phe Thr Leu Thr
 65                  70                  75                  80

Ile Ser Ser Val Gln Ala Glu Asp Val Ala Val Tyr Tyr Cys Gln Asn
                 85                  90                  95

Val Tyr Ile Tyr Pro Leu Thr Phe Gly Gln Gly Thr Lys Leu Glu Ile
                100                 105                 110

Lys Gly Gly Gly Gly Ser Gly Gly Gly Gly Ser Gly Gly Gly Gly Ser
        115                 120                 125

Glu Val Gln Leu Val Glu Ser Gly Gly Leu Val Gln Pro Gly Gly
        130                 135                 140

Ser Leu Arg Leu Ser Cys Ala Val Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Tyr Ile Ser Ser Gly Thr Thr Asn Ile Tyr Tyr Ala Asp Ser Val
                180                 185                 190

Lys Gly Arg Phe Thr Val Ser Arg Asp Asn Ala Lys Asn Ser Leu Tyr
                195                 200                 205

Leu Gln Met Asn Ser Leu Arg Ala Glu Asp Thr Ala Val Tyr Tyr Cys
210                 215                 220

Val Arg Ser Gly Tyr Tyr Gly Asn Ser Leu Asp Tyr Trp Gly Gln Gly
225                 230                 235                 240

Thr Leu Val Thr Val Ser Ser Gly Gly Gly Ser Asp Ile Lys Leu
                245                 250                 255

Gln Gln Ser Gly Ala Glu Leu Ala Arg Pro Gly Ala Ser Val Lys Met
                260                 265                 270

Ser Cys Lys Thr Ser Gly Tyr Thr Phe Thr Arg Tyr Thr Met His Trp
        275                 280                 285

Val Lys Gln Arg Pro Gly Gln Gly Leu Glu Trp Ile Gly Tyr Ile Asn
        290                 295                 300

Pro Ser Arg Gly Tyr Thr Asn Tyr Asn Gln Lys Phe Lys Asp Lys Ala
305                 310                 315                 320

Thr Leu Thr Thr Asp Lys Ser Ser Thr Ala Tyr Met Gln Leu Ser
                325                 330                 335

Ser Leu Thr Ser Glu Asp Ser Ala Val Tyr Tyr Cys Ala Arg Tyr Tyr
        340                 345                 350

Asp Asp His Tyr Cys Leu Asp Tyr Trp Gly Gln Gly Thr Thr Leu Thr
        355                 360                 365

Val Ser Ser Val Glu Gly Gly Ser Gly Gly Ser Gly Gly Ser Gly Gly
        370                 375                 380

Ser Gly Gly Val Asp Asp Ile Gln Leu Thr Gln Ser Pro Ala Ile Met
385                 390                 395                 400

Ser Ala Ser Pro Gly Glu Lys Val Thr Met Thr Cys Arg Ala Ser Ser
                405                 410                 415

Ser Val Ser Tyr Met Asn Trp Tyr Gln Gln Lys Ser Gly Thr Ser Pro
                420                 425                 430

Lys Arg Trp Ile Tyr Asp Thr Ser Lys Val Ala Ser Gly Val Pro Tyr
```

Arg Phe Ser Gly Ser Gly Ser Gly Thr Ser Tyr Ser Leu Thr Ile Ser
            435                 440                 445

Ser Met Glu Ala Glu Asp Ala Ala Thr Tyr Tyr Cys Gln Gln Trp Ser
450                 455                 460

Ser Asn Pro Leu Thr Phe Gly Ala Gly Thr Lys Leu Glu Leu Lys His
465                 470                 475                 480

His His His His His
            485                 490                 495

<210> SEQ ID NO 146
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser Gly Gly Ser Gly Gly Ser Gly Gly
        115                 120                 125

Ser Asp Ile Val Met Thr Gln Ser Pro Asp Ser Leu Ala Val Ser Leu
    130                 135                 140

Gly Glu Arg Val Thr Met Asn Cys Lys Ser Ser Gln Ser Leu Phe Asn
145                 150                 155                 160

Ser Gly Asn Gln Arg Asn Tyr Leu Thr Trp Tyr Gln Gln Lys Pro Gly
                165                 170                 175

Gln Pro Pro Lys Leu Leu Ile Tyr Trp Ala Ser Thr Arg Glu Ser Gly
            180                 185                 190

Val Pro Asp Arg Phe Ser Gly Ser Gly Ser Gly Thr Asp Phe Thr Leu
        195                 200                 205

Thr Ile Ser Ser Val Gln Ala Glu Asp Val Ala Val Tyr Tyr Cys Gln
    210                 215                 220

Asn Val Tyr Ile Tyr Pro Leu Thr Phe Gly Gln Gly Thr Lys Leu Glu
225                 230                 235                 240

Ile Lys Gly Gly Ser Gly Gly Ser Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Val Ser Gly Phe Thr Phe Ser Ser Phe Gly Met His Trp Val
        275                 280                 285

```
Arg Gln Ala Pro Gly Lys Gly Leu Glu Trp Val Ala Tyr Ile Ser Ser
    290                 295                 300
Gly Thr Thr Asn Ile Tyr Tyr Ala Asp Ser Val Lys Gly Arg Phe Thr
305                 310                 315                 320
Val Ser Arg Asp Asn Ala Lys Asn Ser Leu Tyr Leu Gln Met Asn Ser
                325                 330                 335
Leu Arg Ala Glu Asp Thr Ala Val Tyr Tyr Cys Val Arg Ser Gly Tyr
            340                 345                 350
Tyr Gly Asn Ser Leu Asp Tyr Trp Gly Gln Gly Thr Leu Val Thr Val
        355                 360                 365
Ser Ser Gly Gly Ser Gly Gly Ser Gly Gly Ser Ser Tyr Val Leu Thr
370                 375                 380
Gln Pro Ser Ser Val Ser Val Ala Pro Gly Gln Thr Ala Thr Ile Ser
385                 390                 395                 400
Cys Gly Gly His Asn Ile Gly Ser Lys Asn Val His Trp Tyr Gln Gln
                405                 410                 415
Arg Pro Gly Gln Ser Pro Val Leu Val Ile Tyr Gln Asp Asn Lys Arg
            420                 425                 430
Pro Ser Gly Ile Pro Glu Arg Phe Ser Gly Ser Asn Ser Gly Asn Thr
        435                 440                 445
Ala Thr Leu Thr Ile Ser Gly Thr Gln Ala Met Asp Glu Ala Asp Tyr
    450                 455                 460
Tyr Cys Gln Val Trp Asp Asn Tyr Ser Val Leu Phe Gly Gly Gly Thr
465                 470                 475                 480
Lys Leu Thr Val Leu His His His His His His
                485                 490

<210> SEQ ID NO 147
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Val Met Thr Gln Ser Pro Asp Ser Leu Ala Val Ser Leu Gly
1               5                   10                  15
Glu Arg Val Thr Met Asn Cys Lys Ser Ser Gln Ser Leu Phe Asn Ser
            20                  25                  30
Gly Asn Gln Arg Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Val Gln Ala Glu Asp Val Ala Val Tyr Tyr Cys Gln Asn
                85                  90                  95
Val Tyr Ile Tyr Pro Leu Thr Phe Gly Gln Gly Thr Lys Leu Glu Ile
            100                 105                 110
Lys

<210> SEQ ID NO 148
<211> LENGTH: 118
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 148

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser
        115

<210> SEQ ID NO 149
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 149

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val Tyr Ile Tyr Pro Leu Thr Phe Gly Gln Gly Thr Lys Leu Glu Ile
            100                 105                 110

Lys

<210> SEQ ID NO 150
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 150

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Phe Asn Ser
            20                  25                  30

Gly Asn Gln Arg Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Val Tyr Ile Tyr Pro Leu Thr Phe Gly Gln Gly Thr Lys Leu Glu Ile
            100                 105                 110

Lys

<210> SEQ ID NO 151
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Cys Asn Met Leu Val Thr Asn Phe Trp Met Ser Thr Ala Asn Met Tyr
1               5                   10                  15

Thr Gly Met Gly Gly Met Val Gln Thr Val Gln Thr Arg Tyr Thr Phe
            20                  25                  30

Gly Ala

<210> SEQ ID NO 152
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asn Met Leu Val Thr Asn Phe Trp Met Ser Thr Ala Asn Met Tyr Thr
1               5                   10                  15

Gly Met Gly Gly Met Val Gln Thr Val Gln Thr Arg Tyr Thr Phe Gly
            20                  25                  30

Ala Cys

<210> SEQ ID NO 153
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Leu Trp Arg Ser Cys Val Arg Glu Ser Ser Gly Phe Thr Glu Cys
1               5                   10                  15

Arg Gly Tyr Phe Thr Leu
            20

<210> SEQ ID NO 154
<211> LENGTH: 24
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 154

Gln Gly Leu Trp Arg Ser Cys Val Arg Glu Ser Ser Gly Phe Thr Glu
1               5                   10                  15

Cys Arg Gly Tyr Phe Thr Leu Lys
            20

<210> SEQ ID NO 155
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Gln Trp Ser Thr Gln Asp Leu Tyr Asn Asn Pro Val Thr Ala Val
1               5                   10                  15

Phe Asn Tyr Gln Gly Leu Trp Arg Ser Cys
            20                  25

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Arg Gly Tyr Phe Thr Leu Leu Gly Leu Pro Ala Met Leu Gln Ala
1               5                   10                  15

Val Arg

<210> SEQ ID NO 157
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Phe Gly
1

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Gly Gly Gly Ser Gly Gly Gly Ser Gly Gly Gly Gly Ser
1               5                   10                  15

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 159

Val Glu Gly Gly Ser Gly Gly Ser Gly Gly Ser Gly Gly
1               5                   10                  15

Val Asp
```

CLAUDIN18 ANTIBODIES AND METHODS OF TREATING CANCER

CROSS-REFERENCE TO RELATED APPLICATIONS

This application is a 371 national-stage application based on International Patent Application No. PCT/US20/42573, filed Jul. 17, 2020, which claims the benefit of U.S. Provisional Application No. 62/875,416, filed on Jul. 17, 2019, the entire contents of said applications are incorporated herein in their entirety by this reference.

FIELD OF THE DISCLOSURE

The present disclosure relates, in general, to antibodies specific for claudin 18.2 and uses thereof to treat cancer.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Jan. 14, 2022, is named "UCH-21001_SL" and is 120,111 bytes in size.

BACKGROUND

Antibodies constitute powerful therapeutic agents characterized by limited side effects due to their ability to specifically target a distinct antigen on a cell, bacteria, virus, or toxin. In 1986, the first therapeutic monoclonal antibody, Orthoclone OKT3, was introduced into the market. Since then, this class of biopharmaceutical products has significantly grown. In late 2014, forty-seven monoclonal antibody products had received approval in the U.S. or Europe for the treatment of a variety of diseases, including cancer and inflammatory, cardiovascular, respiratory, and infectious diseases.

More than a dozen monoclonal antibodies are currently approved by the U.S. Food and Drug Administration to treat cancers. Among these agents are alemtuzumab (Campath®), which is indicated for chronic lymphocytic leukemia (CLL), and trastuzumab (Herceptin®), which is used for treating breast cancer. Some antibodies are labeled with chemotherapeutic drugs, including, for example, brentuximab vedotin (Adcetris(10) and Ado-trastuzumab emtansine (Kadcyla®). Other antibody products, such as blinatumomab (Blincyto) are designed to recognize and bind to two different antigens. Despite the commercial availability of such antibody products, the current cancer incidence and cancer deaths remain high. It has been reported that cancer incidence is greater than 450 per 100,000 men and women per year, and cancer mortality is just over 170 per 100,000 men and women per year.

SUMMARY

Provided herein are antigen-binding proteins which bind to Claudin-18 (CLDN18). In various aspects, the antigen-binding protein of the present disclosure binds to a human CLDN18 and optionally binds to a mouse CLDN18. In various aspects, the antigen-binding protein binds to the extracellular domain (ECD) of CLDN18. In various embodiments, the disclosure provides an antigen binding protein against CLDN18.2. In various instances, the antigen-binding protein binds to Extracellular Loop 1 (EL1) of the ECD of CLDN18.2. In various aspects, the antigen-binding protein binds to EL1 and does not bind to Extracellular Loop 2 (EL2) of the ECD of CLDN18.2. In various embodiments, the antigen binding protein that binds CLDN18.2 binds to an epitope within the amino acid sequence of residues 28 to 74 of CLDN18.2 (SEQ ID NO: 1). In various embodiments, the antigen-binding binds to the amino acid sequence of GLWRSCVRESSGFTECRFYFTL (SEQ ID NO: 4), QGLWRSCVRESSGFTECRGYFTLK (SEQ ID NO: 5), DQWSTQDLYNNPVTAVFNYQG LWRSC (SEQ ID NO: 6) or CRGYFTLLFLPAMLQAVR (SEQ ID NO: 7) of CLDN 18.2.

In various instances, the antigen binding protein binds to CLDN18.2 and does not bind to any other member of the Claudin family. In various aspects, the antigen binding protein binds to CLDN18.2 endogenously expressed by human cancer cells, e.g., HUPT4 pancreatic cells. In various instances, the antigen-binding proteins of the present disclosure inhibit tumor growth in a subject, e.g., a human, without any other moiety attached to the antigen-binding protein. In various instances, the antigen-binding proteins unconjugated to a heterologous moiety (e.g., unconjugated to any chemotherapeutic agent, drug or toxic moiety) inhibit tumor growth in a subject, e.g., a human.

In various aspects, the antigen-binding protein binds to CLDN18.2 expressed by human cancer cells. In various aspects, the antigen-binding protein inhibits a binding interaction between human CLDN18.2 and a reference anti-CLDN18.2 antibody. Without being bound to a particular theory, the inhibiting action of the antigen-binding proteins provided herein allow such entities to be useful in methods of reducing tumor growth and treating a subject with a tumor or cancer. As further discussed herein, in various aspects, the antigen-binding protein is an antibody, antigen-binding antibody fragment thereof, or antibody protein product.

The present disclosure also provides antigen-binding proteins comprising at least 3, 4, 5, or all amino acid sequences of a specified group of amino acid sequences. In various aspects, the antigen-binding proteins comprise at least 3, 4, 5, or 6 complementary determining region (CDR) amino acid sequences of CLDN18.2 antibodies disclosed herein.

The present disclosure further provides antigen-binding proteins comprising amino acid sequences as detailed herein. In various aspects, the antigen-binding protein comprises an amino acid sequence of a SEQ ID NO: listed in Table A, Table B, Table C, Table D, Table 6, Table 8, Table 9, Table 10, Table 11, or a combination thereof, as further described herein.

The present disclosure provides a bispecific antigen-binding protein that binds to CLDN18.2 and a second antigen. The bispecific antigen-binding protein may comprise any one of the antigen-binding protein described here. The second antigen may be a cell surface protein, optionally a protein whose binding modulates immune response. The bispecific antigen-binding protein may take any structure, e.g., diabody, TandAb (tandem diabody), BiTE (bispecific T cell engager), etc. Exemplary bispecific antigen-binding protein comprises a sequence set forth in Table 11.

The present disclosure also provides a conjugate that comprises an antigen-binding protein or a bispecific antigen-binding protein and a heterologous moiety (e.g., a cytotoxic drug). The conjugate may comprise a cleavable linker or a noncleavable linker. The conjugate may have a various number of heterologous moiety (an agent) conjugated to the antigen-binding protein or a bispecific antigen-binding protein described herein, preferably 1-8 agents per protein or 3-8 agents per protein. The conjugate may be a site-specific conjugate. The conjugate may be a homogenous conjugate or a heterogeneous conjugate.

Related polypeptides, nucleic acids, vectors, host cells, and conjugates are further provided herein. Kits and pharmaceutical compositions comprising such entities are moreover contemplated.

Also provided are methods of making an antigen-binding protein. In various embodiments, the method comprises culturing a host cell comprising a nucleic acid encoding an antigen-binding protein or a polypeptide as described herein so as to express the antigen-binding protein or polypeptide.

Methods of treating a subject having cancer are additionally provided herein. In various embodiments, the method comprises administering to the subject the pharmaceutical composition of the present disclosure in an amount effective for treating the cancer in the subject.

Also provided are methods of treating a subject with a CLDN18.2-expressing cancer comprising administering to the subject a pharmaceutical composition described herein. In various embodiments, the CLDN18.2-expressing cancer expresses CLDN18.2. Further contemplated is a method of inhibiting tumor growth in a subject, comprising administering to the subject a pharmaceutical composition described herein.

A method of reducing tumor size in a subject, or preventing the recurrence of cancer in a subject comprising administering to the subject a pharmaceutical composition described herein.

Also provided herein is a method of treating cancer in a subject diagnosed to be a low over-expresser of CLDN18, such as CLDN18.2, comprising administering to the subject a pharmaceutical composition described herein.

In various embodiments, the administering induces apoptosis in tumor cells, for example in cells expressing CLDN18, in particular CLDN18.2. In various embodiments, the administration induces antibody-dependent cell-mediated cytotoxicity (ADCC) or Complement-dependent cytotoxicity (CDC), tumor necrosis and death or depletion of cells, and/or disruption of tumor cell adherence, each of which result tumor regression or slowing of tumor growth.

BRIEF DESCRIPTION OF THE DRAWINGS

FIG. 3 represents a graph of CLDN18.1 and CLDN18.2 expression in cancer cell lines as determined by RNASeq.

FIG. 5A represents a graph of tumor volume ($mm^3$) of tumors in mice bearing upper gastrointestinal tract (SNU601) tumors as a function of time (days) after treatment with chimeric anti-CLDN18.2 antibodies. FIG. 5B represents a graph of the mean change in tumor volume ($mm^3$) at Day 30 in the same treatment groups.

FIG. 7A represents a graph of tumor volume ($mm^3$) of tumors in mice bearing pancreatic (HUPT4) tumors as a function of time (days) after treatment with humanized anti-CLDN18.2 antibodies. FIG. 7B represents a graph of the mean change in tumor volume ($mm^3$) at Day 42 in the same treatment groups.

FIG. 8A depicts the difference in tumor volume in mice bearing pancreatic (HUPT4) tumors after different dosing schedules as a function of time (days) after treatment with humanized anti-CLDN 18.2 antibody. FIG. 8B represents a graph of the mean change in tumor volume ($mm^3$) at Day 42 in the same treatment groups.

FIG. 9A represents a graph of tumor volume ($mm^3$) of tumors in mice bearing pancreatic (HUPT4) tumors as a function of time (days) after treatment with humanized anti-CLDN18.2 antibody drug conjugate (ADC). FIG. 9B represents a graph of the tumor volume ($mm^3$) in mice treated with a single dose of anti-CLDN18.2 ADC or control antibody.

FIG. 12A represents a graph of tumor volume ($mm^3$) of tumors in mice bearing pancreatic (HUPT4) tumors as a function of time (days) after treatment with different doses of humanized anti-CLDN 18.2 antibody drug conjugate (ADC). FIG. 12B represents a graph of the tumor volume ($mm^3$) at Day 32 in the same treatment groups.

FIG. 13 sets out the amino acid sequences of the heavy chain and light chain variable regions of the CLDN18.2 antibodies described herein.

FIG. 14A represents a graph of tumor volume ($mm^3$) of tumors in mice bearing pancreatic patient-derived (PDX) tumors, which express CLDN18.2, as a function of time (days) after treatment with different doses of humanized anti-CLDN18.2 antibody drug conjugate (ADC). FIG. 14B represents a graph of the tumor volume ($mm^3$) at Day 27 in the same treatment groups. FIG. 14C represents the immunohistochemistry (IHC) showing the CLDN 18.2 expression on the PDX model.

FIG. 15A represents a graph of tumor volume ($mm^3$) of tumors in mice bearing pancreatic patient-derived (PDX) tumors, which do not express CLDN 18.2, as a function of time (days) after treatment with different doses of humanized anti-CLDN 18.2 antibody drug conjugate (ADC). FIG. 15B represents a graph of the tumor volume ($mm^3$) at Day 18 in the same treatment groups. FIG. 15C represents the immunohistochemistry (IHC) showing the lack of CLDN18.2 expression on the PDX model.

FIG. 16A represents a graph of tumor volume ($mm^3$) of tumors in mice bearing melanoma (M202) tumors, which do not express CLDN18.2, as a function of time (days) after treatment with different doses of humanized anti-CLDN18.2 antibody drug conjugates (ADCs). FIG. 16B represents a graph of the tumor volume ($mm^3$) at Day 23 in the same treatment groups.

FIG. 17 represents sequences for antibodies 307-4h and 358-h3 and additional sequence variations. These antibodies were generated to provide additional information on potential manufacturability sequence liabilities.

FIG. 18 represents the humanized antibody binding activity to native positive cells (cells with endogenous expression of CLDN18.2) or artificially overexpressed cells (cells engineered to overexpress CLDN 18.2) as analyzed by flow cytometry.

FIG. 19 represents the humanized antibody binding activity to human CLDN18.2, human CLDN 18.1, mouse CLDN18.2, dog CLDN18, and rat CLDN18.

FIG. 21A represents the binding affinity (KD) of the humanized CLDN18.2 antibodies to cells endogenously expressing CLDN18.2 or cells engineered to overexpress CLDN18.2. FIG. 21B represents the CLDN18.2 expression level on various cancer cell lines. pNK-307-h1F06-4 refers to 307-h4 antibody; pNK-358-h2c10-3 refers to 358-h3 antibody; #307-6h refers to 307-6h antibody; and #358-5h refers to 358-5h antibody.

FIG. 22A represents a graph of tumor volume (mm$^3$) of tumors in mice bearing pancreatic (HUPT4) tumors as a function of time (days) after treatment with different doses of humanized anti-CLDN18.2 antibodies (307-4h, 307-6h, 358-3h, and 358-5h). FIG. 22B represents a graph of the tumor volume (mm$^3$) at Day 24 in the same treatment groups.

FIG. 23A-FIG. 23C represent the sequence of CLDN 18.2-CD3 bispecific T cell engagers (BiTEs) (FIG. 23A and FIG. 23C) and CLDN18.2-CD16 TandAbs (FIG. 23B and FIG. 23C).

FIG. 25A-FIG. 25E represent the binding activity of CLDN18.2-CD16 TandAbs to cells endogenously expressing CLDN 18.2 or cells engineered to overexpress CLDN 18.2. The binding activity was analyzed by flow cytometry.

FIG. 26A-FIG. 26E represent the binding activity of CLDN18.2-CD16 TandAbs to cells endogenously expressing CLDN18.2 or cells engineered to overexpress CLDN18.2. The binding activity was analyzed by flow cytometry.

FIG. 28 represents the T-cell activation assay using Jurkat cells with NFAT-RE reporter and CLDN18.2-CD3 BiTEs using cells endogenously expressing CLDN18.2 or cells engineered to overexpress CLDN18.2.

FIG. 30A-FIG. 30F show the representative images of CLDN I8.2-CD3 BiTEs cytotoxicity assay 5 days post treatment.

FIG. 33A represents a graph of tumor volume (mm$^3$) of tumors in humanized BLT mice bearing pancreatic (HUPT4) tumors as a function of time (days) after treatment with different doses of humanized anti-CLDN18.2 BiTEs. FIG. 33B represents a graph of the tumor volume (mm$^3$) at Day 28 in the same treatment groups.

DETAILED DESCRIPTION

Figure 1:
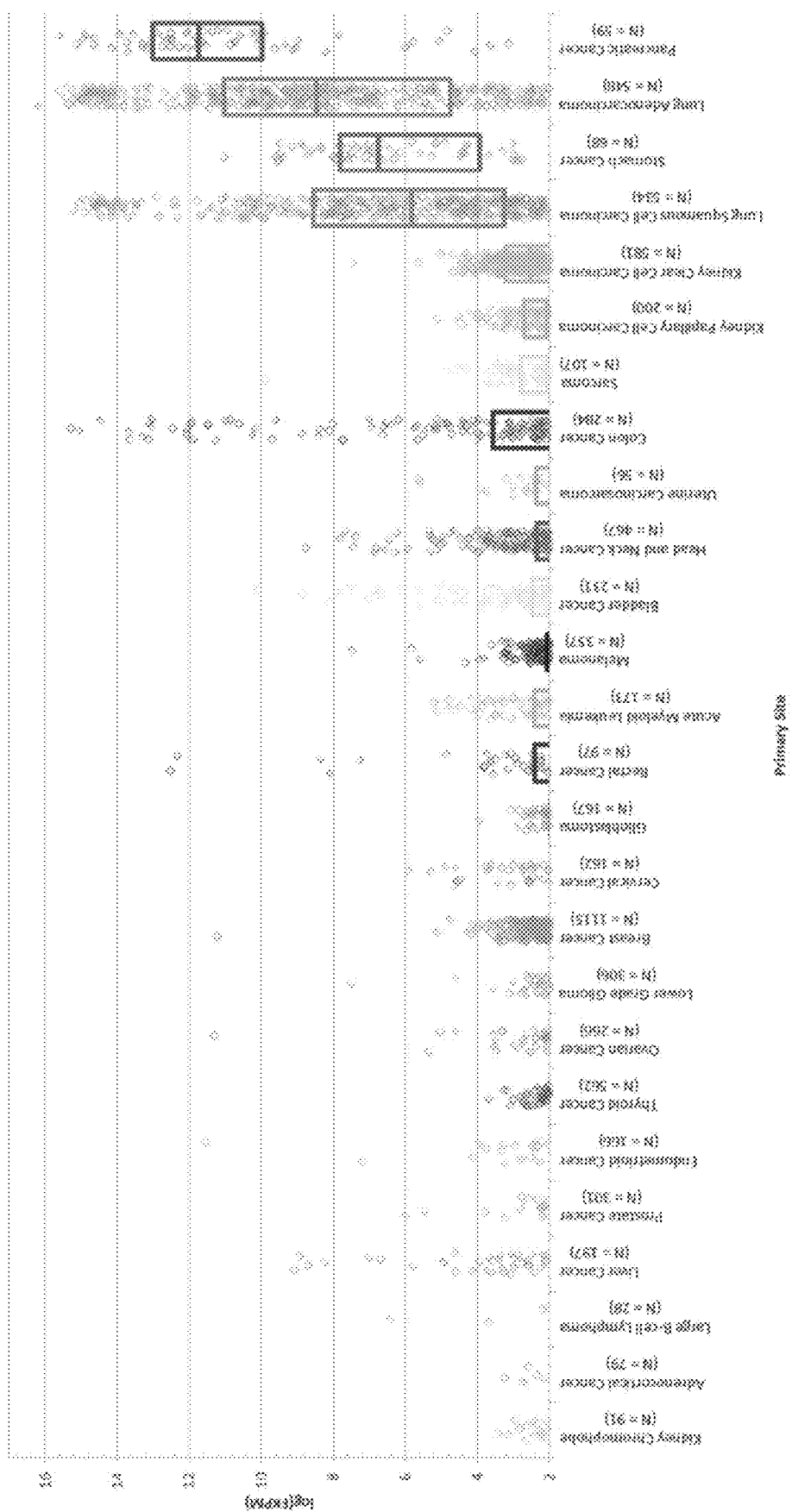
FIG. 1 represents a graph of CLDN18.2 expression in a panel of cancer types.

The present disclosure describes an antigen binding protein against CLDN18, e.g., specific for CLDN18.2, to treat CLDN18.2-expressing cancers. It is believed that the anti-CLDN 18.2 antibodies are effective via direct blocking of CLDN 18.2 function in cell-cell junctions as well as via immune recruitment.

The Claudia Family

Tight junctions, also known as occluding junctions or zonulae occludentes, are vertebrate structures located between two adjacent cells that regulate paracellular permeability and maintain cell polarity in epithelial and endothelial cell sheets. The claudin (CLDN) family of genes encodes membrane proteins that are important components of tight junctions. CLDN proteins comprise four transmembrane (TM) helices (TM1, TM2, TM3, and TM4) and two extracellular loops (EL1 and EL2). The extracellular loops of the CLDN proteins of adjacent cells interact with one another to seal the cellular sheet and regulate paracellular transport between the luminal and basolateral spaces.

CLDN proteins play a role in various human diseases and pathologies. For example, mutations in the CLDN1 gene have been shown to result in progressive scaling of the skin along with obstruction of bile ducts. Mutants of the CLDN16 gene cause a magnesium wasting disorder. CLDN19 mutations lead to ocular conditions, such as macular colobomata and myopia, while CLDN14 mutations can lead to nonsyndromic recessive deafness. CLDN3 and CLDN4 are known to be surface receptors for the *Clostridium perfringens* enterotoxin in the gut, and CLDN1, CLDN6, and CLDN9 are co-receptors for hepatitis C virus (HCV) entry. Several CLDN proteins have been shown to be abnormally expressed in cancers. For instance, CLDN1 is downregulated in breast and colon cancer, whereas CLDN3 and CLDN4 are highly upregulated in multiple cancers.

Claudin-6 (CLDN6) is a member of the CLDN family. The gene encoding the human CLDN6 protein is located on the p arm of human chromosome 16 at 16p13.3 and is conserved in chimpanzee, Rhesus monkey, dog, cow, mouse, rat, zebrafish, and frog. CLDN6 is generally expressed in humans as a 220-amino acid precursor protein; the first 21 amino acids of which constitute the signal peptide.

Claudin-18 (CLDN18) is a tight junction protein mostly absent in non-germline adult tissues. CLDN18.2 is elevated in stem cells relative to non-stem cells. The human CLDN18 gene has two alternative first exons, giving rise to two protein isoforms (CLDN18.1 and CLDN18.2) differing in the N-terminal 69 amino acids (Niimi et al., Mol Cell Biol 2001; 21:7380-90), including the first extracellular loop The two variants are different at 8/51 amino acids in the first extracellular domain, and the sequences of their second extracellular loops are identical. CLDN18.2 is only present in normal gastric tissue. CLDN18.2 is overexpressed in pancreatic, esophageal and lung cancers. The high tumor-normal expression differential as well as it's putative role in tumor biology make CLDN18.2 a highly attractive therapeutic target. The amino acid sequence of the CLDN18.2 precursor protein is publically available at the National Center for Biotechnology Information (NCBI) website as NCBI Reference Sequence NP_001002026 and is provided herein as SEQ ID NO: 1. Extracellular Loop 1 runs from amino acids 28 to 80 of SEQ ID NO: 1 and EL2 is between amino acids 144 to 174 of SEQ ID NO: 1. Antibodies that bind Claudin-18.2 are described in U.S. Pat. No. 10,137,195.

Antigen Binding Proteins

Provided herein are antigen-binding proteins that bind to Claudin-18 (CLDN18). In various embodiments, the antigen binding proteins bind to isoform CLDN18.2. The antigen-binding proteins of the present disclosure can take any one of many forms of antigen-binding proteins known in the art. In various embodiments, the antigen-binding proteins of the present disclosure take the form of an antibody, or antigen-binding antibody fragment, or an antibody protein product.

In various embodiments of the present disclosure, the antigen-binding protein comprises, consists essentially of, or consists of an antibody. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, $4^{th}$ ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra). In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in various embodiments, the antibody is an antibody of isotype IgA, IgD, IgE, IgG, or IgM, including any one of IgG1, IgG2, IgG3 or IgG4. In various aspects, the antibody comprises a constant region comprising one or more amino acid modifications, relative to the naturally-occurring counterpart, in order to improve half-life/stability or to render the antibody more suitable for expression/manufacturability. In various instances, the antibody comprises a constant region wherein the C-terminal Lys residue that is present in the naturally-occurring counterpart is removed or clipped.

The antibody can be a monoclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antigen-binding protein is an antibody, such as a human antibody. In certain aspects, the antigen-binding protein is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non human sequence more similar to a human sequence. Information, including sequence information for human antibody heavy and light chain constant regions is publicly available through the Uniprot database as well as other databases well-known to those in the field of antibody engineering and production. For example, the IgG2 constant region is available from the Uniprot database as Uniprot number P01859, incorporated herein by reference.

An antibody can be cleaved into fragments by enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment. In various aspects of the present disclosure, the antigen-binding protein of the present disclosure is an antigen-binding fragment of an antibody (a.k.a., antigen-binding antibody fragment, antigen-binding fragment, antigen-binding portion). In various instances, the antigen-binding antibody fragment is a Fab fragment or a F(ab')$_2$ fragment.

The architecture of antibodies has been exploited to create a growing range of alternative antibody formats that spans a molecular-weight range of at least about 12-150 kDa and has a valency (n) range from monomeric (n=1), to dimeric (n=2), to trimeric (n=3), to tetrameric (n=4), and potentially higher; such alternative antibody formats are referred to herein as "antibody protein products". Antibody protein products include those based on the full antibody structure and those that mimic antibody fragments which retain full antigen-binding capacity, e.g., scFvs, Fabs and VHH/VH (discussed below). The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (mini Abs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, bispecific antibody (BsAb) fragments, bispecific fusion proteins, and BsAb conjugates. See, e.g., Spiess et al., Molecular Immunology 67(2) Part A: 97-106 (2015).

In various aspects, the antigen-binding protein of the present disclosure comprises, consists essentially of, or consists of any one of these antibody protein products. In various aspects, the antigen-binding protein of the present disclosure comprises, consists essentially of, or consists of any one of an scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate.

In various instances, the antigen-binding protein of the present disclosure is an antibody protein product in monomeric form, or polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

In various embodiments, an anti-CLDN18.2 antibody or antibody variant thereof is selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, an IgG1 antibody, an IgG2 antibody, an IgG3 antibody, and an IgG4 antibody.

In various aspects, the antigen-binding protein of the present disclosure is linked to a therapeutic agent. As described below, the therapeutic agent may be any known in the art, including, but not limited to, chemotherapeutic agents, cytokines and growth factors, cytotoxic agents, and the like. See "Conjugates" below.

Bispecific Formats

In exemplary aspects, the antigen-binding protein is bispecific and thus capable of binding two different and distinct antigens. In exemplary embodiments, the antigen binding protein is bispecific and binds to CLDN18.2 and a second antigen.

In exemplary instances, the second antigen is a cell surface protein expressed by a T-cell. In exemplary aspects, the cell surface protein is a component of the T-cell receptor (TCR), for example, CD3 In exemplary instances, the second antigen is a costimulatory molecule which assists in T-cell activation, e.g., CD40 or 4-1BB (CD137). In exemplary aspects, the second antigen is an Fc receptor. In various aspects, the Fc receptor is a Fc gamma receptor, Fc-alpha receptor, Fc-epsilon receptor. In exemplary aspects, the Fc receptor is CD64 (Fc-gamma RI), CD32 (Fc-gamma RIIA), CD16A (Fc-gamma RIIIA), CD16b (Fc-gamma RIIIb), FcεRI, CD23 (Fc-epsilon RII), CD89 (Fc-epsilon RI), Fcα/μR, or FcRn. In exemplary aspects, the Fc receptor is CD16A. In exemplary instances, the second antigen is an immune checkpoint molecule, e.g., a protein involved in the immune checkpoint pathway. The immune checkpoint pathway and molecules or proteins that function in it are known in the art. See, e.g., Pardoll, Nat Rev Genet 12(4). 252-264 (2012). In exemplary instances, the immune checkpoint molecule is A2AR, B7-H3, B7-H4, BTLA, CTLA4, IDO, KIR, LAG3, NOX2, PD-1, TIM3, VISTA, or SIGLEC7. Optionally, the immune checkpoint molecule is PD-1, LAG3, TIM3, or CTLA4.

Over fifty formats of bispecific antigen-binding proteins are known in the art, some of which are described in Kontermann and Brinkmann, Drug Discovery Today 20(7): 838-847 (2015); Zhang et al., Exp Hematol Oncol 6:12 (2017); Spiess et al., Mol Immunol.; 67(2 Pt A):95-106 (2015). In exemplary aspects, the bispecific antigen-binding protein of the present disclosure is made through chemical engineering, genetic engineering, or quadroma technology.

In exemplary aspects, the bispecific antigen-binding protein is constructed with some or all of the constant domains of an antibody. In exemplary aspects, the bispecific antigen-binding protein of the present disclosure comprises an Fc polypeptide and retains Fc-mediated effector functions. In various instances, the bispecific antigen-binding protein is a bispecific monoclonal antibody formed by, e.g., chemical cross-linking of two monoclonal antibodies (mabs), or by knob and hold technology. In exemplary aspects, the bispecific antigen-binding protein is made through "knobs-into-holes" technology in which H chain heterodimerization is forced by introducing different mutations into the two CH3 domains resulting in asymmetric antibodies. A "knob" mutation is made into one HC and a "hole" mutation is created in the other HC to promote heterodimerization. In exemplary aspects, the bispecific antigen-binding protein is a bispecifc antibody produced by quadroma technology which is based on the somatic fusion of two different hybridoma cells producing monoclonal antibodies with the desired specificity. Zhang et al., 2017, supra. In exemplary aspects, the bispecific antigen-binding protein is a crossMab, ortho-Fab IgG, DVD-Ig, two in one IgG, IgG-scFv and scFv2-Fc (Kontermann and Brinkmann, 2015, supra. In various aspects, the bispecific antigen-binding protein is an Ig-scFv fusion wherein a new antigen-binding moiety is added to a full length IgG resulting in a fusion protein with tetravalency for two distinct antigens, e.g., IgG C-terminal scFv fusion and IgG N-terminal scFv fusion. In exemplary instances, the bispecific antigen-binding protein is a dual-variable-domain-IgG (DVD-IgG), wherein the LC and HC variable regions of an IgG specific for one antigen are fused to the N-terminal LC and HC variable regions of an IgG specific for a second antigen through a linker to form a DVD-IgG. In exemplary aspects, the bispecific antigen-binding protein is a diabody-Fc fusion which involves the replacement of a Fab fragment of an IgG with a bispecific diabody In alternative instances, the bispecific antigen-binding protein of the present disclosure does not comprise an Fc polypeptide. In exemplary aspects, the bispecific antigen-binding protein comprises the variable domains of each parental monoclonal antibody, and linkers are cloned and linked to form a single-chain bispecific antibody. In exemplary aspects, the bispecific antigen-binding protein is a tandem scFvs, diabody format, single-chain diabodies, tandem diabodies (TandAbs), dual-affinity retargeting molecules (DARTs), dock-and-lock (DNL), and nanobodies (Fan et al., J Hematol Oncol. 2015; 8:130). In various aspects, the bispecific antigen-binding protein is a bispecific F(mab$^1$)$_2$, an scFv, a bispecific diabody (BsDb), single-chain bispecific diabody (scBsDb), single-chain bispecific tandem variable domain (scBsTaFv), dock-and-lock trivalent Fab (DNL-(Fab)3), single-domain antibody (sdAb), or a bispecific single-domain antibody (BssdAb). In exemplary aspects, the bispecific antigen-binding protein is a tandem scFv comprising two scFv fragments linked by an extra peptide linker such as glycine-serine repeat motifs. Optionally, the tandem scFv comprises the structure: VL$_A$-linker1-VH$_A$-linker2-VH$_B$-linker3-VL$_B$ (VL and VH derive from the single chain antibody fragment; A and B represent the parental monoclonal antibody A and B). In exemplary aspects, the bispecific antigen-binding protein is a TandAb which contains two pairs of VL and VH domains connected in a single polypeptide chain (Reusch et al., MAbs. 2015; 7(3):584-604). Two polypeptide products dimerize in a head-to-tail fashion, forming homodimers with large molecular weight (~105 kDa) upon expression. In exemplary aspects, the bispecific antigen-binding protein is one produced using crossMab technology which is described in PNAS 108(27): 11187-92 (2011). CrossMabs do not have any chemical linkers or connectors and are produced by a method that enforces correct light chain association in bispecific heterodimeric IgG antibodies. In exemplary aspects, the CrossMab is a bi-(1+1), iii-(2+1) and tetra-(2+2) valent bispecific crossMab, or is a non-Fc tandem antigen-binding fragment (Fab)-based crossMab. In exemplary instances, the crossMab is a crossMab$^{Fab}$, a crossMab$^{VH-VL}$, or a crossMab$^{CH1-CL}$.

In exemplary aspects, the bispecific antigen-binding protein comprises a single-domain antibody, or a nanobody, comprising a single monomeric variable antibody domain. Optionally, the variable domain is based on the heavy chain variable domain. In alternative aspects, the variable domain is based on the light chain variable domain.

In exemplary aspects, the bispecific antigen-binding protein is a bispecific T cell engager or BiTE®. BiTEs are bivalent small molecules comprising only the variable regions of antibodies in the form of scFvs which are connected by flexible peptidic linkers. In exemplary aspects, the bispecific antigen-binding protein comprises an scFV comprising the LC and HC variable regions of the presently disclosed CLDN 18.2 antibodies and the LC and HC variable regions of a second antibody specific for a second antigen. In some embodiments, the BiTE comprises the LC and HC variable region of a second antibody specific for CD3. In some embodiments, the CD3 is CD3E.

In exemplary instances, the bispecific antigen-binding protein is a dual affinity retargeting (DART), which unlike BiTEs®, the covalent linkage between the two chains of DARTs limits the freedom of the antigen-binding sites. Therefore, DARTs are structurally compact and can form stable contacts between target and effector cells. The DART comprises two engineered Fv fragments which have their own VH exchanged with the VH of the other one. The inter-exchanged Fv domains advantageously releases variant fragments from the conformational constraint by the short linking peptide.

In exemplary aspects, the bispecific antigen binding protein is an HSABody comprising two scFvs fused to modified HSA. HSABodies are described in McDonagh et al., Mol Cancer Ther. 2012; 11(3):582-93.

Accordingly, in exemplary aspects, the bispecific antigen-binding protein comprises an antigen binding fragment of any of the presently disclosed CLDN 18.2 antibodies. In exemplary aspects, the antigen binding fragment is a Fab. In exemplary aspects, the bispecific antigen-binding protein comprises an F(ab)$^{2'}$ of any of the presently disclosed CLDN18.2 antibodies. In exemplary aspects, the bispecific antigen-binding protein comprises an scFv comprising the LC and HC variable regions of any of the presently disclosed CLDN18.2 antibodies. In exemplary aspects, the scFv comprises the amino acid sequence of SEQ ID NO: 514 or 515. In various aspects, the antigen binding fragment is based on the heavy chain variable region and in other aspects, the antigen binding fragment is based on the light chain variable region. In exemplary aspects, the antigen binding fragment comprises at least part of both HC variable region and LC variable region. In exemplary aspects, the bispecific antigen-binding protein comprises at least one if not both of the LC or HC variable regions of the presently disclosed CLDN18.2 antibodies and at least one if not both of the LC and HC variable regions of a second antibody specific for a second antigen. In exemplary instances, the bispecific antigen-binding protein comprises an scFV comprising the LC and HC variable regions of the presently disclosed CLDN18.2 antibodies and the LC and HC variable regions of a second antibody specific for a second antigen.

CLDN18 and Epilopes

The antigen-binding proteins of the present disclosure bind to CLDN18.2. In various aspects, the CLDN18.2 is a human CLDN18.2 isoform having the amino acid sequence of:

(SEQ ID NO: 1)
MAVTACQGLGFVVSLIGIAGIIAATCMDQWSTQDLYNNPVTAVFNY

QGLWRSCVRESSGFTECRGYFTLLGLPAMLQAVRALMIVGIVLGAIG

LLVSIFALKCIRIGSMEDSAKANMTLTSGIMFIVSGLCAIAGVSVFAN

MLVTNFWMSTANMYTGMGGMVQTVQTRYTFGAALFVGWVAGGL

TLIGGVMMCIACRGLAPEETNYKAVSYHASGHSVAYKPGGFKASTG

FGSNTKNKKIYDGGARTEDEVQSYPSKHDYV,

In various aspects, the antigen-binding proteins of the present disclosure bind to an epitope within an amino acid sequence of CLDN18.2. In various aspects, CLDN 18.2 is a human CLDN18.2 and the antigen-binding proteins of the present disclosure bind to an epitope within an amino acid sequence of human CLDN 18.2, e.g., SEQ ID NOs: 1. By "epitope" is meant the region of or within CLDN 18.2 which is bound by the antigen-binding protein. In some embodiments, the epitope is a linear epitope. "Linear epitope" refers to the region of or within the CLDN18.2 which is bound by the antigen-binding protein and which region is composed of contiguous amino acids of the amino acid sequence of the CLDN18.2. The amino acids of a linear epitope are adjacent to each other in the primary structure of the CLDN18.2. Accordingly, a linear epitope is a fragment or portion of the amino acid sequence of the antigen, i.e., CLDN 18.2. In other various embodiments, the epitope is a conformational or structural epitope. By "conformational epitope" or "structural epitope" is meant an epitope which is composed of amino acids which are located in close proximity to one another only when the CLDN18.2 is in its properly folded state. Unlike linear epitopes, the amino acids of a conformational or structural epitope are not adjacent to each other in the primary structure (i.e., amino acid sequence) of the CLDN18.2. A conformational or structural epitope is not made of contiguous amino acids of the amino acid sequence of the antigen (CLDN18.2).

In various aspects, the epitope is located within the extracellular domain (ECD) of CLDN18.2, e.g., human CLDN18.2. In various aspects, the antigen binding protein binds to Extracellular Loop 1 (EL1) of the ECD of CLDN18.2 having the amino acid sequence of residues 28 to 80 of SEQ ID NO: 1. In various aspects, the epitope to which the antigen-binding protein binds is within GLWRSCVRESSGFTECRFYFTL (SEQ ID NO: 4), QGLWRSCVRESSGFTECRGYFTLK (SEQ ID NO: 5), DQWSTQDLYNNPVTAVFNYQG LWRSC (SEQ ID NO: 6) or CRGYFTLLFLPAMLQAVR (SEQ ID NO: 7) of CLDN 18.2. In various instances, the antigen-binding protein of the present disclosure binds to EL1, but not to Extracellular Loop 2 (EL2) of CLDN 18.2. In various aspects, the epitope(s) to which the antigen binding proteins of the present disclosure bind to is different from the epitope bound by an anti-CLDN18.2 antibody comprising a light chain variable region comprising the sequence of SEQ ID NO: 58 and a heavy chain variable region comprising the sequence of SEQ ID NO: 59 or comprising a light chain variable region comprising the sequence of SEQ ID NO: 60, and a heavy chain variable sequence encoded by SEQ ID NO: 61, or a light chain variable region comprising the sequence of SEQ ID NO: 62, and a heavy chain variable sequence encoded by SEQ ID NO: 63.

In various aspects, the antigen-binding proteins bind to human CLDN18.2 and a non-human CLDN18.2. In various instances, the non-human CLDN18.2 is a CLDN18.2 of chimpanzee, Rhesus monkey, dog, cow, mouse, rat, zebrafish, or frog. In various instances, the antigen-binding proteins bind to human CLDN 18.2 and mouse CLDN 18.2.

Affinity and Avidity

The antigen-binding proteins provided herein bind to CLDN18.2 in a non-covalent and reversible manner. In various embodiments, the binding strength of the antigen-binding protein to CLDN 18.2 may be described in terms of its affinity, a measure of the strength of interaction between the binding site of the antigen-binding protein and the epitope. In various aspects, the antigen-binding proteins provided herein have high-affinity for CLDN18.2 and thus will bind a greater amount of CLDN18.2 in a shorter period of time than low-affinity antigen-binding proteins. In various aspects, the antigen-binding protein has an equilibrium association constant, KA, which is at least $10^5$ mol$^{-1}$, at least $10^6$ mol$^{-1}$, at least $10^7$ mol$^{-1}$, at least $10^8$ mol$^{-1}$, at least $10^9$ mol$^{-1}$, or at least $10^{10}$ mol$^{-1}$ or at least $10^{10}$ mol$^{-1}$ least $10^{10}$ mol$^{-1}$. As understood by the artisan of ordinary skill, KA can be influenced by factors including pH, temperature and buffer composition.

In various embodiments, the binding strength of the antigen-binding protein to CLDN18.2 may be described in terms of its sensitivity. $K_D$ is the equilibrium dissociation constant, a ratio of $k_{off}/k_{on}$, between the antigen-binding protein and CLDN 18.2. $K_D$ and KA are inversely related. The $K_D$ value relates to the concentration of the antigen-binding protein (the amount of antigen-binding protein needed for a particular experiment) and so the lower the $K_D$ value (lower concentration) the higher the affinity of the antigen-binding protein. In various aspects, the binding strength of the antigen-binding protein to CLDN 18.2 may be described in terms of $K_D$. In various aspects, the $K_D$ of the antigen-binding proteins provided herein is about $10^{-1}$, about $10^{-2}$, about $10^{-3}$, about $10^{-4}$, about $10^{-5}$, about $10^{-6}$, or less. In various aspects, the $K_D$ of the antigen-binding proteins provided herein is micromolar, nanomolar, picomolar or femtomolar. In various aspects, the $K_D$ of the antigen-binding proteins provided herein is within a range of about $10^{-4}$ to $10^{-6}$ or $10^{-7}$ to $10^{-9}$ or $10^{-10}$ to $10^{-12}$ or $10^{-13}$ to $10^{-15}$ or $10^{-9}$ to $10^{-12}$ or $10^{-9}$ to $10^{-15}$. In various aspects, the $K_D$ of the antigen-binding proteins provided herein is within a range of about $1.0 \times 10^{-12}$ M to about $1.0 \times 10^{-8}$ M. In various aspects, the $K_D$ of the antigen-binding proteins is within a range of about $1.0 \times 10^{-11}$ M to about $1.0 \times 10^{-9}$ M.

In various aspects, the affinity of the antigen-binding proteins are measured or ranked using a flow cytometry- or Fluorescence-Activated Cell Sorting (FACS)-based assay. Flow cytometry-based binding assays are known in the art. See, e.g., Cedeno-Arias et al., Sci Pharm 79(3): 569-581 (2011); Rathanaswami et al., Analytical Biochem 373:52-60 (2008); and Geuijen et al., J Immunol Methods 302(1-2): 68-77 (2005). In various aspects, the affinity of the antigen-binding proteins are measured or ranked using a competition assay as described in Trikha et al., Int J Cancer 110: 326-335 (2004) and Tarn et al., Circulation 98(11): 1085-1091 (1998), as well as below. See section titled "*Competition Assays*" below. In Trikh et al., cells that express the antigen were used in a radioassay. The binding of $^{125}$I-labeled antigen-binding protein (e.g., antibody) to the cell surface antigen is measured with the cells in suspension. In various aspects, the relative affinity of a CLDN18.2 antibody is determined via a FACS-based assay in which different concentrations of a CLDN18.2 antibody conjugated to a fluorophore are incubated with cells expressing CLDN18.2 and the fluorescence emitted (which is a direct measure of antibody-antigen binding) is determined. A curve plotting the fluorescence for each dose or concentration is made. The max value is the lowest concentration at which the fluorescence plateaus or reaches a maximum, which is when binding saturation occurs. Half of the max value is considered an EC50 or an IC50 and the antibody with the lowest EC50/IC50 is considered as having the highest affinity relative to other antibodies tested in the same manner. Such an assay is described herein at Example 5.

In various aspects, the $IC_{50}$ value, as determined in a competitive binding inhibition assay, approximates the Kr) of the antigen-binding protein. In various instances, as discussed below, the competition assay is a FACS-based assay carried out with a reference antibody, fluorophore-conjugated secondary antibody, and cells which express CLDN 18.2. In various aspects, the cells are genetically-engineered to overexpress CLDN18.2. In some aspects, the cells are HEK293T cells transduced with a viral vector to express CLDN18.2. In alternative aspects, the cells endogenously express CLDN18.2. Before the FACS-based assay is carried out, in some aspects, the cells which endogenously express CLDN18.2 are pre-determined as low CLDN18.2-expressing cells or high CLDN 18.2-expressing cells. In some aspects, the cells are cancer or tumor cells. In various aspects, the cells are cells from a cell line, e.g., an ovarian cell line, endometrial cell line, bladder cell line, lung cell line, gastrointestinal (GI) cell line, liver cell line, lung cell line, and the like. In various aspects, the cells which endogenously express CLDN18.2 are selected from the group consisting of HUPT4 pancreas cells, UMUC-4 bladder cells, MKN7, KATO III, SNU601, NUGC4, NUGC3, SNU620 SNU520 and OE19 upper GI cells. In various aspects, the antigen-binding protein inhibits the binding interaction between human CLDN18.2 expressed by the cells and the reference antibody, which reference antibody is known to bind to CLDN 18.2 but is not an antigen-binding protein of the present disclosure. In various instances, the antigen-binding proteins of the present disclosure compete with the reference antibody for binding to human CLDN18.2 and thereby reduce the amount of human CLDN 18.2 bound to the reference antibody as determined by an in vitro competitive binding assay. In various aspects, the antigen-binding proteins of the present disclosure inhibit the binding interaction between human CLDN18.2 and the reference antibody and the inhibition is characterized by an $IC_{50}$. In various aspects, the antigen-binding proteins exhibit an $IC_{50}$ of less than about 2500 nM for inhibiting the binding interaction between human CLDN18.2 and the reference antibody. In various aspects, the antigen-binding proteins exhibit an $IC_{50}$ of less than about 2000 nM, less than about 1500 nM, less than about 1000 nM, less than about 900 nm, less than about 800 nm, less than about 700 nm, less than about 600 nm, less than about 500 nm, less than about 400 nm, less than about 300 nm, less than about 200 nm, or less than about 100 nm. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM. In various instances, the antigen binding proteins of the present disclosure compete against a reference antibody known to bind to CLDN18.2 (which reference antibody is different from any of the antigen-binding proteins of the present disclosure) for binding to CLDN18.2. See further description under Competition assays.

Avidity gives a measure of the overall strength of an antibody-antigen complex. It is dependent on three major parameters: affinity of the antigen-binding protein for the epitope, valency of both the antigen-binding protein and CLDN 18.2, and structural arrangement of the parts that interact. The greater an antigen-binding protein's valency (number of antigen binding sites), the greater the amount of antigen (CLDN18.2) it can bind. In various aspects, the antigen-binding proteins have a strong avidity for CLDN18.2. In various aspects, the antigen-binding proteins are multivalent. In various aspects, the antigen-binding proteins are bivalent. In various instances, the antigen antigen-binding proteins are monovalent.

Cross-Reactivity

In various embodiments, the antigen-binding proteins of the present disclosure bind to CLDN 18.2 and do not bind to any other member of the CLDN family, e.g., do not cross-react with any other member of the CLDN family. In various instances, the antigen-binding proteins of the present disclosure are CLDN18.2-specific. In various embodiments, the antigen-binding proteins of the present disclosure have a selectivity for CLDN18.2 which is at least 10-fold, 5-fold, 4-fold, 3-fold, 2-fold greater than the selectivity of the antigen-binding protein for CLDN18.1, or another CLDN protein. In various embodiments, the antigen-binding proteins of the present disclosure have a selectivity for CLDN 18.2 which is at least 10-fold, 5-fold, 4-fold, 3-fold, 2-fold greater than the selectivity of the antigen-binding protein for each of CLDN 18.1 or any other CLDN protein. Selectivity may be based on the $K_D$ exhibited by the antigen binding protein for CLDN 18.2, or a CLDN family member, wherein the $K_D$ may be determined by techniques known in the art, e.g., surface plasmon resonance, FACS-based affinity assays.

Competition Assays

In various embodiments, the antigen-binding protein inhibits a binding interaction between human CLDN18.2 and a reference antibody, which reference antibody is known to bind to CLDN18.2 but is not an antigen-binding protein of the present disclosure. In various instances, the antigen-binding proteins of the present disclosure compete with the reference antibody for binding to human CLDN18.2 and thereby reduce the amount of human CLDN18.2 bound to the reference antibody as determined by an in vitro competitive binding assay. In various embodiments, the reference antibody binds to an epitope within the amino acid sequence of the extracellular domain of human CLDN18.2, optionally, within EL2 or EL1. In various aspects, the reference antibody comprises a light chain variable sequence encoded by SEQ ID NO: 58, and a heavy chain variable sequence encoded by SEQ ID NO: 59 or comprises a light chain variable region comprising the sequence of SEQ ID NO: 60, and a heavy chain variable sequence encoded by SEQ ID NO: 61, or a light chain variable region comprising the sequence of SEQ ID NO: 62, and a heavy chain variable sequence encoded by SEQ ID NO: 63. In various aspects, the antigen-binding proteins of the present disclosure inhibit the binding interaction between human CLDN 18.2 and the reference antibody and the inhibition is characterized by an $IC_{50}$. In various aspects, the antigen-binding proteins exhibit an IC50 of less than about 2500 nM for inhibiting the binding interaction between human CLDN18.2 and the reference antibody. In various aspects, the antigen-binding proteins exhibit an $IC_{50}$ of less than about 2000 nM, less than about 1500 nM, less than about 1000 nM, less than about 900 nm, less than about 800 nm, less than about 700 nm, less than about 600 nm, less than about 500 nm, less than about 400 nm, less than about 300 nm, less than about 200 nm, or less than about 100 nm. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM.

In various instances, the antigen-binding proteins of the present disclosure compete with the reference antibody for binding to human CLDN18.2 and thereby reduce the amount of human CLDN18.2 bound to the reference antibody as determined by an in vitro competitive binding assay. In various aspects, the in vitro competitive binding assay is a FACS-based assay in which the fluorescence of a fluorophore-conjugated secondary antibody which binds to the Fc of the reference antibody is measured in the absence or presence of a particular amount of the antigen-binding protein of the present disclosure. Such a FACS-based assay is described herein in the EXAMPLES. In various aspects, the FACS-based assay is carried out with the reference antibody, fluorphore-conjugated secondary antibody and cells which express CLDN18.2. In various aspects, the cells are genetically-engineered to overexpress CLDN18.2. In some aspects, the cells are HEK293T cells transduced with a viral vector to express CLDN18.2. In alternative aspects, the cells endogenously express CLDN18.2. Before the FACS-based assay is carried out, in some aspects, the cells which endogenously express CLDN18.2 are pre-determined as low CLDN18.2-expressing cells or high CLDN18.2-expressing cells. In some aspects, the cells are cancer or tumor cells. In various aspects, the cells are cells from a cell line, e.g., an ovarian cell line, endometrial cell line, bladder cell line, lung cell line, gastrointestinal (GI) cell line, liver cell line, lung cell line, and the like. In various aspects, the cells which endogenously express CLDN18.2 are selected from the group consisting of HUPT4 pancreas cells, UMUC-4 bladder cells, MKN7, KATO III, SNU601, NUGC4, NUGC3, SNU620 SNU520 and OE19 upper GI cells. In various instances, the antigen binding proteins of the present disclosure bind to CLDN 18.2 endogenously expressed by one or more of the cells that endogenously express CLDN18.2 with high affinity. In various aspects, the antigen binding proteins exhibit an $IC_{50}$ of less than about 3000 nM as determined in a FACS-based competitive binding inhibition assay using one or more of HUPT4, UMUC-4, MKN7, KATO III, SNU601, NUGC4, NUGC3, SNU620 SNU520 and OE19 cells described herein. In various aspects, the antigen binding proteins exhibit an $IC_{50}$ of less than about 2500 nM, less than about 2000 nM, less than about 1750 nM, less than about 1500 nM, less than about 1250 nM, less than about 1000 nM, less than about 750 nM, or less than about 500 nM, as determined in a FACS-based competitive binding inhibition assay using one or more of HUPT4, UMUC-4, MKN7, KATO III, SNU601, NUGC4, NUGC3, SNU620 SNU520 and OE19 cells. In various aspects, the antigen binding proteins exhibit an $IC_{50}$ of less than about 400 nM, less than about 300 nM, less than about 200 nM, less than about 100 nM, less than about 75 nM, less than about 50 nM, less than about 25 nM, or less than about 10 nM, as determined in a FACS-based competitive binding inhibition assay using one or more of HUPT4, UMUC-4, MKN7, KATO Iii, SNU601, NUGC4, NUGC3, SNU620 SNU520 and OE19 cells.

Other binding assays, e.g., competitive binding assays or competition assays, which test the ability of an antibody to compete with a second antibody for binding to an antigen, or to an epitope thereof, are known in the art. See, e.g., Trikha et al., Int J Cancer 110: 326-335 (2004); Tam et al., Circulation 98(11): 1085-1091 (1998). U.S. Patent Application Publication No. US20140178905, Chand et al., Biologicals 46: 168-171 (2017); Liu et al., Anal Biochem 525: 89-91 (2017); and Goolia et al., J Vet Diagn Invest 29(2): 250-253 (2017). Also, other methods of comparing two antibodies are known in the art, and include, for example, surface plasmon resonance (SPR). SPR can be used to determine the binding constants of the antibody and second antibody and the two binding constants can be compared.

Methods of Antibody Production and Related Methods

Suitable methods of making antigen-binding proteins (e.g., antibodies, antigen-binding antibody fragments, and antibody protein products) are known in the art. For instance, standard hybridoma methods for producing antibodies are described in, e.g., Harlow and Lane (eds.), Antibodies: A Laboratory Manual, CSH Press (1988), and CA. Janeway et al. (eds.), Immunobiology, 5$^{th}$ Ed., Garland Publishing, New York, N.Y. (2001)). A various method of preparing CLDN 18.2 monoclonal antibodies or the present disclosure is provided herein in the EXAMPLES.

Depending on the host species, various adjuvants can be used to increase the immunological response leading to greater antibody production by the host. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Other methods of antibody production are summarized in Table 1.

TABLE 1

| Technique | Various references |
| --- | --- |
| EBV-hybridoma methods and Bacteriophage vector expression systems | Haskard and Archer, J. Immunol. Methods, 74(2), 361-67 (1984), Roder et al. Methods Enzymol., 121, 140-67 (1986), and Huse et al., Science, 246, 1275-81 (1989)). |
| methods of producing antibodies in non-human animals | U.S. Pat. Nos. 5,545,806, 5,569,825, and 5,714,352, and U.S. Patent Application Publication No. 2002/0197266 |
| inducing in vivo production in the lymphocyte population or by screening recombinant immunoglobulin libraries or panels of highly specific binding reagents | Orlandi et al (Proc Natl Acad Sci 86: 3833-3837; 1989), and Winter G and Milstein C (Nature 349: 293-299, 1991). |
| methods of producing recombinant proteins | Protein production and purification" Nat Methods 5(2): 135-146 (2008). |
| Phage display | Janeway et al., supra. Huse et al., supra, and U.S. Pat. No. 6,265,150). Related methods also are described in U.S. Pat. No. 5,403,484; U.S. Pat. No. 5,571,698; U.S. Pat. No. 5,837,500; U.S. Pat. No. 5,702,892. The techniques described in |

TABLE 1-continued

| Technique | Various references |
|---|---|
| | U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; and U.S. Pat. No. 6,225,447 |
| Antibodies can be produced by transgenic mice | U.S. Pat. Nos. 5,545,806 and 5,569,825, and Janeway et al., supra. |

Methods of testing antibodies for the ability to bind to the epitope of CLDN18.2 regardless of how the antibodies are produced are known in the art and include any antibody-antigen binding assay, such as, for example, radioimmunoassay (RIA), MASA, Western blot, immunoprecipitation, SPR, and competitive inhibition assays (see, e.g., Janeway et al., infra, and U.S. Patent Application Publication No. 2002/0197266, and the above section relating to competition assays).

Sequences/Structure

Provided herein are antigen-binding proteins comprising (a) a heavy chain (HC) complementarity-determining region (CDR) 1 amino acid sequence set forth in Table A or a sequence selected from the group consisting of: SEQ ID NOs: 64, 88, 69, 89, 72, 75, 91, 94, 95, 97, 99, 101, 103, 106, 109; or a variant sequence thereof which differs by only one or two amino acids or which has at least or about 70% (e.g., at least about 80%, at least about 85%, at least about 90%, at least about 95%) sequence identity; (b) an HC CDR2 amino acid sequence set forth in Table A or a sequence selected from the group consisting of: SEQ ID NOs: 65, 67, 70, 90, 73, 76, 92, 73, 96, 98, 100, 102, 104, 107, 110; or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A or a sequence selected from the group consisting of: SEQ ID NOs: 66, 68, 71, 77, 74, 77, 93, 74, 105, 108, 111; or a variant sequence thereof which differs by only one or two amino acids or which has at least or about 70% (e.g., at least about 80%, at least about 85%, at least about 90%, at least about 95%) sequence identity; (d) a light chain (LC) CDR1 amino acid sequence set forth in Table A or a sequence selected from the group consisting of: SEQ ID NOs: 78, 81, 82, 86, 114, 120, 123, 126; or a variant sequence thereof which differs by only one or two amino acids or which has at least or about 70% (e.g., at least about 80%, at least about 85%, at least about 90%, at least about 95%) sequence identity; (e) an LC CDR2 amino acid sequence set forth in Table A or a sequence selected from the group consisting of: SEQ ID NOs: 79, 112, 79, 84, 116, 118, 119, 129, 121, 124, 127; or a variant sequence thereof which differs by only one or two amino acids or which has at least or about 70% (e.g., at least about 80%, at least about 85%, at least about 90%, at least about 95%) sequence identity; (f) an LC CDR3 amino acid sequence set forth in Table A or a sequence selected from the group consisting of: SEQ ID NOs: 80, 83, 113, 85, 87, 115, 117, 122, 125, 128; or a variant sequence thereof which differs by only one or two amino acids or which has at least or about 70% (e.g., at least about 80%, at least about 85%, at least about 90%, at least about 95%) sequence identity; or (g) a combination of any two or more of (a)-(f).

TABLE A

| | LC CDR1 | LC CDR2 | LC CDR3 | HC CDR1 | HC CDR2 | HC CDR3 |
|---|---|---|---|---|---|---|
| Ab 307 | 78 | 79 | 80 | 64 | 65 | 66 |
| Ab 369 | 81 | 112 | 80 | 88 | 65 | 66 |
| Ab 376 | 81 | 79 | 80 | 64 | 67 | 68 |
| Ab 358 | 82 | 79 | 83 | 39 | 70 | 71 |
| Ab 384 | 81 | 79 | 113 | 89 | 90 | 77 |
| Ab 360 | 81 | 84 | 85 | 72 | 73 | 74 |
| Ab 432 | 86 | 79 | 87 | 75 | 76 | 77 |
| Ab 400 | 114 | 79 | 115 | 91 | 92 | 93 |
| Ab 331 | 81 | 116 | 117 | 94 | 73 | 74 |
| Ab 347 | 81 | 118 | 117 | 95 | 96 | 74 |
| Ab 339 | 81 | 119 | 117 | 97 | 98 | 74 |
| Ab 301 | 81 | 118 | 85 | 99 | 100 | 74 |
| Ab 392 | 81 | 129 | 117 | 101 | 102 | 74 |
| Ab 416 | 120 | 121 | 122 | 103 | 104 | 105 |
| Ab 409 | 123 | 124 | 125 | 106 | 107 | 108 |
| Ab 424 | 126 | 127 | 128 | 109 | 110 | 111 |

In various aspects, the antigen-binding protein comprises a LC CDR1 amino acid sequence, a LC CDR2 amino acid sequence, and a LC CDR3 amino acid sequence set forth in Table A and at least 1 or 2 of the HC CDR amino acid sequences set forth in Table A. In various aspects, the antigen-binding protein comprises a HC CDR1 amino acid sequence, a HC CDR2 amino acid sequence, and a HC CDR3 amino acid sequence set forth in Table A and at least 1 or 2 of the LC CDR amino acid sequences set forth in Table A.

In various embodiments, the antigen-binding protein comprises at least 3, 4, or 5 of the amino acid sequences designated by the SEQ ID NOs: in a single row of Table A. In various embodiments, the antigen-binding protein comprises each of the LC CDR amino acid sequences designated by the SEQ ID NOs: of a single row of Table A and at least 1 or 2 of the HC CDR amino acid sequences designated by the SEQ ID NOs: in of a single row of Table A. In various embodiments, the antigen-binding protein comprises each of the HC CDR amino acid sequences designated by the SEQ ID NOs: of a single row of Table A and at least 1 or 2 of the LC CDR amino acid sequences designated by the SEQ ID NOs: of a single row of Table A. In various embodiments, the antigen-binding protein comprises all 6 of the CDR amino acid sequences designated by the SEQ ID NOs: of a single row of Table A. In various embodiments, the antigen-binding protein comprises six CDR amino acid sequences selected from the group consisting of: (a) SEQ ID NOs: 78, 79, 80, 64, 65, 66; (b) SEQ ID NOs: 81, 112, 80, 88, 65, 66; (c) SEQ ID NOs: 81, 79, 80, 64, 67, 68; (d) SEQ ID NOs: 82, 79, 83, 39, 70, 71; (e) SEQ ID NOs: 81, 79, 113, 89, 90, 77; (f) SEQ ID NOs: 81, 84, 85, 72, 73, 74; (g) SEQ ID NOs: 86, 79, 87, 75, 76, 77; (h) SEQ ID NOs: 114, 79, 115, 91, 92, 93; (i) SEQ ID NOs: 81, 116, 117, 94, 73, 74; (j) SEQ ID NOs: 81, 118, 117, 95, 96, 74; (k) SEQ ID NOs: 81, 119, 117, 97, 98, 74; (l) SEQ ID NOs: 81, 118, 85, 99, 100, 74;

(m) SEQ ID NOs: 81, 129, 117, 101, 102, 74; (n) SEQ ID NOs: 120, 121, 122, 103, 104, 105; (o) SEQ ID NOs: 123, 124, 125, 106, 107, 108; and (p) SEQ ID NOs: 126, 127, 128, 109, 110, 111.

Also contemplated are HCDR and/or LCDR sequences disclosed herein that comprise an amino acid sequence that contains one or more amino acid changes (e.g., substitution, insertion or deletion) compared to any HCDR or LCDR amino acid sequence identified in Table A. Preferable substitutions include a substitution to an amino acid at the corresponding position within another HCDR1, HCDR2, HCDR3 or LCDR1, LCDR2 or LCDR3 of Table A. Alternatively, the HCDR1, HCDR2, HCDR3 and/or LCDR1, LCDR2 or LCDR3 sequence may comprise a consensus amino acid sequence of the HCDR1, HCDR2, HCDR3 or LCDR1, LCDR2 or LCDR3 described herein.

In various instances, the amino acid sequences of Table A are separated by at least one or more (e.g., at least 2, 3, 4, 5, 6, 7, 8, 9, 10, or more) intervening amino acid(s). In various instances, there are about 10 to about 20 amino acids between the sequences of the LC CDR1 and the LC CDR2 and about 25 to about 40 amino acids between the sequences of the LC CDR2 and the LC CDR3. In various instances, there are about 14 to about 16 amino acids between the sequences of the LC CDR1 and the LC CDR2 and about 30 to about 35 amino acids between the sequences of LC CDR2 and the LC CDR3. In various instances, there are about 10 to about 20 amino acids between the sequences of the HC CDR1 and HC CDR2 and about 25 to about 40 amino acids between the sequences of the HC CDR2 and the HC CDR3. In various instances, there are about 14 to about 16 amino acids between the sequences of the HC CDR1 and HC CDR2 and about 30 to about 35 amino acids between the sequences of the HC CDR2 and HC CDR3.

In various embodiments, the antigen-binding protein comprises (a) a heavy chain variable region amino acid sequence set forth in in Table B or a sequence selected from the group consisting of SEQ ID NOs: 10, 12, 14, 16, 18, 20, 22, 24, 26, 28, 30, 2, 34, 36, 38 and 40, or a variant sequence thereof which differs by only one or two amino acids or which has at least or about 70% (e.g., at least about 80%, at least about 85%, at least about 90%, at least about 95%) sequence identity; or (b) a light chain variable region amino acid sequence set forth in Table B or a sequence selected from the group consisting of: SEQ ID NOs: 11, 13, 15, 17, 19, 21, 23, 25, 27, 29, 31, 33, 35, 37, 39 and 41, or a variant sequence thereof which differs by only one or two amino acids or which has at least or about 70% (e.g., at least about 80%, at least about 85%, at least about 90%, at least about 95%) sequence identity; or (c) both (a) and (b).

TABLE B

|  | Heavy Chain Variable Region | Light Chain Variable Region |
|---|---|---|
| Ab 307 | 10 | 11 |
| Ab 369 | 12 | 13 |
| Ab 376 | 14 | 15 |
| Ab 358 | 16 | 17 |
| Ab 384 | 18 | 19 |
| Ab 360 | 20 | 21 |
| Ab 432 | 22 | 23 |
| Ab 400 | 24 | 25 |
| Ab 331 | 26 | 27 |
| Ab 347 | 28 | 29 |
| Ab 339 | 30 | 31 |

TABLE B-continued

|  | Heavy Chain Variable Region | Light Chain Variable Region |
|---|---|---|
| Ab 301 | 32 | 33 |
| Ab 392 | 34 | 35 |
| Ab 416 | 36 | 37 |
| Ab 409 | 48 | 39 |
| Ab 424 | 40 | 41 |

In various embodiments, the antigen-binding protein comprises a pair of amino acid sequences selected from the group consisting of: (a) SEQ ID NOs: 10 and 11; (b) SEQ ID NOs: 12 and 13; (c) SEQ ID NOs: 14 and 15; (d) SEQ ID NOs: 16 and 17; (e) SEQ ID NOs: 18 and 19; (f) SEQ ID NOs: 20 and 21; (g) SEQ ID NOs: 22 and 23; (h) SEQ ID NOs: 24 and 25; (i) SEQ ID NOs: 26 and 27; (j) SEQ ID NOs: 28 and 29; (k) SEQ ID NOs: 30 and 31; (l) SEQ ID NOs: 32 and 33; (m) SEQ ID NOs: 34 and 35; (n) SEQ ID NOs: 36 and 37; (o) SEQ ID NOs: 38 and 39; (p) SEQ ID NOs: 40 and 41.

Also contemplated are VH and/or VL sequences disclosed herein that comprise an amino acid sequence that contains one or more amino acid changes (e.g., substitution, insertion or deletion) compared to any VH or VL amino acid sequence identified in Table B. Preferable substitutions include a substitution to an amino acid at the corresponding position within another VH or VL of Table B. Alternatively, the VH and/or VL sequence may comprise a consensus amino acid sequence of the VH or VL described herein. For example, a CDR or VH or VL may be substituted with an amino acid identified as different from the parent sequence set out in FIG. 13. Amino acid changes in the humanized sequences are highlighted. Contemplated herein is a consensus sequence of the humanized VH or VL sequences described herein.

In various aspects, the antigen-binding protein does not comprise a pair of amino acid sequences encoded by the sequences of SEQ ID NOs: 58 and 59. In various aspects, the antigen-binding protein does not comprise a pair of amino acid sequences of SEQ ID NOs: 60 and 61. In various aspects, the antigen-binding protein does not comprise a pair of amino acid sequences of SEQ ID NOs: 62 and 63.

In various aspects, the antigen-binding protein comprises an amino acid sequence which is similar to an above-referenced amino acid sequence, yet the antigen-binding protein substantially retains its biological function, e.g., its ability to bind to human CLDN18.2, reduce tumor growth, treat cancer.

In various aspects, the antigen-binding protein comprises an amino acid sequence which differs by only 1, 2, 3, 4, 5, 6, or more amino acids, relative to the above-referenced amino acid sequence(s). In various aspects, the antigen-binding protein comprises a variant sequence of the referenced sequence, which variant sequence differs by only one or two amino acids, relative to the referenced sequence. In various aspects, the antigen-binding protein comprising one or more amino acid substitutions that occur outside of the CDRs, e.g., the one or more amino acid substitutions occur within the framework region(s) of the heavy or light chain. In various aspects, the antigen-binding protein comprising one or more amino acid substitutions yet the antigen-binding protein retains the amino acid sequences of the six CDRs. In various aspects, the antigen-binding protein comprises an amino acid sequence having only 1, 2, 3, 4, 5, 6, or more conservative amino acid substitutions, relative to the above-referenced amino acid sequence(s). As used herein, the term "conservative amino acid substitution" refers to the substitution of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues: Ala, Ser, Thr, Pro, Gly;
II. Polar, negatively charged residues and their amides and esters: Asp, Asn, Glu, Gln, cysteic acid and homocysteic acid;
III. Polar, positively charged residues: His, Arg, Lys; Ornithine (Orn)
IV. Large, aliphatic, nonpolar residues: Met, Leu, Ile, Val, Cys, Norleucine (Nle), homocysteine
V. Large, aromatic residues: Phe, Tyr, Trp, acetyl phenylalanine In various aspects, the conservative amino acid substitution is an exchange within one of the following groups of amino acids:

I. aliphatic amino acids: Gly, Ala, Val, Leu, Ile
II. non-aromatic amino acids comprising a side chain hydroxyl: Sere Thr
III. amino acids comprising a sulfur side chain: Cys, Met
IV: amino acids comprising a side chain aromatic ring: Phe, Tyr, Trp
V: acidic amino acid: Glu; Asp
VI: basic amino acid: Arg; Lys
VII: amino acid comprising a side chain amide: Gln, Asn
VIII: amino acid comprising a side chain imidazole: His, alpha-dimethyl imidazole acetic acid (DMIA)
IX: imino acid: Pro, 4-hydroxy-Pro, 4-amino-Pro In various aspects, the antigen-binding protein comprises an amino acid sequence which has greater than or about 30%, greater than or about 50%, or greater than or about 70% sequence identity to the above-referenced amino acid sequence. In various aspects, the antigen-binding protein comprises an amino acid sequence which has at least 30%, at least 40%, at least 50%, at least 60%, at least 70%, at least 80%, at least 85%, at least 90% or has greater than 90% sequence identity to the above-referenced amino acid sequence. In various aspects, the antigen-binding protein comprises an amino acid sequence that has at least 70%, at least 80%, at least 85%, at least 90% or has greater than 90% sequence identity along the full-length of the above-referenced amino acid sequence. In various aspects, the antigen-binding protein comprises an amino acid sequence having at least 95%, 96%, 97%, 98% or 99% sequence identity along the full-length of the above-referenced amino acid sequence.

In various aspects, the antigen-binding protein comprises a variant sequence of the referenced sequence, which variant sequence has at least or about 70% sequence identity, relative to the above-referenced sequence. In various aspects, the antigen-binding protein comprises a variant sequence of the referenced sequence, which variant sequence has at least or about 80% sequence identity, relative to the above-referenced sequence. In various aspects, the antigen-binding protein comprises a variant sequence of the referenced sequence, which variant sequence has at least or about 90° c. sequence identity, relative to the above-referenced sequence. In various aspects, the antigen-binding protein comprises a variant sequence of the referenced sequence, which variant sequence has at least or about 95% sequence identity, relative to the above-referenced sequence.

In various embodiments, the antigen-binding protein comprises one, two, three, four, or five sequences of the SEQ ID NOs. in a single row of Table A and at least one variant sequence having at least or about 70% (e.g., at least about 80°ro, at least about 85°ro, at least about 90%, at least about 95%) sequence identity to any of SEQ ID NOs: 64-129. In various embodiments, the antigen-binding protein comprises one, two, three, four, or five sequences of a set of sequences selected from: (a) SEQ ID NOs: 78, 79, 80, 64, 65, 66; (b) SEQ ID NOs: 81, 112, 80, 88, 65, 66; (c) SEQ ID NOs: 81, 79, 80, 64, 67, 68; (d) SEQ ID NOs: 82, 79, 83, 39, 70, 71; (e) SEQ ID NOs: 81, 79, 113, 89, 90, 77; (1) SEQ ID NOs: 81, 84, 85, 72, 73, 74; (g) SEQ IT) NOs: 86, 79, 87, 75, 76, 77; (h) SEQ ID NOs: 114, 79, 115, 91, 92, 93; (i) SEQ ID NOs: 81, 116, 117, 94, 73, 74; (j) SEQ ID NOs: 81, 118, 117, 95, 96, 74, (k) SEQ ID NOs: 81, 119, 117, 97, 98, 74; (1) SEQ ID NOs: 81, 118, 85, 99, 100, 74; (m) SEQ ID NOs: 81, 129, 117, 101, 102, 74; (n) SEQ ID NOs: 120, 121, 122, 103, 104, 105; (o) SEQ ID NOs: 123, 124, 125, 106, 107, 108; and (p) SEQ ID NOs: 126, 127, 128, 109, 110, 111, wherein the antigen-binding protein further comprises at least one variant sequence having at least or about 70% (e.g., at least about 80%, at least about 85%, at least about 90%, at least about 95%) sequence identity to at least one of the sequences of the set.

In various embodiments, the antigen-binding protein comprises a pair of variant sequences having at least or about 70% (e.g., at least about 80°ro, at least about 85°ro, at least about 90%, at least about 95%) sequence identity to any of SEQ ID NOs: 10-41. In various instances, the antigen binding protein comprises a pair of variant sequences which have at least or about 70% (e.g., at least about 80%, at least about 85%, at least about 90%, at least about 95%) sequence identity to (a) SEQ ID NOs: 10 and 11; (b) SEQ ID NOs: 12 and 13; (c) SEQ ID NOs: 14 and 15; (d) SEQ ID NOs: 16 and 17; (e) SEQ ID NOs: 18 and 19; (f) SEQ ID NOs: 20 and 21; (g) SEQ ID NOs: 22 and 23; (h) SEQ ID NOs: 24 and 25; (i) SEQ ID NOs: 26 and 27; (j) SEQ ID NOs. 28 and 29, (k) SEQ ID NOs: 30 and 31, (1) SEQ ID NOs: 32 and 33; (m) SEQ ID NOs: 34 and 35; (n) SEQ ID NOs: 36 and 37; (o) SEQ ID NOs: 38 and 39; and (p) SEQ ID NOs: 40 and 41. In various embodiments, the antigen-binding protein comprises a pair of sequences: one sequence of Table B and another sequence which is a variant sequence having at least or about 70% (e.g., at least about 80%, at least about 85%, at least about 90%, at least about 95%) sequence identity to any of SEQ ID NOs: 10-41. In various embodiments, the antigen-binding protein comprises a pair of sequences: one sequence selected from (a) SEQ ID NOs: 10 and 11; (b) SEQ ID NOs: 12 and 13; (c) SEQ ID NOs: 14 and 15; (d) SEQ ID NOs: 16 and 17; (e) SEQ ID NOs: 18 and 19; (f) SEQ ID NOs: 20 and 21; (g) SEQ ID NOs: 22 and 23; (h) SEQ ID NOs: 24 and 25; (i) SEQ ID NOs: 26 and 27; (j) SEQ ID NOs: 28 and 29; (k) SEQ ID NOs: 30 and 31; (1) SEQ ID NOs: 32 and 33; (m) SEQ ID NOs: 34 and 35; (n) SEQ ID NOs: 36 and 37; (o) SEQ ID NOs: 38 and 39; (p) SEQ ID NOs: 40 and 41, and another sequence which is a variant sequence having at least or about 70% (e.g., at least about 80%, at least about 85%, at least about 90%, at least about 95%) sequence identity to a sequence of (a)-(p). For instance, in various aspects, the antigen-binding protein comprises a sequence of SEQ ID NO: 10 and the antigen-binding protein further comprises a variant sequence having at least or about 70% (e.g., at least about 80%, at least about 85%, at least about 90%, at least about 95%) sequence identity to SEQ ID NO 11.

In various instances, the antigen-binding protein comprises an amino acid sequence of an above-referenced amino acid sequence with one or more amino acid substitutions to reduce or eliminate reactive amino acids to decrease or prevent unwanted side chain reactions. For instance, the antigen-binding protein comprises an amino acid sequence of an above-referenced amino acid sequence with one or more (i) Trp residues substituted with His, Tyr, or Phe; (ii) Asn residues substituted with Gln, Ser, Ala, or Asp; (iii) Asp residues occurring immediately before a Pro residue substituted with Ala, Ser, or Glu, (iv) Asn residues substituted with Gln, Ser, or Ala; and/or (v) Cys residues substituted with Tyr, Ser, or Ala. In various aspects, the antigen-binding protein comprises an amino acid sequence of an above-referenced amino acid sequence with an amino acid substitution predicted to have greater binding affinity, greater stability, or other positive attribute, based on SHM events or based on statistical analyses of a multitude of other similar antibody sequences.

Humanized Antibodies

In various aspects, the antigen-binding protein is a humanized version of an antigen binding protein described in Table A or Table B.

In various aspects, the antigen-binding protein is a humanized version of an antibody as set forth in Table B with one or more (e.g, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) amino acid substitutions in the heavy chain or light chain variable region at a position shown in FIG. 13, or a consensus sequence thereof.

In various embodiments, the antigen-binding protein comprises (a) a heavy chain variable region amino acid sequence set forth in in Table C or a sequence selected from the group consisting of: 42, 46, 49, 52, 55, 56, 57, and 131, or a variant sequence thereof which differs by only one or two amino acids or which has at least or about 70%, or about 80%, or about 85%, or about 90%, or about 95% sequence identity; or (b) a light chain variable region amino acid sequence set forth in Table C or a sequence selected from the group consisting of: 43-45, 47-48, 50-51, 53-54, 149, and 150, or a variant sequence thereof which differs by only one or two amino acids or which has at least or about 70%, or about 80%, or about 85%, or about 90%, or about 95% sequence identity; or (c) both (a) and (b).

TABLE C

| | Humanized Heavy Chain Variable Region SEQ ID NO. | Humanized Light Chain Variable Region SEQ ID NO. |
|---|---|---|
| HuAB307 | 42 | 43, 44, 45 |
| HuAB376 | 46 | 47, 48 |
| HuAB358 | 131 | 149, 150 |
| HuAB360 | 52, 55, 56 | 53, 54, |
| HuAB432 | 49, 57 | 50, 51 |

In various embodiments, the humanized antigen-binding protein comprises a pair of amino acid sequences as shown in Table D.

TABLE D

| Humanized AB | HC SEQ ID NO. | LG SEQ ID NO. |
|---|---|---|
| HuAb307-1 | 42 | 43 |
| HuAb307-2 | 42 | 44 |

TABLE D-continued

| Humanized AB | HC SEQ ID NO. | LG SEQ ID NO. |
|---|---|---|
| HuAb307-3 | 42 | 45 |
| HuAb376-1 | 46 | 47 |
| HuAb376-2 | 46 | 48 |
| HuAb358-1 | 131 | 149 |
| HuAb358-2 | 131 | 150 |
| HuAb360-1 | 52 | 53 |
| HuAb360-2 | 52 | 54 |
| HuAb360-3 | 55 | 53 |
| HuAb360-4 | 55 | 54 |
| HuAb360-5 | 56 | 53 |
| HuAb360-6 | 56 | 54 |
| HuAb432-1 | 57 | 50 |
| HuAb432-2 | 57 | 51 |
| HuAb432-3 | 49 | 50 |
| HuAb432-4 | 49 | 51 |

In various embodiments, the antigen-binding protein comprises a pair of variant sequences, each having at least or about 70% (e.g., at least about 80%, at least about 85%, at least about 90%, at least about 95%) sequence identity to a SEQ ID NO listed in Table C. In various embodiments, the antigen-binding protein comprises a pair of sequences: one sequence selected from a SEQ ID NO: listed in Table C and another sequence which is a variant sequence having at least or about 70% (e.g., at least about 80%, at least about 85%, at least about 90%, at least about 95%) sequence identity to a sequence having a SEQ ID NO: listed in Table D a sequence having a SEQ ID NO: listed in Table C.

In various embodiments, the antigen-binding protein comprises a pair of sequences: one sequence selected from a SEQ ID NO: listed in Table D, and another sequence which is a variant sequence having at least or about 70% (e.g., at least about 80%, at least about 85%, at least about 90%, at least about 95%) sequence identity to a sequence having a SEQ ID NO: listed in Table D. For instance, in various aspects, the antigen-binding protein comprises a sequences of SEQ ID NO: 42 and the antigen-binding protein further comprises a variant sequence having at least or about 70% (e.g., at least about 80%, at least about 85%, at least about 90%, at least about 95%) sequence identity to SEQ ID NO 43.

Afucosylated Antibodies

Many secreted proteins undergo post-translational glycosylation, a process by which sugar moieties (e.g., glycans, saccharides) are covalently attached to specific amino acids of a protein. In eukaryotic cells, two types of glycosylation reactions occur: (1) N-linked glycosylation, in which glycans are attached to the asparagine of the recognition sequence Asn-X-Thr/Ser, where "X" is any amino acid except proline, and (2) O-linked glycosylation in which glycans are attached to serine or threonine. Regardless of the glycosylation type (N-linked or O-linked), microheterogeneity of protein glycoforms exists due to the large range of glycan structures associated with each site (O or N).

All N-glycans have a common core sugar sequence: Manα1-6(Manα1-3)Manβ1-4GlcNAcβ1-4GlcNAcβI-Asn-X-Ser/Thr (Man$_3$GlcNAc$_2$Asn) and are categorized into one of three types: (A) a high mannose (HM) or oligomannose (OM) type, which consists of two N-acetylglucosamine (GalNAc) moieties and a large number (e.g., 5, 6, 7, 8 or 9) of mannose (Man) residues (B) a complex type, which comprises more than two GlcNAc moieties and any number of other sugar types or (C) a hybrid type, which comprises a Man residue on one side of the branch and GlcNAc at the base of a complex branch. FIG. 1A (taken from Stanley et al., Chapter 8: N-Glycans, Essentials of Glycobiology, 2$^{nd}$ ed., Cold Spring Harbor Laboratory Press; 2009) shows the three types of N-glycans.

N-linked glycans typically comprise one or more monosaccharides of galactose (Gal), N-acetylgalactosamine (GalNAc), galactosamine (GalN), glucose (GLc), N-acetylglucoasamine (ClcNAc), glucoasamine (GlcN), mannose (Man), N-Acetylmannosamine (ManNAc), Mannosamine (ManN), xylose (Xyl), NOAcetylneuraininic acid (Neu5Ac), N-Glycolylneuraminic acid (NeuSGc), 2-keto-3-doxynononic acid (Kdn), fucose (Fuc), Glucuronic acid (GLcA), Iduronic acid (IdoA), Galacturonic acid (Gal A), mannuronic acid (Man A). The commonly used symbols for such saccharides are shown in FIG. 29A.

N-linked glycosylation begins in the endoplasmic reticulum (ER), where a complex set of reactions result in the attachment of a core glycan structure made essentially of two GlcNAc residues and three Man residues. The glycan complex formed in the ER is modified by action of enzymes in the Golgi apparatus. If the saccharide is relatively inaccessible to the enzymes, it typically stays in the original HM form. If enzymes can access the saccharide, then many of the Man residues are cleaved off and the saccharide is further modified, resulting in the complex type N-glycans structure. For example, mannosidase-1 located in the cis-Golgi, can cleave or hydrolyze a HM glycan, while fucosyltransferase FUT-8, located in the medial-Golgi, fucosylates the glycan (Hanrue Imai-Nishiya (2007), BMC Biotechnology, 7:84).

Accordingly, the sugar composition and the structural configuration of a glycan structure varies, depending on the glycosylation machinery in the ER and the Golgi apparatus, the accessibility of the machinery enzymes to the glycan structure, the order of action of each enzyme and the stage at which the protein is released from the glycosylation machinery, among other factors.

In exemplary embodiments of the present disclosure, the antigen-binding proteins comprise an Fc polypeptide. The term "Fc polypeptide" as used herein includes native and mutein forms of polypeptides derived from the Fc region of an antibody. In exemplary aspects, the Fc polypeptide of the presently disclosed antigen-binding protein comprises a glycan. In various instances, the glycan lacks fucose or is afucosylated. In exemplary aspects, the antigen-binding protein comprises an afucosylated glycan. As used herein, the term "afucosylated glycan" or "afuco glycan" or "afucosylated glycoform" or "Afuc" refers to glycoforms which lack a core fucose, e.g., an α1,6-linked fucose on the GIcNAc residue involved in the amide bond with the Asn of the N-glycosylation site. Afucosylated glycoforms include, but are not limited to, A1G0, A2G0, A2G1a, A2G1b, A2G2, and A1G1M5. Additional afucosylated glycans include, e.g., A1G1a, G0[H3N4], G0[H4N4], G0[H5N4], FO-N[H3N3]. See, e.g., Reusch and Tejada, Glycobiology 25(12): 1325-1334 (2015).

The present disclosure also provides a composition, e.g., a pharmaceutical composition, comprising an antigen binding protein comprising an Fc polypeptide comprising an afucosylated glycan. In exemplary aspects, at least or about 25% of the antigen-binding proteins present in the composition are antigen-binding proteins comprising an Fc polypeptide comprising an afucosylated glycan. In exemplary aspects, at least or about 25% of the antigen-binding proteins present in the composition are afucosylated. Optionally, at least 30%, 40%, 50%, 60%, 70%, 80%, or 90% or more of the antigen-binding proteins present in the composition are afucosylated. Methods of producing compositions comprising antigen-binding proteins of a particular glycoprofile are known in the art. In exemplary embodiments, the antigen binding proteins are recombinant produced in cells that are genetically modified to alter the activity of an enzyme of the de novo pathway or the salvage pathway. These two pathways of fucose metabolism are shown in FIG. 29B. In exemplary embodiments, the cells are genetically modified to alter the activity of any one or more of: a fucosyltransferase (FUT, e.g., FUT1, FUT2, FUT3, FUT4, FUT5, FUT6, FUT7, FUT8, FUT9), a fucose kinase, a GDP-fucose pyrophosphorylase, GDP-D-mannose-4,6-dehydratase (GMD), and GDP-keto-6-deoxymannose-3,5-epimerase, 4-reductase (FX). In exemplary embodiments, the cells are genetically modified to knock-out a gene encoding FX. See, e.g., International Patent Publication No. WO2017/079165 A1; Kanda et al., J Biotechnol 130, 2007, 300-310, Yamane-Ohunuki et al., Biotechnol Bioeng 87, 2004, 614-622, Malphettes et al., Biotechnol Bioeng 106, 2010, 774-783.

Nucleic Acids

The present disclosure further provides nucleic acids comprising a nucleotide sequence encoding an antigen-binding protein of the present disclosure. By "nucleic acid" as used herein includes "polynucleotide," "oligonucleotide," and "nucleic acid molecule," and generally means a polymer of DNA or RNA, or modified forms thereof, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. The nucleic acid can comprise any nucleotide sequence which encodes any of the antigen-binding proteins of the present disclosure. In various aspects, the nucleic acid comprises a nucleotide sequence which encodes an antigen-binding protein comprising (a) a heavy chain (HC) complementarity-determining region (CDR) 1 amino acid sequence set forth in Table A or a sequence selected from the group consisting of: SEQ ID NOs: 64, 88, 69, 89, 72, 75, 91, 94, 95, 97, 99, 101, 103, 106, 109; or a variant sequence thereof which differs by only one or two amino acids or which has at least or about 70% (e.g., at least about 804% at least about 85%, at least about 90%, at least about 95%) sequence identity; (b) an HC CDR2 amino acid sequence set forth in Table A or a sequence selected from the group consisting of SEQ ID NOs 65, 67, 70, 90, 73, 76, 92, 73, 96, 98, 100, 102, 104, 107, 110; or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A or a sequence selected from the group consisting of: SEQ ID NOs: 66, 68, 71, 77, 74, 77, 93, 74, 105, 108, 111; or a variant sequence thereof which differs by only one or two amino acids or which has at least or about 70% (e.g., at least about 80%, at least about 85%, at least about 90%, at least about 95%) sequence identity; (d) a light chain (LC) CDR1 amino acid sequence set forth in Table A or a sequence selected from the group consisting of: SEQ ID NOs: 78, 81, 82, 86, 114, 120, 123, 126; or a variant sequence thereof which differs by only one or two amino acids or which has at least or about 70% (e.g., at least about 80%, at least about 85%, at least about 90%, at least about 95%) sequence identity; (e) an LC CDR2 amino acid sequence set forth in Table A or a sequence selected from the group consisting of: SEQ ID NOs: 79, 112, 79, 84, 116, 118, 119, 129, 121, 124, 127; or a variant sequence thereof which differs by only one or two amino acids or which has at least or about 70% (e.g., at least about 80%, at least about 85%, at least about 90%, at least about 95%) sequence identity; (f) an LC CDR3 amino acid sequence set forth in Table A or a sequence selected from the group consisting of: SEQ ID NOs: 80, 83, 113, 85, 87, 115, 117, 122, 125, 128 or a variant sequence thereof which differs by only one or two amino acids or which has at least or about 70% (e.g., at least or about 80%, at least or about 85%, at least or about 90%, at least or about 95%) sequence identity; or (g) a combination of any two or more of (a)-(f). In various aspects, the nucleic acid comprises a nucleotide sequence encoding an antigen-binding protein comprising a LC CDR1 amino acid sequence, a LC CDR2 amino acid sequence, and a LC CDR3 amino acid sequence set forth in Table A and at least 1 or 2 of the HC CDR amino acid sequences set forth in Table A. In various aspects, the nucleic acid comprises a nucleotide sequence encoding an antigen-binding protein comprising a HC CDR1 amino acid sequence, a HC CDR2 amino acid sequence, and a HC CDR3 amino acid sequence set forth in Table A and at least 1 or 2 of the LC CDR amino acid sequences set forth in Table A. In various embodiments, the nucleic acid comprises a nucleotide sequence encoding an antigen-binding protein comprising (a) at least 3, 4, or 5 of the amino acid sequences designated by the SEQ ID NOs: in a single row of Table A, (b) each of the LC CDR amino acid sequences designated by the SEQ ID NOs: of a single row of Table A and at least 1 or 2 of the HC CDR amino acid sequences designated by the SEQ ID NOs: in of a single row of Table A, (c) each of the HC CDR amino acid sequences designated by the SEQ ID NOs: of a single row of Table A and at least 1 or 2 of the LC CDR amino acid sequences designated by the SEQ ID NOs: of a single row of Table A, (d) all 6 of the CDR amino acid sequences designated by the SEQ ID NOs: of a single row of Table A, and/or (e) six CDR amino acid sequences selected from the group consisting of: (a) SEQ ID NOs: 78, 79, 80, 64, 65, 66; (b) SEQ ID NOs: 81, 112, 80, 88, 65, 66; (c) SEQ ID NOs: 81, 79, 80, 64, 67, 68; (d) SEQ ID NOs: 82, 79, 83, 39, 70, 71; (e) SEQ ID NOs: 81, 79, 113, 89, 90, 77; (1) SEQ ID NOs: 81, 84, 85, 72, 73, 74; (g) SEQ ID NOs: 86, 79, 87, 75, 76, 77; (h) SEQ ID NOs: 114, 79, 115, 91, 92, 93; (i) SEQ ID NOs: 81, 116, 117, 94, 73, 74; (j) SEQ ID NOs: 81, 118, 117, 95, 96, 74; (k) SEQ ID NOs: 81, 119, 117, 97, 98, 74; (1) SEQ ID NOs: 81, 118, 85, 99, 100, 74; (m) SEQ ID NOs: 81, 129, 117, 101, 102, 74; (n) SEQ ID NOs: 120, 121, 122, 103, 104, 105; (o) SEQ ID NOs: 123, 124, 125, 106, 107, 108; and (p) SEQ ID NOs: 126, 127, 128, 109, 110, 111.

In various embodiments, the nucleic acid comprises a nucleotide sequence encoding an antigen-binding protein comprising (a) a heavy chain variable region amino acid sequence set forth in in Table B or a sequence selected from the group consisting of: SEQ ID NO: 10, 12, 14, 16, 18, 20, 22, 24, 26, 28, 30, 32, 34, 36, 38, or 40, or a variant sequence thereof which differs by only one or two amino acids or which has at least or about 70% (e.g., at least or about 80%, at least or about 85%, at least or about 90%, at least or about 95%) sequence identity; or (b) a light chain variable region amino acid sequence set forth in Table B or a sequence selected from the group consisting of SEQ ID NO: 11, 13, 15, 17, 19, 21, 23, 25, 27, 29, 31, 33, 35, 37, 39 or 41, or a variant sequence thereof which differs by only one or two amino acids or which has at least or about 70% (e.g., at least or about 80%, at least or about 85%, at least or about 90%, at least or about 95%) sequence identity; or (c) both (a) and (b). In various embodiments, the nucleic acid comprises a nucleotide sequence encoding an antigen-binding protein comprising a pair of amino acid sequences selected from the group consisting of: (a) SEQ ID NOs: 10 and 11; (b) SEQ ID NOs: 12 and 13; (c) SEQ ID NOs: 14 and 15; (d) SEQ ID NOs: 16 and 17; (e) SEQ ID NOs: 18 and 19; (f) SEQ ID NOs: 20 and 21; (g) SEQ ID NOs: 22 and 23; (h) SEQ ID NOs: 24 and 25; (i) SEQ ID NOs: 26 and 27; (j) SEQ ID NOs: 28 and 29; (k) SEQ ID NOs: 30 and 31; (1) SEQ ID NOs: 32 and 33; (m) SEQ ID NOs: 34 and 35; (n) SEQ ID NOs: 36 and 37; (o) SEQ 11) NOs: 38 and 39; (p) SEQ ID NOs: 40 and 41. In various embodiments, the nucleic acid comprises a nucleotide sequence encoding an antigen-binding protein comprising a pair of amino acid sequences selected from the group consisting of the pairs listed in Table D. In various aspects, the nucleic acid comprises a nucleotide sequence comprising a sequence encoding the amino acid set out in of any one or more of SEQ ID NOs: 42-57. In some embodiments, the nucleic acid does not comprise any insertions, deletions, inversions, and/or substitutions. In other embodiments, the nucleic acid comprises one or more insertions, deletions, inversions, and/or substitutions.

In some aspects, the nucleic acids of the present disclosure are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids in some aspects are constructed based on chemical synthesis and/or enzymatic ligation reactions using procedures known in the art. See, for example, Sambrook et al., supra; and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydmuracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the present disclosure can be purchased from companies, such as Macromolecular Resources (Fort Collins, Colo.) and Synthegen (Houston, Tex.).

Vector

The nucleic acids of the present disclosure in some aspects are incorporated into a vector. In this regard, the present disclosure provides vectors comprising any of the presently disclosed nucleic acids. In various aspects, the vector is a recombinant expression vector. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the present disclosure are not naturally-occurring as a whole. However, parts of the vectors can be naturally-occurring. The presently disclosed vectors can comprise any type of nucleotides, including, but not limited to DNA and RNA, which can be single-stranded or double-stranded, synthesized or obtained in part from natural sources, and which can contain natural, non-natural or altered nucleotides. The vectors can comprise naturally-occurring or non-naturally-occurring internucleotide linkages, or both types of linkages. In some aspects, the altered nucleotides or non-naturally occurring internucleotide linkages do not hinder the transcription or replication of the vector.

The vector of the present disclosure can be any suitable vector, and can be used to transduce, transform or transfect any suitable host. Suitable vectors include those designed for propagation and expansion or for expression or both, such as plasmids and viruses. The vector can be a plasmid based expression vector. In various aspects, the vector is selected from the group consisting of the pUC series (Fermentas Life Sciences), the pBluescript series (Stratagene, LaJoIIa, CA), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGT1 1, λZapII (Stratagene), λEMBL4, and λNMI 149, also can be used. Examples of plant expression vectors include pBIOl, pB1101.2, pB1101.3, pB1121 and pBIN 19 (Clontech). Examples of animal expression vectors include pEUK-Cl, pMAM and pMAMneo (Clontech). in some aspects, the vector is a viral vector, e.g., a retroviral vector. In various aspects, the vector is an adenovirus vector, an adeno-associated virus (AAV) vector, a Herpes Simplex Virus (HSV) vector, a Vesicular stomatitis virus (VSV) vector, vaccinia virus vector, or lentivirus vector. See, e.g., Howarth et al., Cell Biol. Toxicol. 26(1): 1-20 (2010). In various aspects, the vector is a baculovirus vector which infects arthropods, e.g., insects. In various aspects, the baculovirus vector is an Autographa-californica multiple nuclear virus (AcMNPV) or a Bombyxmorinuclear polyhedrosis (BmNPV). See, e.g., Khan, Adv Pharm Bull 3(2): 257-263 (2013); Miller, Bioessays 11(4): 91-96 (1989); Atkinson et al., Pestic Sci 28: 215-224 (1990).

The vectors of the present disclosure can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

In some aspects, the vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the presently disclosed expression vectors include, for instance, neomycin/G418 resistance genes, hygromycin resistance genes, histidinol resistance genes, tetracycline resistance genes, and ampicillin resistance genes.

The vector can comprise a native or normative promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovinxs (CMV) promoter, an SV40 promoter, an RSV promoter, and a promoter found in the long-terminal repeat of the murine stem cell virus.

Host Cells

Provided herein are host cells comprising a nucleic acid or vector of the present disclosure. As used herein, the term "host cell" refers to any type of cell that can contain the presently disclosed vector and is capable of producing an expression product encoded by the nucleic acid (e.g., mRNA, protein). The host cell in some aspects is an adherent cell or a suspended cell, i.e., a cell that grows in suspension. The host cell in various aspects is a cultured cell or a primary cell, i.e., isolated directly from an organism, e.g., a human. The host cell can be of any cell type, can originate from any type of tissue, and can be of any developmental stage.

In various aspects, the antigen-binding protein is a glycosylated protein and the host cell is a glycosylation-competent cell. In various aspects, the glycosylation-competent cell is an eukaryotic cell, including, but not limited to, a yeast cell, filamentous fungi cell, protozoa cell, algae cell, insect cell, or mammalian cell. Such host cells are described in the art. See, e.g., Frenzel, et al., *Front Immunol* 4: 217 (2013). In various aspects, the eukaryotic cells are mammalian cells. In various aspects, the mammalian cells are non human mammalian cells. In some aspects, the cells are Chinese Hamster Ovary (CHO) cells and derivatives thereof (e.g., CHO-K1, CHO pro-3), mouse myeloma cells (e.g., NSO, GS-NSO, Sp2/0), cells engineered to be deficient in dihydrofolatereductase (DHFR) activity (e.g., DUKX-X11, DG44), human embryonic kidney 293 (HEK293) cells or derivatives thereof (e.g., HEK293T, HEK293-EBNA), green African monkey kidney cells (e.g., COS cells, VERO cells), human cervical cancer cells (e.g., HeLa), human bone osteosarcoma epithelial cells U2-OS, adenocarcinomic human alveolar basal epithelial cells A549, human fibrosarcoma cells HT1080, mouse brain tumor cells CAD, embryonic carcinoma cells P19, mouse embryo fibroblast cells NIH 3T3, mouse fibroblast cells L929, mouse neuroblastoma cells N2a, human breast cancer cells MCF-7, retinoblastoma cells Y79, human retinoblastoma cells SO-Rb50, human liver cancer cells Hep G2, mouse B myeloma cells J558L, or baby hamster kidney (BHK) cells (Gaillet et al. 2007; Khan, Adv Pharm Bull 3(2): 257-263 (2013)).

For purposes of amplifying or replicating the vector, the host cell is in some aspects is a prokaryotic cell, e.g., a bacterial cell.

Also provided by the present disclosure is a population of cells comprising at least one host cell described herein. The population of cells in some aspects is a heterogeneous population comprising the host cell comprising vectors described, in addition to at least one other cell, which does not comprise any of the vectors. Alternatively, in some aspects, the population of cells is a substantially homogeneous population, in which the population comprises mainly host cells (e.g., consisting essentially of) comprising the vector. The population in some aspects is a clonal population of cells, in which all cells of the population are clones of a single host cell comprising a vector, such that all cells of the population comprise the vector. In various embodiments of the present disclosure, the population of cells is a clonal population comprising host cells comprising a vector as described herein.

Manufacture Methods

Also provided herein are methods of producing an antigen-binding protein which binds to CLDN18.2. In various embodiments, the method comprises culturing a host cell comprising a nucleic acid comprising a nucleotide sequence encoding the antigen-binding protein as described herein in a cell culture medium and harvesting the antigen-binding protein from the cell culture medium. The host cell can be any of the host cells described herein. In various aspects, the host cell is selected from the group consisting of: CHO cells, NSO cells, COS cells, VERO cells, and BHK cells. In various aspects, the step of culturing a host cell comprises culturing the host cell in a growth medium to support the growth and expansion of the host cell. In various aspects, the growth medium increases cell density, culture viability and productivity in a timely manner. In various aspects, the growth medium comprises amino acids, vitamins, inorganic salts, glucose, and serum as a source of growth factors, hormones, and attachment factors. In various aspects, the growth medium is a fully chemically defined media consisting of amino acids, vitamins, trace elements, inorganic salts, lipids and insulin or insulin-like growth factors. In addition to nutrients, the growth medium also helps maintain pH and osmolality. Several growth media are commercially available and are described in the art. See, e.g., Arora, "Cell Culture Media: A Review" MATER METHODS 3:175 (2013).

In various aspects, the method comprises culturing the host cell in a feed medium. In various aspects, the method comprises culturing in a feed medium in a fed-batch mode. Methods of recombinant protein production are known in the art. See, e.g., Li et al., "Cell culture processes for monoclonal antibody production" MAbs 2(5): 466-477 (2010).

The method making an antigen-binding protein can comprise one or more steps for purifying the protein from a cell culture or the supernatant thereof and preferably recovering the purified protein. In various aspects, the method comprises one or more chromatography steps, e.g., affinity chromatography (e.g., protein A affinity chromatography), ion exchange chromatography, hydrophobic interaction chromatography. In various aspects, the method comprises purifying the protein using a Protein A affinity chromatography resin.

In various embodiments, the method further comprises steps for formulating the purified protein, etc., thereby obtaining a formulation comprising the purified protein. Such steps are described in Formulation and Process Development Strategies for Manufacturing, eds. Jameel and Hershenson, John Wiley & Sons, Inc. (Hoboken, N.J.), 2010.

In various aspects, the antigen-binding protein linked to a polypeptide and the antigen-binding protein is part of a fusion protein. Thus, the present disclosure further provides methods of producing a fusion protein comprising an antigen-binding protein which binds to CLDN18.2. In various embodiments, the method comprises culturing a host cell comprising a nucleic acid comprising a nucleotide sequence encoding the fusion protein as described herein in a cell culture medium and harvesting the fusion protein from the cell culture medium.

Conjugates

The present disclosure also provides antigen-binding proteins attached, linked or conjugated to a second moiety (e.g., a heterologous moiety, a conjugate moiety). Accordingly, the present disclosure provides a conjugate comprising an antigen-binding protein and a heterologous moiety. As used herein, the term "heterologous moiety" is synonymous with "conjugate moiety" and refers to any molecule (chemical or biochemical, naturally-occurring or non-coded) which is different from the antigen-binding proteins of the present disclosure. Various heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent.

In some embodiments, the heterologous moiety is a polymer. The polymer can be branched or unbranched. The polymer can be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa.

In some embodiments, the polymer is modified to have a single reactive group, such as an active ester for acylation or an aldehyde for alkylation, so that the degree of polymerization can be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer.

In some embodiments, the polymer is selected from the group consisting of polyamides, polycarbonates, polyalkylenes and derivatives thereof including, polyalkylene glycols, polyalkylene oxides, polyalkylene terepthalates, polymers of acrylic and methacrylic esters, including poly (methyl methacrylate), poly(ethyl methacrylate), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is a therapeutic agent. The therapeutic agent can be any of those known in the art. Examples of therapeutic agents that are contemplated herein include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin 1I receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-HT4 partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-A2 inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptase inhibitors, protease inhibitors, anemia, Kaposi's sarcoma, aminoglycosides, carbapenems, cephalosporins, glycopoptides, lincosamides, macrolies, oxazolidinones, penicillins, streptogramins, sulfonamides, trimethoprirn and derivatives, tetracyclines, anthelmintics, amebicies, biguanides, cinchona alkaloids, folic acid antagonists, quinoline derivatives, *Pneumocystis carinii* therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, *vinca* alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, di phenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opoid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

The antigen-binding proteins of the present disclosure can be conjugated to one or more cytokines and growth factors that are effective in inhibiting tumor metastasis, and wherein the cytokine or growth factor has been shown to have an antiproliferative effect on at least one cell population. Such cytokines, lymphokines, growth factors, or other hematopoietic factors include, but are not limited to: M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors for use herein include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2α, cytokine-induced neutrophil chemotactic factor 2β,β endothelial cell growth factor, endothelin 1, epithelial-derived neutrophil attractant, glial cell line-derived neutrophic factor receptor α 1, glial cell line-derived neutrophic factor receptor α 2, growth related protein, growth related protein α, growth related protein β, growth related protein 7, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein 1, transforming growth factor β binding protein II, transforming growth factor f3 binding protein III, tumor necrosis factor receptor type I, tumor necrosis factor receptor type II, urokinase-type plasminogen activator receptor, and chimeric proteins and biologically or immunologically active fragments thereof.

In some embodiments, the conjugate comprises an antigen-binding protein as described herein and a cytotoxic agent. The cytotoxic agent is any molecule (chemical or biochemical) which is toxic to a cell. In some aspects, when a cytotoxic agent is conjugated to an antigen-binding protein of the present disclosure, the results obtained are synergistic. That is to say, the effectiveness of the combination therapy of an antigen-binding protein and the cytotoxic agent is synergistic, i.e., the effectiveness is greater than the effectiveness expected from the additive individual effects of each. Therefore, the dosage of the cytotoxic agent can be reduced and thus, the risk of the toxicity problems and other side effects is concomitantly reduced. In some embodiments, the cytotoxic agent is a chemotherapeutic agent. Chemotherapeutic agents are known in the art and include, but not limited to, platinum coordination compounds, topoisomerase inhibitors, antibiotics, antimitotic alkaloids and difluoronucleosides, as described in U.S. Pat. No. 6,630,124.

In some embodiments, the chemotherapeutic agent is a platinum coordination compound. The term "platinum coordination compound" refers to any tumor cell growth inhibiting platinum coordination compound that provides the platinum in the form of an ion.

In some embodiments, the platinum coordination compound is cis-diamminediaquoplatinum (II)-ion; chloro(diethylenetriamine)-platinum(II)chloride; dichloro(ethylenediamine)-platinum(II), diammine(1,1-cyclobutanedicarboxylato) platinum(II) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(11); (1,2-diaminocyclohexane)oxalatoplatinum(II); ormaplatin; and tetraplatin.

In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type if and type H. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

In some aspects, the topoisomerase inhibitor is camptothecin or a camptothecin analog. Camptothecin is a water-insoluble, cytotoxic alkaloid produced by Camptotheca accuminata trees indigenous to China and Nothapodytes *foetida* trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to; topotecan, irinotecan and 9-amino-camptothecin.

In additional embodiments, the cytotoxic agent is any tumor cell growth inhibiting camptothecin analog claimed or described in: U.S. Pat. No. 5,004,758, issued on Apr. 2, 1991 and European Patent Application Number 88311366.4, published on Jun. 21, 1989 as 20' Publication Number EP 0 321 122; U.S. Pat. No. 4,604,463, issued on Aug. 5, 1986 and European Patent Application Publication Number EP 0 137 145, published on Apr. 17, 1985; U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983; European Patent Application Publication Number EP 0 088 642, published on Sep. 14, 1983; Wani et al., J. Med. Chem., 29, 2358-2363 (1986); Nitta et al., Proc. 14th International Congr. Chemotherapy, Kyoto, 1985, Tokyo Press, Anticancer Section 1, p. 28-30, especially a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776, issued on Aug. 3, 1982; U.S. patent application Ser. No. 581,916, filed on Sep. 13, 1990 and European Patent Application Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399,276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

In some embodiments, the camptothecin analog is an active metabolite of irinotecan (CPT-11). In some such embodiments, the camptothecin analog is 7-ethyl-10-hydroxycamptothecin (SN-38). As a metabolite, SN-38 is formed by hydrolysis of irinotecan by carboxylesterases. In some embodiments, SN-38 has one of the following structures:

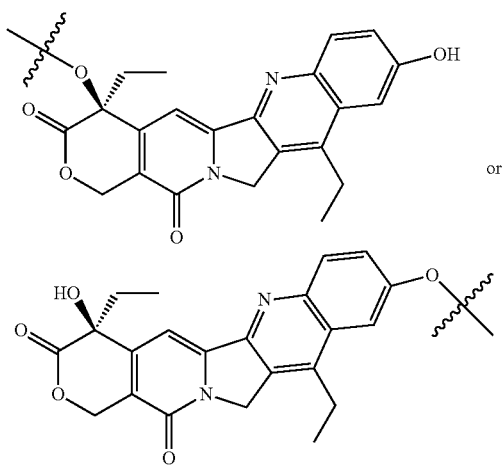

SN-38 has been described in U.S. Pat. Nos. 7,999,083; 8,080,250; 8,759,496; 8,999,344; 10,195,288; and 9,808,537.

In some embodiments, the camptothecin analog is exatecan methanesulfonate. Exatecan methanesulfonate is a water-soluble camptothecin (CPT) that exhibits more potent topoisomerase I inhibitory activity and antitumor activity than other CPT analogs. In addition, exatecan is effective against p-glycoprotein (P-gp)-mediated multi-drug resistant cells.

In some embodiments, the camptothecin analog is deruxtecan (Dxd), a potent derivative of exatecan, which has 10-fold higher topoisomerase I inhibitory potency than SN-38. In some embodiments, Dxd has the following structure:

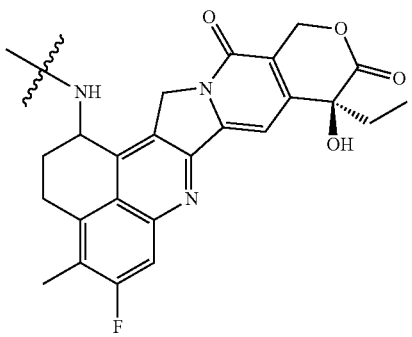 [SMILES: *NC1CCc2c(C)c(F)cc3nc4c(c1c23)Cn1c-4cc2c(c1=O)COC(=O)[C@]2(O)CC]

Dxd has been described in U.S. Pat. Nos. 6,407,115; 10,195,288; 9,808,537; and 6,407,115.

The preparation of numerous compounds of the camptothecin analog class (including pharmaceutically acceptable salts, hydrates and solvates thereof) as well as the preparation of oral and parenteral pharmaceutical compositions comprising such a compounds of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet other embodiments of the invention, the chemotherapeutic agent is an antibiotic compound. Suitable antibiotic include, but are not limited to, doxorubicin, mitomycin, bleomycin, daunorubicin and streptozocin.

In some embodiments, the chemotherapeutic agent is an antimitotic alkaloid. In general, antimitotic alkaloids can be extracted from *Cantharanthus roseus*, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620,985). In one embodiment, the antimitotic alkaloid is vinorelbine.

In other embodiments of the invention, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. In certain aspects, the 2'-deoxy-2',2'-difluoronucleoside used in the compositions and methods of the present invention is 2'-deoxy-2',2'-difluorocytidine hydrochloride, also known as gemcitabine hydrochloride. Gemcitabine is commercially available or can be synthesized in a multi-step process as disclosed and taught in U.S. Pat. Nos. 4,526,988, 4,808,614 and 5,223,608, the teachings of which are incorporated herein by reference.

In various aspects, the chemotherapeutic agent is an anti-mitotic agent which inhibits cell division by blocking tubulin polymerization, destabilizing microtubules, or altering microtubule dynamics, e.g., maytansinoid or a derivative thereof (e.g., DM1 or DM4), auristatin or a derivative thereof. In various instances, the chemotherapeutic agent is an auristatin. For instance, the auristatin is in some aspects, dolastatin, Monomethyl auristatin E (MMAE), Monomethyl auristatin E (MMAE), or PF-06380101. Auristatins are described in the art. See, e.g., Maderna, A.; et al., Mol Pharmaceutics 12(6): 1798-1812 (2015). In various aspects, the conjugate comprises an antibody of the present disclosure in combination with MMAE. Optionally, the conjugate comprises a linker. In some aspects, the linker comprises a cleavable linking moiety. In various instances, the conjugate comprises an antibody of the present disclosure linked to an attachment group which is linked to a cathepsin-cleavable linker, which in turn is linked to a spacer which is linked to MMAE. In aspects, the attachment group is attached to the antibody via a Cys residue of the Fc region of the antibody. In exemplary aspects, the attachment group comprises the structure of Formula I:

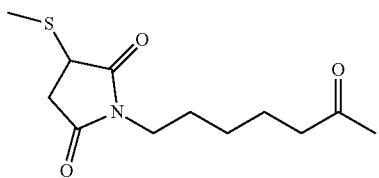

[Formula I]

In exemplary aspects, the cathepsin cleavable linker comprises the structure of Formula II:

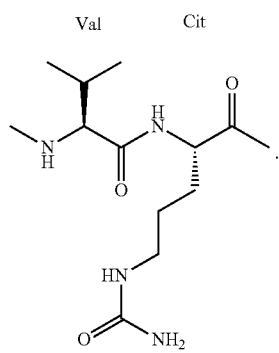

[Formula II]

In exemplary aspects, the spacer comprises the structure of Formula III:

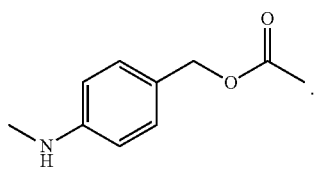

[Formula III]

In some embodiments, MMAE has the following structure:

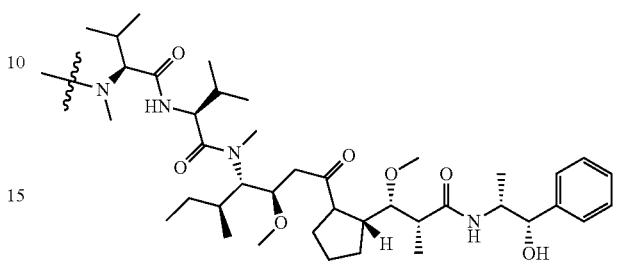

The present disclosure also provides conjugates comprising an antigen-binding protein of the present disclosure linked to a polypeptide, such that the conjugate is a fusion protein. Therefore, the present disclosure provides fusion proteins comprising an antigen-binding protein of the present disclosure linked to a polypeptide. In various embodiments, the polypeptide is a diagnostic label, e.g., a fluorescent protein, such as green fluorescent protein, or other tag, e.g., Myc tag. In various aspects, the polypeptide is one of the cytokines, lymphokines, growth factors, or other hematopoietic factors listed above.

Linkers

In some embodiments, the conjugate is directly linked to the heterologous moiety. In alternative embodiments, the conjugate comprises a linker that joins the compound of the present disclosure to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers can be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. In some embodiments, the linker is an amino acid or a peptidyl linker. Such peptidyl linkers can be any length. Various linkers are from about 1 to 50 amino acids in length, 5 to 50, 3 to 5, 5 to 10, 5 to 15, or 10 to 30 amino acids in length.

A variety of suitable linkers are known in the art. The linker can be cleavable (a cleavable linker), e.g., under physiological conditions, e.g., under intracellular conditions, such that cleavage of the linker releases the drug in the intracellular environment. Alternatively, the linker can be cleavable under extracellular conditions, e.g., outside the tumor cells or in the vicinity of the tumor mass, such that cleavage of the linker releases the drug that permeates preferentially inside the tumor cells. In other embodiments, the linker is not cleavable (a non-cleavable linker), and the drug is released, for example, by antibody degradation.

The linker can be bonded to a chemically reactive group on the antibody moiety, e.g., to a free amino, imino, hydroxyl, thiol, or carboxyl group (e.g., to the N- or C-terminus, to the epsilon amino group of one or more lysine residues, to the free carboxylic acid group of one or more glutamic acid or aspartic acid residues, to the sulfhydryl group of one or more cysteinyl residues, or to the hydroxyl group of one or more serine or threonine residues). The site to which the linker is bound can be a natural residue in the amino acid sequence of the antibody moiety, or it can be introduced into the antibody moiety, e.g., by DNA recombinant technology (e.g., by introducing a cysteine or protease cleavage site in the amino acid sequence) or by protein biochemistry (e.g., reduction, pH adjustment, or proteolysis). The site to which the linker is bound can also be a non-natural amino acids. The site to which the linker is bound can also be a glycan on the antibody.

Typically, the linker is substantially inert under conditions for which the two groups it is connecting are linked. The term "bifunctional crosslinking agent," "bifunctional linker" or "crosslinking agent" refers to a modifying agent that possess two reactive groups at each end of the linker, such that one reactive group can be first reacted with the cytotoxic compound to provide a compound bearing the linker moiety and a second reactive group, which can then react with the antibody. Alternatively, one end of the bifunctional crosslinking agent can be first reacted with the antibody to provide an antibody bearing a linker moiety and a second reactive group, which can then react with the cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, protease/peptidase labile bonds, and esterase labile bonds. See, for example, U.S. Pat. Nos. 5,208,020; 5,475,092; 6,441,163; 6,716,821; 6,913,748; 7,276,497; 7,276,499; 7,368,565; 7,388,026 and 7,414,073. In some embodiments, the bonds are disulfide bonds, thioether, and/or protease/peptidase labile bonds. Other linkers that can be used in the present invention include non-cleavable linkers, such as those described in detail in US 20050169933, charged linkers, or hydrophilic linkers, such as those described in US 2009/0274713, US 2010/0129314, and WO 2009/134976, each of which is expressly incorporated herein by reference.

In some embodiments, the linker is a hydrophilic linker that confers hydrophilicity to the conjugate. In some embodiments, the hydrophilic linker comprises polyethylene glycol (PEG). In some embodiments, the hydrophilic linker is CLA2. In some embodiments, the CLA2 linker has the following structure:

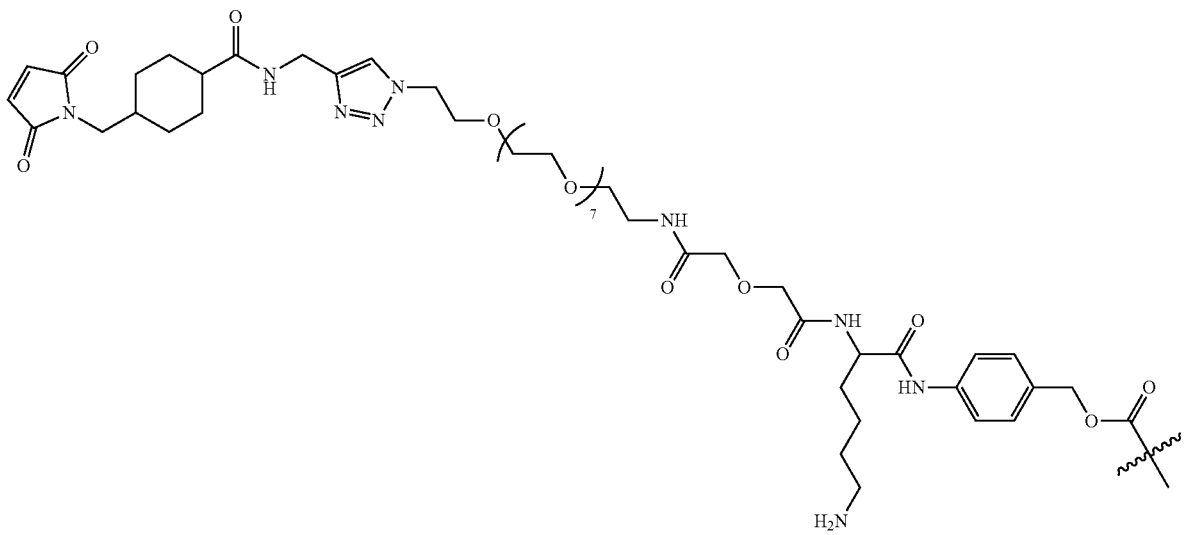

CLA2 has been described in U.S. Pat. Nos. 8,080,250; 8,759,496; and 10,195,288.

In some embodiments, the hydrophilic linker is CL2E. In some embodiments, the CL2E has the following structure:

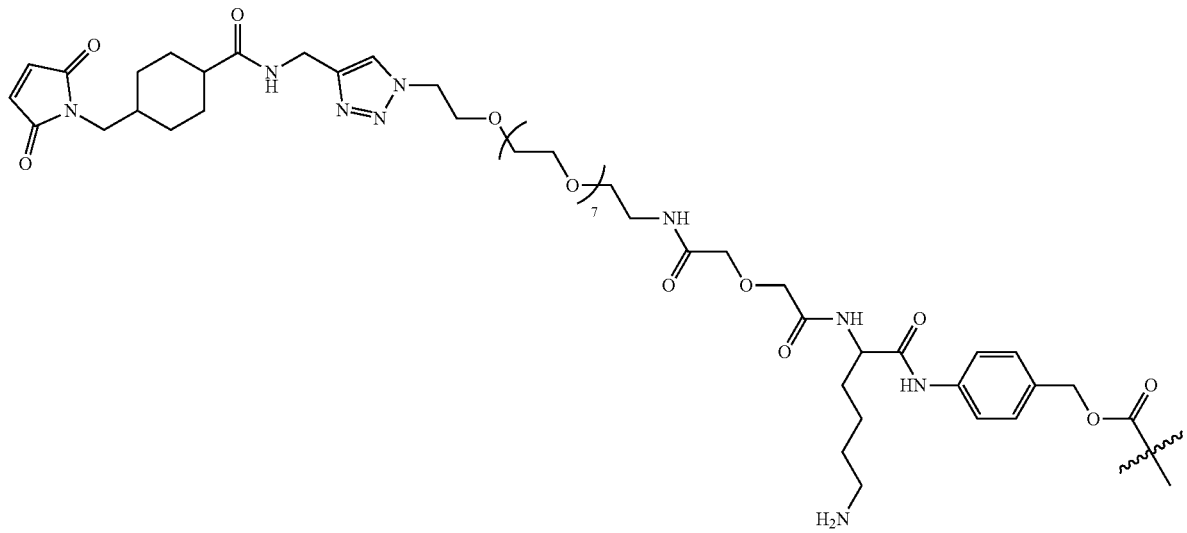

CL2E has been described in U.S. Pat. Nos. 8,080,250; 8,759,496; and 10,195,288.

In some embodiments, the linker is cleavable by a cleaving agent that is present in the intracellular environment (e.g., within a lysosome or endosome or caveolea). The linker can be, e.g., a peptide linker that is cleaved by an intracellular or extracellular peptidase or protease enzyme, including, but not limited to, a lysosomal or endosomal protease. In some embodiments, the peptide linker comprises at least two, at least three, at least four, or at least five amino acids long.

In some embodiments, the peptide linker is MC-VC-PAB, comprising valine and citruline residues. In some embodiments, the MC-VC-PAB linker has the following structure:

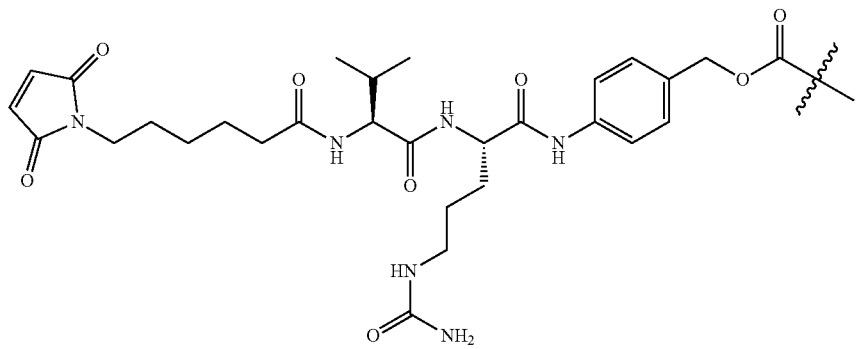 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

MC-VC-PAB has been described in U.S. Pat. Nos. 7,659,241; 7,829,531; 6,884,869; 6,214,345; and 6,214,345.

In some embodiments, the peptide linker is maleimidocaproyl glycine-glycine-phenylalanine-glycine (MC-GGFG). In some embodiments, the MC-GGFG linker has the following structure:

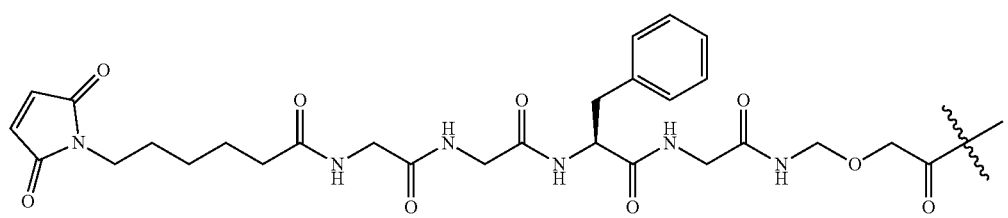

MC-GGFG has been described in U.S. Pat. Nos. 9,808,537 and 10,195,288.

In other embodiments, the cleavable linker is pH-sensitive, i.e., sensitive to hydrolysis at certain pH values. In some embodiments, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used (see, e.g., U.S. Pat. Nos. 5,122,368; 5,824,805; 5,622,929; Dubowchik and Walker, 1999, Pharm. Therapeutics 83:67-123; Neville et al, 1989, Biol. Chem. 264: 14653-14661). Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). Bifunctional cross-linking agents that enable the linkage of an antibody with cytotoxic compounds via disulfide bonds include, but are not limited to, N-succinimidyl-4-(4-nitropyridyl-2-dithio)butanoate, N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)-2-sulfo butanoate (sulfo-SPDB). Sulfo-SPDB is described, e.g., in U.S. Pat. No. 8,236,319, incorporated herein by reference. Alternatively, crosslinking agents that introduce thiol groups such as 2-iminothiolane, homocysteine thiolactone, or S-acetylsuccinic anhydride can be used. In other embodiments, the linker may contain a combination of one or more of the peptide, pH-sensitive, or disulfide linkers described previously.

"Heterobifunctional crosslinking agents" are bifunctional crosslinking agents having two different reactive groups. Heterobifunctional crosslinking agents containing both an amine-reactive N-hydroxysuccinimide group (NHS group) and a carbonyl-reactive hydrazine group can also be used to link cytotoxic compounds with an antibody. Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

The linkers described herein may be used in any combination with the heterologous moiety described herein. All of the above-listed linkers and heterologous moiety described herein are available commercially and/or can be prepared by conventional techniques including those described in the above-listed references.

Conjugation

The heterologous moiety-to-antigen-binding protein ratio (HAR) represents the number of a heterologous moiety linked per antigen-binding molecule. In some embodiments, the HAR ranges from 1 to 15, 1 to 10, 1 to 9, 1 to 8, 1 to 7, 1 to 6, 1 to 5, 1 to 4, 1 to 3, or 1 to 2. In some embodiments, the HAR ranges from 2 to 10, 2 to 9, 2 to 8, 2 to 7, 2 to 6, 2 to 5, 2 to 4 or 2 to 3. In other embodiments, the HAR is about 2, about 2.5, about 3, about 4, about 5, or about 6. In some embodiments, the HAR ranges from about 2 to about 4. The HAR may be characterized by conventional means such as mass spectrometry, UVN is spectroscopy, EL1SA assay, and/or HPLC.

In some embodiments, the conjugates are heterogeneous conjugates (also referred to as "conventional"), wherein the antigen-binding proteins are conjugated to a different number of the heterologous moiety. In some embodiments, the heterogeneous conjugates follow a Gaussian distribution or quasi-Gaussian distribution of the conjugates, wherein the distribution centers on the average heterologous moiety loading value with some antigen-binding proteins conjugated with higher than average and some antigen-binding proteins conjugated with lower than the average.

In some embodiments, the conjugates are homogeneous conjugates, wherein the substantial percentage of the antigen-binding proteins are conjugated to a defined number of the heterologous moiety. In some embodiments, the homogeneous conjugates comprise the HAR of 1, 2, 3, 4, 5, 6, 7, 8, 9, or 10. In some embodiments, the homogeneous conjugates comprise the HAR of 2, 4, 6, or 8. In preferred embodiments, the homogeneous conjugates comprise the HAR of 4. In other preferred embodiments, the homogeneous conjugates comprise the HAR of 2. In some embodiments, the homogeneous conjugates comprise greater than or equal to 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent conjugates with the defined HAR. In some embodiments, the homogeneous conjugates comprise about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent conjugates with the defined HAR. In some embodiments, the homogeneous conjugates comprise at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent conjugates with the defined HAR. In some embodiments, the homogeneous conjugates comprise the HAR distribution that is not Gaussian or quasi-Gaussian distribution. In some embodiments, the homogeneity of the homogeneous conjugates is determined by a chromatogram, e.g., HPLC or any suitable chromatography. In some embodiments, the chromatogram is a HIC chromatogram. The homogeneous conjugate may be generated by a site-specific conjugation.

In some embodiments, the heterologous moiety is conjugated to the antigen-binding protein (e.g., antibody) in a site-specific manner. Various site-specific conjugation methods are known in the art, e.g., thiomab or TDC or conjugation at an unpaired cysteine residue (Junutula et al. (2008) Nat. Biotechnol. 26:925-932; Dimasi et al. (2017)Mol. Pharm. 14:1501-1516; Shen et al. (2012) Nat. Biotechnol. 30:184-9); thiol bridge linker (Behrens et al. (2015) Mol. Pharm. 12:3986-98); conjugation at glutamine using a transglutaminase (Dennler et al. (2013) Methods Mol. Rio. 1045: 205-15; Dennler et al. (2014) Bioconjug Chem. 25:569-78); conjugation at engineered unnatural amino acid residues (Axup et al. (2012) Proc Ncril Acad Sci U.S.A. 104-16101-6; Tian et al. (2014) Proc Natl Acad Sci U.S.A. 111:1766-71; VanBrunt et al. (2015) Bioconjug Chem 26:2249 60; Zimmerman et al. (2014) Bioconjug Chem 25:351-61); selenocysteine conjugation (Li et al. (2017) Cell Chem Bio124: 433-442); glycan-mediated conjugation (Okeley et al. (2013) Bioconjug Chem 24:1650-5); conjugation at galactose or GalNAc analogues (Ramakrishnan and Qasba (2002) J Biol Chem 277:20833-9; van Geel et at (2015) Bioconjug Chem 26:2233-42); via glycan engineering (Zhou et al. (2014) Bioconjug Chem 25:510-20; Tang et al. (2017) Nat Protoc 12:1702-1721); via a short peptide tag, such as engineering a glutamine tag or sortase A-mediated transpeptidation (Strop et al. (2013) *Chem Biol* 20:161-7; Beerli ei al. (2015) *PLoS One* 10:e0131177); and via an aldehyde tag (Wu et al. (2009) *Proc Natl Acad Sci U.S.A.* 106:3000-5).

*Unpredictability of conjugate* (e.g., ADC)

It is not possible to predict in advance, simply based on an antibody profile, or a drug payload profile, which antibody-drug conjugates will be sufficiently safe and effective for clinical applications. For example, a particular drug payload may function perfectly well when conjugated to an antibody directed to one target, but it may not work nearly as well when conjugated to an antibody directed to a different target, or even to a different antibody directed to the same target. Why different antibody-drug conjugates display different anti-tumor activity in vivo is not sufficiently well understood to allow accurate predictions in the design of new antibody-drug conjugates. It is speculated that an unpredictable interplay of many factors play a role. These factors may include, for example, the binding affinity of an antibody-drug conjugate to a target antigen, the ability of the conjugate to penetrate solid tumors, as well as the half-life in circulation for proper exposure to tumors without causing toxicity.

The complexity and unpredictability is well demonstrated by antibody affinity alone. Antibodies or antibody-drug conjugates with high affinity track with better cellular uptake, which leads to a higher level of the cytotoxic payloads released inside the cells. Higher affinity is also known to enhance the antibody-dependent cellular cytotoxicity (ADCC). All these attributes favor the cell killing property of antibody-drug conjugates. However, it is also known that high affinity of an antibody or antibody-drug conjugate can prevent efficient tumor penetration via an "antigen barrier effect," suggesting that in order to achieve a strong anti-tumor activity in vivo, affinity of the antibody-drug conjugate has to be just right: not too high or not too low. To date, it is not known how to predict what will be the most efficient or effective level of affinity for an antibody-drug conjugate.

In addition, in vivo anti-tumor activity cannot be predicted by the mechanism of linkers and payloads alone. For example, O. Ab et al, *Mol. Cancer Ther.* 14(&):1605-1613 (2015) demonstrated that, when tested in pre-clinical cancer models, the same antibody conjugated to the same anti-tubulin toxin via different linkers exhibited dramatically different anti-tumor activity. This example is particularly surprising because the chemical structures of the two linkers are very similar. Moreover, the linker present in the superior conjugate contained a hydrophilic moiety. Hydrophilic metabolites are generally less membrane-permeable, and are thought to be slower in efflux from the lysosomes (the site of conjugate degradation), leading to a delay in the anti-tubulin activity of the released payload. This finding argues for an "ideal" kinetics of payload delivery, but to date, there is no insight into what constitutes such kinetics. Adding to this complexity is the open question of whether ideal kinetics of payload delivery, even if defined for a particular cell type, would apply to all cell types. Thus, it is not possible to predict the most effective in vivo anti-tumor activity merely from the chemical composition of the linker or payload.

Compositions, Pharmaceutical Compositions and Formulations

Compositions comprising an antigen-binding protein, a nucleic acid, a vector, a host cell, or a conjugate as presently disclosed are provided herein. The compositions in some aspects comprise the antigen-binding proteins in isolated and/or purified form. In some aspects, the composition comprises a single type (e.g., structure) of an antigen-binding protein of the present disclosure or comprises a combination of two or more antigen-binding proteins of the present disclosure, wherein the combination comprises two or more antigen-binding proteins of different types (e.g., structures).

In some aspects, the composition comprises agents which enhance the chemico-physico features of the antigen-binding protein, e.g., via stabilizing the antigen-binding protein at certain temperatures, e.g., room temperature, increasing shelf life, reducing degradation, e.g., oxidation protease mediated degradation, increasing half-life of the antigen-binding protein, etc. In some aspects, the composition comprises any of the agents disclosed herein as a heterologous moiety or conjugate moiety, optionally in admixture with the antigen-binding proteins of the present disclosure or conjugated to the antigen-binding proteins.

In various aspects of the present disclosure, the composition additionally comprises a pharmaceutically acceptable carrier, diluents, or excipient. In some embodiments, the antigen-binding protein, a nucleic acid, a vector, a host cell, or a conjugate as presently disclosed (hereinafter referred to as "active agents") is formulated into a pharmaceutical composition comprising the active agent, along with a pharmaceutically acceptable carrier, diluent, or excipient. In this regard, the present disclosure further provides pharmaceutical compositions comprising an active agent which is intended for administration to a subject, e.g., a mammal.

In some embodiments, the active agent is present in the pharmaceutical composition at a purity level suitable for administration to a patient. In some embodiments, the active agent has a purity level of at least about 90%, about 91%, about 92%, about 93%, about 94%, about 95%, about 96%, about 97%, about 98% or about 99%, and a pharmaceutically acceptable diluent, carrier or excipient. In some embodiments, the compositions contain an active agent at a concentration of about 0.001 to about 30.0 mg/ml.

In various aspects, the pharmaceutical compositions comprise a pharmaceutically acceptable carrier. As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The pharmaceutical composition can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, watermiscible cosolvents, water softeners, or wetting agents. See, e.g., the *Handbook of Pharmaceutical Excipients*, Third Edition, A. H. Kibbe (Pharmaceutical Press, London, U K, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

In various aspects, the pharmaceutical composition comprises formulation materials that are nontoxic to recipients at the dosages and concentrations employed. In specific embodiments, pharmaceutical compositions comprising an active agent and one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents. In various aspects, the pharmaceutical composition comprises one or more polyols and/or one or more surfactants, optionally, in addition to one or more excipients, including but not limited to, pharmaceutically acceptable salts; osmotic balancing agents (tonicity agents); anti-oxidants; antibiotics; antimycotics; bulking agents; lyoprotectants; anti-foaming agents; chelating agents; preservatives; colorants; and analgesics.

In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides, salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

The pharmaceutical compositions can be formulated to achieve a physiologically compatible pH. In some embodiments, the pH of the pharmaceutical composition can be for example between about 4 or about 5 and about 8.0 or about 4.5 and about 7.5 or about 5.0 to about 7.5. In various embodiments, the pH of the pharmaceutical composition is between 5.5 and 7.5.

The present disclosure provides methods of producing a pharmaceutical composition. In various aspects, the method comprises combining the antigen-binding protein, conjugate, fusion protein, nucleic acid, vector, host cell, or a combination thereof, with a pharmaceutically acceptable carrier, diluent, or excipient.

Routes of Administration

With regard to the present disclosure, the active agent, or pharmaceutical composition comprising the same, can be administered to the subject via any suitable route of administration. For example, the active agent can be administered to a subject via parenteral, nasal, oral, pulmonary, topical, vaginal, or rectal administration. The following discussion on routes of administration is merely provided to illustrate various embodiments and should not be construed as limiting the scope in any way.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the active agent of the present disclosure in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the present disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Dosages

The active agents of the disclosure are believed to be useful in methods of inhibiting tumor growth, as well as other methods, as further described herein, including methods of treating or preventing cancer. For purposes of the disclosure, the amount or dose of the active agent administered should be sufficient to effect, e.g., a therapeutic or prophylactic response, in the subject or animal over a reasonable time frame. For example, the dose of the active agent of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which cancer is treated upon administration of a given dose of the active agent of the present disclosure to a mammal among a set of mammals, each set of which is given a different dose of the active agent, could be used to determine a starting dose to be administered to a mammal. The extent to which cancer is treated upon administration of a certain dose can be represented by, for example, the extent of tumor regression achieved with the active agent in a mouse xenograft model. Methods of assaying tumor regression are known in the art and described herein in EXAMPLES.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the present disclosure, the dose of the active agent of the present disclosure can be about 0.0001 to about 1 g/kg body weight of the subject being treated/day, from about 0.0001 to about 0.001 g/kg body weight/day, or about 0.01 mg to about 1 g/kg body weight/day.

Controlled Release Formulations

In some embodiments, the active agents described herein can be modified into a depot form, such that the manner in which the active agent of the present disclosure is released into the body to which it is administered is controlled with respect to time and location within the body (see, for example, U.S. Pat. No. 4,450,150). Depot forms of active agents of the present disclosure can be, for example, an implantable composition comprising the active agents and a porous or non-porous material, such as a polymer, wherein the active agent is encapsulated by or diffused throughout the material and/or degradation of the non-porous material. The depot is then implanted into the desired location within the body of the subject and the active agent is released from the implant at a predetermined rate.

The pharmaceutical composition comprising the active agent in certain aspects is modified to have any type of in vivo release profile. In some aspects, the pharmaceutical composition is an immediate release, controlled release, sustained release, extended release, delayed release, or biphasic release formulation. Methods of formulating peptides for controlled release are known in the art. See, for example, Qian et al., J Pharm 374: 46-52 (2009) and International Patent Application Publication Nos. WO 2008/130158, WO2004/033036; WO2000/032218; and WO 1999/040942.

The instant compositions can further comprise, for example, micelles or liposomes, or some other encapsulated form, or can be administered in an extended release form to provide a prolonged storage and/or delivery effect.

Use

The antigen-binding proteins of the present disclosure are useful for inhibiting tumor growth. Without being bound to a particular theory, the inhibiting action of the antigen-binding proteins provided herein allow such entities to be useful in methods of treating cancer.

Accordingly, provided herein are methods of inhibiting tumor growth in a subject and methods of reducing tumor size in a subject. In various embodiments, the methods comprise administering to the subject the pharmaceutical composition of the present disclosure in an amount effective for inhibiting tumor growth or reducing tumor size in the subject. In various aspects, the growth of an ovarian tumor, melanoma tumor, bladder tumor, or endometrial tumor is inhibited. In various aspects, the size of an ovarian tumor, melanoma tumor, bladder tumor, or endometrial tumor is reduced.

As used herein, the term "inhibit" or "reduce" and words stemming therefrom may not be a 100% or complete inhibition or reduction. Rather, there are varying degrees of inhibition or reduction of which one of ordinary skill in the art recognizes as having a potential benefit or therapeutic effect. In this respect, the antigen-binding proteins of the present disclosure may inhibit tumor growth or reduce tumor size to any amount or level. In various embodiments, the inhibition provided by the methods of the present disclosure is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition). In various embodiments, the reduction provided by the methods of the present disclosure is at least or about a 10% reduction (e.g., at least or about a 20% reduction, at least or about a 30% reduction, at least or about a 40% reduction, at least or about a 50% reduction, at least or about a 60% reduction, at least or about a 70% reduction, at least or about a 80% reduction, at least or about a 90% reduction, at least or about a 95% reduction, at least or about a 98% reduction).

Additionally provided herein are methods of treating a subject with cancer, e.g., CLDN18.2-expressing cancer. In various embodiments, the method comprises administering to the subject the pharmaceutical composition of the present disclosure in an amount effective for treating the cancer in the subject.

For purposes herein, the cancer of the methods disclosed herein can be any cancer, e.g., any malignant growth or tumor caused by abnormal and uncontrolled cell division that may spread to other parts of the body through the lymphatic system or the blood stream. The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In various aspects, the cancer is pancreatic cancer, gastrointestinal cancer, bladder cancer, colon cancer, lung cancer, liver cancer, endometrial cancer. In various aspects, the cancer is any cancer characterized by moderate to high expression of CLDN18.2. See, e.g., FIG. 1-FIG. 2. In various aspects, the cancer is acute myeloid leukemia, large B-cell lymphoma, stomach cancer, prostate cancer, melanoma, colon cancer, rectal cancer, bladder cancer, cervical cancer, liver cancer, breast cancer, kidney clear cell carcinoma, head and neck cancer, sarcoma, kidney chroinophobe cancer, lower grade glioma, adrenocortical cancer, glioblastoma, kidney papillary cell carcinoma, lung squamous cell carcinoma, thyroid cancer, lung adenocarcinoma, pancreatic cancer, endometroid cancer, uterine carcinsarcoma, or ovarian cancer. In various aspects, the cancer is selected from pancreatic cancer, gastrointestinal cancer, bladder cancer, colon cancer, lung cancer, liver cancer, ovarian cancer, endometrioid cancer, uterine cancer, lung cancer, gastric cancer, breast cancer Head and Neck Squamous Cell Carcinoma (IINSCC) cancer, and cervical cancer.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the method of the present disclosure can include treatment of one or more conditions or symptoms or signs of the cancer being treated. Also, the treatment provided by the methods of the present disclosure can encompass slowing the progression of the cancer. For example, the methods can treat cancer by virtue of enhancing the T cell activity or an immune response against the cancer, reducing tumor or cancer growth, reducing metastasis of tumor cells, increasing cell death of tumor or cancer cells, and the like. In various aspects, the methods treat by way of delaying the onset or recurrence of the cancer by at least 1 day, 2 days, 4 days, 6 days, 8 days, 10 days, 15 days, 30 days, two months, 3 months, 4 months, 6 months, 1 year, 2 years, 3 years, 4 years, or more. In various aspects, the methods treat by way increasing the survival of the subject.

The antigen binding proteins of the present disclosure also may be used to detect CLDN18.2 in a sample or diagnose a CLDN18.2-positive cancer. Therefore, the present disclosure provides methods of detecting CLDN18.2 in a sample. In various embodiments, the method comprises contacting the sample with an antigen-binding protein, a conjugate, or a fusion protein, as described herein, and assaying for an immunocomplex comprising the antigen-binding protein, conjugate or fusion protein bound to CLDN18.2. The present disclosure also provides methods of diagnosing a CLDN18.2-positive cancer in a subject. In various embodiments, the method comprises contacting a biological sample comprising cells or tissue obtained from the subject with an antigen-binding protein, a conjugate, or a fusion protein, as described herein, and assaying for an immunocomplex comprising the antigen-binding protein, conjugate or fusion protein bound to CLDN18.2.

Subjects

In some embodiments of the present disclosure, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human.

Kits

In some embodiments, the antigen-binding proteins of the present disclosure are provided in a kit. In various aspects, the kit comprises the antigen-binding protein(s) as a unit dose. For purposes herein "unit dose" refers to a discrete amount dispersed in a suitable carrier. In various aspects, the unit dose is the amount sufficient to provide a subject with a desired effect, e.g., inhibition of tumor growth, reduction of tumor size, treatment of cancer. Accordingly, provided herein are kits comprising an antigen-binding protein of the present disclosure optionally provided in unit doses. In various aspects, the kit comprises several unit doses, e.g., a week or month supply of unit doses, optionally, each of which is individually packaged or otherwise separated from other unit doses. In some embodiments, the components of the kit/unit dose are packaged with instructions for administration to a patient. In some embodiments, the kit comprises one or more devices for administration to a patient, e.g., a needle and syringe, and the like. In some aspects, the antigen-binding protein of the present disclosure, a pharmaceutically acceptable salt thereof, a conjugate comprising the antigen-binding protein, or a multimer or dimer comprising the antigen-binding protein, is pre-packaged in a ready to use form, e.g., a syringe, an intravenous bag, etc. In some aspects, the kit further comprises other therapeutic or diagnostic agents or pharmaceutically acceptable carriers (e.g., solvents, buffers, diluents, etc.), including any of those described herein. In particular aspects, the kit comprises an antigen-binding protein of the present disclosure, along with an agent, e.g., a therapeutic agent, used in chemotherapy or radiation therapy.

Various Embodiments

In various embodiments of the present disclosure, the antigen-binding protein binds to a human CLDN18.2 protein (SEQ ID NO: 1), wherein (a) the antigen-binding protein binds to Extracellular Loop 1 (EL1) of an extracellular domain (ECD) of CLDN 18.2 and does not bind to Extracellular Loop 2 (EL2) of the ECD of CLDN 18.2; or (b) does not bind to Claudin 18.1 (CLDN 18.1), or any other claudin protein, and binds to CLDN 18.2 endogenously expressed by HUPT4 cells with an affinity greater than 1.5 times that of a reference antibody; or (c) a combination thereof. In various embodiments, the antigen binding protein herein binds to a cell endogenously expressing CLDN18.2 (e.g., HUPT4 or other cell) with an affinity at least 1.5, 2.0, 2.5, 3.0, 3.5, 4.0, 4.5, or 5.0 or more tunes greater than a references antibody.

In various instances, the antigen-binding protein binds to an epitope within the amino acid sequence of GLWRSCVRESSGFTECRFYFTL (SEQ ID NO: 4), QGLWRSCVRESSGFTECRGYFTLK (SEQ ID NO: 5), DQWSTQDLYNNPVTAVFNYQG LWRSC (SEQ ID NO: 6) or CRGYFTLLFLPAMLQAVR (SEQ ID NO: 7) of CLDN 18.2.

In various embodiments, the antigen-binding protein comprises (a) a heavy chain (CDR) 1 amino acid sequence set forth in Table A or a sequence selected from the group consisting of: SEQ ID NOs: 64, 88, 69, 89, 72, 75, 91, 94, 9.5, 97, 99, 101, 103, 106, 109; or a variant sequence thereof which differs by only one or two amino acids or which has at least or about 70% (e.g., at least about 80%, at least about 85%, at least about 90%, at least about 95%) sequence identity; (b) an HC CDR2 amino acid sequence set forth in Table A or a sequence selected from the group consisting of: SEQ ID NOs: 65, 67, 70, 90, 73, 76, 92, 73, 96, 98, 100, 102, 104, 107, 110; or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A or a sequence selected from the group consisting of: SEQ ID NOs: 66, 68, 71, 77, 74, 77, 93, 74, 105, 108, 111; or a variant sequence thereof which differs by only one or two amino acids or which has at least or about 70% (e.g., at least about 80%, at least about 85%, at least about 90%, at least about 95%) sequence identity; (d) a light chain (LC) CDR1 amino acid sequence set forth in Table A or a sequence selected from the group consisting of: SEQ ID NOs: 78, 81, 82, 86, 114, 120, 123, 126; or a variant sequence thereof which differs by only one or two amino acids or which has at least or about 70%/o (e.g., at least about 80%, at least about 85%, at least about 90%, at least about 95%) sequence identity; (e) an LC CDR2 amino acid sequence set forth in Table A or a sequence selected from the group consisting of: SEQ ID NOs: 79, 112, 79, 84, 116, 118, 119, 129, 121, 124, 127; or a variant sequence thereof which differs by only one or two amino acids or which has at least or about 70% (e.g., at least about 80%, at least about 85%, at least about 90%, at least about 95%) sequence identity; (t) an LC CDR3 amino acid sequence set forth in Table A or a sequence selected from the group consisting of: SEQ ID NOs: 80, 83, 113, 85, 87, 115, 117, 122, 125, 128 or a variant sequence thereof which differs by only one or two amino acids or which has at least or about 70% (e.g., at least or about 85%, at least or about 90%) sequence identity; (g) a combination of any two or more of (a)-(t).

In various aspects, the antigen-binding protein comprises a light chain CDR1 amino acid sequence, a light chain CDR2 amino acid sequence, and a light chain CDR3 amino acid sequence set forth in Table A and 1 or 2 of the heavy chain CDR amino acid sequences set forth in Table A. In some instances, the antigen-binding protein comprises a heavy chain CDR1 amino acid sequence, a heavy chain CDR2 amino acid sequence, and a heavy chain CDR3 amino acid sequence set forth in Table A and 1 or 2 of the light chain CDR amino acid sequences set forth in Table A. In various aspects, the antigen-binding protein comprises six CDR amino acid sequences selected from the group consisting of: (a) SEQ ID NOs: 78, 79, 80, 64, 65, 66; (b) SEQ ID NOs: 81, 112, 80, 88, 65, 66; (c) SEQ ID NOs: 81, 79, 80, 64, 67, 68; (d) SEQ ID NOs: 82, 79, 83, 39, 70, 71; (e) SEQ ID NOs: 81, 79, 113, 89, 90, 77; (f) SEQ ID NOs: 81, 84, 85, 72, 73, 74; (g) SEQ ID NOs: 86, 79, 87, 75, 76, 77; (h) SEQ ID NOs. 114, 79, 115, 91, 92, 93; (i) SEQ ID NOs: 81, 116, 117, 94, 73, 74; (j) SEQ ID NOs: 81, 118, 117, 95, 96, 74; (k) SEQ ID NOs: 81, 119, 117, 97, 98, 74; (1) SEQ ID NOs: 81, 118, 85, 99, 100, 74; (m) SEQ ID NOs: 81, 129, 117, 101, 102, 74; (n) SEQ ID NOs: 120, 121, 122, 103, 104, 105; (o) SEQ ID NOs: 123, 124, 125, 106, 107, 108; and (p) SEQ ID NOs: 126, 127, 128, 109, 110, 111.

In various aspects, the antigen-binding protein of comprises (a) a heavy chain variable region amino acid sequence set forth in in Table B or a sequence selected from the group consisting of: SEQ ID NOs: 10, 12, 14, 16, 18, 20, 22, 24, 26, 28, 30, 2, 34, 36, 38 and 40, or a variant sequence thereof which differs by only one or two amino acids or which has at least or about 70% (e.g., at least or about 85%, at least or about 90%) sequence identity; or (b) a light chain variable region amino acid sequence set forth in in Table B or a sequence selected from the group consisting of: SEQ ID NOs: 11, 13, 15, 17, 19, 21, 23, 25, 27, 29, 31, 33, 35, 37, 39 and 41, or a variant sequence thereof which differs by only one or two amino acids or which has at least or about 70% (e.g., at least or about 85%, at least or about 90%) sequence identity; or both (a) and (b). In various aspects, the antigen-binding protein comprises a pair of amino acid sequences selected from the group consisting of: (a) SEQ ID NOs: 10 and 11; (b) SEQ ID NOs: 12 and 13; (c) SEQ ID NOs: 14 and 15; (d) SEQ ID NOs: 16 and 17; (e) SEQ ID NOs: 18 and 19; (f) SEQ ID NOs: 20 and 21; (g) SEQ ID NOs: 22 and 23; (h) SEQ ID NOs: 24 and 25; (i) SEQ ID NOs: 26 and 27; (j) SEQ ID NOs: 28 and 29; (k) SEQ ID NOs: 30 and 31; (1) SEQ ID NOs: 32 and 33; (m) SEQ ID NOs: 34 and 35; (n) SEQ ID NOs: 36 and 37; (o) SEQ ID NOs: 38 and 39; (p) SEQ ID NOs: 40 and 41.

In various embodiments, the antigen-binding protein comprises (a) a heavy chain variable region amino acid sequence set forth in in Table C, Table D, Table 6, Table 8, Table 9, Table 10, or a sequence selected from the group consisting of: SEQ ID NOs: 42, 46, 49, 52, 55, 56, 57, and 131, or a variant sequence thereof which differs by only one or two amino acids or which has at least or about 70%, or about 80%, or about 90%, or about 95% sequence identity; or (b) a light chain variable region amino acid sequence set forth in Table C, Table D, Table 6, Table 8, Table 9, Table 10, or a sequence selected from the group consisting of: SEQ ID NOs: 43-45, 47-48, 50-51, 53-54, 130, 132, 147, 149, and 150, or a variant sequence thereof which differs by only one or two amino acids or which has at least or about 70%, or about 80%, or about 90%, or about 95% sequence identity; or (c) both (a) and (b). In various aspects, the antigen-binding protein comprises a pair of amino acid sequences as listed in Table D.

In various aspects the antigen-binding protein of the present disclosure comprises a pair of amino acid sequences selected from the group consisting of: (a) SEQ ID NOs: 42 and 43; (b) SEQ ID NOs: 42 and 44; (c) SEQ ID NOs: 42 and 45; (d) SEQ ID NOs: 46 and 47; (e) SEQ ID NOs: 46 and 48; (f) SEQ ID NOs: 131 and 149; (g) SEQ ID NOs: 131 and 150; (h) SEQ ID NOs: 52 and 53; (i) SEQ ID NOs: 52 and 54; (j) SEQ ID NOs: 55 and 53; (k) SEQ ID NOs: 55 and 54; (l) SEQ ID NOs: 56 and 53; (m) SEQ ID NOs: 56 and 54; (n) SEQ ID NOs: 57 and 50; (o) SEQ ID NOs: 57 and 51; (p) SEQ ID NOs: 49 and 50; (q) SEQ ID NOs: 49 and 51; (r) SEQ ID NO: 42 and 130; (s) SEQ ID NO: 131 and 147; and (t) SEQ ID NO: 131 and 132.

In some embodiments, the antigen-binding protein of the present disclosure comprises a Fc polypeptide. In some embodiments, the antigen-binding protein of the present disclosure comprises a Fc polypeptide comprising an afucosylated glycan.

In various aspects, the antigen-binding protein of the present disclosure is an antibody, e.g., a monoclonal antibody. In various instances, the antigen-binding protein is an IgG. In various aspects, the antigen-binding protein inhibits at least about 50% colony growth in a soft agar 3D proliferation assays or inhibits tumor growth in xenograft mice injected with human cancer cells. In various aspects, the antigen-binding protein inhibits tumor growth of in xenograft mice injected with ovarian cancer cells, melanoma cancer cells, bladder cancer cells, or endometrial cancer cells. In various instances, the antigen-binding protein inhibits at least 50% tumor growth in xenograft mice injected with ovarian cancer cells, bladder cancer cells, or endometrial cancer cells.

The present disclosure provides a bispecific antigen-binding protein that binds CLDN18.2 and a second antigen, wherein the antigen-binding protein that binds CLDN18.2 is any one of the antigen-binding protein described herein. In some embodiments, the bispecific antigen-binding protein comprises: (a) a heavy chain variable region amino acid sequence set forth in Table B, Table C, Table D, Table 6, Table 8, Table 9, Table 10, or a variant sequence thereof which differs by only one or two amino acids or which has at least or about 70% sequence identity; (b) a light chain variable region amino acid sequence set forth in Table B, Table D, Table 6, Table 8, Table 9, Table 10, or a variant sequence thereof which differs by only one or two amino acids or which has at least or about 70% sequence identity; or (c) both (a) and (b). In some embodiments, the variant sequence has at least about 75%, 80%, 85%, 90%, 95%, 96%, 97%, 98%, 99%, or 100% sequence identity. In some embodiments, the bispecific antigen-binding protein comprises a Fc polypeptide. In some embodiments, the bispecific antigen-binding protein comprises a Fc polypeptide comprising an afucosylated glycan.

In various aspects, a bispecific antigen-binding protein binds CLDN18.2 and a second antigen. In some embodiments, a bispecific antigen-binding protein comprises an antigen-binding fragment of an antibody specific for the second antigen. In various embodiments, the second antigen is a cell surface protein expressed by a T cell, optionally a component of the T-cell receptor (TCR), for example CD3. In some embodiments, the second antigen is CD3. In some embodiments, the second antigen is CD3E.

In various embodiments, the second antigen is a costimulatory molecule which assists in T-cell activation, e.g., CD40 or 4-1BB (CD137). In various embodiments, the second antigen is an Fc receptor, optionally, a Fc gamma receptor, Fc-alpha receptor, or Fc-epsilon receptor. In some embodiments, the Fc receptor is CD64 (Fc-gamma RI), CD32 (Fc-gamma RIIA), CD16A (Fc-gamma RIIIA), CD16b (Fc-gamma RIIIb), FcεRI, CD23 (Fc-epsilon RI), CD89 (Fc-epsilon RI), Fcα/μR, or FcRn. In some embodiments, the Fc receptor is CD16A.

In various embodiments, the second antigen is an immune checkpoint molecule, e.g., a protein involved in the immune checkpoint pathway, optionally, A2AR, B7-H3, B7-H4, BTLA, CTLA4, 1130, KIR, LAG3, NOX2, PD-1, TIM3, VISTA, or SIGLEC7. In some embodiments, the immune checkpoint molecule is PD-1, LAG3, TIM3, or CTLA4. In various embodiments, the bispecific antigen-binding protein comprises an scFv, a Fab, or a F(ab)2' of any of the presently disclosed CLDN18.2 antibodies (e.g., Table B, Table C, Table D, Table 6, Table 8, FIG. 13, or FIG. 17).

In various embodiments, the bispecific antigen-binding protein comprises an antigen-binding protein comprising a sequence set forth in Table 11 or SEQ ID NO: 143, 144, 145, or 146, or a variant sequence thereof which differs by only 1-5 amino acids or which has at least or about 70% sequence identity. In some embodiments, the variant sequence has at least or about 75%, 80%, 85% 90%, 95%, 96%, 97%, 98%, 99%, or 100% sequence identity. In various embodiments, the bispecific antigen-binding protein comprises a structure of a nanobody, a diabody, a BiTE®, DART, TandAb, CrossMab, or HSAbody. The present disclosure provides a conjugate comprising an antigen-binding protein or a bispecific antigen-binding protein described herein and a heterologous moiety. In some embodiments, the antigen-binding protein comprises the amino acid sequence set forth in SEQ ID NO: 42 and SEQ ID NO: 45. In some embodiments, the conjugate comprises a cytotoxic agent or a chemotherapeutic agent. In some embodiments, the chemotherapeutic agent is an anti-mitotic agent which inhibits cell division by blocking tubulin polymerization. In some embodiments, the anti-mitotic agent is an auristatin. In some embodiments, the auristatin is MMAE.

In various embodiments, the conjugate of the present disclosure is conjugated to the antigen-binding protein via a cleavable linker. In some embodiments, the cleavable linker is MC-VC-PAB.

In some embodiments, the conjugate comprises an antigen-binding protein that is an antibody, i.e., the conjugate is an antibody conjugate. In some embodiments, the antibody is a monoclonal antibody, optionally wherein the monoclonal antibody is an IgG antibody. In some embodiments, the antibody is a human antibody, humanized antibody, or a chimeric antibody.

In various embodiments, the conjugate of the present disclosure has an average number of units of the agent conjugated per antigen-binding protein in a range of 1 to 8, preferably wherein the average number of units of the agent conjugated per antigen-binding protein is in a range of 3-8.

In some embodiments, the conjugate is a heterogeneous conjugate. In other embodiments, the conjugate is a homogeneous conjugate. In some embodiments, the conjugate comprises a heterologous moiety or an agent, wherein the agent is conjugated at a specific site of the antigen-binding protein. In some embodiments, the specific site is an unpaired cysteine residue. In some embodiments, the conjugate comprises a polypeptide comprising the amino acid set forth in SEQ ID NO: 42 and SEQ ID NO: 45 conjugated to MC-VC-PAB-MMAE.

The present disclosure also provides a fusion protein comprising an antigen-binding protein or a bispecific antigen-binding protein described herein. The present disclosure further provides a nucleic acid comprising a nucleotide sequence encoding an antigen-binding protein, a bispecific antigen-binding protein, a conjugate, or a fusion protein, of the present disclosure. The present disclosure provides a vector comprising the nucleic acid comprising a nucleotide sequence encoding an antigen binding protein, a conjugate, or a fusion protein, of the present disclosure. The present disclosure additionally provides a host cell comprising the nucleic acid or the vector of the present disclosure.

The present disclosure provides a method of producing an antigen-binding protein or a bispecific antigen-binding protein that binds to a Claudin18.2 (CLDN18.2) protein, comprising (i) culturing the host cell of the present disclosure in a cell culture medium, wherein the host cell comprises a nucleic acid comprising a nucleotide sequence encoding an antigen binding protein or a bispecific antigen-binding protein described herein, and (ii) harvesting the antigen-binding protein or a bispecific antigen-binding protein from the cell culture medium. Also, provided is a method of producing a fusion protein comprising an antigen-binding protein or a bispecific antigen-binding protein that binds to a Claudin18.2 (CLDN18.2) protein, comprising (i) culturing the host cell of the present disclosure in a cell culture medium, wherein the host cell comprises a nucleic acid comprising a nucleotide sequence encoding a fusion protein of the present disclosure, and (ii) harvesting the fusion protein from the cell culture medium.

The present disclosure furthermore provides a method of producing a pharmaceutical composition comprising combining an antigen-binding protein, a bispecific antigen-binding protein, a conjugate, a fusion protein, a nucleic acid, a vector, a host cell, of the present disclosure, or a combination thereof, and a pharmaceutically acceptable carrier, diluent or excipient. Also provided are pharmaceutical compositions comprising antigen-binding protein, a bispecific antigen-binding protein, a conjugate, a fusion protein, a nucleic acid, a vector, a host cell, of the present disclosure, or a combination thereof, and a pharmaceutically acceptable carrier, diluent or excipient.

Provided herein is a method of treating a subject with a CLDN18.2-expressing cancer comprising administering to the subject a pharmaceutical composition described herein in an amount effective to treat the cancer. Also provided is a method of inhibiting tumor growth in a subject, comprising administering to the subject a pharmaceutical composition described herein in an amount effective to inhibit tumor growth. The present disclosure provides a method of reducing tumor size in a subject, comprising administering to the subject a pharmaceutical composition described herein in an amount effective to reduce tumor size. Further provided is a method of preventing the recurrence of cancer in a subject, comprising administering to the subject a pharmaceutical composition described herein in an amount effective to prevent the recurrence of cancer.

The present disclosure provides a method of detecting Claudin18.2 (CLD18.2) in a sample, comprising contacting the sample with an antigen-binding protein, a bispecific antigen-binding protein, a conjugate, or a fusion protein, of the present disclosure, and assaying for an immunocomplex comprising the antigen-binding protein, conjugate or fusion protein bound to CLD18.2. Also provided herein is a method of diagnosing a Claudin18.2 (CLD18.2)-positive cancer in a subject, comprising contacting a biological sample comprising cells or tissue obtained from the subject with an antigen-binding protein, a bispecific antigen-binding protein, a conjugate, or a fusion protein, of the present disclosure, and assaying for an immunocomplex comprising the antigen-binding protein, conjugate or fusion protein bound to CLD 18.2.

The present disclosure also provides a method of treating cancer in a subject diagnosed to be a low over-expresser of CLDN18.2. In various embodiments, the method comprises administering to the subject a presently disclosed pharmaceutical composition in an amount effective to prevent the recurrence of cancer. In some aspects, the administering induces apoptosis in tumor cells, optionally, the administering induces apoptosis in cells expressing CLDN18.2. In various aspects, the subject has a tumor and the tumor is semi-quantitatively categorized into one of four groups: high expressers, moderate expressers, low expressers, and non-expressers. In various instances, high expressers are defined as CLDN8.2 RNA greater than 12 log Fragments Per Kilobase Million (FPKM), wherein the CLDN8.2 RNA is measured by RNASeq, or CLDN 18.2 protein levels are greater than 3+ as measured by immunohistochemistry (IHC). In various instances, moderate expressers are defined as CLDN8.2 RNA greater than 10 log FPKM, wherein the CLDN18.2 RNA is measured by RNASeq, or CLDN18.2 protein levels are greater than 2+ as measured by IHC. In various instances, low expressers are defined as CLDN18.2 RNA greater than 6 log FPKM, wherein the CLDN8.2 RNA is measured by RNASeq, or CLDN18.2 protein levels are greater than 1+ as measured by IHC. In various instances, non-expressers are defined as CLDN8.2 RNA less than than 6 log FPKM, wherein the CLDN18.2 RNA is measured by RNASeq, or CLDN 18.2 protein levels are below IHC detection limits. In various aspects, the subject having said tumor is likewise described as a high expresser, moderate expresser, low expresser, or non-expresser of CLDN18.2.

The following examples are given merely to illustrate the present disclosure and not in any way to limit its scope.

EXAMPLES

Example 1

This example demonstrates an analysis of CLDN18.2 RNA levels in different cell and tissue sources.

In order to establish a baseline for expression of CLDN18.2 in different source materials, expression levels of CLDN18.2 expression in patient samples and cell lines created by the Translational Oncology Research laboratory (TORL) were assayed.

Levels of CLDN8.2 RNA in patient samples were measured using information contained in The Cancer Genome Atlas (TCGA) database managed by the National Cancer Institute (NCI). CLDN18.2 levels in normal tissue were measured using information in the Genotype-Tissue Expression (GTEX) database maintained by the Common Fund. The analysis of tissues from the GTEX database showed that CLDN18.2 is detectable in various sites, including the lung, stomach, prostate, colon, pancreas, and breast, among other tissues.

Figure 2:
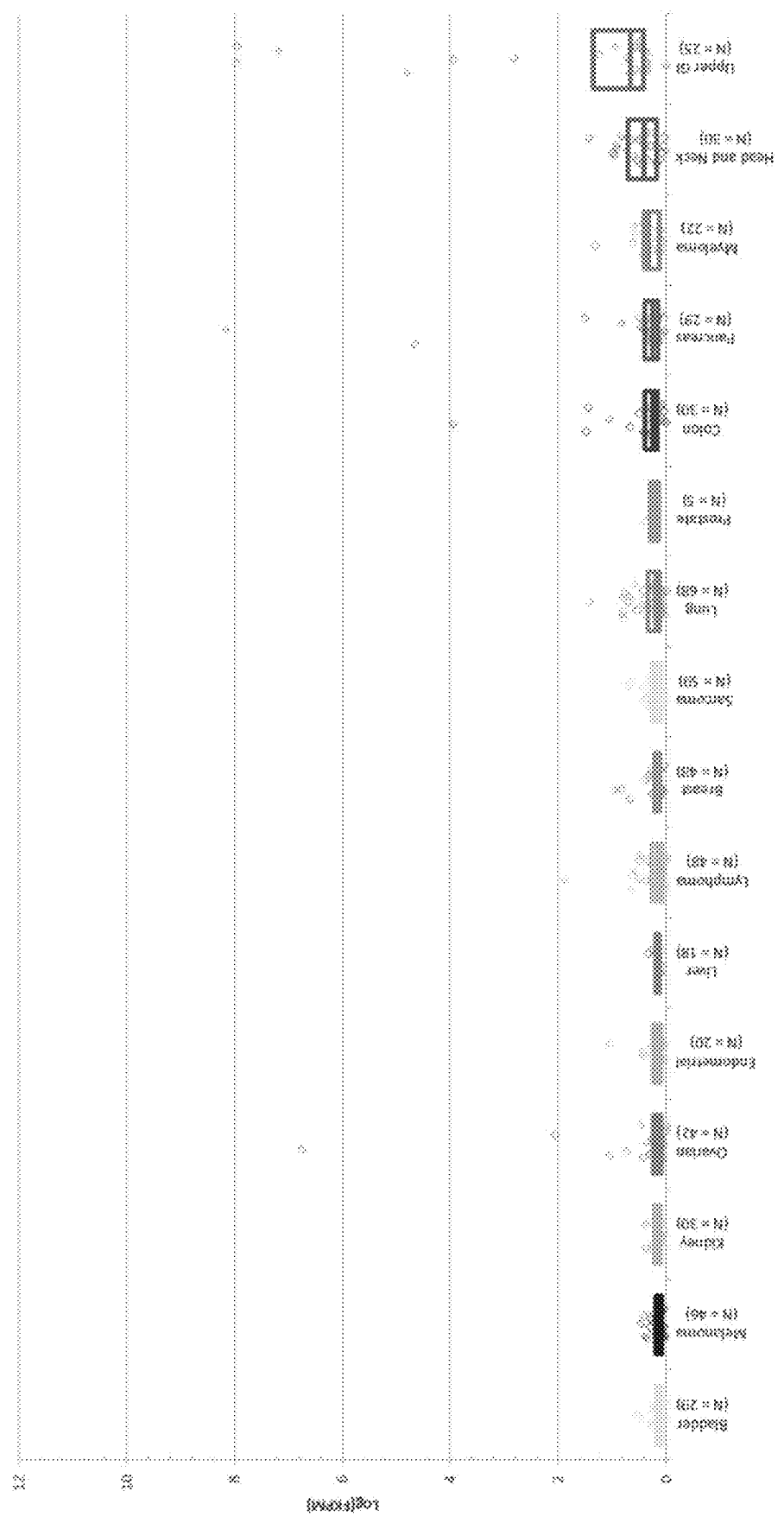
FIG. 2 represents a graph of CLDN18.2 expression in additional cancer types.

CLDN 18.2 expression levels were measured in TORL cancer cell lines using Agilent 44K microarrays (4×44K array chip, Agilent Technologies, Santa Clara, Calif.) and RNA sequencing (RNA-Seq) assays. RNASeq was performed by BGI Americas (Cambridge, Mass.) using their "RNASeq for quantification" service. As shown in FIG. 1 and FIG. 2, upper gastrointestinal (GI), pancreas and colon cancer cells expressed the highest levels of CLDN18.2, though CLDN18.2 expression levels were detectable in head and neck, melanoma, breast, lung, prostate, sarcoma and lymphoma cancer cells.

Figure 4:
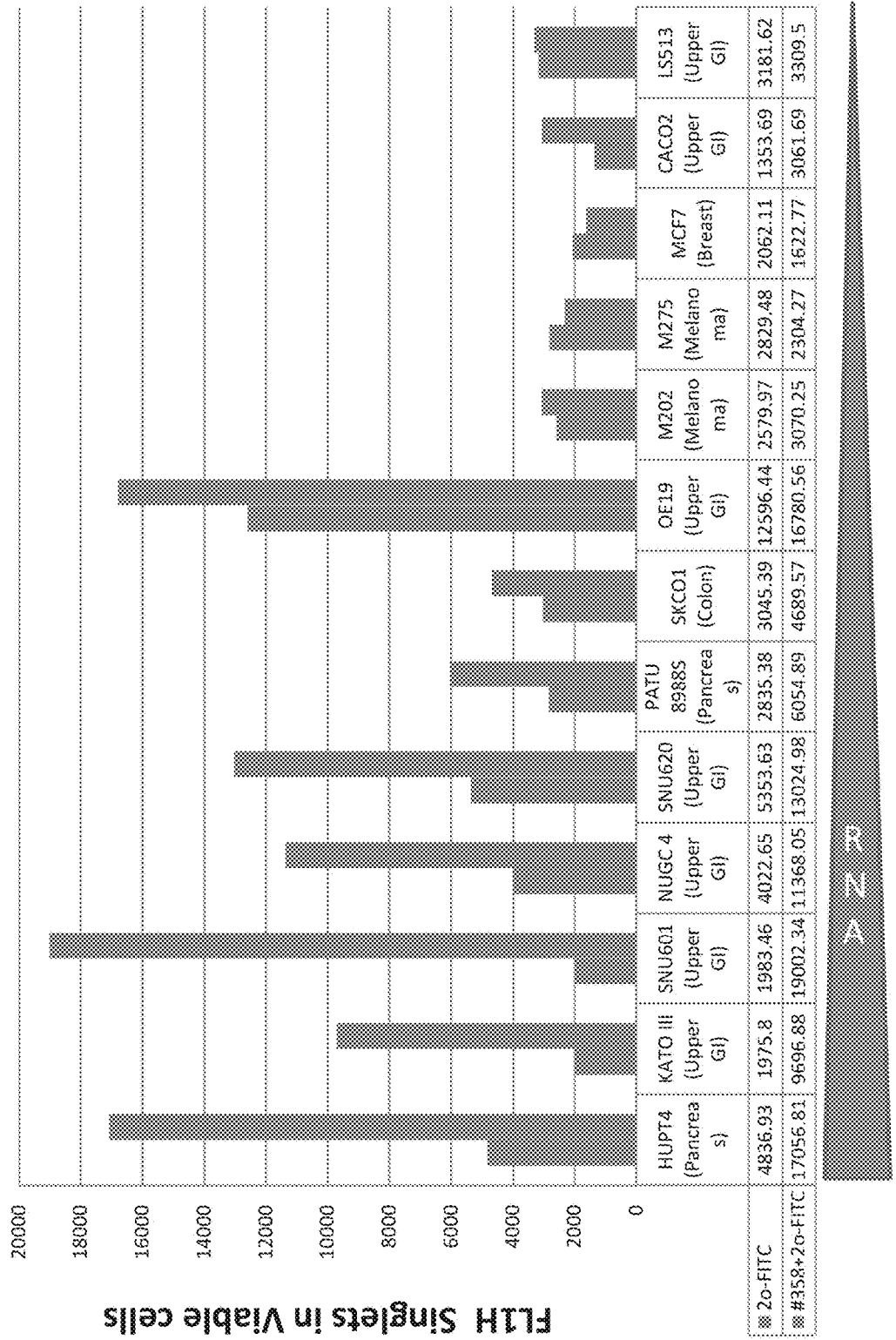
FIG. 4 illustrates the ability of an anti-CLDN18.2 antibody described herein to detect CLDN18.2 on the surface of cancer cells lines endogenously expressing CLDN18.2.

FIG. 3 shows that those cells that are high CLDN 18.2 expressers do not express CLDN18.1. FIG. 4 shows the distribution of native cell lines expressing CLDN18.2, and demonstrates cells that are CLDN18.2 RNA positive have positive flow signal.

Example 2

This example demonstrates the production of cells engineered to overexpress CLDN18.2.

Models engineered to overexpress CLDN18.2 were generated. These models were used to determine the efficacy of CLDN18.2 antibodies described herein. Briefly, a nucleotide sequence encoding CLDN18.2 was engineered into a lentiviral vector having a CMV promoter and an attenuated Internal ribosome entry site (IRES) of encephalomyocarditis virus (EMCV). The IRES was located between the Gene of Interest (GOI) cDNA (CLDN18.2) and puromycin cDNA. A woodchuck posttranscriptional regulatory element (WPRE) was located downstream of the puromycin cDNA. The vector also expressed either a GFP marker sequence or a MycDDK tag.

The expression vector was virally transduced into HEK293T cells (for screening purposes) and NIH3T3 cells (for immunizations). Positively transduced cells were selected based on survival in medium containing puromycin (1 mg/ml). The positive cells were subcloned to obtain a stable, uniform, clonal population of CLDN18.2 overexpressing cells.

Subclone CLDN18.2 expression was confirmed by fluorescence microscopy using a GFP tag to confirm overexpression of CLDN 18.2.

Example 3

This example demonstrates the production of reference and control antibodies.

Benchmark (reference) CLDN 18.2-specific antibodies and control antibodies were made by cloning the antibody heavy and light chain variable regions into the ExpiCHO™ expression system (ThermoFisher Scientific, Waltham, Mass.) to produce recombinant mouse IgG2A chimeric antibodies. These antibodies were tested alongside newly generated CLDN18.2 specific antibodies described in Example 5.

Briefly, plasmids containing the control and benchmark antibody sequences were transfected using the ExpiCHO™ Expression System (Catalog Number A29133, ThennoFisher Scientific, USA) according to the manufacturer's protocol. The cells were cultured at 37° C. and 8% $CO_2$ at day 1 and then at 32° C. and 5% $CO_2$ post-transfection in media provided in the kit. Antibodies were purified by clarifying the ExpiCHO™ culture medium by centrifugation at 1,000 g for 10 min followed by 5,000 g for 30 min. The supernatant was then filtered using a 0.451 μm filter followed by a 0.22 μm filter. Subsequently, the supernatant was subjected to affinity purification using protein A/G resins (Life Technologies, Carlsbad, Calif.; Catalog #20424) according to the manufacturer's protocol. Prior to EL1SA purification, antibody titer in the culture medium was roughly determined to ensure the amount of medium loaded occupied less than 80% of the resin binding capacity. After incubation, the resins were washed with PBS and eluted with Elution Buffer (Life Technologies, Catalog #21004). The elution fractions were immediately adjusted to physiologic pH by adding Tris Buffer, pH8.0. The purified antibodies were subsequently subjected to buffer exchange and protein concentration using Amicon Ultra-15 Centrifugal Filter Unit (Life Technologies, Catalog # UFC900324) in PBS buffer. Antibody concentration was determined by BCA Protein Assay. SDS-PAGE and Coomassie-staining were carried out to test the antibody purity. The purified protein was aliquoted and stored at −80° C. for long time storage or kept at 4° C. for immediate use.

The integrity of the antibody was validated by SDS-PAGE followed by Coomassie staining under non-reducing vs reducing conditions; under non-reducing condition, one dominating band around 150 kDa, whereas under reducing conditions, two bands were observed, 50 kDa and 25 kDa.

Example 4

This example demonstrates the characterization of cell lines with high endogenous CLDN18.2 expression.

A panel of cancer cell lines was analyzed for their endogenous expression of CLDN18.2 by FACS. Briefly, the binding of antibodies to targets were validated by FACS using cells overexpressing CLDN18.2 (e.g., HEK293T cells overexpressing CLDN18.2, described in Example 2), and cell lines that endogenously express CLDN 18.2 at high or low levels, as determined in Example 1. The CLDN 18.2-expressing cells were incubated with reference or control antibodies (described in Example 3) for 30 min on ice, and, after washing, incubated with Alexa Fluor® 647 conjugated Goat anti-mouse IgG (minimal x-reactivity) antibody, Biolegend cat #405322 for 30 min on ice. Fluorescence was read by a BD Biosciences Accuri™ flow cytometer (San Jose, Calif.).

The overexpressed lines were used to validate the control and reference antibodies, and, once validated, the control and reference antibodies were used to characterize the endogenous cell lines. The cells overexpressing CLDN18.2 were included as positive controls in these assays.

The FAC'S assays showed that four Upper GI cancer cell lines, in addition pancreas, colon and bladder cancer cell line, express CLDN18.2 on the surface at high levels. Endogenous expression levels of CLDN18.2 by the tested cancer cells lines are summarized in Table 2. See also FIG. 4.

TABLE 2

| Cell Line | Histology | CLDN18.2 FKPM | Group | Flow Validated |
|---|---|---|---|---|
| HUPT4 | Pancreas | 285.62 | Pos Con | +++ |
| KATO III | Upper GI | 246.53 | Pos Con | +++ |
| SNU601 | Upper GI | 245.64 | Pos Con | +++ |
| NUGC 4 | Upper GI | 144.16 | Pos Con | ++ |
| SNU620 | Upper GI | 27.06 | Pos Con | ++ |
| PATU | Pancreas | 24.32 | Pos Con | + |

TABLE 2-continued

| Cell Line | Histology | CLDN18.2 FKPM | Group | Flow Validated |
|---|---|---|---|---|
| 8988S | | | | |
| SKCO1 | Colon | 14.48 | Pos Con | + |
| SNU520 | Upper GI | 13.16 | Pos Con | + |
| OE19 | Upper GI | 6.02 | Pos Con | + |
| M202 | Melanoma | 0 | Neg Con | − |
| M275 | Melanoma | 0 | Neg Con | − |
| MCF7 | Breast | 0 | Neg Con | − |
| CACO2 | Colon | 0 | Neg Con | − |
| LS513 | Colon | 0 | Neg Con | − |

This example describes the immunization of mice for the production of CLDN 18.2 specific antibodies.

CLDN18.2-specific antibodies were produced by immunizing Balb/c and CD1 mice with a mixture of six different peptide immunogens following techniques of the Fred Hutchinson Cancer Research Center. The peptides spanned either the first or the second loop in the CLDN 18.2 extracellular domain (i.e., EL1 or EL2). The peptides include the full length of EL1, peptides spanning the first (N-terminal) half of EL1, and peptides spanning the second (C-terminal) half of EH Table 3 provides the sequences of the peptides.

TABLE 3

| Peptide Immunogen | | SEQ ID NO: |
|---|---|---|
| AC-CNMLVTNFWMSTANMYTGMGG MVQTVQTRYTFGA-amide N-terminal Cys conjugation | Full EL2 for counter-screening | 4 |
| Ac-NMLVTNFWMSTANMYTGMGG MVQTVQTRYTFGAC-amide C-terminal Cys conjugation | Full EL2 for counter-screening | 5 |
| H2N-GLWRSCVRESSGFTECRGYFTL- amide Free amine conjugation | Middle EL1 | 6 |
| H2N-QGLWRSCVRESSGFTECRGYFTLK- amide Free amine conjugation | Middle EL1 | 7 |
| Ac-DQWSTQDLYNNPVTAVFNYQGLWRSC- amide C-terminal Cys conjugation | N-terminal EL1 | 8 |
| Ac-CRGYFTLLGLPAMLQAVR-amide N-terminal Cys conjugation | C-terminal EL1 | 9 |

Mice also were immunized with 3T3 cells overexpressing full length CLDN18.2 using a plasmid comprising a human CLDN18.2-myc-DDK expression vector.

Splenocytes were harvested from the immunized mice and fused with myeloma lines by BTX Electrofusion (BTX, Holliston, Mass.) to generate hydridomas. 7000 primary hybridoma cultures were generated and cultured in 384-well plates. The ability of the antibodies to bind peptide was assessed by bead array using beads expressing the three different peptides targets. Approximately 2000 potential positive antibodies were re-arrayed into 96 well plates further screened by flow cytometry against endogenous and artificial cell line models.

Positive hybridoma supernatants were then counter-screened by flow cytometry against endogenous and artificial models of proteins that have sequence similarity to the target region (e.g., other CLDN proteins). From the secondary screen and counterscreen, approximately 20 CLDN18.2-specific antibodies were chosen for additional study. These antibodies were subcloned and the variable heavy and light chain sequences were determined. See Table B and sequence listing.

CLDN18.2 antibodies were formatted as full-length IgG antibodies using ExpiCHO™ expression. The heavy and light chain variable regions of the antibodies were cloned into an antibody expression vector which was engineered in the lab based on a pcDNA™3.4-TOPO® vector (Catalog Number: A14697, ThermoFisher Scientific, USA) and transfected into CHO cells by (According to protocol provided in the kit (ExpiCHO™ Expression System, Catalog Number: A29133, ThermoFisher Scientific, USA)). Antibodies were purified and cell surface binding of the antibodies to CLDN18.2 and the antibody IC50 were determined by FACS in which CLDN18.2 antibodies were directly conjugated with Alexa Fluor® 647 MIS Ester (Succinimidyl Ester), Cat # A20106 (ThermoFisher Scientific) following the manufacturer's protocol. CLDN18.2 antibodies were tested from 0.32 nM to 1000 nM (serial dilution 1:5, 6 points) in a 50 μl volume with 150,000 cells system.

CLDN18.2-expressing cells were used in FACS assays to determine the CLDN18.2 antibody's ability to bind to CLDN18.2 on the surface of cells and to cross-react with other CLDN family members. HEK293 T cells engineered to express human CLDN 18.2 fused to GFP, mouse CLDN18.2 fused to GFP, CLDN 18.1-GFP, or GFP alone (without CLDN 18.2) were used as artificial models of CLDN 18.2 expression. HUPT4, SNU601, and PATU8988S cells were used as endogenous models of CLDN18.2 expression.

For each type of cell tested and for each mAb, cells were detached from the surface of the culture flasks by versene (instead of trypsin) in order to protect the cell surface proteins. The detached cells were then incubated with Alexa Fluor®-labeled CLDN18.2 mAbs for 30 min in the dark on ice at a pre-determined concentration. The CLDN18.2 mAbs were directly labeled with Alexa Fluor® 647 NHS Ester (Succinimidyl Ester). After washing, the cells were read by a BD Accuri™ Flow Cytometer C6 to detect antibody-antigen protein binding in channel FL4H. Each antibody was tested at varied concentrations to establish a dose-fluorescence curve. The EC50/IC50 of the antibodies (the concentration of the antibody at which half the max value were calculated based on the values of FL4H (gated in viable singlet cells) using the Very Simple IC50 Tool kit available online which allows biological dose-response data to be plotted and fitted to curve types to give the EC50/IC50. The max value was the lowest concentration of the antibody at which fluorescence maxes out. The antibodies were also screened for their ability to cross-react with other CLDN18 isoform CLDN18.1. These values were used to determine each antibody's relative affinity among the set of antibodies tested. Cross-reactivity data were obtained using a similar methodology.

Relative affinity data as determined in this manner are set out in Table 4.

TABLE 4

| Antibody | HEK293T CLDN18.2 Clone C12 | HEK293T CLDN18.1 MP | HEK293T mouse CLDN18.2 MP | SNU601 (UP GI) (18.2 +, 18.1 −) | HUPT4 (Pancreatic) (18.2 +, 18.1 −) |
|---|---|---|---|---|---|
| Ref 1 | 1087.33 | Negative | 194.616 | Negative | Negative |
| Ref 2 | 1739.8 | Negative | Negative | Negative | Negative |
| 307 | 39.1103 | Negative | 68.7527 | 221.052 | 336.347 |
| 369 | 39.9668 | Negative | 90.027 | 275.857 | 265.104 |
| 376 | 52.086 | Negative | Negative | Negative | Negative |
| 358 | 54.516 | 1521.2 | 40.5826 | 414.028 | 111.152 |
| 384 | 595.065 | Negative | Negative | Negative | Negative |
| 360 | 39.6599 | 1764.71 | 57.7089 | 119.333 | 693.06 |
| 432 | 42.3122 | Negative | 96.7865 | 245.495 | 348.164 |
| 400 | 31.2122 | Negative | Negative | 270.384 | 97.7672 |
| 331 | 23.075 | 1676.34 | 810.04 | 106.452 | 606.235 |
| 347 | 70.4383 | 1231 | 1349.89 | 275.857 | 294.152 |
| 339 | 37.62 | 594.402 | 433.276 | 285.293 | 302.185 |
| 301 | 22.0736 | 674.874 | 1608.73 | 256.108 | 142.614 |
| 392 | 446 | Negative | Negative | Negative | Negative |
| 416 | 597.23 | Negative | 591.243 | Negative | Negative |
| 409 | 604.874 | Negative | 1044 | Negative | Negative |

Example 6

This example demonstrates the characterization of chimeric mouse IgG mAbs.

In vivo binding studies were carried out in xenograft mice injected with human cancer cell lines. Briefly, xenograft models of human cancer cell lines were established in six-week-old CD-1 athymic nude mice (Charles River Laboratories). The following conditions were followed for subcutaneous injection of each cell line: HUPT4 $1.0 \times 10^7$ cells, SNU601 $1.0 \times 10^7$ cells with 50% matrigel (BD Biosciences). Sufficient numbers of mice were injected to achieve 8 mice per treatment arm. When tumors reached an average size of 150 to 300 $mm^3$, mice were randomized into treatment groups. For treatment, each therapeutic antibody (Ab384, Ab400, Reference Ab1, Reference Ab2, and non-targeting IgG2-control were diluted in sterile saline to a working concentration of 1 mg/ml for intravenous tail vein (IV) injection. Tumor xenografts were measured with calipers three times per week, and tumor volume in $mm^3$ was determined by multiplying height×width×length. Mice were treated for 2-5 weeks. At the end of study, animals were euthanized and tumor tissue was excised and divided to be stored as snap-frozen or formalin fixed paraffin embedded (FFPE) tissue for biomarker analysis. All animal work was carried out under a protocol approved by IACUC and the University of California at Los Angeles Animal Research Committee. Data was analyzed using StudyLog software from StudyDirector (San Francisco, Calif.). Results are presented as mean volumes for each group. Error bars represent the standard error (SE) of the mean.

Figures 6A, 6B:
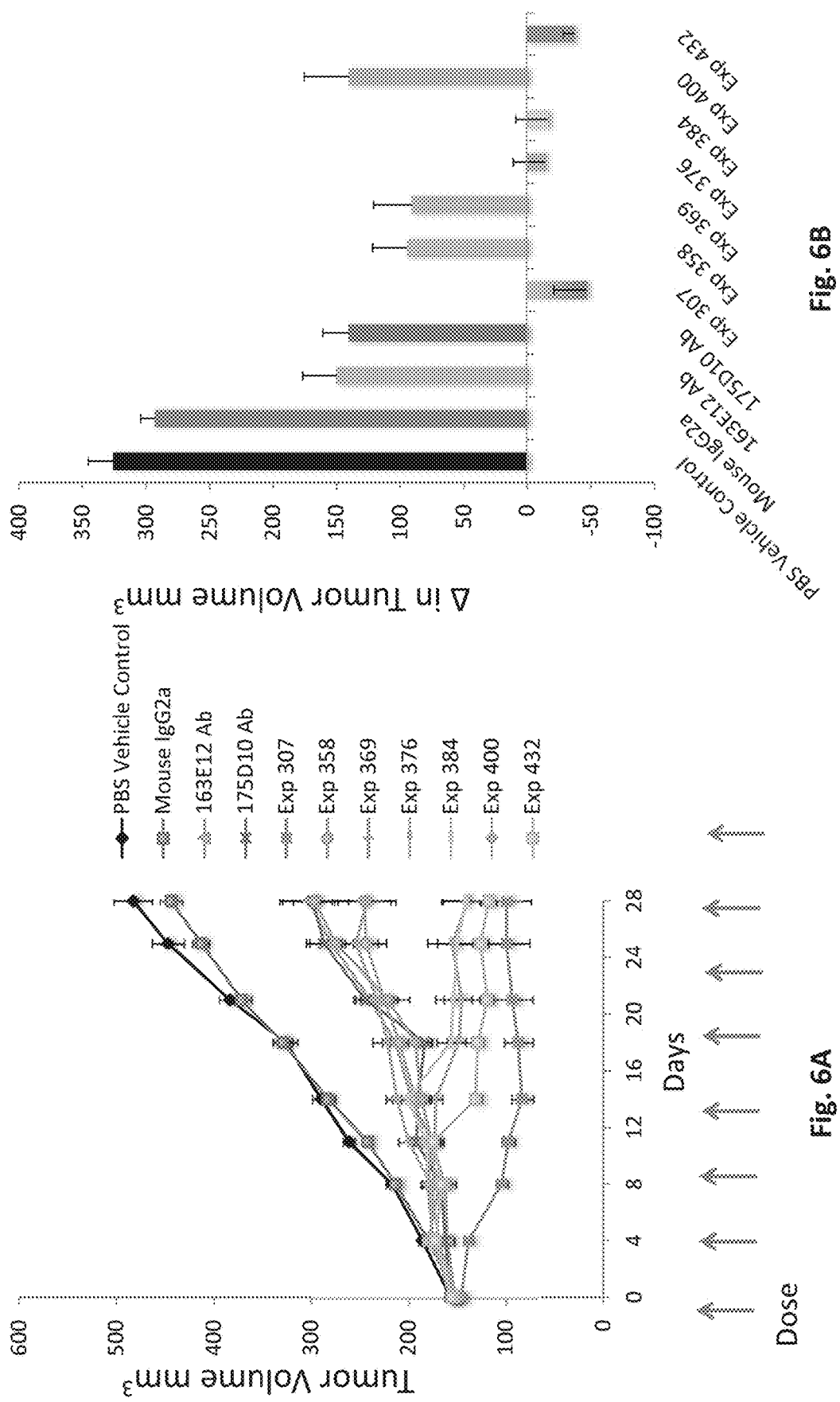
FIG. 6A represents a graph of tumor volume ($mm^3$) of tumors in mice bearing pancreatic (HUPT4) tumors as a function of time (days) after treatment with chimeric anti-CLDN18.2 antibodies.
FIG. 6B represents a graph of the mean change in tumor volume ($mm^3$) at Day 28 in the same treatment groups.

The results of the xenograft assays are shown in FIG. 5-FIG. 6. As shown in FIG. 5A and FIG. 5B, each of Ab384 and Ab400 caused a substantial mean change in tumor volume at Day 30, relative to control IgG2 antibody, in mice bearing gastrointestinal tumors. As shown in FIG. 6A and FIG. 6B, clone Ab384, Ab376, Ab307, and Ab432 caused a substantial mean change in tumor volume at Day 28, relative to control IgG2 antibody, in mice bearing pancreatic tumors.

Example 7

This example demonstrates the humanization of antibodies of the present disclosures.

A subset of antibodies listed in Table A/Table B were selected for humanization analysis. The heavy chain variable (VH) and light chain variable (VL) sequences of Ab307, Ab376, Ab358, Ab360 and Ab432 antibodies were compared to a library of known human germline sequences from human VH genes and human VLkappa genes (IMGT® the international ImMunoGeneTics information system® www.imgt.org; founder and director: Marie-Paule Lefranc, Montpellier, France).; the databases used were IMGT human VH genes (F+ORF, 273 germline sequences) and IMGT human VLkappa genes (F+ORF, 74 germline sequences). The acceptor human germline was chosen from those closest in sequence to the parental antibody.

CDRs were defined according to the AbM definition (see the website of Dr. Andrew C. R. Martin www.bioint.org.uk-Jabs/for a table comparing CDR definitions).

Alteration of human germline framework (i.e., non-CDR residues in VH and VL) positions to corresponding parental murine sequence might be required to optimize binding of the humanized antibody. The sequences for versions of humanized antibodies are provided as SEQ ID NOs: 42-57.

Table 6 shows a scheme for combining the humanized VH and VL. If none of the humanized versions is equivalent to the chimeric mAb.

TABLE 6

| Parental | Humanized Ab # | VH (SEQ ID NO:) | VL (SEQ ID NO:) |
|---|---|---|---|
| AB307 | AB307-1 | 42 | 43 |
| | AB307-2 | 42 | 44 |
| | AB307-3 (also known as 02-0307-h4 or 307-h4) | 42 | 45 |
| AB376 | AB376-1 | 46 | 47 |
| | AB376-2 | 46 | 48 |
| AB358 | AB358-1 | 131 | 149 |
| | AB358-2 | 131 | 150 |
| AB360 | AB360-1 | 52 | 53 |
| | AB360-2 | 52 | 54 |
| | AB360-3 | 55 | 53 |
| | AB360-4 | 55 | 54 |
| | AB360-5 | 56 | 53 |
| | AB360-6 | 56 | 54 |
| AB432 | AB432-1 | 57 | 50 |
| | AB432-2 | 57 | 51 |
| | AB432-3 | 49 | 50 |
| | AB432-4 | 49 | 51 |

Humanized antibodies described in Table 6 were constructed and expressed as essentially described in Example 5. FACS assays were carried out to determine relative antigen binding strengths of the humanized antibodies (at either 1.5 μg or 0.3 μg) for binding to CLDN18.2 as expressed by the indicated cancer cell lines. The results of the assays are provided in Table 7. Zolbetuximab, 163E12 and 175D10 were used as reference antibodies Corresponding Parental antibodies (antibodies prior to humanization) were used as controls and designated with "chim".

TABLE 7

| KW Seq # | HEK293T-CLDN18.2 C12 clone 1.5 ug | HUPT4 (+) 1.5 ug | M202 (−) new thaw 1.5 ug | HEK293T parental (−) 1.5 ug |
| --- | --- | --- | --- | --- |
| Ref 1 | 80,615.36 | 2,445.92 | 3,894.39 | 2,898.86 |
| Ref 2 | 125,202.94 | 11,064.14 | 2,216.52 | 998.59 |
| zolbetuximab | 109,075.36 | 10,591.27 | 1,904.84 | 678.45 |
| HuAb307-1 | 125,796.09 | 30,241.74 | 8,682.10 | 4,289.50 |
| HuAb307-2 | 132,787.03 | 32,521.62 | 1,592.42 | 5,408.69 |
| HuAb307-3 | 150,985.45 | 33,950.44 | 3,775.04 | 3,360.29 |
| 307-Chim | 141,127.14 | 34,706.06 | 3,080.84 | 1,129.30 |
| HuAb376-1 | 140,433.38 | 29,690.76 | 2,299.00 | 6,632.66 |
| HuAb376-2 | 119,002.68 | 28,320.51 | 3,041.69 | 1,541.68 |
| 376-Chim | 136,939.09 | 31,333.80 | 31,708.31 | 810.22 |
| HuAb358-1 | 130,607.65 | 52,729.98 | 6,152.96 | 21,348.56 |
| HuAb358-2 | 122,419.18 | 29,784.78 | 11,218.61 | 3,402.99 |
| 358-Chim | 139,047.66 | 33,303.64 | 3,367.47 | 2,137.99 |
| HuAb360-1 | 119,957.83 | 26,419.25 | 19,069.64 | 6,776.90 |
| HuAb360-2 | 138,043.18 | 24,936.06 | 48,715.77 | 9,009.25 |
| HuAb360-3 | 156,608.12 | 27,378.40 | 969.43 | 3,333.84 |
| HuAb360-4 | 149,257.62 | 27,974.01 | 17,782.36 | 20,416.84 |
| HuAb360-5 | 138,037.24 | 28,632.32 | 6,854.33 | 9,633.66 |
| HuAb360-6 | 158,583.85 | 34,575.76 | 43,042.33 | 37344.48 |
| 360-Chim | 116,699.09 | 26,165.33 | 947.91 | 1,096.91 |
| HuAb432-1 | 97,364.68 | 30,614.48 | 36,682.10 | 10,710.48 |
| HuAb432-2 | 127,823.22 | 36,110.09 | 37,613.03 | 14,253.88 |
| HuAb432-3 | 88,782.75 | 27,081.55 | 2,166.10 | 926.51 |
| HuAb432-4 | 172,520.93 | 23,114.08 | 39,687.76 | 16,580.43 |
| 432-Chim | 161,087.95 | 27,883.51 | 1,900.93 | 951.57 |

Based on the in vitro antigen binding data, five humanized antibodies were selected for further testing and development. The antibodies were derived from Ab307, Ab376, Ab358, Ab360, and Ab432.

In vivo binding studies of the humanized versions of Ab307, Ab376, Ab358, Ab360, and Ab432 were carried out in xenograft mice injected with pancreatic cancer cell line HUPT4, as essentially described in Example 6. Briefly, xenograft models of HUPT4 were established in six-week-old CD-1 athymic nude mice (Charles River Laboratories). After tumors reached an average size of 150 to 300 mm$^3$, mice were randomized into treatment groups. Humanized antibodies were diluted in sterile saline to a working concentration of 1 mg/ml for intravenous tail vein (IV) injection. Tumor xenografts were measured with calipers three times a week, and tumor volume in mm$^3$ was determined by multiplying height×width×length. Mice were treated for 2-7 weeks. At the end of study, animals were euthanized and tumor tissue was excised and divided to be stored as snap-frozen or formalin fixed paraffin embedded (FFPE) tissue for biomarker analysis.

The results of the xenograft assays are shown in FIG. 7-FIG. 12. FIG. 7A-FIG. 7B shows the xenograft assay results for humanized Ab307, Ab376, Ab358, Ab360, Ab432, wherein antibody was administered 1 time per week for 5 weeks. Controls included vehicle control (PBS), human IgG1 (10 mg/kg Q4D), and the murine version of 307 (10 mg/kg Q4D). As shown in FIG. 7, animals treated with humanized Ab307 (HuAb307) and HuAb358 demonstrated a the highest decrease in tumor volume over the 42 day treatment period, while HuAb 360 and HuAb 432 treatment induced a moderate decrease in tumor volume.

FIG. 8A-FIG. 8B shows xenograft assay results for treatments of HUPT4 pancreatic cancer with varying doses of the HuAb307 antibody, e.g., 10 mg/kg, given every 4 days (q4d), weekly (qw), every 3 weeks (q3w) or 2.5 mg/kg given every 4 days. Weekly or every 4 day treatment showed better results compared to antibody given every 3 weeks by day 42 post treatment.

Example 8

Antibodies were also tested for their ability to carry a cytotoxic payload. Humanized antibodies carrying MMAE were tested at varying doses and dose schedules to assess the ability of the antibody to mediate cell cytotoxicity in a model for pancreatic or bladder cancer.

Briefly, CD-1 nude mice (8 mice per group) were subcutaneously injected into the right flank with HUPT4 or PATU8988S pancreatic cells, or SNU601 bladder cells. When tumors reached an average size of 150 to 300 mm$^3$, mice were randomized into treatment groups. For treatment, mice were administered once weekly by tail vein injection either humanized anti-CLDN18.2 MMAE antibody, or a human IgG control antibody. Tumor xenografts were measured with calipers three times a week, and tumor volume in mm$^3$ was determined by multiplying height×width×length. Mice were treated for 20-42 days. At the end of the study, animals were euthanized and tumor tissue was excised and divided to be stored as snap-frozen or formalin fixed paraffin embedded (FFPE) tissue for biomarker analysis. All animal work was carried out under a protocol approved by IACUC and the University of California at Los Angeles Animal Research Committee. Data was analyzed using StudyLog software from StudyDirector (San Francisco, Calif.). Results are presented as mean volumes for each group. Error bars represent the standard error (SE) of the mean.

FIG. 9A-FIG. 9B show the results of treatment in a pancreatic tumor model with antibody HuAb307-MMAE and HuAb358-MMAE administered weekly at 5 mg/kg, 2.5 mg/kg or 1 mg/kg for three weeks. Anti-CLDN18.2-ADCs were more effective at reducing tumor volume than the payload alone. A single dose of HuAb307 at 5 mg/kg also was effective at killing tumor cells out to day 40.

Figure 10A:
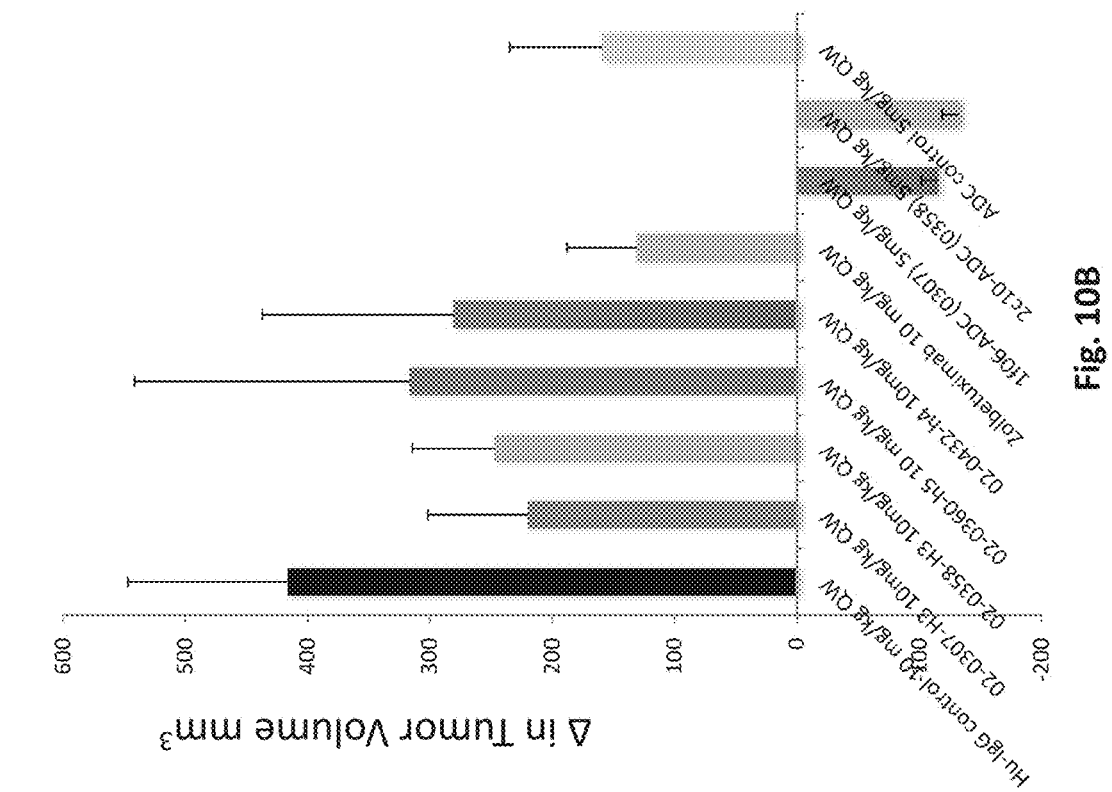
FIG. 10A represents a graph of tumor volume ($mm^3$) of tumors in mice bearing pancreatic (PATU8988S) tumors as a function of time (days) after treatment with different doses of humanized anti-CLDN18.2 ADC.
Figure 10B:
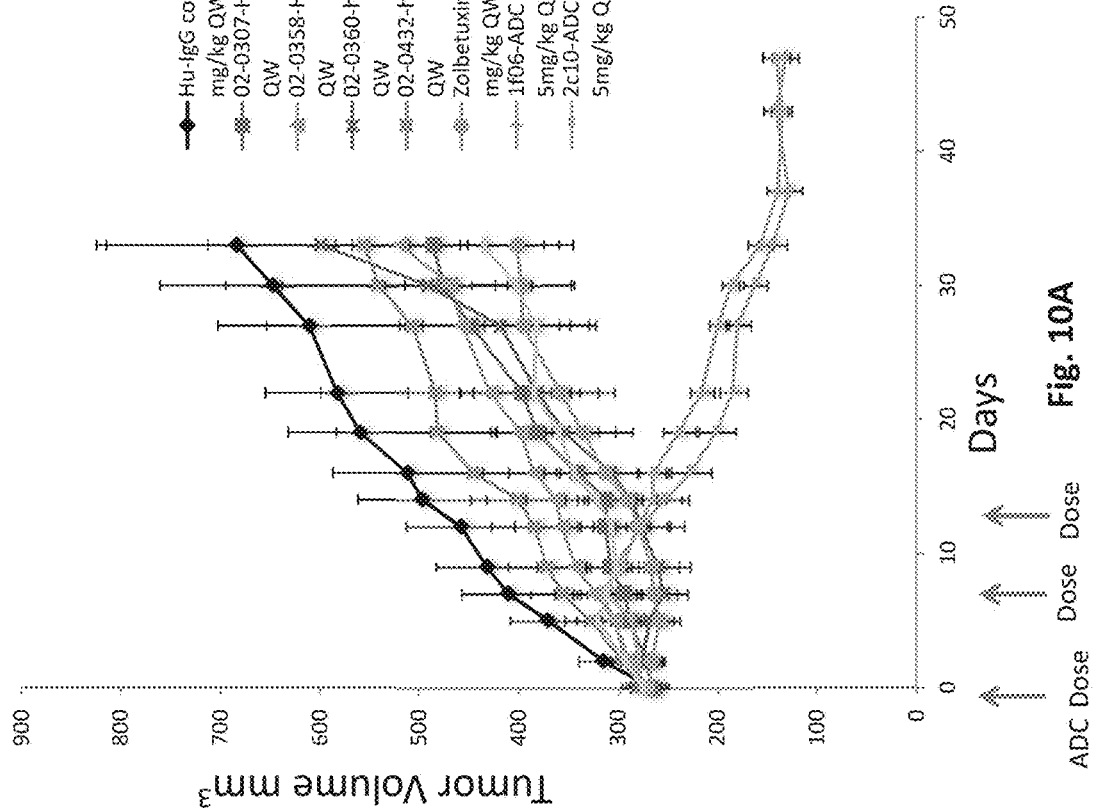
FIG. 10B represents a graph of the mean change in tumor volume ($mm^3$) at Day 33 in the same treatment groups.
Figure 11:
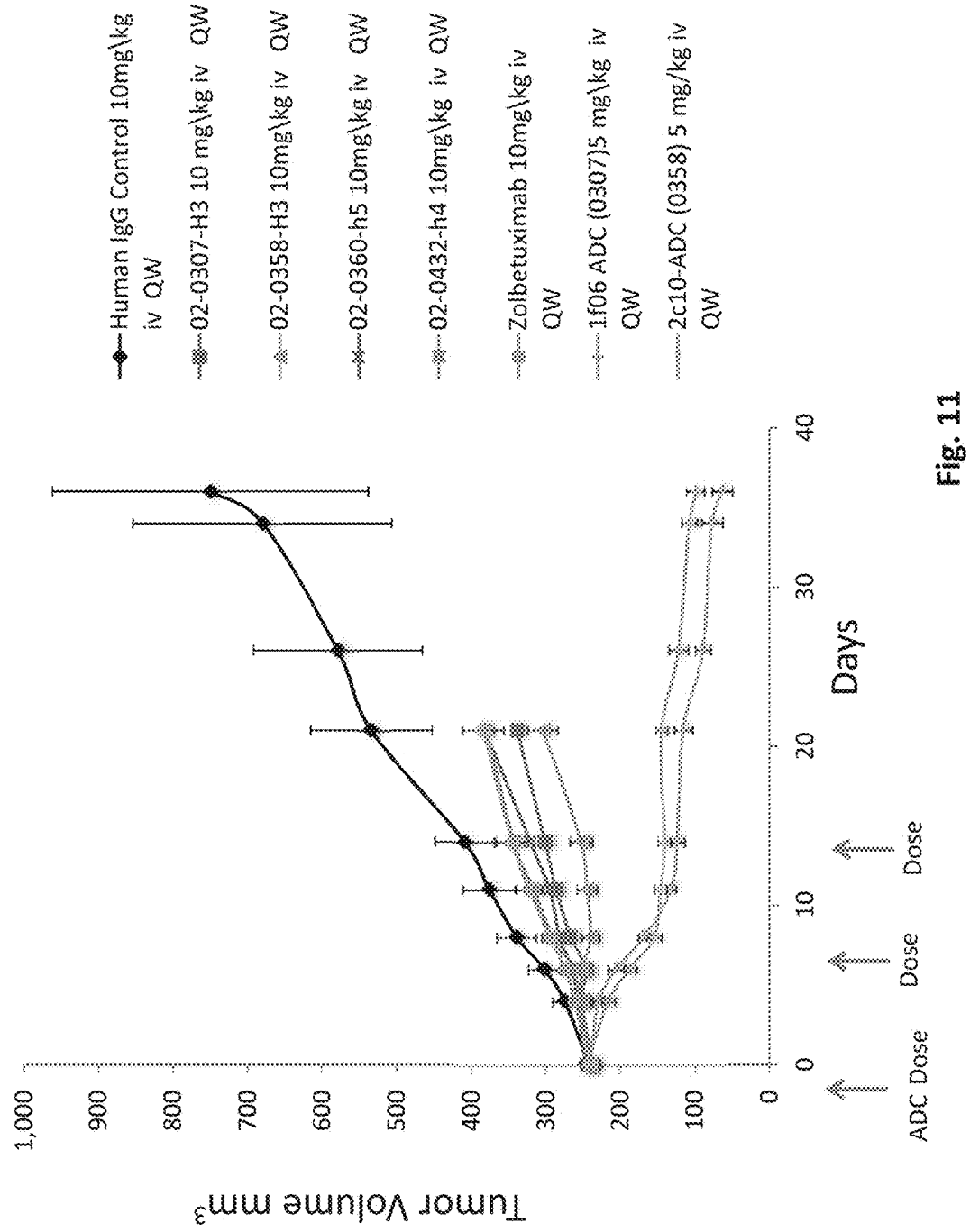
FIG. 11 represents a graph of tumor volume ($mm^3$) of tumors in mice bearing SNIJ601 gastric carcinoma as a function of time (days) after treatment with different doses of humanized anti-CLDN18.2 ADC.

Efficacy of antibodies HuAb307, HuAb368, HuAb360 and HuAb432 administered at 10 mg/kg were compared to HuAb307 and HuAb358-ADC conjugated to MMAE and administered in a pancreatic cancer cell model at 5 mg/kg weekly. Antibody alone decreased tumor volume size, but anti-CLDN18.2-ADC showed improved tumor killing out to 48 days (FIG. 10A-FIG. 10B). Similar results were observed in a gastric carcinoma model (FIG. 11).

In an additional experiment, Ab307 and Ab358-ADC conjugates were administered in different doses intravenously. Results show that i.v. treatment is dose dependent (FIG. 12A-FIG. 12B).

These results show that the antibody is a useful delivery system for cyotoxic agents into solid tumors.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or various language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Example 9

This example demonstrates the in vivo activity of humanized anti-CLDN18.2-307 antibody drug conjugate (ADC) in pancreas cancer patient derived xenografts (PDXs).

Method: The anti-tumor activity of the CLDN18.2 directed ADC (CLDN18.2-307-ADC (conjugated to MC-VC-PAB-MMAE)), and the CLDN18.2 directed mAb CLDN 18.2-307, were assessed in two patient derived xenografts of pancreatic cancer. Each PDX has previously been shown to be positive (XWR6) or negative (XWR187) for CLDN18.2 protein by IHC (FIG. 14C and FIG. 15C). Patient derived xenografts were established in six-week-old CD-1 athymic nude mice (Charles River Laboratories) through in vivo passage of tumor tissue in mice by subcutaneous implantation of tumor pieces into the right rear flank of the animal. Once sufficient numbers of xenograft tumor bearing mice had been achieved and tumor volumes ranged between 200-300 mm³, mice were randomized into treatment groups to receive either non-targeting IgG2A control antibody (10 mg/kg QW IV), humanized mAb CLDN18.2-307 (10 mg/kg QW IV) or CLDN18.2-307-ADC (5 mg/kg QW IV) for 3 repeat doses. For all experiments, tumor xenografts were measured with calipers 3 times/week, and tumor volume in mm³ was determined by multiplying height×width×length. All animal work was carried out under a protocol approved by IACUC and the UCLA Animal Research Committee. Data were analyzed using StudyLog software from StudyDirector (San Francisco, Calif.).

Brief Summary: In the CLDN18.2 positive XWR6 model, treatment with mAb CLDN18.2-307 slowed the mean rate of progression of the PDXs relative to the non-targeting control, however the 307-ADC induced complete regression of xenograft tumor burden in each of the 4 mice in the group (FIG. 14A and FIG. 14B). In contrast to the CLDN18.2 positive model, CLDN18.2-307-ADC or mAb CLDN18.2-307 showed no impact on xenograft tumor progression in the CLDN18.2 negative PDX, XWR187 (FIG. 15A and FIG. 15B).

Example 10

This example demonstrates the evaluation of humanized CLDN18.2 mAb and humanized CLDN 18.2 ADC activity in target negative cancer cell line xenografts.

Method: The target selective activity of two CLDN18.2 ADCs (conjugated to MC-VC-PAB-MMAE) and two CLDN18.2 mAbs was assessed in a cell line xenograft model of human melanoma (M202) that has previously been shown to be negative to CLDN18.2 protein (i.e., lacks expression of the CLDN18.2 protein). Cancer cell line xenografts were established in six-week-old CD-1 athymic nude mice (Charles River Laboratories) by injection of $1.0\times10^7$ cells with 50% matrigel (BD Biosciences) into the right rear flank of the animal. When tumors reached an average size of 250 mm³ to 300 mm³ mice were randomized into groups for treatment with either non-targeting humanized-IgG1 control antibody (10 mg/kg QW IV), mAb CLDN18.2-307 (10 mg/kg QW IV), mAb CLDN18.2-358 (10 mg/kg QW IV), CLDN18.2-307-ADC (5 mg/kg QW IV) or CLDN18.2-338-ADC (5 mg/kg QW IV) for three repeat doses. For all experiments, tumor xenografts were measured with calipers 3 times/week, and tumor volume in mm³ was determined by multiplying height×width×length. All animal work was carried out under a protocol approved by IACUC and the UCLA Animal Research Committee. Data were analyzed using StudyLog software from StudyDirector (San Francisco, Calif.).

Brief Summary: No significant anti-tumor activity was observed with either of these mAbs or ADC in this CLDN18.2-negative model (FIG. 16A and FIG. 16B). These data indicate that these molecules have very little off-target activity.

Example 11

This example demonstrates the humanized antibody binding activity to native positive cells (cells with endogenous expression of CLDN 18.2) or artificially overexpressed cells (cells engineered to overexpress CLDN18.2) as analyzed by flow cytometry Method: The humanized antibodies at three different concentrations were incubated with 150,000 cells in 50 µl 2% FBS/PBS at 4° C. for 30 mins followed by washing with 2% FBS/PBS; then incubated with Alexa Fluor® anti-human IgG Fc Antibody from Biolegend (409320) at 4° C. for 30 mins. The samples were then measured by Lntellicyt® iQue Advanced Flow Cytometry Platform.

Brief Summary: 8 humanized antibodies modified based on 307 (h1F06) and 8 humanized antibodies modified based on 358 against CLDN18.2 show various binding affinity by flow cytometry compared with their parental antibody in native CLDN18.2 expressing HUPT4 cells, or in artificial CLDN18.2 overexpressing HEK293T cells while showing no activity against negative control M202 cells and HEK293T parental cells (FIG. 18).

Example 12

The following Table 8 shows additional humanized antibodies and sequences.

CellLight™ Lysosomes-GFP, BacMam 2.0 (C10507), transfected at 37° C., 2 ul/10k cells overnight. CLDN18.2 antibodies are primarily labeled with AF647. HUPT4 cells are stained with 8 ug antibody/300 ul growth media at 4° C. for 30 min.

Brief Summary: All 4 antibodies tested (02-0307-h4, 02-0307-h6, 02-0358-h3 and 02-0358-h5) are completely

TABLE 8

| Antibody | VH or VL | SEQ ID NO | Amino acid sequence |
|---|---|---|---|
| 02-0307-h4 | 02-0307-h4_VH | 42 | EVQLLESGGGLVQPGGSLRLSCAASGFTFSSYTMSWRQ APGKGLEWVATIIIGGSYTYYADSVKGRFTISRDNSKNTLYL QMNSLRAEDTAVYYCTRLVKGNAMDYWGQGTLVTVSS |
| | 02-0307-h4_VL | 45 | DIVMTQSPDSLAVSLGERVTMNCKSSQSLLNSGNQKNYLS WYQQKPGQPPKLLFYWASTRESGVPDRFSGSGSGTDFTL TISSVQAEDVAVYYCQNDYSYPFTFGQGTKLEIK |
| 02-0307-h6 | 02-0307-h6_VH | 42 | EVQLLESGGGLVQPGGSLRLSCAASGFTFSSYTMSWVRQ APGKGLEWVATIIIGGSYTYYADSVKGRFTISRDNSKNTLYL QMNSLRAEDTAVYYCTRLVKGNAMDYWGQGTLVTVSS |
| | 02-0307-h6_VL | 130 | DIVMTQSPDSLAVSLGERVTMNCKSSQSLLSSGNQKNYLS WYQQKPGQPPKLLFYWASTRESGVPDRFSGSGSGTDFTL TISSVQAEDVAVYYCQNDYSYPFTFGQGTKLEiK |
| 02-0358-h3 | 02-0358-h3_VH | 131 | EVQLVESGGGLVQPGGSLRLSCAVSGFTFSSFGMHWVRQ APGKGLEWVAYISSGTTNIYYADSVKGRFTVSRDNAKNSL YLQMNSLRAEDTAVYYCVRSGYYGNSLDYWGQGTLVTVS S |
| | 02-0358-h3_VL | 147 | DIVMTQSPDSLAVSLGERVTMNCKSSQSLFNSGNQRNYLT WYQQKPGQPPKLLIYWASTRESGVPDRFSGSGSGTDFTL TISSVQAEDVAVYYCQNVYIYPLTFGQGTKLEIK |
| 02-0358-h5 | 02-0358-h5_VH | 131 | EVQLVESGGGLVQPGGSLRLSCAVSGFTFSSFGMHVWRQ APGKGLEWVAYISSGTTNIYYADSVKGRFTVSRDNAKNSL YLQMNSLRAEDTAVYYCVRSGYYGNSLDYWGQGTLVTVS S |
| | 02-0358-h5_VL | 132 | DIVMTQSPDSLAVSLGERVTMNCKSSQSLFSSGNQRNYLT WYQQKPGQPPKLLIYWASTRESGVPDRFSGSGSGTDFTL TISSVQAEDVAVYYCQNVYIYPLTFGQGTKLEIK |

Example 13

This example demonstrates the humanized antibody binding activity to species orthologs of CLDN 18.1 and CLDN 18.2 on cells engineered to overexpress the orthologs. The binding activity was analyzed by flow cytometry.

Method: The 4 humanized antibodies at three different concentrations were incubated with 150,000 cells in 50 μl 2% FBS/PBS at 4° C. for 30 mins followed by washing with 2% FBS/PBS; then incubated with Alexa Fluor® 647 anti-human IgG Fc Antibody from Biolegend (409320) at 4'C for 30 mins. The samples were then measured by Lntellicyt® iQue Advanced Flow Cytometry Platform.

Brief Summary: 4 humanized antibodies modified based on 307 and 358 show significantly different binding affinity by flow cytometry with human CLDN 18.2, human CLDN 18.1, mouse CLDN 18.2, dog CLDN 18, and rat CLDN 18 (FIG. 19). Both loop 1 and loop2 are identical between human and *Macaca fascicularis* (Crab-eating macaque) (Cynomolgus monkey), so monkey CLDN18.2 OE line was not included into this assay.

Example 14

This example demonstrates the in vitro characterization of antibody internalization with CLDN18.2 humanized antibodies in HUPT4 cells.

Figure 20:
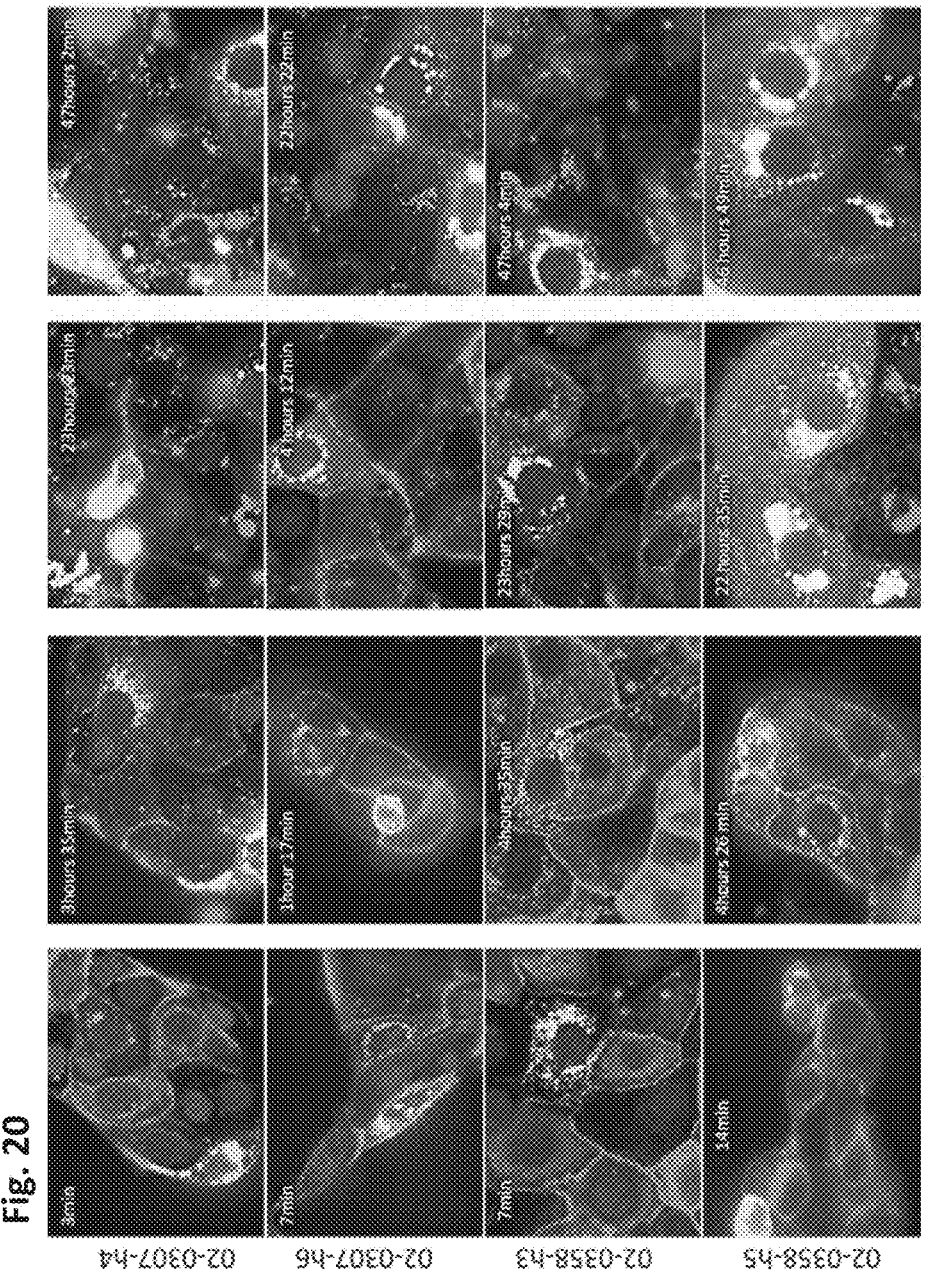
FIG. 20 shows the in vitro characterization of antibody internalization with CLDN 18.2 humanized antibodies in HUPT4 cells.
Figures 24A, 24B:
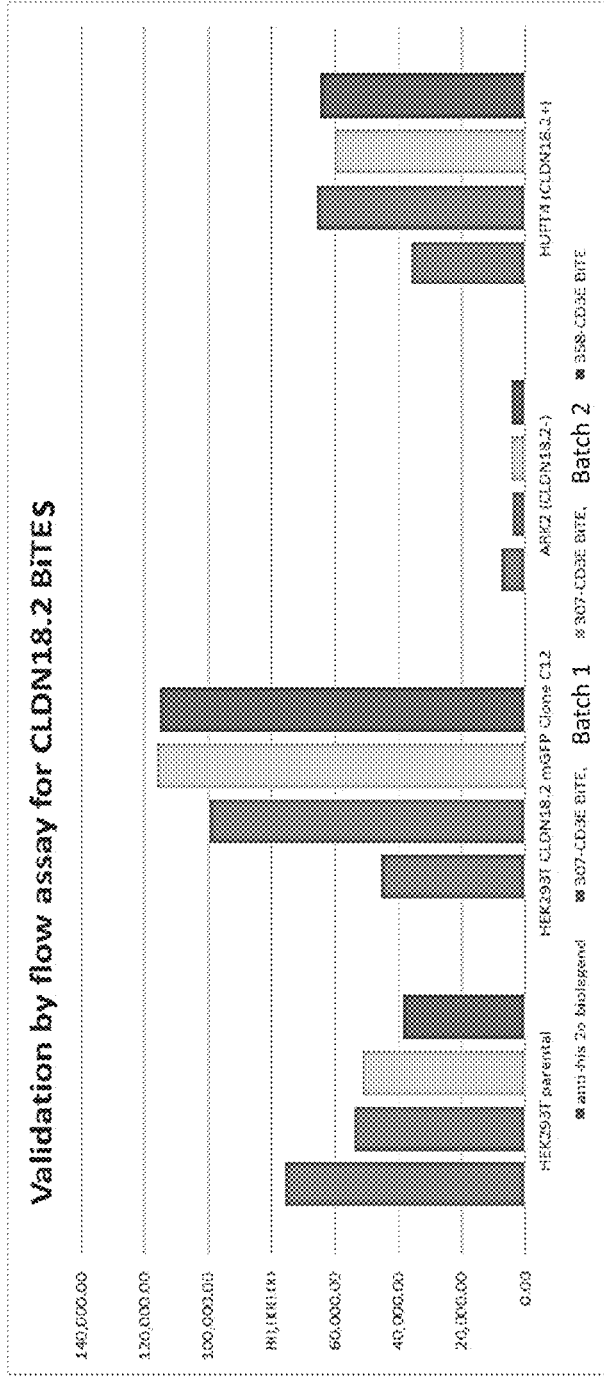
FIG. 24A-FIG. 24E represent the binding activity of CLDN18.2-CD3 BiTEs to cells endogenously expressing CLDN18.2 or cells engineered to overexpress CLDN18.2. The binding activity was analyzed by flow cytometry.
Figure 24E:
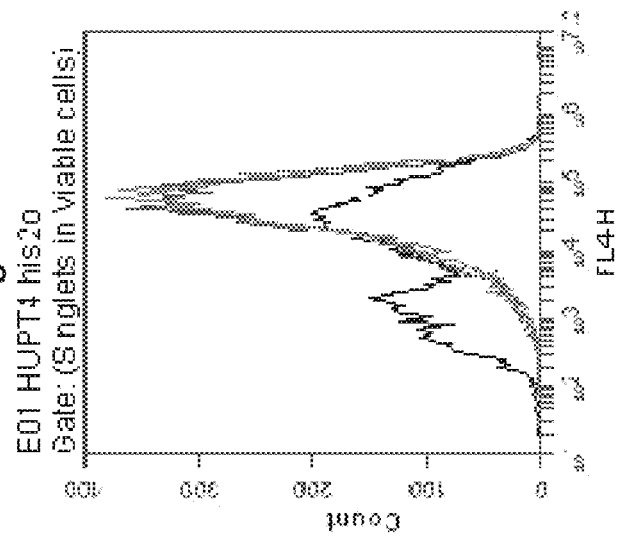
Figure 24D:
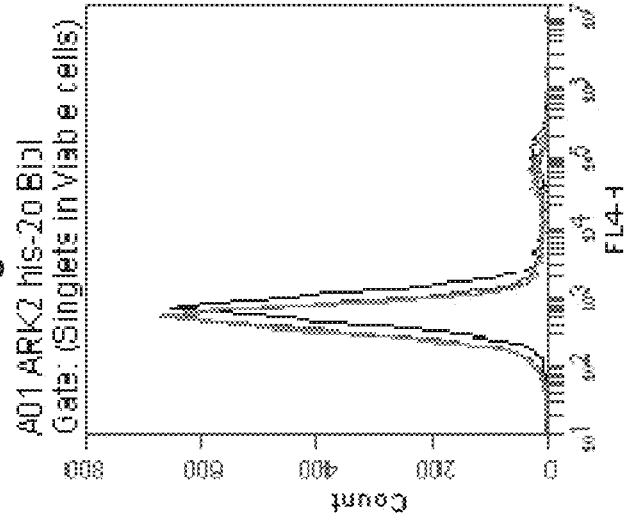
Figure 24C:
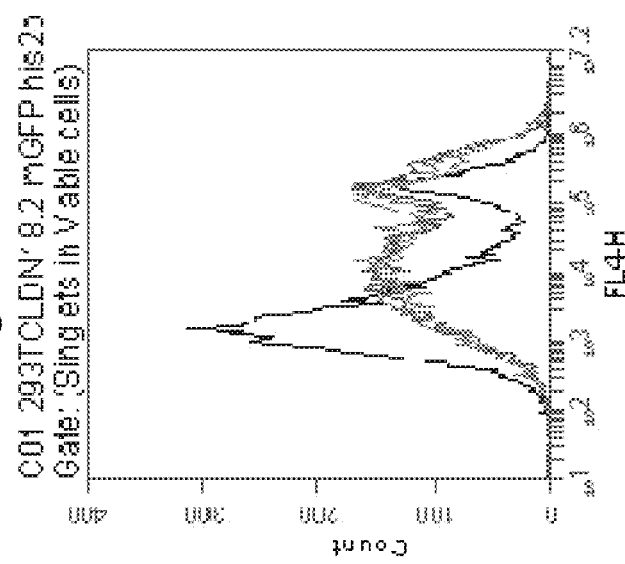
Figure 25B:
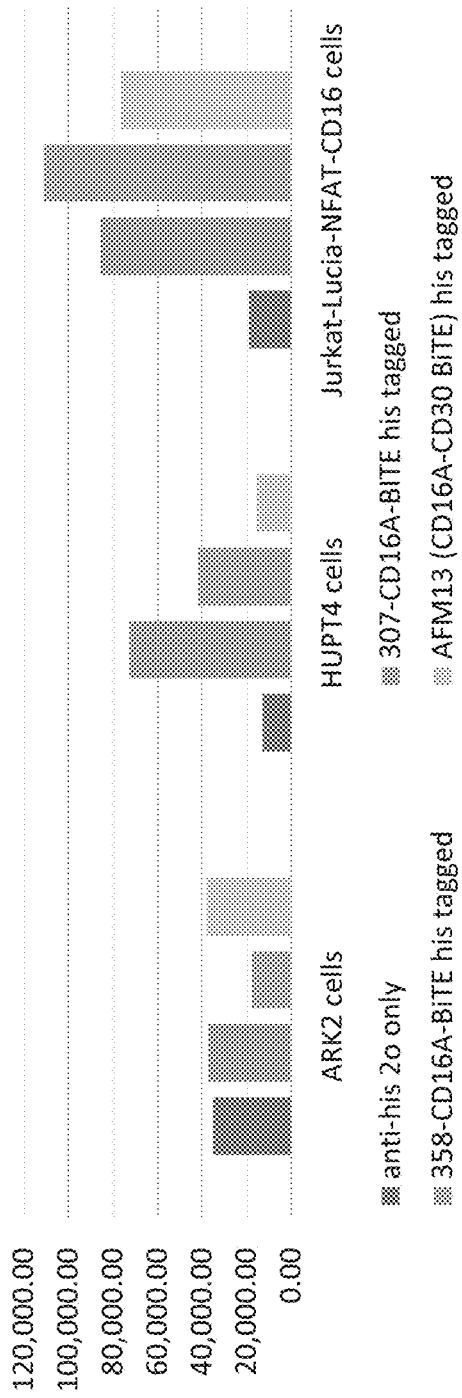

Method: Nucleus stained with DNA dye Hoechst 33342 in 1 ug/ml media overnight at 37° C. Lysosome stained with internalized between 24-48 hours after staining (FIG. 20). After being internalized, antibodies (red) merged into lysosomes (green) and form yellow color spots around nucleus (blue) (FIG. 20).

Example 15

This example demonstrates the binding affinity (KD) of the humanized CLDN18.2 antibodies, and the CLDN18.2 expression level on the surface of various cancer cell lines.

Method: The cell-based antibody affinity $K_D$ was measured by KinExA 4000 from Sapidye (FIG. 21A). For each $K_D$ measurement, in general, at least two antibody concentration curves were prepared using the same batch of cells (same passage) to avoid changes in expression level from passage to passage. Briefly, either HEK293T CLDN18.2-mGFP C12 cells (engineered overexpression cell line) or HUPT4 cells (native positive cell line) were detached using Versene. Cells were then equilibrated in different concentrations of the antibody solutions, respectively, in 2°, 0FBS/DMEM or 2% FBS/RPMI at 4° C. overnight. Cells concentrations started with $1.8 \times 10^7$ cells/ml and 2-fold serial dilution was performed to 10 points. In addition, antibody solution only (Signal 100%) and nonspecific binding (NSB) buffer only were included in each curve. Next day, spin the cells at 1500 rpm for 10 mins and saved the supernatant for measurement. The PMMA beads (Sapidye, 440176) were precoated with goat-anti-human IgG (Jackson ImmunoResearch Labs, 109 005-003) at 30 μg/ml, followed by incubating with 10 mg/ml BSA/PBS at RT for 1 hr. Fluorescent Alexa Fluor® 647 AffiniPure Goat Anti-Human IgG (Jackson ImmunoResearch Labs, 109-605-088) was diluted in 1% BSA/PBS at 0.5 µg/ml. The KD and antigen expression level were calculated using two antibody curves analyzed by n-curve analysis.

Cell surface antigen expression levels were also performed via quantitative flow cytometric measurement (FIG. 21B) by using the combination of Quantum MESF kit (four fluorescent microsphere populations labeled with varying amounts of Alexa Fluor 647, Bangs Laboratories Inc, Catalog #647) and Quantum Simply Cellular (4 standards, Bangs Laboratories Inc, Catalog #816) or Simply Cellular Kit (1 standard, Cat #812). Briefly, cells were detached using Versene solution; stained the cells and QSC beads with CLDN18.2 antibodies primary labeled with Alexa Fluor 647 dye at 4° C. for 30 min; after washing with 2% FBS/PBS, analyze cells, MESF, and QSC beads on Accuri C6 at the same setting gating around the singlet population. Using QuickCal analysis template provided with each kit, MESF kit was used to generate a standard curve and quantify fluorescence; cell samples are then read against the curve for determination of expression. In addition, Quantum Simply Cellular or Simply Cellular Kit were used to quantify the Fluorophore: Protein (F/P) ratio. Using QuickCal analysis template. Subsequently, convert the results from MESF to ABC units using F/P ratio. Finally, multiplying 2 of the calculated monovalent ABC is the ABC value with bivalent binding.

Brief Summary: 4 humanized CLDN18.2 antibodies showed different binding affinities to CLDN18.2 positive cell lines; higher binding affinity to native CLDN18.2 positive cells compared with CLDN18.2 overexpressed artificial cells (FIG. 21A). The expression levels of CLDN18.2 on the cell surface varied in the endogenous cell lines among different histology (FIG. 21B).

Example 16

This example demonstrates the CLDN18.2 humanized mAb efficacy in CLDN18.2+ pancreas cancer cell line (HUPT4) xenografts.

Methods: Anti-tumor activity of four CLD18.2 directed antibodies were compared in a HUPT4 cell line xenograft model of human pancreas cancer. Cancer cell line xenografts were established in six-week-old CD-1 athymic nude mice (Charles River Laboratories) by injection of $1.1 \times 10^7$ cells with 50% matrigel (BD Biosciences) into the right rear flank of the animal. When tumors reached an average size of 200 mm³, mice were randomized into treatment groups. Mice were treated once weekly (QW) by intravenous (N) injection of either non-targeting humanized-IgG1 control antibody, CLDN 18.2 antibody clone #307-4, #02-307-6h, #358-3 or #02-358-5h at 10 mg/kg. For all experiments, tumor xenografts were measured with calipers 3 times/week, and tumor volume in mm³ was determined by multiplying height×width×length. All animal work was carried out under a protocol approved by IACUC and the UCLA Animal Research Committee. Data were analyzed using StudyLog software from StudyDirector (San Francisco, Calif.).

Brief Summary: Treatment with each antibody induced a complete block of xenograft tumor progression over the 24 days of dosing. Of the four CLDN18.2 mAbs tested, clone #307-4 showed marginally improved efficacy over the other three clones (FIG. 22A and FIG. 22B).

Example 17

This example demonstrates the CLDN18.2-CD3-bispecific T cell engager (BiTE) binding activity to native positive cells or artificially overexpressed cells by flow cytometry.

Method: The #307-CD3E-BiTE (2 batches) and 358-CD3E-BiTE were incubated with 150,000 cells in 50 µl 2% FBS/PBS at 4° C. for 30 mins followed by washing with 2% FBS/PBS; then incubated with anti-his Alexa Fluor® 647 antibody (Biolegend #652513) at 4° C. for 30 mins. The samples were then measured by BD Accuri™ C6 Flow Cytometer.

Brief Summary: CLDN18.2 BiTEs [#307-CD3E-BiTE (2 batches) and 358-CD3E-BiTE] showed good binding affinity by flow assay with native CLDN18.2 expressing HUPT4 cells, and artificial CLDN18.2 overexpressing HEK293T cells while showing no activity against negative control ARK2 cells (FIG. 24A-FIG. 24E). However, anti-his-AF647 (Biolegend #652513) has very high background/non-specific binding with HEK293T parental cells.

Example 18

This example demonstrates the CLDN18.2-CD16-TandAb (Tandem diabody) binding activity to native positive cells or artificial overexpressed cells by flow cytometry.

Method: A TandAb comprising antigen-binding moieties that each binds CD16A or CLDN18.2 was constructed using an antigen binding protein of 307 or 358 antibody. The structure of TandAb described herein is: CD16A VH-(G2S) 3-CLDN18.2AbVL-(G2S)3-CLDN18.2AbVH-(G2S)3-CD16A VL-His Tag (FIG. 23A-FIG. 23C). The TandAb 307-CD16A and TandAb 358-CD16A as well as AFM13 were incubated with 150,000 cells in 50 µl 2% FBS/PBS at 4° C. for 30 mins followed by washing with 2% FBS/PBS; then incubated with anti-his Alexa Fluor® 647 antibody (Biolegend #652513) at 4° C. for 30 mins. The samples were then measured by BD Accuri™ C6 Flow Cytometer.

Brief Summary: The TandAb 307-CD16A and TandAb 358-CD16A showed good binding affinity by flow assay with native CLDN18.2 expressing HUPT4 cells, while showing less activity against negative control ARK2 cells. However, anti-his-AF647 (Biolegend #652513) has very high background/non-specific binding. AFM 13 antibody (bispecific to CD16A and CD30) was used as positive control for binding to CD16A in Jurkat-Lucia-NFAT-CD16A cells. The results in this flow assay demonstrated that the TandAbs of 307-CD16A and 358-CD16A successfully bind to both CLDN18.2 and CD16A (FIG. 25A-FIG. 25E).

Example 19

This example demonstrates the CLDN18.2-CD16-Tand-Abbinding activity to native positive cells or artificial overexpressed cells by flow cytometry.

Method: Tandab 307-CD16A and Tandab 358-CD16A as well as AFM13 were incubated with 150,000 cells in 50 µl 2% FBS/PBS at 4° C. for 30 mins followed by washing with 2% FBS/PBS; then incubated with anti-his Alexa Fluor® 647 antibody (Biolegend #652513) at 4° C. for 30 mins. The samples were then measured by BD Accuri™ C6 Flow Cytometer.

Figure 26B:
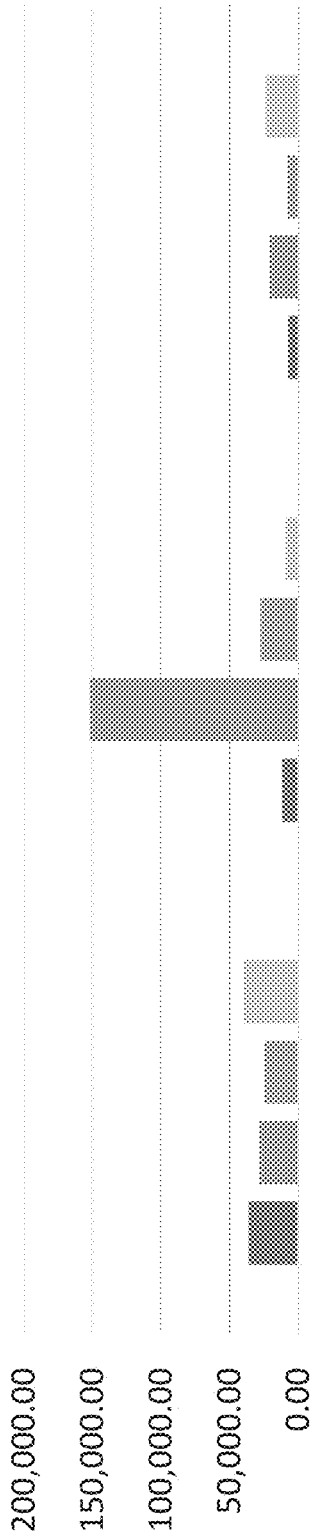

Brief Summary: The Tandab 307-CD16A and Tandab 358-CD16A showed good binding affinity with native CLDN18.2 expressing HUPT4 cells, while showing less activity against CLDN18.2 negative ARK2 cells (FIG. 26A-

Figure 26E:
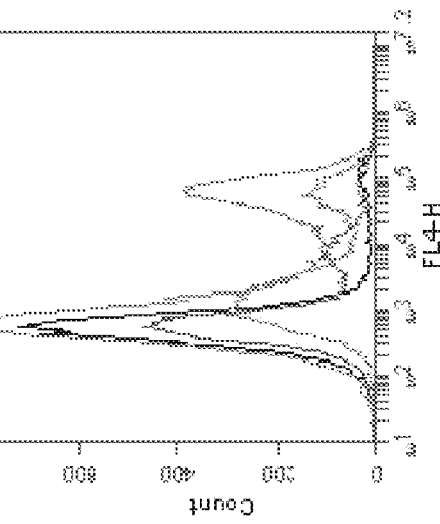
Figure 26D:
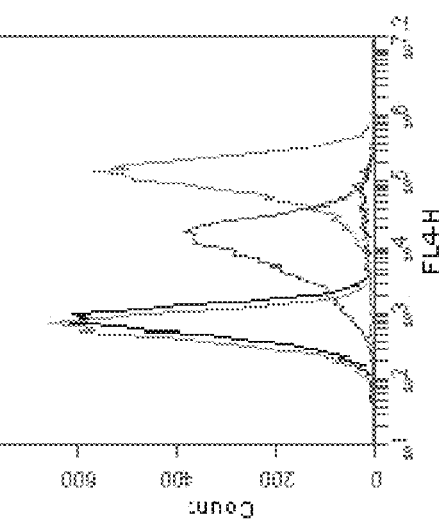
Figure 26C:
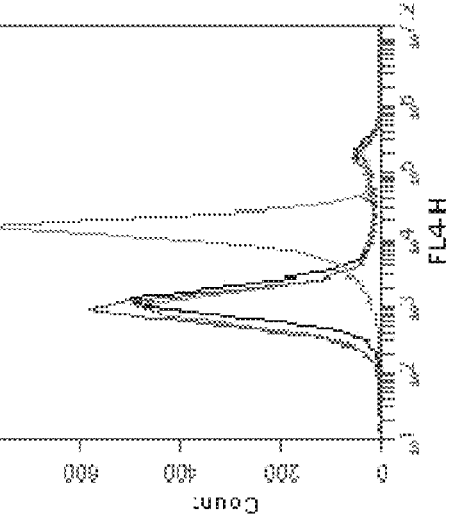

FIG. 26E). However, anti-his-AF647 (Biolegend #652513) has high background/non-specific binding. AFM13 antibody (bispecific to CD16A and CD30) was used as positive control for binding to CD16A in Jurkat-Lucia-NFAT-CD16A cells. The results in this flow assay showed that the Tandab 307-CD16A and Tandab 358-CD16A successfully bind to both CLDN 18.2 and CD16A (FIG. 26A-FIG. 26E).

Example 20

This example shows the CLDN18.2-CD3 BiTE binding activity to Jurkat cells by flow cytometry Method: Jurkat cells, endogenously positive for CD3, were incubated with 1 ug of each BiTE of interest (Blincyto-His tag, p307 BiTE-His tag, p358 BiTE-His tag), incubated in 4° C. for at least 30 minutes, washed and incubated with 0.5 ug of anti-His secondary antibody. Samples were washed and run for flow cytometry the same day. For the negative control, Jurkat cells were incubated with only the anti-His secondary antibody.

Figure 27B:
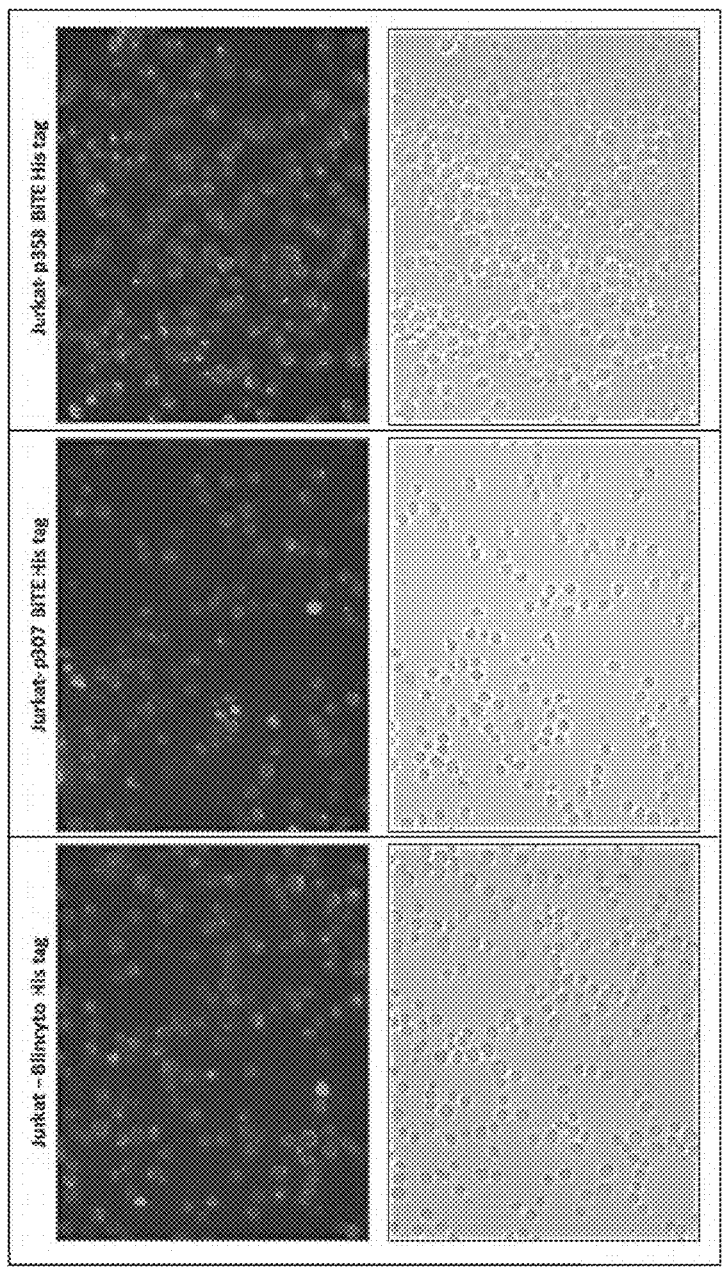
FIG. 27B shows the surface staining of the Jurkat cells with the BiTEs.
Figure 27A:
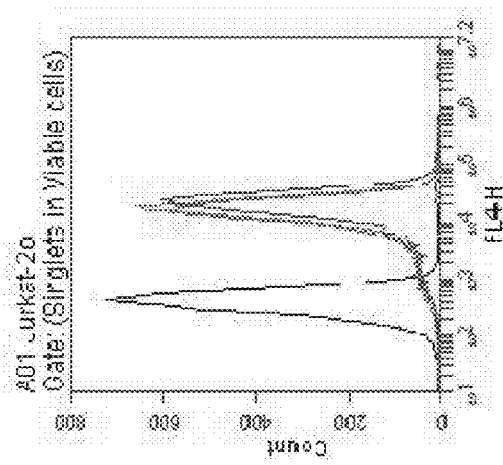
FIG. 27A represents the binding activity of CLDN19.2-CD3 BiTEs to Jurkat cells as analyzed by flow cytometry.

Brief Summary: Flow results indicate anti-CD3 binding capability of the benchmark antibody (Blincyto) as well as our CLDN18.2 BiTES p307 and p358 (as shown in FIG. 27A). The 40× Keyence images indicate consistent surface staining (FIG. 27B).

Example 21

This example shows a T-cell activation assay using Jurkat cells with NFAT-RE reporter and CLDN18.2-CD3 BiTEs using native or artificially overexpressed cells.

Method: Assays were run using Promega's T Cell Activation Bioassay kits (NFAT-RE J1621). Target cells were seeded at a density of 40,000 cells/well in white 96 well plate wells and incubated at 37° C. overnight, after which thaw-and-use Jurkat T cells included in the assay kit (engineered to luminesce when activated) were added to the seeded cells (1:1 cell ratio) along with the BiTE treatments. BiTE treatments were added in nine serial 1:4 dilutions at a starting concentration of 10 nM. Treated plates were incubated in 37° C. for over a 6 hour period, after which Bio-Glo reagent (included in kit) was added and immediately read on the Victor 3V luminometer at units of counts per second (CPS).

Brief Summary: The luminescence data demonstrate that the p307 BiTE induces CLDN 18.2 specific activation of the CD3+ Jurkat cells (FIG. 28). In other words, cells positive for the tumor associated antigen (TAA) need to be present for the BiTE's to induce relative levels of activation.

Example 22

This example demonstrates a T-Cell activation assay using Jurkat cells with NFAT-RE reporter and CLDN18.2-CD3 BiTEs using artificial overexpressed cells and endogenous cell lines.

Method: (Same as FIG. 28 but with both CLDN18.2 BiTEs) Assays were run using Promega's T Cell Activation Bioassay kits (NFAT-RE J1621). Target cells were seeded at a density of 40,000 cells/well in white 96 well plate wells and incubated at 37.0 overnight, after which thaw-and-use Jurkat T cells included in the assay kit (engineered to luminesce when activated) were added to the seeded cells (1:1 cell ratio) along with the BiTE treatments. BiTE treatments were added in nine serial 1:4 dilutions at a starting concentration of 10 nM. Treated plates were incubated in 37° C. over a 6 hour period, after which Bio-Glo reagent (included in kit) was added and immediately read on the Victor 3V luminometer at units of counts per second (CPS).

Figure 29:
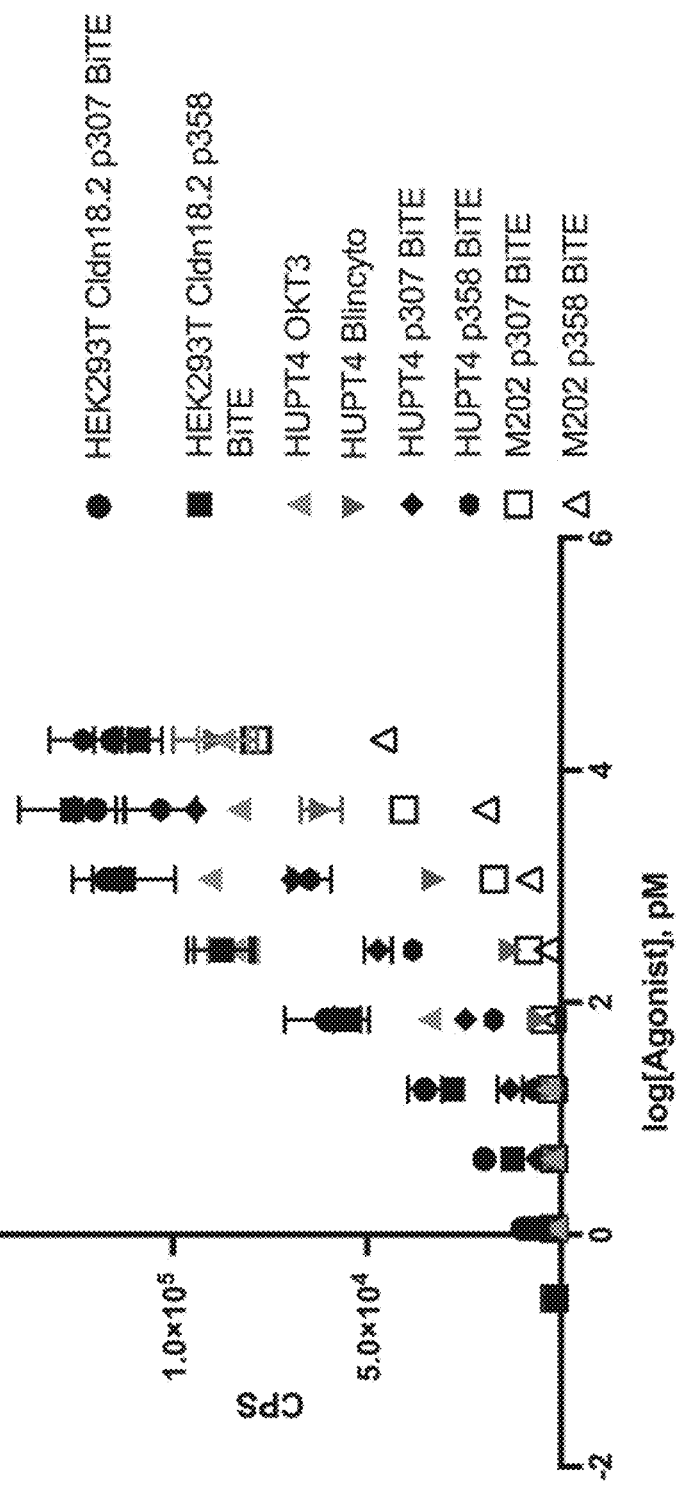
FIG. 29 represents the T-cell activation assay using Jurkat cells with NFAT-RE reporter and CLDN18.2-CD3 BiTEs using cells endogenously expressing CLDN18.2 or cells engineered to overexpress CLDN18.2.

Brief Summary: The luminescence data demonstrate that the p307 and p358 BiTEs induce CLDN18.2 specific activation of the CD3+ Jurkat cells (FIG. 29). In other words, cells positive for the tumor associated antigen (TAA) are required for the BiTEs to induce relative levels of activation.

Example 23

This example shows representative images of CLDN18.2-CD3 bispecific cytotoxicity assay 5 days post treatment.

Method: In a 96 well plate, pan CD3+ human PBMCs (purchased from HumanCells Bio) were co-cultured with HUPT4, a Cldn18.2+ cell line, at different Effector:Target ratios and treated with either p307 CLDN18.2 BiTE or negative control Blincyto. The concentration of treatment started at 125 ng/mL and was serially diluted at a 1:10 ratio. After five days post treatment, the plate was imaged with a Cellavista imaging system to determine if the co-culture and treatment would induce cytotoxic effects on the HUPT4 cells and to which extent.

Brief Summary: The Cellavista images demonstrate that p307 CLDN18.2 BiTE induce cytotoxic effects on the HUPT4 cells. In contrast, a negative control Blincyto which is specific to CD19 and not CLDN18.2, did not affect the HUPT4 cells at the same concentrations (FIG. 30A-FIG. 30F).

Example 24

This example demonstrates the LDH activity of CLDN18.2-CD3 BiTEs 5 days post treatment.

Method: Media from the experiment detailed in Example 22 were collected and spun at 14,500 rpm for 10 min to prepare for an LDH assay (Sigma: MAK066). 6 µl of culture medium from each well was used for the LDH activity assay. RPMI with 10% FBS was used as a negative control. The assays were performed at 37° C. and the OD450 nM was measured every 15 mins with 30 second interval using a microplate reader (Molecular Device).

Figure 31:
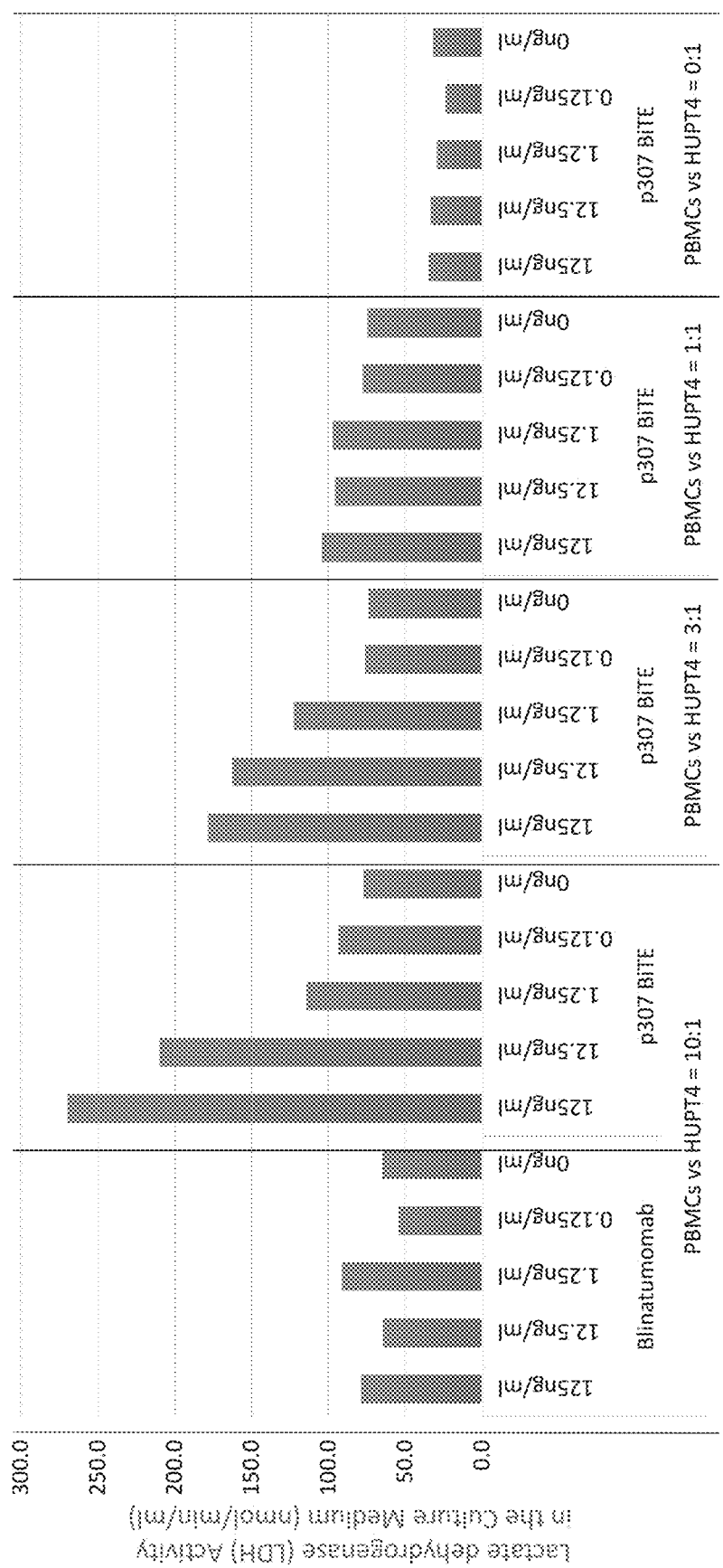
FIG. 31 represents the lactate dehydrogenase (LDH) activity of CLDN18.2-CD3 BiTEs 5 days post treatment.

Brief Summary: An LDH colorimetric assay was used as a simple method to measure relative levels of cytotoxicity. Results demonstrate target-specific cytotoxicity and a dose-dependent response; HUPT4 cells co-cultured with CD3+ human PBMCs and treated with p307 BiTE released noticeably higher levels of LDH in comparison to cells treated with a negative control blinatumomab (Blincyto). An effector cell to target cell ratio-dependent response is also observed, indicating that CD3+ cells are required for cytotoxic effects (FIG. 31).

Example 25

This example demonstrates the in vivo activity of CLDN18.2-directed BiTEs (CD3) in CLDN18.2 positive HUPT4 pancreas cancer cell line xenografts of human PBMC injected mice.

Method: The anti-tumor activity of CLDN18.2 directed BiTEs were evaluated in cell line xenograft studies using immunocompromised mice supplemented with human PBMC injection. Immunocompromised (NSG) mice were injected with $1.0 \times 10^7$ HUPT4 pancreas cancer cells 12 days prior to intraperitoneal injection of either $1.1 \times 10^7$ human donor peripheral blood mononuclear cells (PBMCs) stimulated with IL-2. The day after injection of PBMCs, mice were randomized into groups based on mean tumor volume (150-200 mm$^3$) and treated continuously for 7 days with daily intravenous (IV) injection of either 1 mg/kg Blincyto (non-targeting control), 1 mg/kg CLDN18.2-BiTE-307 or 1 mg/kg CLDN18.2-BiTE-358. Additional controls groups were also treated with non-targeting human IgG1 antibody (10 mg/kg IV QW), CLDN18.2-mAb-307 (10 mg/kg IV QW) or CLDN18.2-mAb-358 (10 mg/kg IV QW).

Figure 32:
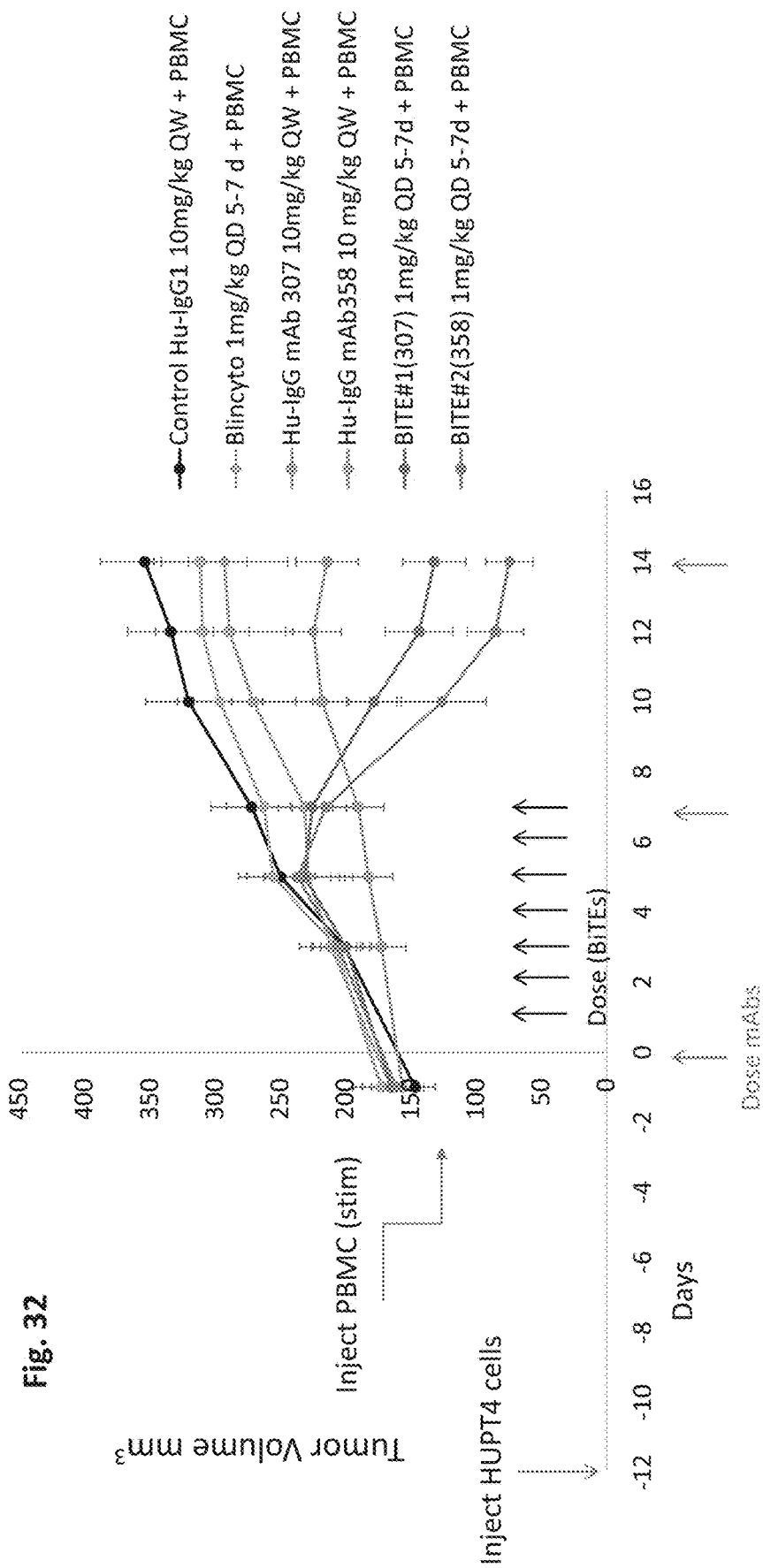
FIG. 32 represents a graph of tumor volume (mm$^3$) of tumors in mice bearing pancreatic (HUPT4) tumors and injected with human PBMCs as a function of time (days) after treatment with different doses of anti-CLDN18.2 BiTEs.

Brief Summary: Significant tumor regressions of the CLDN 18.2-positive HUPT4 xenografts were observed only in mice treated with CLDN18.2-BiTE-307 or CLDN18.2-BiTE-358 (FIG. 32). No anti-tumor activity was observed in response to treatment with the CD19-directed BiTE, Blincyto. HUPT4 cells do not express CD19 protein. mAbs directed against CLDN18.2 also had no activity in this model (FIG. 32). These data illustrate the potent activity of CLDN 18.2 BiTEs and advantage in targeting CLND 18.2 using the BiTE technology.

Example 26

This example demonstrates the in vivo activity of CLDN 18.2-directed BiTEs (CD3) in CLDN 18.2-positive HUPT4 cancer cell line xenografts in humanized BLT mice.

Method: The anti-tumor activity of CLDN 18.2 directed BiTEs were evaluated in cell line xenograft studies using immunocompromised (NSG) mice implanted with fetal donor CD38+ stem cells and fragments of donor liver and thymus to generate a fully humanized immune system. Reconstitution of human immune cells was confirmed in these BLT (Bone marrow Liver Thymus) mice prior to injection with $1.0 \times 10^7$ HUPT4 pancreas cancer cells. Once tumors reached a mean volume of 200 mm$^3$, mice were treated with either 10 mg/kg Hu-IgG1 control IV QW or 1 mg/kg CLDN18.2-BiTE-307 IV for 5 consecutive days.

Brief Summary: Significant tumor regressions were observed in mice treated with CLDN18.2-BiTE-307 (FIG. 33A and FIG. 33B). These data demonstrate that the CLDN18.2-targeting BiTE described herein induces significant anti-tumor activity in humanized mice bearing CLDN18.2-positive cancer cell line xenografts.

Following Tables 9-11 represent various antigen-binding proteins or bispecific antigen-binding proteins that bind to CLDN 18.2.

TABLE 9

(also shown in FIG. 13)

| SEQ ID NO: | Ab Clone | Amino Acid Sequence |
|---|---|---|
| | | Light Chain Variable Region |
| 11 | 307 | DIVMTQSPSSLTVTTGEKVTMSCKSSQSLLNSGNQKNYLSWYQQIPGQPPKLLFYWASTRESGVPDRFTGSGSGTDFTLTISNVQAEDLAVYYCQNDYSYPFTFGAGTKLELR |
| 13 | 369 | DILMTQSPSSLTVTAGEKVTMTCKSSQSLLNSGNQKNYLTWYQQKPGQPPKLLIYWASSRESGVPDRFTGSGSGTDFTLTISSVQAEDLAVYYCQNDYSYPFTFGAGTKLELK |
| 15 | 376 | DIVMTQSPSSLTVTAGEKVTMSCKSSQSLLNSGNQKNYLTWYQQKPGQPPKLLIYWASTRESGVPDRFTGSGSGTGFTLTISSVQAEDLAVYYCQNDYSYPFTFGAGTKLELK |
| 17 | 358 | DIVMTQSPSSLTVTAGEKVTMSCKSSQSLFNSGNQRNYLTWYQQKPGQPPKLLIYWASTRESGVPDRFTGSGSGTGFTLTISSVQAEDLAFYYCQNVYIYPLTFGLGTKLELR |
| 19 | 384 | DIVMTQSPSSLTVTAGEKVTMSCKSSQSLLNSGNQKNYLTWYQQRPGQPPKLLIYWASTRESGVPDRFTGSGSGTDFTLTISSVQAEDLAVYCCQNNYYPFTFGGGTKLGIK |
| 21 | 360 | DIVMTQSPSSLAVTAGEQVTMSCKSSQSLLNSGNQKNYLTWYQQKPGQPPKLLIYWASIRQSGVPDRFTGSGSGTDFTLTISSVQAEDLAVYYCLNDYGFPLTFGAGTKLELK |
| 23 | 432 | DIVMTQSPSSLTVTAREKVTMNCKSTQSLLNSGNQKNYLTWYQQKPGQPPKLLIYWASTRESGVPDRFTGSGSGTDFTLTISSVQAEDLAVYYCQNAYYYPFTFGGGTKLEIK |
| 25 | 400 | DVVMTQSPSSLTVTAGEKVTMNCKSSQSLLNSGNQRSYLTWYQQKPGQPPKLLIYWASTRESGAPDRFTGSGSGADFTLTISSVQAEDLAIYYCQNNYNYPFTFGSGTKLEIK |
| 27 | 331 | DIVMTQSPSSLTVTAGEKVTMSCKSSQSLLNSGNQKNYLTWYQQKPGQPPKLLFYWASTKKSGVPDRFTGSGSRTDFTLTISSVQAEDLAVYYCLNDYSFPLTFGAGTKLELK |
| 29 | 347 | DIVMTQSPSSLTVTAGEKVTMSCKSSQSLLNSGNQKNYLTWYQQKPGQPPKLLIYWASTRQSGVPDRFTGSGSGTDFTLTISSVQAEDLTVYYCLNDYSFPLTFGAGTKLELK |
| 31 | 339 | DIVMTQSPSSLTVTAGEKVTMTCKSSQSLLNSGNQKNYLTWYQQKPGQPPKLLIYWASTGASGVPDRFTGSGSGTDFTLTISSAQAADLAVYYCLNDYSFPLTFGAGTKLELK |

TABLE 9-continued (also shown in FIG. 13)

| SEQ ID NO: | Ab Clone | Amino Acid Sequence |
|---|---|---|
| 33 | 301 | DIVMTQSPSSLAVTTGEQVTMNCKSSQSLLNSGNQKNYLTWYQQKTGQ SPKLLIYWASTRQSGVPDRFTGSGSGTDFTLTISSVQAEDLAVYYCLN DYGFPLTFGAGTKLELK |
| 35 | 392 | DIVMTQSPSSLTVTTGEKVTMDCKSSQSLLNSGNQKNYLTWYQQKSGQ PPKLLIYWASIRKSGVPDRFTGSGSGTDFTLTISSVQAEDLAVYYCLN DYSFPLTFGAGTKLELK |
| 37 | 416 | QIVLTQSPAIMSASPGQKVTITCSASSTTNYMHWYQQKLGSSPKLWTY DTSKLAPGVPARFSGSGSGTSYSLTISSMEAEDAASYFCHQWSSYPPT FGSGTKLELK |
| 39 | 409 | DIQMTQTTSSLSASLGDRVTISCRASQDISNYLNWYQQKPDGTVKLLI YYTSRLHSGVPSRFSGSGSGTDYSLTISNLEPEDIATYYCQHYSKLPP TFGSGTKLEIK |
| 41 | 424 | DIVITQDELSNPVTSGESVSISCRSSKSLLYKDGKTYLNWFLQRPGQS PQLLVYWMSTRASGVSDRFSGSGSGTDFTLEISRVKAEDVGVYYCQQV VYYPYTFGSGTKLEIK |
| 58 | Benchmark 1-175D10 | DIVMTQSPSSLTVTAGEKVTMSCKSSQSLLNSGNQKNYLTWYQQKPGQ PPKLLIYWASTRESGVPDRFTGSGSGTDFTLTISSVQAEDLAVYYCQN DYSYPFTFGSGTKLEIK |
| 60 | Benchmark 2-163E12 | DIVMTQSPSSLTVTAGEKVTMSCKSSQSLLNSGNQKNYLTWYQQKPGQ PPKLLIYWASTRESGVPDRFTGSGSGTDFTLTISSVQAEDLAVYYCQN DYSYPLTFGAGTKLELK |
| 62 | Benchmark 3-zoletuximab | DIVMTQSPSSLTVTAGEKVTMSCKSSQSLLNSGNQKNYLTWYQQKPGQ PPKLLIYWASTRESGVPDRFTGSGSGTDFTLTISSVQAEDLAVYYCQN DYSYPFTFGSGTKLETK |
| Heavy Chain Variable Region | | |
| 10 | 307 | DVKLVESGGGLVKPGGSLKLSCAASGFTFSSYTMSWVRQTPEKRLEWV ATIIIGGSYTYYPDSVKGRFTISRDNAKNTLYLQMSSLKSEDTAMYYC TRLVKGNAMDYWGQGTSLAVSS |
| 12 | 369 | DVKLVESGGGLVKPGGSLKLSCAASGFTFSSYTMSWVRQTPEKRLEWV ATIIIGGSYTYYPDSVKGRFTISRDNAKNTLYLQMSSLKSEDTAMYYC TRLVKGNAMDYWGQGTSVTVSS |
| 14 | 376 | DVKLVESGGGLVKPGGSLKLSCAASGFTFSSYTMSWVRQTPEKRLYWV ATISSGVSYTYYPDSVKGRFTISRDNAKNTLYLQMSSLKSEDTAMYYC TRLTKGNAMDYWGQGTSVTVSS |
| 16 | 358 | VVQLVESGGDFVQPGGSRKLSCAVSGFTFSSFGMHWVRQAPEKGLEWV AYISSGTTNIYYADTVKGRFTVSRDNPKNSLFLHMTSLRSEDTAMYYC VRSGYYGNSLDYWGQGTPLTVSS |
| 18 | 384 | QVQLQQSGAELARPGASVKLSCKASDYTFTSYVISWVKQRTGQGLEWI GEIYPRNGNTYYNEKFKGKATLTADKSSSTAYMELRSLTSEDSAVYFC ARSYYGNSFAYWGQGTLVTVSA |
| 20 | 360 | VVQLQQSGPELVKPGASVKMSCKASGYTFTSYLMHWVRQKPGLGLDWI GYINPYNDGTNYNAKFIDKATLTSDKSSSTAYMELSSLTSEDSAIYYC TRGDYWGQGTSVTVSS |
| 22 | 432 | QIQLQQSGAELARPRASVKLSCKASGYTFTSDVISWVKQRPGQGLEWI GESYLRNGNTYYNENFKGKATLTADKSSSTAYMELRSLTSEDSAVYFC ARSYYGNSFAYWGQGTLVTVSA |
| 24 | 400 | QVQLKESGPGLVAPSQSLSITCTVSGFSLNSYGVSWVRQPPGKGLEWL GVIWGDGSTNYHSALKSRLNINKDKSKSQVFLKLNSLQTDDTATYYCA RPTRGNAMDYWGQGTSVTVSS |
| 26 | 331 | EVQLQQSGPELVKPGASVRMSCKASGYTFTSYIMHWVKQKPGQGPEWM GYINPYNDGTNYNEKFKDKATLTSDKSSSTAYMDLSSLTSEDSAVYYC TRGDYWGQGTSVTVSS |
| 28 | 347 | EVQLQQSGPELVKPGASVKMSCKASGYTFTSYLIHWVKQKPGQGLEWI GYINPYNDATYYNEKFKAKATLTSDKSSSTAYMELSSLTSEDTAIYYC TRGDYWSQGTSVTVSS |

TABLE 9-continued (also shown in FIG. 13)

| SEQ ID NO: | Ab Clone | Amino Acid Sequence |
|---|---|---|
| 30 | 339 | EVQLQQSGPELVKPGASVKMSCKASGYTFTSYVMHWVKQKPGQGLEWI GYFNPYNDDTKYNEKFKGKATLTSDKSSSTAYMDLSSLTSEDSAVYXC TRGDYWGQGTSVTVSS |
| 32 | 301 | VVQLQQSGPELVKPGASVKMSCKASGYTFTSFLIHWVRQKPGLGLEWI GYINPYDYGINYNVKFMDKVTLTSDKTSSTAYMELSSLTSADSAIYYC TRGDYWGQGTSVIVSS |
| 34 | 392 | EVQLQQSGPELVKPGASVKMSCKASGFTFTSYVMHWVKQKSGQGLEWI GYINPYNDDIKYNAKFEDKATLTSDRSSSTAYMELSSLTSDDSAVYFC TRGDYWGQGTTLTVSS |
| 36 | 416 | EFQLQQSGPELVKPGASVKISCKASVYSFTGYNMNWVKQSNGKSLEWI GVINPNYGNTNYNQRFKGKATLTVDQSSSTAYMQLNSLTSEDSAVYYC ARSEDYYNIRGASWGQGTLVTVSA |
| 38 | 409 | QVQLQQSGAELARPGASVKLSCKASGYTFTSYGTSWVKQRTGQGLEWI GEISPRSGNTYYNEKFKGKATLTADKSSSTAYMELRSLTSEDSAVYFC ATGVITTVIPTDWYFDVWGTGTTVTVSS |
| 40 | 424 | EVQLQQSGPELVKPGASVKISCKASGYSFTVYYMNWVKQSPEKSLEWI GEINPSTGGTTYNPKFKAKATLTVDKSSSTAYMQLKSLTSEDSAIYFC VRWADYWGQGTTLTVSS |
| 59 | Benchmark 1 | QVQLQQPGAELVRPGASVKLSCKASGYTFTSYWINWVKQRPGQGLEWI GNIYPSDSYTNYNQKFKDKATLTVDKSSSTAYMQLSSPTSEDSAVYYC TRSWRGNSFDYWGQGTTLTVSS |
| 61 | Benchmark 2 | QVQLQQSGAELARPGASVKLSCKASGYTFTDYYINWVKQRTGQGLEWI GEIYPGSGNTYYNEKFKGKATLTADKSSSTAYMQLSSLTSEDSAVYFC ARSYGAFDYWGQGTTLTVSS |
| 148 | Benchmark 2-1 | QIQLVQSGPELKKPGETVKISCKASGYTFTNYGMNWVKQAPGKGLKWM GWINTNTGEPTYAEEFKGRFAFSLETSASTAYLQINNLKNEDTATYFC ARLGFGNAMDYWGQGTSVTVSS |
| 63 | Benchmark 3-zoletuximab | QVQLQQPGAELVRPGASVKLSCKASGYTFTSYWINWVKQRPGQGLEWI GNIYPSDSYTNYNQKFKDKATLTVDKSSSTAYMQLSSPTSEDSAVYYC TRSWRGNSFDYWGQGTTLTVSS |

Humanized Light Chain Variable Region

| 43 | HuAb307-1 (L1) | DIVMTQSPDSLAVSLGERATINCKSSQSLLNSGNQKNYLSWYQQKPGQ PPKLLIYWASTRESGVPDRFSGSGSGTDFTLTISSLQAEDVAVYYCQN DYSYPFTFGQGTKLEIK |
| 44 | HuAb307-2 (L2) | DIVMTQSPDSLAVSLGERATINCKSSQSLLNSGNQKNYLSWYQQKPGQ PPKLLFYWASTRESGVPDRFSGSGSGTDFTLTISSLQAEDVAVYYCQN DYSYPFTFGQGTKLEIK |
| 45 | HuAb307-3 (L3) | DIVMTQSPDSLAVSLGERVTMNCKSSQSLLNSGNQKNYLSWYQQKPGQ PPKLLFYWASTRESGVPDRFSGSGSGTDFTLTISSVQAEDVAVYYCQN DYSYPFTFGQGTKLEIK |
| 47 | HuAb376-1 (L1) | DIVMTQSPDSLAVSLGERATINCKSSQSLLNSGNQKNYLTWYQQKPGQ PPKLLIYWASTRESGVPDRFSGSGSGTDFTLTISSLQAEDVAVYYCQN DYSYPFTFGQGTKLEIK |
| 48 | HuAb376-2 (L2) | DIVMTQSPDSLAVSLGERVTMNCKSSQSLLNSGNQKNYLTWYQQKPGQ PPKLLIYWASTRESGVPDRFSGSGSGTDFTLTISSVQAEDVAVYYCQN DYSYPFTFGQGTKLEIK |
| 149 | HuAb358-1 (L1) | DIVMTQSPDSLAVSLGERATINCKSSQSLFNSGNQRNYLTWYQQKPGQ PPKLLIYWASTRESGVPDRFSGSGSGTDFTLTISSLQAEDVAVYYCQN VYIYPLTFGQGTKLEIK |
| 150 | HuAb358-2 (L2) | DIVMTQSPDSLAVSLGERVTMNCKSSQSLFNSGNQRNYLTWYQQKPGQ PPKLLIYWASTRESGVPDRFSGSGSGTDFTLTISSVQAEDVAVYYCQN VYIYPLTFGQGTKLEIK |
| 53 | HuAb360-1 (L1) | DIVMTQSPDSLAVSLGERATINCKSSQSLLNSGNQKNYLTWYQQKPGQ PPKLLIYWASIRQSGVPDRFSGSGSGTDFTLTISSLQAEDVAVYYCLN DYGFPLFGQGTKLEIK |

TABLE 9-continued (also shown in FIG. 13)

| SEQ ID NO: | Ab Clone | Amino Acid Sequence |
|---|---|---|
| 54 | HuAb360-2 (L2) | DIVMTQSPDSLAVSLGERVTMNCKSSQSLLNSGNQKNYLTWYQQKPGQPPKLLIYWASIRQSGVPDRFSGSGSGTDFTLTISSVQAEDVAVYYCLNDYGFPLTFGQGTKLEIK |
| 53 | HuAb360-3 (L1) | DIVMTQSPDSLAVSLGERATINCKSSQSLLNSGNQKNYLTWYQQKPGQPPKLLIYWASIRQSGVPDRFSGSGSGTDFTLTISSLQAEDVAVYYCLNDYGFPLTFGQGTKLEIK |
| 54 | HuAb360-4 (L2) | DIVMTQSPDSLAVSLGERVTMNCKSSQSLLNSGNQKNYLTWYQQKPGQPPKLLIYWASIRQSGVPDRFSGSGSGTDFTLTISSVQAEDVAVYYCLNDYGFPLTFGQGTKLEIK |
| 53 | HuAb360-5 (L1) | DIVMTQSPDSLAVSLGERATINCKSSQSLLNSGNQKNYLTWYQQKPGQPPKLLIYWASIRQSGVPDRFSGSGSGTDFTLTISSLQAEDVAVYYCLNDYGFPLTFGQGTKLEIK |
| 54 | HuAb360-6 (L2) | DIVMTQSPDSLAVSLGERVTMNCKSSQSLLNSGNQKNYLTWYQQKPGQPPKLLIYWASIRQSGVPDRFSGSGSGTDFTLTISSVQAEDVAVYYCLNDYGFPLTFGQGTKLEIK |
| 50 | HuAb432-1 (L1) | DIVMTQSPDSLAVSLGERATINCKSTQSLLNSGNQKNYLTWYQQKPGQPPKLLIYWASTRESGVPDRFSGSGSGTDFTLTISSLQAEDVAVYYCQNAYYYPFTFGQGTKLEIK |
| 51 | HuAb432-2 (L2) | DIVMTQSPDSLAVSLGERVTMNCKSTQSLLNSGNQKNYLTWYQQKPGQPPKLLIYWASTRESGVPDRFSGSGSGTDFTLTISSVQAEDVAVYYCQNAYYYPFTFGQGTKLEIK |
| 50 | HuAb432-3 (L1) | DIVMTQSPDSLAVSLGERATINCKSTQSLLNSGNQKNYLTWYQQKPGQPPKLLIYWASTRESGVPDRFSGSGSGTDFTLTISSLQAEDVAVYYCQNAYYYPFTFGQGTKLEIK |
| 51 | HuAb432-4 (L2) | DIVMTQSPDSLAVSLGERVTMNCKSTQSLLNSGNQKNYLTWYQQKPGQPPKLLIYWASTRESGVPDRFSGSGSGTDFTLTISSVQAEDVAVYYCQNAYYYPFTFGQGTKLEIK |
| Humanized Heavy Chain Variable Region | | |
| 42 | HuAb307-1 (H2) | EVQLLESGGGLVQPGGSLRLSCAASGFTFSSYTMSWVRQAPGKGLEWVATIIIGGSYTYYADSVKGRPTISRDNSKNTLYLQMNSLRAEDTAVYYCTRLVKGNAMDYWGQGTLVTVSS |
| 42 | HuAb307-2 (H2) | EVQLLESGGGLVQPGGSLRLSCAASGFTFSSYTMSWVRQAPGKGLEWVATIIIGGSYTYYADSVKGRFTISRDNSKNTLYLQMNSLRAEDTAVYYCTRLVKGNAMDYWGQGTLVTVSS |
| 42 | HuAb307-3 (H2) | EVQLLESGGGLVQPGGSLRLSCAASGFTFSSYTMSWVRQAPGKGLEWVATIIIGGSYTYYADSVKGRFTISRDNSKNTLYLQMNSLRAEDTAVYYCTRLVKGNAMDYWGQGTLVTVSS |
| 46 | HuAb376-1 (H2) | EVQLLESGGGLVQPGGSLRLSCAASGFTFSSYTMSWVRQAPGKGLEWVATISSGVSYTYYADSVKGRFTISRDNSKNTLYLQMNSLRAEDTAVYYCTRLTKGNAMDYWGQGTLVTVSS |
| 46 | HuAb376-2 (H2) | EVQLLESGGGLVQPGGSLRLSCAASGFTFSSYTMSWVRQAPGKGLEWVATISSGVSYTYYADSVKGRFTISRDNSKNTLYLQMNSLRAEDTAVYYCTRLTKGNAMDYWGQGTLVTVSS |
| 131 | HuAb358-1 (H2) | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGNSLDYWGQGTLVTVSS |
| 131 | HuAb358-2 (H2) | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGNSLDYWGQGTLVTVSS |
| 52 | HuAb360-1 (H2) | QVQLVQSGAEVKKPGASVKVSCKASGYTFTSYLMHWVRQAPGQGLEWIGYINPYNDGTNYAQKFQGRVTMTSDTSTSTVYMELSSLRSEDTAVYYCTRGDYWGQGTLVTVSS |
| 52 | HuAb360-2 (H2) | QVQLVQSGAEVKKPGASVKVSCKASGYTFTSYLMHWVRQAPGQGLEWIGYINPYNDGTNYAQKFQGRVTMTSDTSTSTVYMELSSLRSEDTAVYYCTRGDYWGQGTLVTVSS |

TABLE 9-continued (also shown in FIG. 13)

| SEQ ID NO: | Ab Clone | Amino Acid Sequence |
|---|---|---|
| 55 | HuAb360-3 (H3) | QVQLVQSGAEVKKPGASVKMSCKASGYTFTSYLMHWVRQAPGQGLEWI GYINPYNDGTNYAQKFQGRATLTSDTSTSTAYMELSSLRSEDTAVYYC TRGDYWGQGTLVTVSS |
| 55 | HuAb360-4 (H3) | QVQLVQSGAEVKKPGASVKMSCKASGYTFTSYLMHWVRQAPGQGLEWI GYINPYNDGTNYAQKFQGRATLTSDTSTSTAYMELSSLRSEDTAVYYC TRGDYWGQGTLVTVSS |
| 56 | HuAb360-5 (H4) | QVQLVQSGAEVKKPGASVKMSCKASGYTFTSYLMHWVRQAPGQGLEWI GYINPYNDGTNYAQKFQGRATLTSDKSTSTAYMELSSLRSEDTAVYYC TRGDYWGQGTLVTVSS |
| 56 | HuAb360-6 (H4) | QVQLVQSGAEVKKPGASVKMSCKASGYTFTSYLMHWVRQAPGQGLEWI GYINPYNDGTNYAQKFQGRATLTSDKSTSTAYMELSSLRSEDTAVYYC TRGDYWGQGTLVTVSS |
| 57 | HuAb432-1 (H1) | QVQLVQSGAEVKKPGSSVKVSCKASGYTFTSDVISWVRQAPGQGLEWM GESYLRNGNTYYAQKFQGRVTITADKSTSTAYMELSSLRSEDTAVYYC ARSYYGNSFAYWGQGTLVTVSS |
| 57 | HuAb432-2 (H1) | QVQLVQSGAEVKKPGSSVKVSCKASGYTFTSDVISWVRQAPGQGLEWM GESYLRNGNTYYAQKFQGRVTITADKSTSTAYMELSSLRSEDTAVYYC ARSYYGNSFAYWGQGTLVTVSS |
| 49 | HuAb432-3 (H2) | QVQLVQSGAEVKKPGSSVKLSCKASGYTFTSDVISWVRQAPGQGLEWI GESYLRNGNTYYAQKFQGRATLTADKSTSTAYMELSSLRSEDTAVYYC ARSYYGNSFAYWGQGTLVTVSS |
| 49 | HuAb432-4 (H2) | QVQLVQSGAEVKKPGSSVKLSCKASGYTFTSDVISWVRQAPGQGLEWI GESYLRNGNTYYAQKFQGRATLTADKSTSTAYMELSSLRSEDTAVYYC ARSYYGNSFAYWGQGTLVTVSS |

TABLE 10

(also shown in FIG. 17)

| SEQ ID NO | Name | Description | Sequence |
|---|---|---|---|
| 131 | 02-0358-4h_VH | 02-0358-4h antibody | EVQLVESGGGLVQPGGSLRLSCAVSGFTFSSFGMHVWRQAP GKGLEVWVAYISSGTTNIYYADSVKGRFTVSRDNAKNSLYLQM NSLRAEDTAVYYCVRSGYYGNSLDYWGQGTLVTVSS |
| 135 | 02-0358-4h_VL | 02-0358-4h antibody | DIVMTQSPDSLAVSLGERVTMNCKSSQSLFQSGNQRNYLTW YQQKPGQPPKLLIYWASTRESGVPDRFSGSGSGTDFTLTISS VQAEDVAVYYCQNVYIYPLTFGQGTKLEIK |
| 131 | 02-0358-5h_VH | 02-0358-5h antibody | EVQLVESGGGLVQPGGSLRLSCAVSGFTFSSFGMHVWRQAP GKGLEVWVAYISSGTTNIYYADSVKGRFTVSRDNAKNSLYLQM NSLRAEDTAVYYCVRSGYYGNSLDYWGQGTLVTVSS |
| 136 | 02-0358-5h_VL | 02-0358-5h antibody | DIVMTQSPDSLAVSLGERVTMNCKSSQSLFSSGNQRNYLTW YQQKPGQPPKLLIYWASTRESGVPDRFSGSGSGTDFTLTISS VQAEDVAVYYCQNVYIYPLTFGQGTKLEIK |
| 133 | 02-0358-6h_VH | 02-0358-6h antibody | EVQLVESGGGLVQPGGSLRLSCAVSGFTFSSFGMHVWRQAP GKGLEVWVAYISSGTTNIYYADSVKGRFTVSRDNAKNSLYLQM NSLRAEDTAVYYCVRSGYYGQSLDYWGQGTLVTVSS |
| 137 | 02-0358-6h_VL | 02-0358-6h antibody | DIVMTQSPDSLAVSLGERVTMNCKSSQSLFNSGNQRNYLTW YQQKPGQPPKLLIYWASTRESGVPDRFSGSGSGTDFTLTISS VQAEDVAVYYCQNVYIYPLTFGQGTKLEIK |
| 134 | 02-0358-7h_VH | 02-0358-7h antibody | EVQLVESGGGLVQPGGSLRLSCAVSGFTFSSFGMHVWRQAP GKGLEVWVAYISSGTTNIYYADSVKGRFTVSRDNAKNSLYLQM NSLRAEDTAVYYCVRSGYYGSSLDYWGQGTLVTVSS |
| 137 | 02-0358-7h_VL | 02-0358-7h antibody | DIVMTQSPDSLAVSLGERVTMNCKSSQSLFNSGNQRNYLTW YQQKPGQPPKLLIYWASTRESGVPDRFSGSGSGTDFTLTISS VQAEDVAVYYCQNVYIYPLTFGQGTKLEIK |

TABLE 10-continued (also shown in FIG. 17)

| SEQ ID NO | Name | Description | Sequence |
|---|---|---|---|
| 133 | 02-0358-8h_VH | 02-0358-8h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGQSLDYWGQGTLVTVSS |
| 135 | 02-0358-8h_VL | 02-0358-8h antibody | DIVMTQSPDSLAVSLGERVTMNCKSSQSLFQSGNQRNYLTWYQQKPGQPPKLLIYWASTRESGVPDRFSGSGSGTDFTLTISSVQAEDVAVYYCQNVYIYPLTFGQGTKLEIK |
| 133 | 02-0358-9h_VH | 02-0358-9h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGQSLDYWGQGTLVTVSS |
| 136 | 02-0358-9h_VL | 02-0358-9h antibody | DIVMTQSPDSLAVSLGERVTMNCKSSQSLFSSGNQRNYLTWYQQKPGQPPKLLIYWASTRESGVPDRFSGSGSGTDFTLTISSVQAEDVAVYYCQNVYIYPLTFGQGTKLEIK |
| 134 | 02-0358-10h_VH | 02-0358-10h antibody | EVQLVESGGGLVQPGGSLRLSCAVSGFTFSSFGMHVWRQAPGKGLEWVAYISSGTTNIYYADSVKGRFTVSRDNAKNSLYLQMNSLRAEDTAVYYCVRSGYYGSSLDYWGQGTLVTVSS |
| 135 | 02-0358-10h_VL | 02-0358-10h antibody | DIVMTQSPDSLAVSLGERVTMNCKSSQSLFQSGNQRNYLTWYQQKPGQPPKLLIYWASTRESGVPDRFSGSGSGTDFTLTISSVQAEDVAVYYCQNVYIYPLTFGQGTKLEIK |
| 134 | 02-0358-11h_VH | 02-0358-11h antibody | EVQLVESGGGLVQPGGSLRLSCAVSGFTFSSFGMHWVRQAPGKGLEWVAYISSGTTNIYYADSVKGRFTVSRDNAKNSLYLQMNSLRAEDTAVYYCVRSGYYGSSLDYWGQGTLVTVSS |
| 136 | 02-0358-11h_VL | 02-0358-11h antibody | DIVMTQSPDSLAVSLGERVTMNCKSSQSLFSSGNQRNYLTWYQQKPGQPPKLLIYWASTRESGVPDRFSGSGSGTDFTLTISSVQAEDVAVYYCQNVYIYPLTFGQGTKLEIK |
| 42 | 02-h1F06-5h_VH | 02-0307-5h antibody | EVQLLESGGGLVQPGGSLRLSCAASGFTFSSYTMSWVRQAPGKGLEWVATIIIGGSYTYYADSVKGRFTISRDNSKNTLYLQMNSLRAEDTAVYYCTRLVKGNAMDYWGQGTLVTVSS |
| 140 | 02-h1F06-5h_VL | 02-0307-5h antibody | DIVMTQSPDSLAVSLGERVTMNCKSSQSLLQSGNQKNYLSWYQQKPGQPPKLLFYWASTRESGVPDRFSGSGSGTDFTLTISSVQAEDVAVYYCQNDYSYPFTFGQGTKLEIK |
| 42 | 02-h1F06-6h_VH | 02-0307-6h antibody | EVQLLESGGGLVQPGGSLRLSCAASGFTFSSYTMSWVRQAPGKGLEWVATIIIGGSYTYYADSVKGRFTISRDNSKNTLYLQMNSLRAEDTAVYYCTRLVKGNAMDYWGQGTLVTVSS |
| 141 | 02-h1F06-6h_VL | 02-0307-6h antibody | DIVMTQSPDSLAVSLGERVTMNCKSSQSLLSSGNQKNYLSWYQQKPGQPPKLLFYWASTRESGVPDRFSGSGSGTDFTLTISSVQAEDVAVYYCQNDYSYPFTFGQGTKLEIK |
| 138 | 02-h1F06-7h_VH | 02-0307-7h antibody | EVQLLESGGGLVQPGGSLRLSCAASGFTFSSYTMSWVRQAPGKGLEWVATIIIGGSYTYYADSVKGRFTISRDNSKNTLYLQMNSLRAEDTAVYYCTRLVKGQAMDYWGQGTLVTVSS |
| 142 | 02-h1F06-7h_VL | 02-0307-7h antibody | DIVMTQSPDSLAVSLGERVTMNCKSSQSLLNSGNQKNYLSWYQQKPGQPPKLLFYWASTRESGVPDRFSGSGSGTDFTLTISSVQAEDVAVYYCQNDYSYPFTFGQGTKLEIK |
| 138 | 02-h1F06-8h_VH | 02-0307-8h antibody | EVQLLESGGGLVQPGGSLRLSCAASGFTFSSYTMSWVRQAPGKGLEVWVATIIIGGSYTYYADSVKGRFTISRDNSKNTLYLQMNSLRAEDTAVYYCTRLVKGQAMDYWGQGTLVTVSS |
| 140 | 02-h1F06-8h_VL | 02-0307-8h antibody | DIVMTQSPDSLAVSLGERVTMNCKSSQSLLQSGNQKNYLSWYQQKPGQPPKLLFYWASTRESGVPDRFSGSGSGTDFTLTISSVQAEDVAVYYCQNDYSYPFTFGQGTKLEIK |
| 138 | 02-h1F06-9h_VH | 02-0307-9h antibody | EVQLLESGGGLVQPGGSLRLSCAASGFTFSSYTMSWVRQAPGKGLEVWVATIIIGGSYTYYADSVKGRFTISRDNSKNTLYLQMNSLRAEDTAVYYCTRLVKGQAMDYWGQGTLVTVSS |
| 141 | 02-h1F06-9h_VL | 02-0307-9h antibody | DIVMTQSPDSLAVSLGERVTMNCKSSQSLLSSGNQKNYLSWYQQKPGQPPKLLFYWASTRESGVPDRFSGSGSGTDFTLTISSVQAEDVAVYYCQNDYSYPFTFGQGTKLEIK |

TABLE 10-continued (also shown in FIG. 17)

| SEQ ID NO | Name | Description | Sequence |
|---|---|---|---|
| 139 | 02-h1F06-10h_VH | 02-0307-10h antibody | EVQLLESGGGLVQPGGSLRLSCAASGFTFSSYTMSWVRQAP GKGLEWVATIIIGGSYTYYADSVKGRFTISRDNSKNTLYLQMN SLRAEDTAVYYCTRLVKGSAMDYWGQGTLVTVSS |
| 142 | 02-h1FQ6-10h_VL | 02-0307-10h antibody | DIVMTQSPDSLAVSLGERVTMNCKSSQSLLNSGNQKNYLSW YQQKPGQPPKLLFYWASTRESGVPDRFSGSGSGTDFTLTISS VQAEDVAVYYCQNDYSYPFTFGQGTKLEIK |
| 139 | 02-h1F06-11h_VH | 02-0307-11h antibody | EVQLLESGGGLVQPGGSLRLSCAASGFTFSSYTMSWVRQAP GKGLEWVATIIIGGSYTYYADSVKGRFTISRDNSKNTLYLQMN SLRAEDTAVYYCTRLVKGSAMDYWGQGTLVTVSS |
| 140 | 02-h1F06-11h_VL | 02-0307-11h antibody | DIVMTQSPDSLAVSLGERVTMNCKSSQSLLQSGNQKNYLSW YQQKPGQPPKLLFYWASTRESGVPDRFSGSGSGTDFTLTISS VQAEDVAVYYCQNDYSYPFTFGQGTKLEIK |
| 139 | 02-h1F06-12h_VH | 02-0307-12h antibody | EVQLLESGGGLVQPGGSLRLSCAASGFTFSSYTMSWVRQAP GKGLEWVATIIIGGSYTYYADSVKGRFTISRDNSKNTLYLQMN SLRAEDTAVYYCTRLVKGSAMDYWGQGTLVTVSS |
| 141 | 02-h1F06-12h_VL | 02-0307-12h antibody | DIVMTQSPDSLAVSLGERVTMNCKSSQSLLSSGNQKNYLSWY QQKPGQPPKLLFYWASTRESGVPDRFSGSGSGTDFTLTISSV QAEDVAVYYCQNDYSYPFTFGQGTKLEIK |

The antibodies in Table 10 represent sequences for antibodies 307-4h and 358 h3 and additional sequence variations. These antibodies were generated to provide additional information on potential manufacturability sequence liabilities.

TABLE 11

(also shown in FIG. 23)

| Name | Description | Sequence |
|---|---|---|
| 02-0307-h4-Bs (SEQ ID NO: 143) | CLDN18.2-CD3E BiTE (Bispecific T cell engager) | DIVMTQSPDSLAVSLGERVTMNCKSSQSLLNSGNQKN YLSWYQQKPGQPPKLLFYWASTRESGVPDRFSGSGS GTDFTLTISSVQAEDVAVYYCQNDYSYPFTFGQGTKLE IKGGGGSGGGGSGGGGSEVQLLESGGGLVQPGGSL RLSCAASGFTFSSYTMSVWRQAPGKGLEWVATIIIGGS YTYYADSVKGRFTISRDNSKNTLYLQMNSLRAEDTAVY YCTRLVKGNAMDYWGQGTLVTVSSGGGGSDIKLQQS GAELARPGASVKMSCKTSGYTFTRYTMHWVKQRPGQ GLEWIGYINPSRGYTNYNQKFKDKATLTTDKSSSTAYM QLSSLTSEDSAVYYCARYYDDHYCLDYWGQGTTLTVS SVEGGSGGSGGSGGSGGVDDIQLTQSPAIMSASPGE KVTMTCRASSSVSYMNWYQQKSGTSPKRWIYDTSKV ASGVPYRFSGSGSGTSYSLTISSMEAEDAATYYCQQW SSNPLTFGAGTKLELKHHHHHH* |
| 02-0307-h4-CD16A_His (SEQ ID NO: 144) | CLDN18.2-CD16A TandAb | QVQLVQSGAEVKKPGESLKVSCKASGYTFTSYYMHW VRQAPGQGLEWMGIINPSGGSTSYAQKFQGRVTMTR DTSTSTVYMELSSLRSEDTAVYYCARGSAYYYDFADY WGQGTLVTVSSGGSGGSGGSDIVMTQSPDSLAVSLG ERVTMNCKSSQSLLNSGNQKNYLSWYQQKPGQPPKL LFYWASTRESGVPDRFSGSGSGTDFTLTISSVQAEDV AVYYCQNDYSYPFTFGQGTKLEIKGGSGGSGGSEVQL LESGGGLVQPGGSLRLSCAASGFTFSSYTMSWVRQA PGKGLEVWATIIIGGSYTYYADSVKGRFTISRDNSKNTL YLQMNSLRAEDTAVYYCTRLVKGNAMDYWGQGTLVT VSSGGSGGSGGSSYVLTQPSSVSVAPGQTATISCGG HNIGSKNVHWYQQRPGQSPVLVIYQDNKRPSGIPERF SGSNSGNTATLTISGTQAMDEADYYCQVWDNYSVLF GGGTKLTVLHHHHHH* |
| 02-0358-h3-Bs (SEQ ID NO: 145) | CLDN18.2-CD3E BiTE | DIVMTQSPDSLAVSLGERVTMNCKSSQSLFNSGNQRN YLTWYQQKPGQPPKLLIYWASTRESGVPDRFSGSGS GTDFTLTISSVQAEDVAVYYCQNVYIYPLTFGQGTKLEI KGGGGSGGGGSGGGGSEVQLVESGGGLVQPGGSLR |

TABLE 11-continued (also shown in FIG. 23)

| Name | Description | Sequence |
|---|---|---|
| | | LSCAVSGFTFSSFGMHWRQAPGKGLEWVAYISSGT<br>TNIYYADSVKGRFTVSRDNAKNSLYLQMNSLRAEDTA<br>VYYCVRSGYYGNSLDYWGQGTLVTVSSGGGGSDIKL<br>QQSGAELARPGASVKMSCKTSGYTFTRYTMHWVKQR<br>PGQGLEWIGYINPSRGYTNYNQKFKDKATLTTDKSSS<br>TAYMQLSSLTSEDSAVYYCARYYDDHYCLDYWGQGT<br>TLTVSSVEGGSGGSGGSGGSGGVDDIQLTQSPAIMSA<br>SPGEKVTMTCRASSSVSYMNWYQQKSGTSPKRWIYD<br>TSKVASGVPYRFSGSGSGTSYSLTISSMEAEDAATYY<br>CQQWSSNPLTFGAGTKLELKHHHHHH* |
| 02-0358-h3-<br>CD16A-His<br>(SEQ ID<br>NO: 146) | CLDN18.2-<br>CD16A<br>TandAb | QVQLVQSGAEVKKPGESLKVSCKASGYTFTSYYMHW<br>VRQAPGQGLEWMGIINPSGGSTSYAQKFQGRVTMTR<br>DTSTSTVYMELSSLRSEDTAVYYCARGSAYYYDFADY<br>WGQGTLVTVSSGGSGGSGGSDIVMTQSPDSLAVSLG<br>ERVTMNCKSSQSLFNSGNQRNYLTWYQQKPGQPPKL<br>LIYWASTRESGVPDRFSGSGSGTDFTLTISSVQAEDVA<br>VYYCQNVYIYPLTFGQGTKLEIKGGSGGSGGSEVQLV<br>ESGGGLVQPGGSLRLSCAVSGFTFSSFGMHWVRQAP<br>GKGLEWVAYISSGTTNIYYADSVKGRFTVSRDNAKNSL<br>YLQMNSLRAEDTAVYYCVRSGYYGNSLDYWGQGTLV<br>TVSSGGSGGSGGSSYVLTQPSSVSVAPGQTATISCGG<br>HNIGSKNVHWYQQRPGQSPVLVIYQDNKRPSGIPERF<br>SGSNSGNTATLTISGTQAMDEADYYCQVWDNYSVLF<br>GGGTKLTVLHHHHHH* |

---

What is claimed is:

1. An antigen-binding protein that binds to a human Claudin 18.2 (CLDN 18.2) protein (SEQ ID NO: 1) comprising:
   a. CDR1-3 derived from a heavy chain variable region comprising the amino acid sequence: EVQLLESGG-GLVQPGGSLRLSCAASGFTFS-SYTMSWVRQAPGKGLEWVA TIIIGGSYTYY-ADSVKGRFTISRDNSKNTLYLQMNSLRAEDTAVYYC-TRLV KGNAMDYWGQGTLVTVSS (SEQ ID NO 42) or a variant sequence thereof which differs by 1-5 amino acids; and
   b. CDR1-3 derived from a light chain variable region comprising the amino acid sequence: DIVMTQSPD-SLAVSLGERVTMNCKSSQSLLNSGNQK-NYLSWYQQKPGQP PKLLFYWAST-RESGVPDRFSGSGSGTDFTLTISSVQAEDVAVYYCOND-YS YPFTFGQGTKLEIK (SEQ ID NO 45) or a variant sequence thereof which differs by 1-5 amino acids.

2. The antigen-binding protein of claim 1, comprising:
   a. a heavy chain CDR1 comprising amino acid sequence GFTFSSYTMS (SEQ ID NO: 64), or a variant sequence thereof which differs by one or two amino acids;
   b. a heavy chain CDR2 amino acid sequence TIIIGG-SYTY (SEQ ID NO: 65), or a variant sequence thereof which differs by one or two amino acids;
   C. a heavy chain CDR3 amino acid sequence LVKG-NAMDY (SEQ ID NO: 66), or a variant sequence thereof which differs by one or two amino acids;
   d. a light chain CDR1 amino acid sequence KSSQSLLNSGNQKNYLS (SEQ ID NO: 78), or a variant sequence thereof which differs by one or two amino acids;
   e. a light chain CDR2 amino acid sequence WASTRES (SEQ ID NO: 79), or a variant sequence thereof which differs by one or two amino acids; and
   f. a light chain CDR3 amino acid sequence QNDYSYPFT (SEQ ID NO: 80), or a variant sequence thereof which differs by one or two amino acids.

3. The antigen-binding protein of claim 1, which is an antibody.

4. The antigen-binding protein of claim 3, which is a monoclonal antibody or a humanized antibody.

5. The antigen-binding protein of claim 3, which is an IgG antibody.

6. A bispecific antigen-binding protein that binds CLDN18.2 and a second antigen, wherein the antigen-binding protein that binds CLDN18.2 is an antigen-binding protein of claim 1.

7. The bispecific antigen-binding protein of claim 6, wherein the antigen-binding protein that binds CLDN18.2 comprises:
   a. a heavy chain CDR1 comprising amino acid sequence GFTFSSYTMS (SEQ ID NO: 64), or a variant sequence thereof which differs by one or two amino acids;
   b. a heavy chain CDR2 amino acid sequence TIIIGG-SYTY (SEQ ID NO: 65), or a variant sequence thereof which differs by one or two amino acids;
   C. a heavy chain CDR3 amino acid sequence LVKG-NAMDY (SEQ ID NO: 66), or a variant sequence thereof which differs by one or two amino acids;
   d. a light chain CDR1 amino acid sequence KSSQSLLNSGNOKNYLS (SEQ ID NO: 78), or a variant sequence thereof which differs by one or two amino acids;
   e. a light chain CDR2 amino acid sequence WASTRES (SEQ ID NO: 79), or a variant sequence thereof which differs by one or two amino acids; and
   f. a light chain CDR3 amino acid sequence QNDYSYPFT (SEQ ID NO: 80), or a variant sequence thereof which differs by one or two amino acids.

8. The bispecific antigen-binding protein of claim 6, wherein the second antigen is a cell surface protein expressed by a T cell or a component of the T-cell receptor (TCR).

9. The bispecific antigen-binding protein of claim 6, wherein the bispecific antigen-binding protein comprises an scFv, a Fab, a Fab', a Fv, or a F(ab')$_2$.

10. A conjugate comprising an antigen-binding protein of claim 1.

11. The conjugate of claim 10 comprising a cytotoxic agent or a chemotherapeutic agent.

12. The conjugate of claim 10, wherein the antigen-binding protein is an antibody, which is a humanized antibody or a chimeric antibody.

13. The antigen-binding protein of claim 1, wherein the antigen-binding protein comprises:
   a. a heavy chain variable region comprising the amino acid sequence: EVQLLESGGGLVQPGGSLRLS-CAASGFTFSSYTMSWVRQAPGKGLEWVA TIIIGGSYTYYADSVKGRFTISRDNSKNT-LYLQMNSLRAEDTAVYYCTRLV KGNAMDYWGQGTLVTVSS (SEQ ID NO 42) or a variant sequence thereof which differs by 1-5 amino acids; and
   b. a light chain variable region comprising the amino acid sequence: DIVMTQSPDSLAVSLGERVTMNCK-SSQSLLNSGNQKNYLSWYQQKPGQP PKLLFY-WASTRESGVPDRFSGSGSGTDFTLTISSVQAE-DVAVYYCONDYS YPFTFGQGTKLEIK (SEQ ID NO 45) or a variant sequence thereof which differs by 1-5 amino acids.

14. A bispecific antigen-binding protein that binds CLDN18.2 and a second antigen, wherein the antigen-binding protein that binds CLDN18.2 is an antigen-binding protein of claim 13.

15. A conjugate comprising an antigen-binding protein of claim 13.

* * * * *